US009708414B2

(12) United States Patent
Tremblay et al.

(10) Patent No.: US 9,708,414 B2
(45) Date of Patent: Jul. 18, 2017

(54) METHODS AND PRODUCTS FOR INCREASING FRATAXIN LEVELS AND USES THEREOF

(71) Applicant: UNIVERSITE LAVAL, Quebec (CA)

(72) Inventors: Jacques P. Tremblay, Stoneham-Et-Tewkesbury (CA); Joel Rousseau, Quebec (CA); Pierre Chapdelaine, Saint-Romuald (CA); Zoe Coulombe, Quebec (CA)

(73) Assignee: UNIVERSITÉ LAVAL, Québec (CA)

( * ) Notice: Subject to any disclaimer, the term of this patent is extended or adjusted under 35 U.S.C. 154(b) by 44 days.

(21) Appl. No.: 14/358,156

(22) PCT Filed: Nov. 16, 2012

(86) PCT No.: PCT/CA2012/050817
§ 371 (c)(1),
(2) Date: May 14, 2014

(87) PCT Pub. No.: WO2013/071440
PCT Pub. Date: May 23, 2013

(65) Prior Publication Data
US 2014/0315782 A1    Oct. 23, 2014

Related U.S. Application Data

(60) Provisional application No. 61/561,440, filed on Nov. 18, 2011.

(51) Int. Cl.
| | |
|---|---|
| *A61K 38/16* | (2006.01) |
| *C07K 1/00* | (2006.01) |
| *C07K 14/00* | (2006.01) |
| *C07K 17/00* | (2006.01) |
| *C12N 5/071* | (2010.01) |
| *C12N 5/00* | (2006.01) |
| *C07K 19/00* | (2006.01) |
| *C07K 14/195* | (2006.01) |
| *C07K 14/47* | (2006.01) |
| *A61K 38/00* | (2006.01) |

(52) U.S. Cl.
CPC .............. *C07K 19/00* (2013.01); *A61K 38/16* (2013.01); *C07K 14/195* (2013.01); *C07K 14/47* (2013.01); *A61K 38/00* (2013.01); *C07K 2319/09* (2013.01); *C07K 2319/10* (2013.01); *C07K 2319/21* (2013.01); *C07K 2319/71* (2013.01); *C07K 2319/80* (2013.01)

(58) Field of Classification Search
None
See application file for complete search history.

(56) References Cited

U.S. PATENT DOCUMENTS

2011/0301073 A1* 12/2011 Gregory et al. ............... 514/1.1

FOREIGN PATENT DOCUMENTS

| EP | 2206723 A1 | 7/2010 |
|---|---|---|
| JP | 2014-541496 | 7/2016 |
| WO | WO2010/079430 | 7/2010 |

OTHER PUBLICATIONS

Miyamoto et al., J. Biol. Chem. 272:26375-26381 (1997).*
The American Heritage® New Dictionary of Cultural Literacy, "Plasmid", 3rd Ed., available online at http://www.dictionary.com/browse/plasmid, 2 pages (2005).*
Al-Mahdawi et al.—GAA repeat expansion mutation mouse models of Friedreich ataxia exhibit oxidative stress leading to progressive neuronal and cardiac pathology. Genomics, Nov. 2006; 88(5) 580-90.
Babady et al.—Advancements in the pathophysiology of Friedreich's Ataxia and new prospects for treatments. Molecular Genetics and Metabolism 92 (2007) 23-35.
Bidichandani et al.—Atypical Friedreich ataxia caused by compound heterozygosity for a novel missense mutation and the GAA triplet-repeat expansion. Am J Hum Genet, 60: 1251-1256, 1997.
Boch et al.—Breaking the code of DNA binding specificity of TAL-type III effectors. Science, 326, 1509-1512, 2009.
Boch et al.—Xanthomonas AvrBs3 family-type III effectors: discovery and function. Annu Rev Phytopathol, 2010, 48: 419-436.
Bogdanove et al.—Two new complete genome sequences offer insight into host and tissue specificity of plant pathogenic *Xanthomonas* spp. Journal of Bacteriology, Oct. 2011, vol. 193, No. 19, pp. 5450-5464.
Calmels et al.—The first cellular models based on frataxin missense mutations that reproduce spontaneously the defects associated with Friedreich ataxia. PLoS One, Jul. 9, vol. 4, Issue 7, e6379, pp. 1-11.
Campuzano et al.—Friedreich's ataxia: autosomal recessive disease caused by an intronic GAA triplet repeat expansion. Science,vol. 271, No. 5254, Mar. 8, 1996, pp. 1423-1427.
Cermak et al.—Efficient design and assembly of custom TALEN and other TAL effector-based constructs for DNA targeting. Nucleic Acids Research, 2011, 1-11.
Clark et al.—The GAA triplet-repeat is unstable in the context of the human FXN locus and displays age-dependent expansions in cerebellum and DRG in a transgenic mouse model. Hum Genet (2007) 120: 633-640.
Condo et al.—A pool of extramitochondrial frataxin that promotes cell survival. J. Biol. Chem., 2006, 281: 16750-16756.
Cooper et al.—Friedreich's Ataxia: disease mechanisms, antioxidant and Coenzyme Q10 therapy. Biofactors 18 (2003), 163-171.
Coppola et al.—Gene expression profiling in frataxin deficient mice: microarray evidence for significant expression changes without detectable neurodegeneration. Neurobiology of Disease 22 (2006), 302-311.
Coppola et al.—Functional genomic analysis of frataxin deficiency reveals tissue-specific alterations and identifies the PPARgamma pathway as a therapeutic target in Friedreich's ataxia. Human Molecular Genetics, 2009, vol. 18, No. 13, pp. 2452-2461.

(Continued)

*Primary Examiner* — Hasan Ahmed
*Assistant Examiner* — Thea D'Ambrosio
(74) *Attorney, Agent, or Firm* — S. Serge Shahinian

(57) ABSTRACT

Methods and products (e.g., recombinant proteins) are described for increasing frataxin expression/levels in a cell, as well as uses of such methods and products, for example for the treatment of Friedreich ataxia in a subject suffering therefrom.

8 Claims, 67 Drawing Sheets

(56) References Cited

OTHER PUBLICATIONS

Cossee et al.—Friedreich's ataxia: point mutations and clinical presentation of compound heterozygotes. Annals Neurology, 1999;45: 200-206.
Grant et al.—Rational selection of small molecules that increase transcription through the GAA repeats found in Friedreich's ataxia. FEBS Lett. Oct. 2, 2006; 580(22): 5399-5405.
Guillon et al.—Frataxin deficiency causes upregulation of mitochondrial Lon and ClpP proteases and severe loss of mitochondrial Fe-S proteins. FEBS Journal 276 (2009) 1036-147.
Harding et al.—Friedreich's ataxia: a clinical and genetic study of 90 families with an analysis of early diagnostic criteria and intrafamilial clustering of clinical features. Brain(1981), 104, 589-620.
Li et al.—Expression of Human frataxin is regulated by transcription factors SRF and TFAP2. Plos One, Aug. 2010, vol. 5, Issue 8, e12286.
Lynch et al.—Friedreich ataxia: effects of genetic understanding on clinical evaluation and therapy. Arch Neurol, vol. 59, May 2002, pp. 743-747.
McCormack et al.—Frataxin point mutations in two patients with Friedreich's ataxia and unusual clinical features. J Neurol Neurosurg Psychiatry 2000; 68: 661-644.
Miranda et al.—Frataxin knockin mouse. FEBS Letters, 512(2002) 291-297.
Miranda et al.—Frataxin overexpressing mice. FEBS Letters, 572 (2004) 281-288.
Moscou et al.—A simple cipher governs DNA recognition by TAL effectors. Science, vol. 326, Dec. 11, 2009, 1501.
Pandolfo—Molecular pathogenesis of Friedreich ataxia. Arch Neurol, vol. 56, Oct. 1999, pp. 1201-1208.
Puccio et al.—Mouse models for Friedreich ataxia exhibit cardiomyopathy, sensory nerve defect and Fe-S enzyme deficiency followed by intramitochondrial iron deposits. Nature Genetics, vol. 27, Feb. 2001, 181-186.
Ristow et al.—Frataxin deficiency in pancreatic islets causes diabetes due to loss of beta cell mass. The Journal of Clinical Investigation, Aug. 20013, vol. 112, No. 4, pp. 527-534.
Sarsero et al.—Upregulation of expression from the FRDA genomic locus for the therapy of Friedreich ataxia. The Journal of Gene Medicine, 2003; 5: 72-81.
Sarsero et al.—Evaluation of an FRDA-EGFP genomic reporter assay in transgenic mice. Mamm Genome, vol. 16, pp. 228-241 (2005).
Schoenfeld et al.—Frataxin deficiency alters heme pathway transcripts and decreases mitochondrial heme metabolites in mammalian cells. Human Molecular Genetics, 2005, vol. 14, No. 24, pp. 3787-3799.
Singh et al.—Electroconvulsive therapy and Friedreich's ataxia. The Journal of ECT, 17(1):53-54, 2001.
Tremblay et al.—Transcription activator-like effector proteins induce the expression of the frataxin gene, Human Gene Therapy, Aug. 2012, vol. 23, No. 8, pp. 883-890.
Vyas—TAT conjugated frataxin as a nonviral therapeutic delivery system for Friedreich's ataxia, Circulation Research, Aug. 29, 2008, vol. 103, No. 5, pp. E43-E44.
Yu et al.—Colonization of rice leaf blades by an African strain of Xanthomonas oryzae pv. oryzae depends on a new TAL effector that induces the rice nodulin-3 Os11N3 gene. Mol Plant Microbe Interact, vol. 24, No. 9, 2011, pp. 1102-1113.
Zhang et al.—Efficient construction of sequence-specific TAL effectors for modulating mammalian transcription. Nature Biotechnology,vol. 29, No. 2, Feb. 2011, pp. 149-153.
International Search Report and Written Opinion of corresponding International Application No. PCT/CA2012/050817.
De Biase et al., Epigenetic Silencing in Friedreich Ataxia Is Associated with Depletion of CTCF (CCCTC-Binding Factor) and Antisense Transcription, PLoS One, Nov. 2009, vol. 4, Issue 11: 1-8.
European Search Report and Opinion in respect of European Application No. 12850493.3 (Mar. 19, 2015).
Kumari et al.,—Repeat Expansion Affects Both Transcription Initiation and Elongation in Friedreich Ataxia Cells, J. Biol. Chem., 2011, 286: 4209-4215.
Pandolfo, Massimo, Friedreich Ataxia., Handbook of Clinical Neurology, vol. 103 (3rd series), Chapter 17, 275-294 (2012).
Sandi et al., Epigenetics in Friedreich's Ataxia: Challenges and Opportunities for Therapy, Genetics Research International, vol. 2013, Article ID 852080, 1-12.
Sandi et al., Epigenetic-based therapies for Friedreich ataxia, Frontiers in Genetics, Epigenomics and Epigenetics, Jun. 2014, vol. 5, Article 165, 1-12.
Strum et al., Recombinant human erythropoietin: effects on frataxin expression in vitro, European journal of Clinical Investigation, 2005, 35: 711-717.
Yandim et al., Gene regulation and epigenetics in Friedreich's ataxia, Journal of Neurochemistry, 2013, 126 (Suppl. 1): 21-42.
Kim et al., Protective effects of transduced PEP-1-Frataxin protein on oxidative stress-induced neuronal cell death, JNS-11487; pp. 1-6.

\* cited by examiner

NCBI Reference Sequence: NM_000144.4

```
  1 agtctccctt gggtcagggg tcctggttgc actccgtgct ttgcacaaag caggctctcc
 61 attttgtta aatgcacgaa tagtgctaag ctggaagtt cttcctgagg tctaacctct
121 agctgctccc ccacagaaga gtgcctgcgg ccagtggcca ccaggggtcg cgcagcacc
181 cagcgctgga gggcggagcg ggcggcagac ccggagcagc atgtggactc tcgggcgccg
```

Position and activity of the TALEs targeting the frataxin promoter

The position of the targeted sequence is relative to NCBI Reference Sequence NM_000144.4

| Tale# | Position of target sequence | Targeted sequence | RVD | fluo red Q2 | Fluo green Q2 | Ratio red/green |
|---|---|---|---|---|---|---|
| 1 | 5-18 | tcccttgggtcagg | HD HD HD NG NG NN NN NN NG HD NI NG NN | 5530 | 37800 | 0.15 |
| 2 | 21-34 | tcctgtttgcactc | HD HD NG NN NN NG NG NN HD NI HD NG HD | 5489 | 20404 | 0.27 |
| 3 | 24-37 | tgttgcactccgt | NN NN NG NG NN HD NI HD NG NN HD NN NG | 6652 | 28642 | 0.23 |
| 4 | 37-50 | tgctttgcacaaag | NN HD NG NG NN NN HD NI HD NI NI NN NN | 7636 | 38856 | 0.20 |
| 5 | 73-86 | tgccgaatagtgc | NN HD NI HD NN NI NI NG NI NN NN NN HD | 6923 | 62983 | 0.11 |
| 6 | 81-94 | tagtgctaagctgg | NI NN NG NN HD NG NN NI NI NN HD NG NN | 7663 | 19852 | 0.39 |
| 7 | 92-105 | tgggaagttcttcc | NN NN NN NI NI NN NG NG HD NG HD HD | 5509 | 10237 | 0.54 |
| 8 | 103-116 | tcctgaggtctaac | HD HD NG NN NI NN NN NG HD NG NI NI | 4909 | 16621 | 0.30 |
| 9 | 106-119 | tgaggtctaacctc | NN NI NN NN NG NG NN NI NI HD HD NG | 8159 | 38178 | 0.21 |
| 10 | 124-137 | tgctccccacaga | NN HD NG HD HD HD HD HD NI HD NI NN NI | 4865 | 39668 | 0.12 |
| 11 | 155-168 | tggcaccaggggt | NN NN HD NI HD HD HD HD NI NN NN NN NG | 7150 | 70769 | 0.10 |
| 12 | 168-181 | tcgccgcagcaccc | HD NN HD HD NN HD NI NN HD NI HD HD | 4630 | 61567 | 0.08 |

Figure 8

A
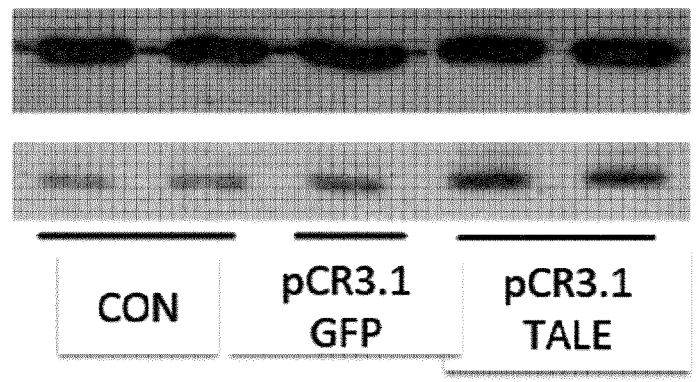
B
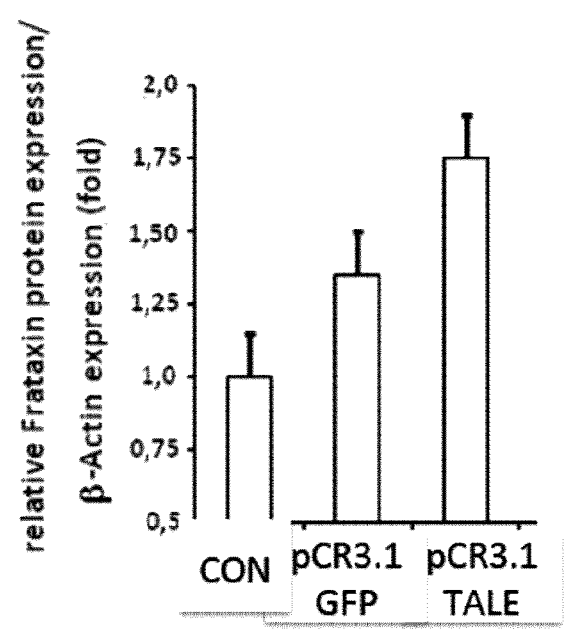
Figure 11

A.
MGHHHHHHSSGGLRSYGRKKRRQRRRGASTGGMSRTRLPSPPAPSPAFSADSFSDLLRQF
DPSLFNTSLFDSLPPFGAHHTEAATGEWDEVQSGLRAADAPPPTMRVAVTAARPPRAKPA
PRRRAAQPSDASPAAQVDLRTLGYSEKIKPKVRSTVAQHHEALVGHGFTHAHIVALSQHP
AALGTVAVKYQDMIAALPEATHEAIVGVGKQWSGARALEALLTVAGELRGPPLQLDTGQL
LKIAKRGGVTAVEAVHAWRNALTGAPLNLTPEQVVAIASHDGGKQALETVQRLLPVLCQA
HGLTPEQVVAIASHDGGKQALETVQRLLPVLCQAHGLTPEQVVAIASNGGGKQALETVQR
LLPVLCQAHGLTPEQVVAIASNNGGKQALETVQRLLPVLCQAHGLTPEQVVAIASNIGGK
QALETVQRLLPVLCQAHGLTPEQVVAIASNNGGKQALETVQRLLPVLCQAHGLTPEQVVA
IASNNGGKQALETVQRLLPVLCQAHGLTPEQVVAIASNGGGKQALETVQRLLPVLCQAHG
LTPEQVVAIASHDGGKQALETVQRLLPVLCQAHGLTPEQVVAIASNGGGKQALETVQRLL
PVLCQAHGLTPEQVVAIASNIGGKQALETVQRLLPVLCQAHGLTPEQVVAIASNIGGKQA
LETVQRLLPVLCQAHGLTPEQVVAIASHDGGRPALESIVAQLSRPDPALAALTNDHLVAL
ACLGGRPALDAVKKGLPHAPALIKRTNRRIPERTSHRVADHAQVVRVLGFFQCHSHPAQA
FDDAMTQFGMSRHGLLQLFRRVGVTELEARSGTLPPASKRWDRILQASGMKRAKPSPTST
QTPDQASLHAFADSLERDLDAPSPMHEGDQTRASASPKKKRKVEASGSGRADALDDFDLD
MLGSDALDDFDLDMLGSDALDDFDLDMLGSDALDDFDLDMLINSR–

B.
MGHHHHHHSSGIKETWWETWWTEWSQPKKKRKVSSGLEGMSRTRLPSPPAPSPAFSADSF
SDLLRQFDPSLFNTSLFDSLPPFGAHHTEAATGEWDEVQSGLRAADAPPPTMRVAVTAAR
PPRAKPAPRRRAAQPSDASPAAQVDLRTLGYSEKIKPKVRSTVAQHHEALVGHGFTHAHI
VALSQHPAALGTVAVKYQDMIAALPEATHEAIVGVGKQWSGARALEALLTVAGELRGPPL
QLDTGQLLKIAKRGGVTAVEAVHAWRNALTGAPLNLTPEQVVAIASHDGGKQALETVQRL
LPVLCQAHGLTPEQVVAIASHDGGKQALETVQRLLPVLCQAHGLTPEQVVAIASNGGGKQ
ALETVQRLLPVLCQAHGLTPEQVVAIASNNGGKQALETVQRLLPVLCQAHGLTPEQVVAI
ASNIGGKQALETVQRLLPVLCQAHGLTPEQVVAIASNNGGKQALETVQRLLPVLCQAHGL
TPEQVVAIASNNGGKQALETVQRLLPVLCQAHGLTPEQVVAIASNGGGKQALETVQRLLP
VLCQAHGLTPEQVVAIASHDGGKQALETVQRLLPVLCQAHGLTPEQVVAIASNGGGKQAL
ETVQRLLPVLCQAHGLTPEQVVAIASNIGGKQALETVQRLLPVLCQAHGLTPEQVVAIAS
NIGGKQALETVQRLLPVLCQAHGLTPEQVVAIASHDGGRPALESIVAQLSRPDPALAALT
NDHLVALACLGGRPALDAVKKGLPHAPALIKRTNRRIPERTSHRVADHAQVVRVLGFFQC
HSHPAQAFDDAMTQFGMSRHGLLQLFRRVGVTELEARSGTLPPASKRWDRILQASGMKRA
KPSPTSTQTPDQASLHAFADSLERDLDAPSPMHEGDQTRASASPKKKRKVEASGSGRADA
LDDFDLDMLGSDALDDFDLDMLGSDALDDFDLDMLGSDALDDFDLDMLINSR--

Figure 13

A.
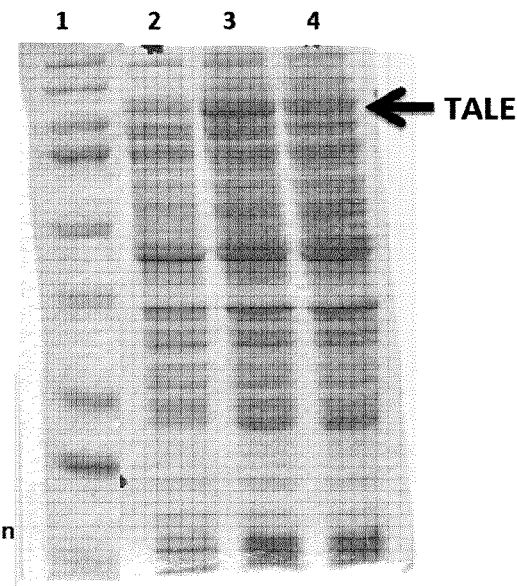
1) Molecular weight markers
2) E. coli total extract no induction
3) E. coli total extract after induction with 1mM IPTG at 37 C
4) E. coli soluble extract after induction with 1mM IPTG at 37 C
B.
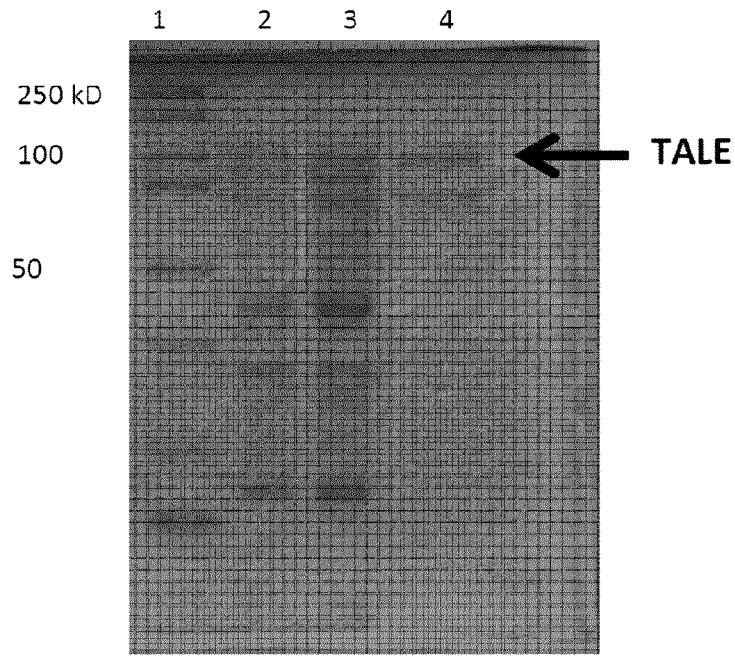
Figure 14

A.
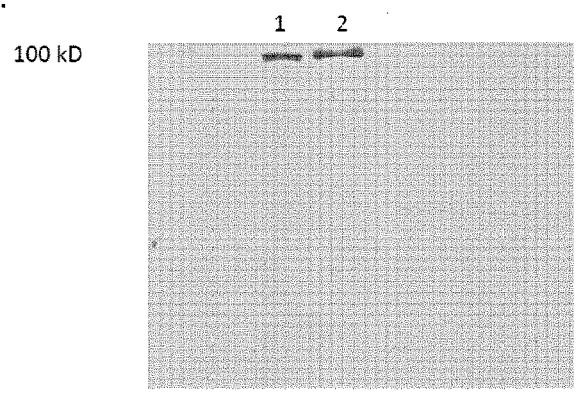
B.
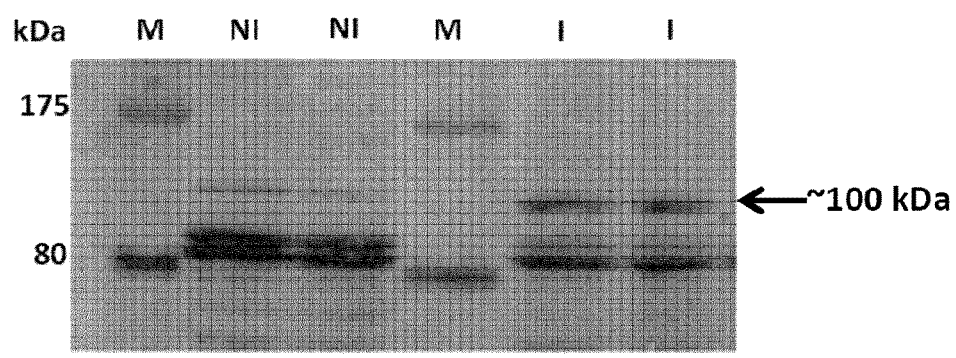
Figure 15

MDPIRSRTPSPARELLSGPQPDGVQPTADRGVSPPAGGPLDGLPARRT**MSRTRLPSPPAPSPAFSADSFS
DLLRQFDPSLFNTSLFDSLPPFGAHHTEAATGEWDEVQSGLRAADAPPPTMRVAVTAARPPRAKPAPRRR
AAQPSDASPAAQVDLRTLGYSQQQQEKIKPKVRSTVAQHHEALVGHGFTHAHIVALSQHPAALGTVAVKY
QDMIAALPEATHEAIVGVGKQWSGARALEALLTVAGELRGPPLQLDTGQLLKIAKRGGVTAVEAVHAWRN
ALTGAPLN**LTPEQVVAIASNIGGKQALETVQRLLPVLCQAHGLTPQQVVAIASHDGGKQALETVQRLLPV
LCQAHGLTPEQVVAIASNIGGKQALETVQALLPVLCQAHGLTPEQVVAIASHDGGKQALETVQRLLPVLC
QAHGLTPQQVVAIASHDGGKQALETVQRLLPVLCQAHGLTPQQVVAIASHDGGKQALETVQRLLPVLCQA
HGLTPQQVVAIASNSGGKQALETVQRLLPVLCQAHGLTPQQVVAIASNSGGKQALETVQRLLPVLCQAHG
LTPQQVVAIASNSGGKQALETVQRLLPVLCQAHGLTPEQVVAIASHDGGKQALETVQRLLPVLCQAHGLT
PEQVVAIASNIGGKQALETVQRLLPVLCQAHGLTPQQVVAIASNGGGRPALESIVAQLSRP**DPALAALTN
DHLVALACLGGRPALDAVKKGLPHAPALIKRTNRRIPERTSHRVADHAQVVRVLGFFQCHSHPAQAFDDA
MTQFGMSRHGLLQLFRRVGVTELEARSGTLPPASQRWDRILQASGMKRAKPSPTSTQTPDQASLHAFADS
LERDLDAPSPMHEGDQTRAS**SRKRSRSDRAVTGPSAQQSFEVRVPEQRDALHLPLLSWGVKRPRTRIGGL
LDPGTPMDADLVASSTVVWEQDADPFAGTADDFPAFNEEELAWLMELLPQ

Figure 19

A. N-terminal nucleotide sequence of Hax3 in pLenti EF1a TALE 2A VP64 EGFP

```
GTACGGCCACCATGTCGCGGACCCGGCTCCCTTCCCCACCCGCACCCAGCCCAGCGTTTT
CGGCCGACTCGTTCTCAGACCTGCTTAGGCAGTTCGACCCCTCACTGTTTAACACATCGT
TGTTCGACTCCCTTCCTCCGTTTGGGGCGCACCATACGGAGGCGGCCACCGGGGAGTGGG
ATGAGGTGCAGTCGGGATTGAGAGCTGCGGATGCACCACCCCCAACCATGCGGGTGGCCG
TCACCGCTGCCCGACCGCCGAGGGCGAAGCCCGCACCAAGGCGGAGGGCAGCGCAACCGT
CCGACGCAAGCCCCGCAGCGCAAGTAGATTTGAGAACTTTGGGATATTCACAGCAGCAGC
AGGAAAAGATCAAGCCCAAAGTGAGGTCGACAGTCGCGCAGCATCACGAAGCGCTGGTGG
GTCATGGGTTTACACATGCCCACATCGTAGCCTTGTCGCAGCACCCTGCAGCCCTTGGCA
CGGTCGCCGTCAAGTACCAGGACATGATTGCGGCGTTGCCGGAAGCCACACATGAGGCGA
TCGTCGGTGTGGGGAAACAGTGGAGCGGAGCCCGAGCGCTTGAGGCCCTGTTGACGGTCG
CGGGAGAGCTGAGAGGGCCTCCCCTTCAGCTGGACACGGGCCAGTTGCTGAAGATCGCGA
AGCGGGGAGGAGTCACGGCGGTCGAGGCGGTGCACGCGTGGCGCAATGCGCTCACGGGAG
CACCCCTCAACCTGACCGAGACGGTACATGAAACGCATGGCACGGCGTCTCAACTCACGC
CTGAGCAGGTAGTGGCTATTGCATCCAATATCGGGGGCAGACCCGCACTGGAGTCAATCG
TGGCCCAGCTTTCGAGGCCG
```

B. C-terminal nucleotide sequence of Hax3 in pLenti EF1a TALE 2A VP64 EGFP

```
GACCCCGCGCTGGCCGCACTCACTAATGATCATCTTGTAGCGCTGGCCTGCCTCGGCGGA
CGACCCGCCTTGGATGCGGTGAAGAAGGGGCTCCCGCACGCGCCTGCATTGATTAAGCGG
ACCAACAGAAGGATTCCCGAGAGGACATCACATCGAGTGGCAGATCACGCGCAAGTGGTC
CGCGTGCTCGGATTCTTCCAGTGTCACTCCCACCCCGCACAAGCGTTCGATGACGCCATG
ACTCAATTTGGTATGTCGAGACACGGACTGCTGCAGCTCTTTCGTAGAGTCGGTGTCACA
GAACTCGAGGCCCGCTCGGGCACACTGCCTCCCGCCTCCCAGCGGTGGGACAGGATTCTC
CAAGCGAGCGGTATGAAACGCGCGAAGCCTTCACCTACGTCAACTCAGACACCTGACCAG
GCGAGCCTTCATGCGTTCGCAGACTCGCTGGAGAGGGATTTGGACGCGCCCTCGCCCATG
CATGAAGGGGACCAAACTCGCGCGTCA
```

Figure 20

```
AAAATATTAACGCTTACAATTTACGCGCGTCGAGtctagaGGCAGAGTACAGATTTACAC
AAGGCATCCGTCTCCTGGCCCCACATACCCAACTGCTGTAAACCCATACCGGCGGCCAAG
CAGCCTCAATTTGTGCATGCAGGGCCACCAGGCTGCAGTCTCCCTTGGGTCAGGGGTCCT
GGTTGCACTCCGTGCTTTGCACAAAGCAGGCTCTCCATTTTTGTTAAATGCACGAATAGT
GCTAAGCTGGGAAGTTCTTCCTGAGGTCTAACCTCTAGCTGCTCCCCCACAGAAGAGTGC
CTGCGGCCAGTGGCCACCAGGGGTCGCCGCAGCACCCAGCGCTGGAGGGCGGAGCGGGCG
GCAGAGGATCCTATCACGAATTCTggatccACGTATGTCGAGGTAGGCGTGTACGGTGGG
AGGCCTATATAAGCAGAGCTCGTTTAGTGAACCGTCAGATCGCCTGGAGGTACCGCCACC
atgGTGAGCAAGGGCGAGGAGGATAACATGGCCATCATCAAGGAGTTCATGCGCTTCAAG
GTGCACATGGAGGGCTCCGTGAACGGCCACGAGTTCGAGATCGAGGGCGAGGGCGAGGGC
CGCCCCTACGAGGGCACCCAGACCGCCAAGCTGAAGGTGACCAAGGGTGGCCCCCTGCCC
TTCGCCTGGGACATCCTGTCCCCTCAGTTCATGTACGGCTCCAAGGCCTACGTGAAGCAC
CCCGCCGACATCCCCGACTACTTGAAGCTGTCCTTCCCCGAGGGCTTCAAGTGGGAGCGC
GTGATGAACTTCGAGGACGGCGGCGTGGTGACCGTGACCCAGGACTCCTCCCTGCAGGAC
GGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGC
GCCCTGAAGGGCGAGATCAAGCAGAGGCTGAAGCTGAAGGACGGCGGCCACTACGACGCT
GAGGTCAAGACCACCTACAAGGCCAAGAAGCCCGTGCAGCTGCCCGGCGCCTACAACGTC
AACATCAAGTTGGACATCACCTCCCACAACGAGGACTACACCATCGTGGAACAGTACGAA
CGCGCCGAGGGCCGCCACTCCACCGGCGGCATGGACGAGCTGTACAAGtaaGAATTCGAt
aaacccgctgatcagcctcgactgtgccttctagttgccagccatctgttgtttgcccct
ccccgtgccttccttgacccggaaggtgccactcccactgtcctttcctaataaaatg
aggaaattgcatcgcattgtctgagtaggtgtcattctattctgggggtggggtgggc
aggacagcaaggggggaggattgggaagacaatagcaggcatgctggggatgcggtgggct
ctatggcttctgaggcggaaagaaccagtggcggtaatacggttatccacagaatcaggg
gataacgcaggaaagaacatgtgagcaaaaggccagcaaaaggccaggaaccgtaaaaag
gccgcgttgctggcgtttttccataggctccgcccccctgacgagcatcacaaaaatcga
cgctcaagtcagaggtggcgaaacccgacaggactataaagataccaggcgtttccccct
ggaagctccctcgtgcgctctcctgttccgaccctgccgcttaccggatacctgtccgcc
tttctcccttcgggaagcgtggcgctttctcatagctcacgctgtaggtatctcagttcg
gtgtaggtcgttcgctccaagctgggctgtgtgcacgaaccccccgttcagcccgaccgc
tgcgccttatccggtaactatcgtcttgagtccaacccggtaagacacgacttatcgcca
ctggcagcagccactggtaacaggattagcagagcgaggtatgtaggcggtgctacagag
ttcttgaagtggtggcctaactacggctacactagaaggacagtatttggtatctgcgct
ctgctgaagccagttaccttcggaaaaagagttggtagctcttgatccggcaaacaaacc
accgctggtagcggtggtttttttgtttgcaagcagcagattacgcgcagaaaaaaagga
tctcaagaagatcctttgatcttttctacggggtctgacgctcagtggaacgaaaactca
cgttaagggattttggtcatgagattatcaaaaaggatcttcacctagatccttttaaat
taaaaatgaagttttaaatcaatctaaagtatatatgagtaacctgaggctatggcaggg
cctgccgccccgacgttggctgcgagccctgggccttcaccgaacttgggggtgggt
ggggaaaaggaagaaacgcgggcgtattggccccaatgggtctcggtggggtatcgaca
gagtgccagccctgggaccgaacccgcgtttatgaacaaacgacccaacaccgtgcgtt
ttattctgtctttttattgccgtcatagcgcgggttccttccggtattgtctccttccgt
gtttcagttagcctcccccctagggtgggcgaagaactccagcatgagatcccgcgctgg
aggatcatccagccggcgtcccggaaaacgattccgaagcccaaccttcatagaaggcg
gcggtggaatcgaaatctcgtgatggcaggttgggcgtcgcttggtcggtcatttcgaac
cccagagtcccgctcagaagaactcgtcaagaaggcgatagaaggcgatgcgctgcgaat
cgggagcggcgataccgtaaagcacgaggaagcggtcagcccattcgccgccaagctctt
cagcaatatcacgggtagccaacgctatgtcctgatagcggtccgccacacccagccggc
cacagtcgatgaatccagaaaagcggccattttccaccatgatattcggcaagcaggcat
cgccatgggtcacgacgagatcctcgccgtcgggcatgctcgccttgagcctggcgaaca
gttcggctggcgcgagcccctgatgctcttgatcatcctgatcgacaagaccggcttcca
tccgagtacgtgctcgctcgatgcgatgtttcgcttggtggtcgaatgggcaggtagccg
```

Figure 21A

```
gatcaagcgtatgcagccgccgcattgcatcagccatgatggatactttctcggcaggag
caaggtgagatgacaggagatcctgccccggcacttcgcccaatagcagccagtcccttc
ccgcttcagtgacaacgtcgagcacagctgcgcaaggaacgcccgtcgtggccagccacg
atagccgcgctgcctcgtcttgcagttcattcagggcaccggacaggtcggtcttgacaa
aaagaaccgggcgccctgcgctgacagccggaacacggcggcatcagagcagccgattg
tctgttgtgccagtcatagccgaatagcctctccacccaagcggccggagaacctgcgt
gcaatccatcttgttcaatcatgcgaaacgatcctcatcctgtctcttgatcgatctttg
caaaagcctaggcctccaaaaaagcctcctcactacttctggaatagctcagaggccgag
gcggcctcggcctctgcataaataaaaaaaattagtcagccatgggcggagaatgggcg
gaactgggcggagttaggggcgggatgggcggagttaggggcgggactatggttgctgac
taattgagatgcatgctttgcatacttctgcctgctggggagcctggggactttccacac
ctggttgctgactaattgagatgcatgctttgcatacttctgcctgctggggagcctggg
gactttccacaccctaactgacacacattccacagctggttcttccgcctcaggactct
tccttttcaataaatcaatctaaagtatatatgagtaaacttggtctgacagttaccaa
tgcttaatcagtgaggcacctatctcagcgatctgtctatttcgttcatccatagttgcc
tgactcccgtcgtgtagataactacgatacgggagggcttaccatctggccccagtgct
gcaatgataccgcgagacccacgctcaccggctccagatttatcagcaataaaccagcca
gccggaagggccgagcgcagaagtggtcctgcaactttatccgcctccatccagtctatt
aattgttgccgggaagctagagtaagtagttcgcagttaatagtttgcgcaacgttgtt
gccattgctacaggcatcgtggtgtcacgctcgtcgtttggtatggcttcattcagctcc
ggttcccaacgatcaaggcgagttacatgatccccatgttgtgcaaaaaagcggttagc
tccttcggtcctccgatcgttgtcagaagtaagttggccgcagtgttatcactcatggtt
atggcagcactgcataattctcttactgtcatgccatccgtaagatgcttttctgtgact
ggtgagtactcaaccaagtcattctgagaatagtgtatgcggcgaccgagttgctcttgc
ccggcgtcaatacgggataataccgcgccacatagcagaactttaaaagtgctcatcatt
ggaaaacgttcttcggggcgaaaactctcaaggatcttaccgctgttgagatccagttcg
atgtaacccactcgtgcacccaactgatcttcagcatcttttactttcaccagcgtttct
gggtgagcaaaaacaggaaggcaaaatgccgcaaaaaagggaataagggcgacacggaaa
tgttgaatactcatactcttcctttttcaatattattgaagcatttatcagggttattgt
ctcatgagcggatacatatttgaatgtatttagaaaaataaacaaatagggg ttccgcgc
acatttccccgaaaagtgccacctgacgcgccctgtagcggcgcattaagcgcggcggt
gtggtggttacgcgcagcgtgaccgctacacttgccagcgccctagcgcccgctcctttc
gctttcttcccttcctttctcgccacgttcgccggctttccccgtcaagctctaaatcgg
gggctccctttagggttccgatttagtgctttacggcacctcgaccccaaaaaacttgat
tagggtgatggttcacgtagtgggccatcgccctgatagacggtttttcgccctttgacg
ttggagtccacgttctttaatagtggactcttgttccaaactggaacaacactcaaccct
atctcggtctattcttttgatttataagggattttgccgatttcggcctattggttaaaa
aatgagctgatttaacaaaaatttaacgcgaattttaac
```

Figure 21B

Restriction map of  plasmid pCR3.1frataxin-promoter-miniCMV-mCherry

```
         Ssp1         SpDon             Xba1                  T7Ter
          |             |                |                      |
       AAAATATTAACGCTTACAATTTACGCGCGTCGAGtctagaGGCAGAGTACAGATTTACAC
  1    ---------+---------+---------+---------+---------+---------+ 60
       TTTTATAATTGCGAATGTTAAATGCGCGCAGCTCagatctCCGTCTCATGTCTAAATGTG BsmB1
                   |
       AAGGCATCCGTCTCCTGGCCCCACATACCCAACTGCTGTAAACCCATACCGGCGGCCAAG
 61    ---------+---------+---------+---------+---------+---------+ 120
       TTCCGTAGGCAGAGGACCGGGGTGTATGGGTTGACGACATTTGGGTATGGCCGCCGGTTC Sph1              Pst1
                    |                 |
       CAGCCTCAATTTGTGCATGCAGGGCCACCAGGCTGCAGTCTCCCTTGGGTCAGGGGTCCT
121    ---------+---------+---------+---------+---------+---------+ 180
       GTCGGAGTTAAACACGTACGTCCCGGTGGTCCGACGTCAGAGGGAACCCAGTCCCCAGGA Dra3
              BstAP
                |
       GGTTGCACTCCGTGCTTTGCACAAAGCAGGCTCTCCATTTTTGTTAAATGCACGAATAGT
181    ---------+---------+---------+---------+---------+---------+ 240
       CCAACGTGAGGCACGAAACGTGTTTCGTCCGAGAGGTAAAAACAATTTACGTGCTTATCA BseY1
       Blp1   |    Xmn1 Bsu36                      Ear1SpAcc
        |     |     |    |                             |
       GCTAAGCTGGGAAGTTCTTCCTGAGGTCTAACCTCTAGCTGCTCCCCCACAGAAGAGTGC
241    ---------+---------+---------+---------+---------+---------+ 300
       CGATTCGACCCTTCAAGAAGGACTCCAGATTGGAGATCGACGAGGGGGTGTCTTCTCACG Msc1                BseY1 Afe1             BsrB1
                   |                   |    |                |
       CTGCGGCCAGTGGCCACCAGGGGTCGCCGCAGCACCCAGCGCTGGAGGGCGGAGCGGGCG
301    ---------+---------+---------+---------+---------+---------+ 360
       GACGCCGGTCACCGGTGGTCCCCAGCGGCGTCGTGGGTCGCGACCTCCCGCCTCGCCCGC BamH1
            Eci1 |
            Bpm1| |    EcoR1  BamH1
             || |       |      |
       GCAGAGGATCCTATCACGAATTCTggatccACGTATGTCGAGGTAGGCGTGTACGGTGGG
361    ---------+---------+---------+---------+---------+---------+ 420
       CGTCTCCTAGGATAGTGCTTAAGAcctaggTGCATACAGCTCCATCCGCACATGCCACCC
```

Figure 22A

```
                    Sac1                                  Kpn1
         Stu1       Ecl2 |                        Acc65     |    Nco1
          |          | |                           |        |     |
          AGGCCTATATAAGCAGAGCTCGTTTAGTGAACCGTCAGATCGCCTGGAGGTACCGCCACC
    421   ---------+---------+---------+---------+---------+---------+ 480
          TCCGGATATATTCGTCTCGAGCAAATCACTTGGCAGTCTAGCGGACCTCCATGGCGGTGG
orf 1     >

SpDon                     Msc1
          Ale1 |                    BseR1
          | |                        |
          atgGTGAGCAAGGGCGAGGAGGATAACATGGCCATCATCAAGGAGTTCATGCGCTTCAAG
    481   ---------+---------+---------+---------+---------+---------+ 540
          tacCACTCGTTCCCGCTCCTCCTATTGTACCGGTAGTAGTTCCTCAAGTACGCGAAGTTC
orf 1     > M   V   S   K   G   E   E   D   N   M   A   I   I   K   E   F   M   R   F   K ApaL1                   BssS1
           |                        |
          GTGCACATGGAGGGCTCCGTGAACGGCCACGAGTTCGAGATCGAGGGCGAGGGCGAGGGC
    541   ---------+---------+---------+---------+---------+---------+ 600
          CACGTGTACCTCCCGAGGCACTTGCCGGTGCTCAAGCTCTAGCTCCCGCTCCCGCTCCCG
orf 1     > V   H   M   E   G   S   V   N   G   H   E   F   E   I   E   G   E   G   E   G SpAcc                        BstE2           Eco57
           |                             |               |
          CGCCCCTACGAGGGCACCCAGACCGCCAAGCTGAAGGTGACCAAGGGTGGCCCCCTGCCC
    601   ---------+---------+---------+---------+---------+---------+ 660
          GCGGGGATGCTCCCGTGGGTCTGGCGGTTCGACTTCCACTGGTTCCCACCGGGGGACGGG
orf 1     > R   P   Y   E   G   T   Q   T   A   K   L   K   V   T   K   G   G   P   L   P Ahd1       SpAcc             Stu1
                     |           |                 |
          TTCGCCTGGGACATCCTGTCCCCTCAGTTCATGTACGGCTCCAAGGCCTACGTGAAGCAC
    661   ---------+---------+---------+---------+---------+---------+ 720
          AAGCGGACCCTGTAGGACAGGGGAGTCAAGTACATGCCGAGGTTCCGGATGCACTTCGTG
orf 1     > F   A   W   D   I   L   S   P   Q   F   M   Y   G   S   K   A   Y   V   K   H CCCGCCGACATCCCCGACTACTTGAAGCTGTCCTTCCCCGAGGGCTTCAAGTGGGAGCGC
    721   ---------+---------+---------+---------+---------+---------+ 780
          GGGCGGCTGTAGGGGCTGATGAACTTCGACAGGAAGGGGCTCCCGAAGTTCACCCTCGCG
orf 1     > P   A   D   I   P   D   Y   L   K   L   S   F   P   E   G   F   K   W   E   R SpAcc
                                                                Sbf1|
                              BstE2     BseR1                   Pst1|
                                |         |                      | |
          GTGATGAACTTCGAGGACGGCGGCGTGGTGACCGTGACCCAGGACTCCTCCCTGCAGGAC
    781   ---------+---------+---------+---------+---------+---------+ 840
          CACTACTTGAAGCTCCTGCCGCCGCACCACTGGCACTGGGTCCTGAGGAGGGACGTCCTG
orf 1     > V   M   N   F   E   D   G   G   V   V   T   V   T   Q   D   S   S   L   Q   D
```

Figure 22B

```
                       SpDon        BsaXb                                    BsaXa
                         |            |                                        |
                GGCGAGTTCATCTACAAGGTGAAGCTGCGCGGCACCAACTTCCCCTCCGACGGCCCCGTA
            841 ---------+---------+---------+---------+---------+---------+ 900
                CCGCTCAAGTAGATGTTCCACTTCGACGCGCCGTGGTTGAAGGGGAGGCTGCCGGGGCAT
    orf 1        > G  E  F  I  Y  K  V  K  L  R  G  T  N  F  P  S  D  G  P  V BseR1
                                  PflM1|
                                  BseY1|
                           Bbs1     ||                                   Nar1
                     Nco1   |       ||       Stu1         BsrB1          Kas1|
                      |     |       ||        |             |              ||
                ATGCAGAAGAAGACCATGGGCTGGGAGGCCTCCTCCGAGCGGATGTACCCCGAGGACGGC
            901 ---------+---------+---------+---------+---------+---------+ 960
                TACGTCTTCTTCTGGTACCCGACCCTCCGGAGGAGGCTCGCCTACATGGGGCTCCTGCCG
    orf 1        > M  Q  K  K  T  M  G  W  E  A  S  S  E  R  M  Y  P  E  D  G Bpu10
                             AlwN1                                        BbvC1
                             Eco57 |                         Eco57  Eco57   |
                                |  |                           |      |    |
                GCCCTGAAGGGCGAGATCAAGCAGAGGCTGAAGCTGAAGGACGGCGGCCACTACGACGCT
            961 ---------+---------+---------+---------+---------+---------+ 1020
                CGGGACTTCCCGCTCTAGTTCGTCTCCGACTTCGACTTCCTGCCGCCGGTGATGCTGCGA
    orf 1        > A  L  K  G  E  I  K  Q  R  L  K  L  K  D  G  G  H  Y  D  A Nar1
          Drd1                                     Pvu2      Kas1|     Bsg1
           |                                         |          ||       |
                GAGGTCAAGACCACCTACAAGGCCAAGAAGCCCGTGCAGCTGCCCGGCGCCTACAACGTC
           1021 ---------+---------+---------+---------+---------+---------+ 1080
                CTCCAGTTCTGGTGGATGTTCCGGTTCTTCGGGCACGTCGACGGGCCGCGGATGTTGCAG
    orf 1        > E  V  K  T  T  Y  K  A  K  K  P  V  Q  L  P  G  A  Y  N  V BsaXb                           BsaXa       Ale1
                        |                               |           |
                AACATCAAGTTGGACATCACCTCCCACAACGAGGACTACACCATCGTGGAACAGTACGAA
           1081 ---------+---------+---------+---------+---------+---------+ 1140
                TTGTAGTTCAACCTGTAGTGGAGGGTGTTGCTCCTGATGTGGTAGCACCTTGTCATGCTT
    orf 1        > N  I  K  L  D  I  T  S  H  N  E  D  Y  T  I  V  E  Q  Y  E SgrA1 Xcm1             BsrG1 SpDonEcoR1
                                   |    |                 |    |   |
                CGCGCCGAGGGCCGCCACTCCACCGGCGGCATGGACGAGCTGTACAAGtaaGAATTCGAt
           1141 ---------+---------+---------+---------+---------+---------+ 1200
                GCGCGGCTCCCGGCGGTGAGGTGGCCGCCGTACCTGCTCGACATGTTCattCTTAAGCTa
    orf 1        > R  A  E  G  R  H  S  T  G  G  M  D  E  L  Y  K  *

T7Ter
                                             |
                aaacccgctgatcagcctcgactgtgccttctagttgccagccatctgttgtttgccct
           1201 ---------+---------+---------+---------+---------+---------+ 1260
                tttgggcgactagtcggagctgacacggaagatcaacggtcggtagacaacaaacggga
```

Figure 22C

```
                                                  BtgZ1
                                          polyA    |
                                            |      |
         ccccccgtgccttccttgaccctggaaggtgccactcccactgtcctttcctaataaaatg
  1261   ---------+---------+---------+---------+---------+---------+ 1320
         gggggcacggaaggaactgggaccttccacggtgagggtgacaggaaaggattatttttac aggaaattgcatcgcattgtctgagtaggtgtcattctattctgggggtggggtggggc
  1321   ---------+---------+---------+---------+---------+---------+ 1380
         tcctttaacgtagcgtaacagactcatccacagtaagataagaccccccacccccacccccg Sph1
                              Bbs1        BseY1
                               |           |
         aggacagcaaggggggaggattgggaagacaatagcaggcatgctggggatgcggtgggct
  1381   ---------+---------+---------+---------+---------+---------+ 1440
         tcctgtcgttccccctcctaaccccttctgttatcgtccgtacgaccccctacgccacccga Eci1
                            |
         ctatggcttctgaggcggaaagaaccagtggcggtaatacggttatccacagaatcaggg
  1441   ---------+---------+---------+---------+---------+---------+ 1500
         gataccgaagactccgcctttcttggtcaccgccattatgccaataggtgtcttagtccc SpDon
             BspLU  |
               |    |
         gataacgcaggaaagaacatgtgagcaaaaggccagcaaaaggccaggaaccgtaaaaag
  1501   ---------+---------+---------+---------+---------+---------+ 1560
         ctattgcgtccttcttgtacactcgttttccggtcgttttccggtccttggcattttttc Eci1  SpAcc                     BpuE1
                      |     |                         |
         gccgcgttgctggcgtttttccataggctccgccccccctgacgagcatcacaaaaatcga
  1561   ---------+---------+---------+---------+---------+---------+ 1620
         cggcgcaacgaccgcaaaaaggtatccgaggcgggggactgctcgtagtgttttagct Drd1                  SpAcc
              |                      |
         cgctcaagtcagaggtggcgaaacccgacaggactataaagataccaggcgtttccccct
  1621   ---------+---------+---------+---------+---------+---------+ 1680
         gcgagttcagtctccaccgctttgggctgtcctgatatttctatggtccgcaaaggggga BssS1                       BciV1 Eci1
               |                           |    |
         ggaagctccctcgtgcgctctcctgttccgaccctgccgcttaccggatacctgtccgcc
  1681   ---------+---------+---------+---------+---------+---------+ 1740
         ccttcgagggagcacgcgagaggacaaggctgggacggcgaatggcctatggacaggcgg SpAcc
                                      |
         tttctcccttcgggaagcgtggcgctttctcatagctcacgctgtaggtatctcagttcg
  1741   ---------+---------+---------+---------+---------+---------+ 1800
         aaagagggaagcccttcgcaccgcgaaagagtatcgagtgcgacatccatagagtcaagc
```

Figure 22D

```
                         BseY1     ApaL1
                           |         |
         gtgtaggtcgttcgctccaagctgggctgtgtgcacgaacccccgttcagcccgaccgc
   1801  ---------+---------+---------+---------+---------+---------+ 1860
         cacatccagcaagcgaggttcgacccgacacacgtgcttggggggcaagtcgggctggcg BpuE1
                                                        |
         tgcgccttatccggtaactatcgtcttgagtccaacccggtaagacacgacttatcgcca
   1861  ---------+---------+---------+---------+---------+---------+ 1920
         acgcggaataggccattgatagcagaactcaggttgggccattctgtgctgaatagcggt AlwN1
                 |
         ctggcagcagccactggtaacaggattagcagagcgaggtatgtaggcggtgctacagag
   1921  ---------+---------+---------+---------+---------+---------+ 1980
         gaccgtcgtcggtgaccattgtcctaatcgtctcgctccatacatccgccacgatgtctc SpAcc
                               |
         ttcttgaagtggtggcctaactacggctacactagaaggacagtatttggtatctgcgct
   1981  ---------+---------+---------+---------+---------+---------+ 2040
         aagaacttcaccaccggattgatgccgatgtgatcttcctgtcataaaccatagacgcga Eco57
                           |
         ctgctgaagccagttaccttcggaaaaagagttggtagctcttgatccggcaaacaaacc
   2041  ---------+---------+---------+---------+---------+---------+ 2100
         gacgacttcggtcaatggaagcctttttctcaaccatcgagaactaggccgtttgtttgg BpuE1
                                                |
         accgctggtagcggtggttttttttgtttgcaagcagcagattacgcgcagaaaaaagga
   2101  ---------+---------+---------+---------+---------+---------+ 2160
         tggcgaccatcgccaccaaaaaaacaaacgttcgtcgtctaatgcgcgtctttttttcct tctcaagaagatcctttgatcttttctacggggtctgacgctcagtggaacgaaaactca
   2161  ---------+---------+---------+---------+---------+---------+ 2220
         agagttcttctaggaaactagaaaagatgccccagactgcgagtcaccttgcttttgagt BspH1                                        Dra1
                 |                                            |
         cgttaagggattttggtcatgagattatcaaaaaggatcttcacctagatccttttaaat
   2221  ---------+---------+---------+---------+---------+---------+ 2280
         gcaattccctaaaaccagtactctaatagttttcctagaagtggatctaggaaaattta Dra1                           Bsu36
                 |                              |
         taaaaatgaagttttaaatcaatctaaagtatatatgagtaacctgaggctatggcaggg
   2281  ---------+---------+---------+---------+---------+---------+ 2340
         attttactccaaaatttagttagatttcatatatactcattggactccgataccgtccc
orf 2          <                        *  L  I  Y  S  Y  G  S  A  I  A  P
```

Figure 22E

```
           BstAP
           AlwN1
              |
              cctgccgccccgacgttggctgcgagccctgggccttcacccgaacttgggggtggggt
       2341 ---------+---------+---------+---------+---------+---------+ 2400
              ggacggcgggggctgcaaccgacgctcgggaccggaagtgggcttgaaccccccacccca
orf 2       <  G  A  A  G  V  N  A  A  L  G  P  G  E  G  S  S  P  P  H  P Bsa1
                                                         |
              ggggaaaaggaagaaacgcgggcgtattggccccaatggggtctcggtggggtatcgaca
       2401 ---------+---------+---------+---------+---------+---------+ 2460
              cccctttccttctttgcgcccgcataaccggggttaccccagagccaccccatagctgt
orf 2       <  P  S  F  S  S  V  R  A  Y  Q  G  W  H  P  R  P  P  T  D  V gagtgccagccctgggaccgaaccccgcgtttatgaacaaacgacccaacaccgtgcgtt
       2461 ---------+---------+---------+---------+---------+---------+ 2520
              ctcacggtcgggaccctggcttgggggcgcaaatacttgtttgctgggttgtggcacgcaa
orf 2       <  S  H  W  G  Q  S  R  V  G  R  K  H  V  F  S  G  V  G  H  T polyA        polyA
              |            |
              ttattctgtcttttttattgccgtcatagcgcgggttccttccggtattgtctccttccgt
       2521 ---------+---------+---------+---------+---------+---------+ 2580
              aataagacagaaaaataacggcagtatcgcgcccaaggaaggccataacagaggaaggca
orf 2       <  K  N  Q  R  K  I  A  T  M  A  R  T  G  E  P  I  T  E  K  R SpAcc
                                   Bpm1|
                              Avr2  ||
                                |   ||
              gtttcagttagcctcccccctagggtgggcgaagaactccagcatgagatccccgcgctgg
       2581 ---------+---------+---------+---------+---------+---------+ 2640
              caaagtcaatcggagggggatcccacccgcttcttgaggtcgtactctagggcgcgacc
orf 2       <  T  E  T  L  R  G  R  P  H  A  F  F  E  L  M  L  D  G  R  Q Bpm1
                         Nae1   |
                       NgoM4 |  |                            SpAcc
                         | |  |                                 |
              aggatcatccagccggcgtcccggaaaacgattccgaagcccaacctttcatagaaggcg
       2641 ---------+---------+---------+---------+---------+---------+ 2700
              tcctagtaggtcggccgcagggccttttgctaaggcttcgggttggaaagtatcttccgc
orf 2       <  L  I  M  W  G  A  D  R  F  V  I  G  F  G  L  R  E  Y  F  A BssS1
                         BspM1                          BstB1
                           |                              |
              gcggtggaatcgaaatctcgtgatggcaggttgggcgtcgcttggtcggtcatttcgaac
       2701 ---------+---------+---------+---------+---------+---------+ 2760
              cgccaccttagctttagagcactaccgtccaacccgcagcgaaccagccagtaaagcttg
orf 2       <  A  T  S  D  F  D  R  S  P  L  N  P  T  A  Q  D  T  M
```

Figure 22F

```
                    BsrB1
                      |
            cccagagtcccgctcagaagaactcgtcaagaaggcgatagaaggcgatgcgctgcgaat
      2761  ---------+---------+---------+---------+---------+---------+  2820
            gggtctcagggcgagtcttcttgagcagttcttccgctatcttccgctacgcgacgctta
orf 3       <         * F F E D L L R Y F A I R Q S BtgZ1 BsrB1                BssS1                 Eco57
              |     |                    |                     |
            cgggagcggcgataccgtaaagcacgaggaagcggtcagcccattcgccgccaagctctt
      2821  ---------+---------+---------+---------+---------+---------+  2880
            gccctcgccgctatggcatttcgtgctccttcgccagtcgggtaagcggcggttcgagaa
orf 3       < D   P   A   A   I   G   Y   L   V   L   F   R   D   A   W   E   G   G   L   E Nae1
            Sap1                                                 NgoM4 |
            Ear1                       Eci1    Rsr2      BseY1   | |
              |                          |       |         |     | | |
            cagcaatatcacgggtagccaacgctatgtcctgatagcggtccgccacacccagccggc
      2881  ---------+---------+---------+---------+---------+---------+  2940
            gtcgttatagtgcccatcggttgcgatacaggactatcgccaggcggtgtgggtcggccg
orf 3       < E   A   I   D   R   T   A   L   A   I   D   Q   Y   R   D   A   V   G   L   R BtgZ1
                                                           |
            cacagtcgatgaatccagaaaagcggccattttccaccatgatattcggcaagcaggcat
      2941  ---------+---------+---------+---------+---------+---------+  3000
            gtgtcagctacttaggtcttttcgccggtaaaaggtggtactataagccgttcgtccgta
orf 3       < G   C   D   I   F   G   S   F   R   G   N   E   V   M   I   N   P   L   C   A Nco1                              Sph1
                |                                 |
            cgccatgggtcacgacgagatcctcgccgtcgggcatgctcgccttgagcctggcgaaca
      3001  ---------+---------+---------+---------+---------+---------+  3060
            gcggtacccagtgctgctctaggagcggcagcccgtacgagcggaactcggaccgcttgt
orf 3       < D   G   H   T   V   V   L   D   E   G   D   P   M   S   A   K   L   R   A   F BpuE1
                |
            gttcggctggcgcgagcccctgatgctcttgatcatcctgatcgacaagaccggcttcca
      3061  ---------+---------+---------+---------+---------+---------+  3120
            caagccgaccgcgctcggggactacgagaactagtaggactagctgttctggccgaaggt
orf 3       < L   E   A   P   A   L   G   Q   H   E   Q   D   D   Q   D   V   L   G   A   E BspM1
                                                  BtgZ1  |
                                                    |    |
            tccgagtacgtgctcgctcgatgcgatgtttcgcttggtggtcgaatgggcaggtagccg
      3121  ---------+---------+---------+---------+---------+---------+  3180
            aggctcatgcacgagcgagctacgctacaaagcgaaccaccagcttacccgtccatcggc
orf 3       < M   R   T   R   A   R   E   I   R   H   K   A   Q   H   D   F   P   C   T   A
```

Figure 22G

```
                                BsrD1          BciV1
                                  |              |
                 gatcaagcgtatgcagccgccgcattgcatcagccatgatggatactttctcggcaggag
           3181  ---------+---------+---------+---------+---------+---------+ 3240
                 ctagttcgcatacgtcggcggcgtaacgtagtcggtactacctatgaaagagccgtcctc
   orf 3       < P  D  L  T  H  L  R  R  M  A  D  A  M  I  S  V  K  E  A  P SpDon                                        Eco57
                     |                                            |
                 caaggtgagatgacaggagatcctgccccggcacttcgcccaatagcagccagtcccttc
           3241  ---------+---------+---------+---------+---------+---------+ 3300
                 gttccactctactgtcctctaggacggggccgtgaagcgggttatcgtcggtcagggaag
   orf 3       < A  L  H  S  S  L  L  D  Q  G  P  V  E  G  L  L  L  W  D  R Fsp1
                         PflF1         Pvu2  |                  Msc1
                           |             |   |                    |
                 ccgcttcagtgacaacgtcgagcacagctgcgcaaggaacgcccgtcgtggccagccacg
           3301  ---------+---------+---------+---------+---------+---------+ 3360
                 ggcgaagtcactgttgcagctcgtgtcgacgcgttccttgcgggcagcaccggtcggtgc
   orf 3       < G  A  E  T  V  V  D  L  V  A  A  C  P  V  G  T  T  A  L  W Drd1
                                                            |
                 atagccgcgctgcctcgtcttgcagttcattcagggcaccggacaggtcggtcttgacaa
           3361  ---------+---------+---------+---------+---------+---------+ 3420
                 tatcggcgcgacggagcagaacgtcaagtaagtcccgtggcctgtccagccagaactgtt
   orf 3       < S  L  R  A  A  E  D  Q  L  E  N  L  A  G  S  L  D  T  K  V Nar1
                        Kas1|
                           ||
                 aaagaaccgggcgcccctgcgctgacagccggaacacggcggcatcagagcagccgattg
           3421  ---------+---------+---------+---------+---------+---------+ 3480
                 tttcttggcccgcggggacgcgactgtcggccttgtgccgccgtagtctcgtcggctaac
   orf 3       < F  L  V  P  R  G  Q  A  S  L  R  F  V  A  A  D  S  C  G  I Bmr1                              Eag1
                       |                                 |
                 tctgttgtgcccagtcatagccgaatagcctctccacccaagcggccggagaacctgcgt
           3481  ---------+---------+---------+---------+---------+---------+ 3540
                 agacaacacgggtcagtatcggcttatcggagaggtgggttcgccggcctcttggacgca
   orf 3       < T  Q  Q  A  W  D  Y  G  F  L  R  E  V  W  A  A  P  S  G  A BspM1
                     |
                 gcaatccatcttgttcaatcatgcgaaacgatcctcatcctgtctcttgatcgatctttg
           3541  ---------+---------+---------+---------+---------+---------+ 3600
                 cgttaggtagaacaagttagtacgctttgctaggagtaggacagagaactagctagaaac
   orf 3       < H  L  G  D  Q  E  I  M
```

Figure 22H

```
              Avr2 Stu1BseR1              SpDon
               |   |   |                    |
              caaaagcctaggcctccaaaaaagcctcctcactacttctggaatagctcagaggccgag
        3601  ---------+---------+---------+---------+---------+---------+  3660
              gttttcggatccggaggttttttcggaggagtgatgaagacctatcgagtctccggctc Sfi1
              Bgl1              polyA              Nco1
               |                  |                  |
              gcggcctcggcctctgcataaataaaaaaaaattagtcagccatggggcggagaatgggcg
        3661  ---------+---------+---------+---------+---------+---------+  3720
              cgccggagccggagacgtatttattttttttaatcagtcggtaccccgcctcttacccgc Eci1
              Eci1        Bmr1        Eci1                    Eci1
               |           |           |                       |
              gaactgggcggagttaggggcgggatgggcggagttaggggcgggactatggttgctgac
        3721  ---------+---------+---------+---------+---------+---------+  3780
              cttgacccgcctcaatcccgccctacccgcctcaatcccgccctgataccaacgactg BstAP
                     Sph1 |
                     Nsi1 | |
                 BfrB1 | | |              BseY1
                     | | | |                |
              taattgagatgcatgctttgcatacttctgcctgctggggagcctggggactttccacac
        3781  ---------+---------+---------+---------+---------+---------+  3840
              attaactctacgtacgaaacgtatgaagacggacgaccccctcggaccctgaaggtgtg BstAP
                         Sph1 |
                         Nsi1 | |
                     BfrB1 | | |              BseY1
                         | | | |                |
              ctggttgctgactaattgagatgcatgctttgcatacttctgcctgctggggagcctggg
        3841  ---------+---------+---------+---------+---------+---------+  3900
              gaccaacgactgattaactctacgtacgaaacgtatgaagacggacgaccccctcggaccc Pvu2
                                  Eci1          Bsu36
                                   |              |
              gactttccacaccctaactgacacacattccacagctggttctttccgcctcaggactct
        3901  ---------+---------+---------+---------+---------+---------+  3960
              ctgaaggtgtgggattgactgtgtgtaaggtgtcgaccaagaaaggcggagtcctgaga Ear1 polyA
               |    |
              tcctttttcaataaatcaatctaaagtatatatgagtaaacttggtctgacagttaccaa
        3961  ---------+---------+---------+---------+---------+---------+  4020
              aggaaaaagttatttagttagatttcatatatactcatttgaaccagactgtcaatggtt
orf 4         <                                                       *  W tgcttaatcagtgaggcacctatctcagcgatctgtctatttcgttcatccatagttgcc
        4021  ---------+---------+---------+---------+---------+---------+  4080
              acgaattagtcactccgtggatagagtcgctagacagataaagcaagtaggtatcaacgg
orf 4         < H  K  I  L  S  A  G  I  E  A  I  Q  R  N  R  E  D  M  T  A
```

Figure 22I

```
                                              Bmr1
              Ahd1                   SpDon     |
               |                       |       |
            tgactccccgtcgtgtagataactacgatacgggagggcttaccatctggccccagtgct
     4081   ---------+---------+---------+---------+---------+---------+ 4140
            actgaggggcagcacatctattgatgctatgccctcccgaatggtagaccggggtcacga
orf 4     < Q  S  G  T  T  Y  I  V  V  I  R  S  P  K  G  D  P  G  L  A BsrD1
              Bsa1      Bpm1                        polyA
               |         |                           |
            gcaatgataccgcgagacccacgctcaccggctccagatttatcagcaataaaccagcca
     4141   ---------+---------+---------+---------+---------+---------+ 4200
            cgttactatggcgctctgggtgcgagtggccgaggtctaaatagtcgttatttggtcggt
orf 4     < A  I  I  G  R  S  G  R  E  G  A  G  S  K  D  A  I  F  W  G Bgl1                Eci1                           Ase1
               |                   |                              |
            gccggaagggccgagcgcagaagtggtcctgcaactttatccgcctccatccagtctatt
     4201   ---------+---------+---------+---------+---------+---------+ 4260
            cggccttcccggctcgcgtcttcaccaggacgttgaaataggcggaggtaggtcagataa
orf 4     < A  P  L  A  S  R  L  L  P  G  A  V  K  D  A  E  M  W  D  I Acl1
                                                    Fsp1  |
                                                     |    |
            aattgttgccgggaagctagagtaagtagttcgccagttaatagtttgcgcaacgttgtt
     4261   ---------+---------+---------+---------+---------+---------+ 4320
            ttaacaacggcccttcgatctcattcatcaagcggtcaattatcaaacgcgttgcaacaa
orf 4     < L  Q  Q  R  S  A  L  T  L  L  E  G  T  L  L  K  R  L  T  T BsrD1
               |
            gccattgctacaggcatcgtggtgtcacgctcgtcgtttggtatggcttcattcagctcc
     4321   ---------+---------+---------+---------+---------+---------+ 4380
            cggtaacgatgtccgtagcaccacagtgcgagcagcaaaccataccgaagtaagtcgagg
orf 4     < A  M  A  V  P  M  T  T  D  R  E  D  N  P  I  A  E  N  L  E ggttcccaacgatcaaggcgagttacatgatcccccatgttgtgcaaaaaagcggttagc
     4381   ---------+---------+---------+---------+---------+---------+ 4440
            ccaagggttgctagttccgctcaatgtactaggggggtacaacacgttttttcgccaatcg
orf 4     < P  E  W  R  D  L  R  T  V  H  D  G  M  N  H  L  F  A  T  L Pvu1      SpDon            Bts1
                        |          |               |
            tccttcggtcctccgatcgttgtcagaagtaagttggccgcagtgttatcactcatggtt
     4441   ---------+---------+---------+---------+---------+---------+ 4500
            aggaagccaggaggctagcaacagtcttcattcaaccggcgtcacaatagtgagtaccaa
orf 4     < E  K  P  G  G  I  T  T  L  L  L  N  A  A  T  N  D  S  M  T
```

Figure 22J

```
             Bts1
              |
          atggcagcactgcataattctcttactgtcatgccatccgtaagatgcttttctgtgact
     4501 ---------+---------+---------+---------+---------+---------+ 4560
          taccgtcgtgacgtattaagagaatgacagtacggtaggcattctacgaaaagacactga
orf 4     < I  A  A  S  C  L  E  R  V  T  M  G  D  T  L  H  K  E  T  V SpDon  Sca1                    Bcg1a
           |     |                        |
          ggtgagtactcaaccaagtcattctgagaatagtgtatgcggcgaccgagttgctcttgc
     4561 ---------+---------+---------+---------+---------+---------+ 4620
          ccactcatgagttggttcagtaagactcttatcacatacgccgctggctcaacgagaacg
orf 4     < P  S  Y  E  V  L  D  N  Q  S  Y  H  I  R  R  G  L  Q  E  Q Bcg1b                              Dra1
             |                                 |
          ccggcgtcaatacgggataataccgcgccacatagcagaactttaaaagtgctcatcatt
     4621 ---------+---------+---------+---------+---------+---------+ 4680
          ggccgcagttatgccctattatggcgcggtgtatcgtcttgaaattttcacgagtagtaa
orf 4     < G  A  D  I  R  S  L  V  A  G  C  L  L  V  K  F  T  S  M  M Xmn1
           Acl1 BpuE1
             |   |
          ggaaaacgttcttcggggcgaaaactctcaaggatcttaccgctgttgagatccagttcg
     4681 ---------+---------+---------+---------+---------+---------+ 4740
          ccttttgcaagaagcccgcttttgagagttcctagaatggcgacaactctaggtcaagc
orf 4     < P  F  R  E  E  P  R  F  S  E  L  I  K  G  S  N  L  D  L  E EcoK
             Eco57 |
             ApaL1 |
            BssS1 | |                        SpDon SpDon
              | | |                            |    |
          atgtaacccactcgtgcacccaactgatcttcagcatcttttactttcaccagcgtttct
     4741 ---------+---------+---------+---------+---------+---------+ 4800
          tacattgggtgagcacgtgggttgactagaagtcgtagaaaatgaaagtggtcgcaaaga
orf 4     < I  Y  G  V  R  A  G  L  Q  D  E  A  D  K  V  K  V  L  T  E gggtgagcaaaaacaggaaggcaaaatgccgcaaaaagggaataagggcgacacggaaa
     4801 ---------+---------+---------+---------+---------+---------+ 4860
          cccactcgttttgtccttccgttttacggcgttttttcccttattcccgctgtgccttt
orf 4     < P  H  A  F  V  P  L  C  F  A  A  F  F  P  I  L  A  V  R  F Ear1    Ssp1
                     |       |
          tgttgaatactcatactcttccttttcaatattattgaagcatttatcagggttattgt
     4861 ---------+---------+---------+---------+---------+---------+ 4920
          acaacttatgagtatgagaaggaaaaagttataataacttcgtaaatagtcccaataaca
orf 4     < H  Q  I  S  M
```

Figure 22K

```
               BsrB1
        BciV1    |
     BspH1 |     |                    polyA
      | |  |     |                      |
         ctcatgagcggatacatatttgaatgtatttagaaaaataaacaaataggggttccgcgc
   4921 ---------+---------+---------+---------+---------+---------+ 4980
         gagtactcgcctatgtataaacttacataaatcttttatttgtttatccccaaggcgcg acatttccccgaaaagtgccacctgacgcgccctgtagcggcgcattaagcgcggcggt
   4981 ---------+---------+---------+---------+---------+---------+ 5040
         tgtaaaggggcttttcacgtggactgcgcgggacatcgccgcgtaattcgcgccgccca BsrB1
                                                              |
         gtggtggttacgcgcagcgtgaccgctacacttgccagcgccctagcgcccgctcctttc
   5041 ---------+---------+---------+---------+---------+---------+ 5100
         caccaccaatgcgcgtcgcactggcgatgtgaacggtcgcgggatcgcgggcgaggaaag Nae1
                              NgoM4 |
                                | |
         gctttcttcccttcctttctcgccacgttcgccggctttccccgtcaagctctaaatcgg
   5101 ---------+---------+---------+---------+---------+---------+ 5160
         cgaaagaagggaaggaaagagcggtgcaagcggccgaaaggggcagttcgagatttagcc SpAcc
                    |
         gggctcccttagggttccgatttagtgctttacggcacctcgaccccaaaaaacttgat
   5161 ---------+---------+---------+---------+---------+---------+ 5220
         cccgagggaaatcccaaggctaaatcacgaaatgccgtggagctgggtttttgaacta BtgZ1     Dra3                              BsaXa
                   |         |                                 |
         tagggtgatggttcacgtagtgggccatcgccctgatagacggttttttcgcccttttgacg
   5221 ---------+---------+---------+---------+---------+---------+ 5280
         atcccactaccaagtgcatcacccggtagcgggactatctgccaaaaagcgggaaactgc Drd1           BsaXb
            |              |
         ttggagtccacgttctttaatagtggactcttgttccaaactggaacaacactcaaccct
   5281 ---------+---------+---------+---------+---------+---------+ 5340
         aacctcaggtgcaagaaattatcacctgagaacaaggtttgaccttgttgtgagttggga Ps11
                          |
         atctcggtctattcttttgatttataagggattttgccgatttcggcctattggttaaaa
   5341 ---------+---------+---------+---------+---------+---------+ 5400
         tagagccagataagaaaactaaatattccctaaaacggctaaagccggataaccaattt aatgagctgatttaacaaaaatttaacgcgaatttaac
   5401 ---------+---------+---------+--------- 5439
         ttactcgactaaattgtttttaaattgcgcttaaaattg
```

Figure 22L

Proximal promoter of human frataxin

GGCAGAGTACAGATTACACAAGGCATCCGTCTCCTGGCCCCACATACCCAACTGCTGTA
AACCCATACCGGCGGCCAAGCAGCCTCAATTTGTGCATGCAGGGCCACCAGGCTGCAGT
CTCCCTTGGGTCAGGGTCCTGTTGCACTCCGTTGCACAAAGCAGGCTCTCCAT
TTTGTTAAATGCACGAATAGTGCTAAGGAAGTTCTTCCTGAGGTCTAACCTCTAG
CTGCTCCCCACAGAAGAGTGCCTGCGCCAGTGGCCACCAGGGGTCGCCGCAGCAC
CCAGGCGCTGGAGGGGCGGGAGCGGGGGGGCAGAGGATCCTATCACGAATTCT

Figure 23

MiniCMV promoter

TAGGCGTGTACGGTGGGAGGCCTATATAAGCAGAGCTCGTTTAGTGAACCGTCAGATCGC

Figure 24

```
atggtgagcaaggccgaggaggataacatggccatcatcaaggagttcatgcgcttcaag
 M  V  S  K  G  E  E  D  N  M  A  I  I  K  E  F  M  R  F  K
gtgcacatggagggctccgtgaacggccacgagttcgagatcgagggcgagggcgagggc
 V  H  M  E  G  S  V  N  G  H  E  F  E  I  E  G  E  G  E  G
cgcccctacgagggtcagacccagaccgccaagctgaaggtgaccaaggtgcccctgccc
 R  P  Y  E  G  T  Q  T  A  K  L  K  V  T  K  V  P  L  P
ttcgcctgggacatcctgtcccctcagttcatgtacggctccaaggcctacgtgaagcac
 F  A  W  D  I  L  S  P  Q  F  M  Y  G  S  K  A  Y  V  K  H
cccgccgacatcccgactacttgaagctgtcctttcccgaggcttcaagtgggagcgc
 P  A  D  I  P  D  Y  L  K  L  S  F  P  E  G  F  K  W  E  R
gtgatgaacttcgaggacggcgtgtacaccgtgacccagcgactcctccctgaccaggac
 V  M  N  F  E  D  G  V  Y  T  V  T  Q  D  S  S  L  Q  D
ggcgagttcatctactacaaggtgaaggtgggaggcctcctccgagccgatgtacccgaggacggc
 G  E  F  I  Y  K  V  K  L  R  G  T  N  F  P  S  D  G  P  V
atgcagaagaagaccatgggctggaggcctcgagcctgaagctgaaggacggcggccactacgacgct
 M  Q  K  K  T  M  G  W  E  A  S  S  E  R  M  Y  P  E  D  G
gccctgaagggcgagatcaagcagaggctcaagaagccaagaagcccgtgcagctgccgggcgcctacaacgtc
 A  L  K  G  E  I  K  Q  R  L  K  L  K  D  G  G  H  Y  D  A
gaggtcaagaccacctactacaaggccacctcccacaacgaggactacaccatcgtggaacagtactacgaa
 E  V  K  T  T  Y  Y  A  K  K  P  V  Q  L  P  G  A  Y  N  V
aacatcaagttggacatcacctccacctccaccggcatgggacgagctgtacaagtaa
 N  I  K  L  D  I  T  S  H  N  E  D  Y  T  I  V  E  Q  Y  E
cgcgccgagggccgccactccaccggcatggacgagctgtacaagtaa
 R  A  E  G  R  H  S  T  G  M  D  E  L  Y  K  -
```

Figure 25

A. Human elongation factor 1 alpha promoter

TGCAAAGATGGATAAAGTTTTAAACAGAGAGGAATCTTTGCAGCTAATGGACCTTCTAGGTCTTGA
AGGAGTGGGAATTGGCTCCGGTGCCCGTCAGTGGGCAGAGCGCACATCGCCCACAGTCCCCGA
GAAGTTGGGGGGAGGGGTCGGCAATTGAACCGGTGCCTAGAGAAGGTGGCGCGGGGTAAACTG
GGAAAGTGATGTCGTGTACTGGCTCCGCCTTTTCCCGAGGGTGGGGGAGAACCGTATATAAGTG
CAGTAGTCGCCGTGAACGTTCTTTTTCGCAACGGGTTTGCGCCAGAACACAGTAAGTGCCGTG
TGTGGTTCCCGCGGGCCTGGCCTCTTACGGGTTATGGCCCTTGCGTGCCTTGAATTACTTCCAC
TGGCTGCAGTACGTGATTCTTGATCCCGAGCTTCGGGTTGGAAGTGGGTGGGAGAGTTCGAGGC
CTTGCGCTTAAGGAGCCCCTTCGCCTCGTCGTTGCTTGAGTTGAGGCCTGGCCTGGGCGCTGGGCCG
CCGCGTGCGAATCTGGTGGCACCTTCGCGCGCACCTTGCTCGCTGTCTCGCTGCTTCGATAAGTCTCTAGCCATT
AAAATTTTGATGACCTGCTGCGACGCTTTTTCGGTTTTCTGCAAGATAGTCTTGTAAATGCGGGCAAG
ATCTGCACACTGGTATTTCGGTTTTGGGGCCGGCCTGCTGCTGCGAGGGCCTGCTGCTGCGAGGGCCCGTGCGTCCAGCG
CACATGTTCGGGGCCTCTGTGTCCACCAGTTGCGTGACCGAGAATCGGACGGGGTAGTCTCA
AGCTGGCCGGCCTGCTGTGCCACCAGTTGCGTGAGCGGAAAGATGGCCGCTTCCCGGCCCTGCGC
AGGCTGCGGAGTCAAAATGGAGGACGCGGCGCTCGGGAGAGCGGGCGGGTGAGTCACCACACAAAG
GAAAAGGGCCTTTCCGTCCTCAGCGCTTCCATGTGACTCGTCTTTAGGTTGGGGGAGGGTTTA
AGGCACCTCGATTAGTTCTCGAGCTTTTGGAGTACGTCGTCTTTAGGTTGGGGGAGGGTTTA
TGCGATGGAGTTTCCCACACTGAGTGGGTGGAGACTGAAGTTAGGCCAGCTTGGCACTTGATGT
AATTCCTTGGAATTTGCCCTTTTGCCCTTTGGATCTTGGTTCATTCTCAAGCCTCAGACAGTGGT
TCAAAGTTTTTCTTCCATTCAGGTGTCGTGA

B. Synthetic transcription activation domain

```
ggttccggacgggctgacgcattgacgattttgatctgacatgctggaagtgacgcc
 G  S  G  R  A  D  A  L  D  D  F  D  L  D  M  L  G  S  D  A
ctcgatgattttgacctgactgcttgttgccttgacatgctttgacctcgac
                    D  A  L  D  D  F  D  L  D  M  L  G  S  D  A
atgctcggacagtgacgccctgatgattcgacctgacatgctgattaactctaga
 L  D  D  F  D  L  D  M  L  G  S  D  A  L  D  D  F  D  L  D  M
                                                       L  I  N  S  R
```

ggcagtggagagggcagagaggaagtctgctaacatgcgtgacgtcgagagaatcctggc
G  S  G  E  G  R  G  S  L  L  T  C  G  D  V  E  E  N  P  G
cca
Pf

B.

gtgagcaagggcgaggagctgttcaccgggtggtgcccatcctggtcgagctggacggc
V  S  K  G  E  E  L  F  T  G  V  V  P  I  L  V  E  L  D  G
gacgtaaacggccacaagttcagcgtgtccggcgaggcgatgccacctacggc
D  V  N  G  H  K  F  S  V  S  G  E  G  D  A  T  Y  G
aagctgaccctgaagttcatctgcaccaccggcaagctgcccgtgccctggcccaccctc
K  L  T  L  K  F  I  C  T  T  G  K  L  P  V  P  W  P  T  L
gtgaccaccctgacctacgtgcagtgcttcagccgctaccccgaccacatgaagcag
V  T  T  L  T  Y  V  Q  C  F  S  R  Y  P  D  H  M  K  Q
cacgacttcttcaagtccgccatgcccgaaggctacgtccaggagcgcaccatcttcttc
H  D  F  F  K  S  A  M  P  E  G  Y  V  Q  E  R  T  I  F  F
aaggacgacggcaactacaagacccgcgccgaggtgaagttcgaggcgacaccctggtg
K  D  D  G  N  Y  K  T  R  A  E  V  K  F  E  G  D  T  L  V
aaccgcatcgagctgaagggcatcgacttcaaggaggacggcaacatcctggggcacaag
N  R  I  E  L  K  G  I  D  F  K  E  D  G  N  I  L  G  H  K
ctggagtacaactacaacagccacaacgtctatatcatggccgacaagcagaagaacggc
L  E  Y  N  Y  N  S  H  N  V  Y  I  M  A  D  K  Q  K  N  G
atcaaggtgaacttcaagatccgccacaacatcgaggacggcagcgtgcagctcgccgac
I  K  V  N  F  K  I  R  H  N  I  E  D  G  S  V  Q  L  A  D
cactaccagcagaacacccccatcggcgacggccccgtgctgctgcccgacaaccactac
H  Y  Q  Q  N  T  P  I  G  D  G  P  V  L  L  P  D  N  H  Y
ctgagcacccagtccgccctgagcaaagacccaacgagaagcgcgatcacatgtcctg
L  S  T  Q  S  A  L  S  K  D  P  N  E  K  R  D  H  M  V  L
ctggagttcgtgaccgccgccgggatcactctcggcatggacgagctgtacaagtaa
L  E  F  V  T  A  A  G  I  T  L  G  M  D  E  L  Y  K  -

Figure 27

Complete sequence of pLenti-EF1α-TALE-VP64-2A-EGFP-WPRE

```
                                                                              1
GTCGACGGAT CGGGAGATCT CCCGATCCCC TATGGTGCAC TCTCAGTACA ATCTGCTCTG ATGCCGCATA GTTAAGCCAG
                                                                             81
TATCTGCTCC CTGCTTGTGT GTTGGAGGTC GCTGAGTAGT GCGCGAGCAA AATTTAAGCT ACAACAAGGC AAGGCTTGAC
                                                                            161
CGACAATTGC ATGAAGAATC TGCTTAGGGT TAGGCGTTTT GCGCTGCTTC GCGATGTACG GGCCAGATAT ACGCGTTGAC
                                                                            241
ATTGATTATT GACTAGTTAT TAATAGTAAT CAATTACGGG GTCATTAGTT CATAGCCCAT ATATGGAGTT CCGCGTTACA
                                                                            321
TAACTTACGG TAAATGGCCC GCCTGGCTGA CCGCCCAACG ACCCCCGCCC ATTGACGTCA ATAATGACGT ATGTTCCCAT
                                                                            401
AGTAACGCCA ATAGGGACTT TCCATTGACG TCAATGGGTG GAGTATTTAC GGTAAACTGC CCACTTGGCA GTACATCAAG
                                                                            481
TGTATCATAT GCCAAGTACG CCCCCTATTG ACGTCAATGA CGGTAAATGG CCCGCCTGGC ATTATGCCCA GTACATGACC
                                                                            561
TTATGGGACT TTCCTACTTG GCAGTACATC TACGTATTAG TCATCGCTAT TACCATGGTG ATGCGGTTTT GGCAGTACAT
                                                                            641
CAATGGGCGT GGATAGCGGT TTGACTCACG GGGATTTCCA AGTCTCCACC CCATTGACGT CAATGGGAGT TTGTTTTGGC
                                                                            721
ACCAAAATCA ACGGGACTTT CCAAAATGTC GTAACAACTC CGCCCCATTG ACGCAAATGG GCGGTAGGCG TGTACGGTGG

5'LTR
                      ~~~~~~ ~~~~~~~~~~ ~~~~~~~~~~ ~~~~~~~~~~ ~~~~~~~~~~
                                                                            801
GAGGTCTATA TAAGCAGCGC GTTTTGCCTG TACTGGGTCT CTCTGGTTAG ACCAGATCTG AGCCTGGGAG CTCTCTGGCT

5'LTR
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                            881
AACTAGGGAA CCCACTGCTT AAGCCTCAAT AAAGCTTGCC TTGAGTGCTT CAAGTAGTGT GTGCCCGTCT GTTGTGTGAC

5'LTR
~~~~~~~~~~ ~~~~~~~~~~ ~~~~~~~~~~ ~~~~~~~~~~ ~~~~~~~~~~ ~~~~~
                                                                            961
TCTGGTAACT AGAGATCCCT CAGACCCTTT TAGTCAGTGT GGAAAATCTC TAGCAGTGGC GCCCGAACAG GGACTTGAAA
                                                                           1041
GCGAAAGGGA AACCAGAGGA GCTCTCTCGA CGCAGGACTC GGCTTGCTGA AGCGCGCACG GCAAGAGGCG AGGGGCGGCG
                                                                           1121
ACTGGTGAGT ACGCCAAAAA TTTTGACTAG CGGAGGCTAG AAGGAGAGAG ATGGGTGCGA GAGCGTCAGT ATTAAGCGGG
                                                                           1201
GGAGAATTAG ATCGCGATGG GAAAAAATTC GGTTAAGGCC AGGGGGAAAG AAAAAATATA AATTAAAACA TATAGTATGG
                                                                           1281
GCAAGCAGGG AGCTAGAACG ATTCGCAGTT AATCCTGGCC TGTTAGAAAC ATCAGAAGGC TGTAGACAAA TACTGGGACA
```

Figure 28A

```
                                                                         1361
GCTACAACCA TCCCTTCAGA CAGGATCAGA AGAACTTAGA TCATTATATA ATACAGTAGC AACCCTCTAT TGTGTGCATC
                                                                         1441
AAAGGATAGA GATAAAAGAC ACCAAGGAAG CTTTAGACAA GATAGAGGAA GAGCAAAACA AAAGTAAGAC CACCGCACAG
                                                                         1521
CAAGCGGCCG CTGATCTTCA GACCTGGAGG AGGAGATATG AGGGACAATT GGAGAAGTGA ATTATATAAA TATAAAGTAG
                                                                         1601
TAAAAATTGA ACCATTAGGA GTAGCACCCA CCAAGGCAAA GAGAAGAGTG GTGCAGAGAG AAAAAAGAGC AGTGGGAATA

RRE

1681
GGAGCTTTGT TCCTTGGGTT CTTGGGAGCA GCAGGAAGCA CTATGGGCGC AGCGTCAATG ACGCTGACGG TACAGGCCAG

RRE

1761
ACAATTATTG TCTGGTATAG TGCAGCAGCA GAACAATTTG CTGAGGGCTA TTGAGGCGCA ACAGCATCTG TTGCAACTCA

RRE

1841
CAGTCTGGGG CATCAAGCAG CTCCAGGCAA GAATCCTGGC TGTGGAAAGA TACCTAAAGG ATCAACAGCT CCTGGGGATT
                                                                         1921
TGGGGTTGCT CTGGAAAACT CATTTGCACC ACTGCTGTGC CTTGGAATGC TAGTTGGAGT AATAAATCTC TGGAACAGAT
                                                                         2001
TTGGAATCAC ACGACCTGGA TGGAGTGGGA CAGAGAAATT AACAATTACA CAAGCTTAAT ACACTCCTTA ATTGAAGAAT
                                                                         2081
CGCAAAACCA GCAAGAAAAG AATGAACAAG AATTATTGGA ATTAGATAAA TGGGCAAGTT TGTGGAATTG GTTTAACATA
                                                                         2161
ACAAATTGGC TGTGGTATAT AAAATTATTC ATAATGATAG TAGGAGGCTT GGTAGGTTTA AGAATAGTTT TTGCTGTACT
                                                                         2241
TTCTATAGTG AATAGAGTTA GGCAGGGATA TTCACCATTA TCGTTTCAGA CCCACCTCCC AACCCCGAGG GGACCCGACA
                                                                         2321
GGCCCGAAGG AATAGAAGAA GAAGGTGGAG AGAGAGACAG AGACAGATCC ATTCGATTAG TGAACGGATC GGCACTGCGT
                                                                         2401
GCGCCAATTC TGCAGACAAA TGGCAGTATT CATCCACAAT TTTAAAAGAA AAGGGGGGAT TGGGGGGTAC AGTGCAGGGG
                                                                         2481
AAAGAATAGT AGACATAATA GCAACAGACA TACAAACTAA AGAATTACAA AAACAAATTA CAAAAATTCA AAATTTTCGG

EF-1a

2561
GTTTATTACA GGGACAGCAG AGATCCAGTT TGGTTAATTA ATGCAAAGAT GGATAAAGTT TTAAACAGAG AGGAATCTTT
```

Figure 28B

```
                                  EF-1a
                                                                          2641
GCAGCTAATG GACCTTCTAG GTCTTGAAAG GAGTGGGAAT TGGCTCCGGT GCCCGTCAGT GGGCAGAGCG CACATCGCCC

EF-1a
                                                                          2721
ACAGTCCCCG AGAAGTTGGG GGGAGGGGTC GGCAATTGAA CCGGTGCCTA GAGAAGGTGG CGCGGGGTAA ACTGGGAAAG

EF-1a
                                                                          2801
TGATGTCGTG TACTGGCTCC GCCTTTTTCC CGAGGGTGGG GGAGAACCGT ATATAAGTGC AGTAGTCGCC GTGAACGTTC

EF-1a
                                                                          2881
TTTTTCGCAA CGGGTTTGCC GCCAGAACAC AGGTAAGTGC CGTGTGTGGT TCCCGCGGGC CTGGCCTCTT TACGGGTTAT

EF-1a
                                                                          2961
GGCCCTTGCG TGCCTTGAAT TACTTCCACT GGCTGCAGTA CGTGATTCTT GATCCCGAGC TTCGGGTTGG AAGTGGGTGG

EF-1a
                                                                          3041
GAGAGTTCGA GGCCTTGCGC TTAAGGAGCC CCTTCGCCTC GTGCTTGAGT TGAGGCCTGG CCTGGGCGCT GGGGCCGCCG

EF-1a
                                                                          3121
CGTGCGAATC TGGTGGCACC TTCGCGCCTG TCTCGCTGCT TTCGATAAGT CTCTAGCCAT TTAAAATTTT TGATGACCTG

EF-1a
                                                                          3201
CTGCGACGCT TTTTTTCTGG CAAGATAGTC TTGTAAATGC GGGCCAAGAT CTGCACACTG GTATTTCGGT TTTTGGGGCC

EF-1a
                                                                          3281
GCGGGCGGCG ACGGGGCCCG TGCGTCCCAG CGCACATGTT CGGCGAGGCG GGGCCTGCGA GCGCGGCCAC CGAGAATCGG
```

Figure 28C

```
                                          EF-1a
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3361
ACGGGGGTAG TCTCAAGCTG GCCGGCCTGC TCTGGTGCCT GGCCTCGCGC CGCCGTGTAT CGCCCCGCCC TGGGCGGCAA

EF-1a
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3441
GGCTGGCCCG GTCGGCACCA GTTGCGTGAG CGGAAAGATG GCCGCTTCCC GGCCCTGCTG CAGGGAGCTC AAAATGGAGG

EF-1a
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3521
ACGCGGCGCT CGGGAGAGCG GGCGGGTGAG TCACCCACAC AAAGGAAAAG GGCCTTTCCG TCCTCAGCCG TCGCTTCATG

EF-1a
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3601
TGACTCCACG GAGTACCGGG CGCCGTCCAG GCACCTCGAT TAGTTCTCGA GCTTTTGGAG TACGTCGTCT TTAGGTTGGG

EF-1a
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3681
GGGAGGGGTT TTATGCGATG GAGTTTCCCC ACACTGAGTG GGTGGAGACT GAAGTTAGGC CAGCTTGGCA CTTGATGTAA

EF-1a
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3761
TTCTCCTTGG AATTTGCCCT TTTTGAGTTT GGATCTTGGT TCATTCTCAA GCCTCAGACA GTGGTTCAAA GTTTTTTTCT

N'term of Hax3
                                          ~~~~~~~~~~ ~~~~~~~~~~ ~~~~~~~~~~ ~~~~~~~~~~ ~~~~~~~~~~
           EF-1a
~~~~~~~~~~ ~~~~~~~~~~
                                                                                    3841
TCCATTTCAG GTGTCGTGAC GTACGGCCAC CATGTCGCGG ACCCGGCTCC CTTCCCCACC CGCACCCAGC CCAGCGTTTT N'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    3921
CGGCCGACTC GTTCTCAGAC CTGCTTAGGC AGTTCGACCC CTCACTGTTT AACACATCGT TGTTCGACTC CCTTCCTCCG N'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    4001
TTTGGGGCGC ACCATACGGA GGCGGCCACC GGGGAGTGGG ATGAGGTGCA GTCGGGATTG AGAGCTGCGG ATGCACCACC
```

Figure 28D

N'term of Hax3

```
                                                                        4081
CCCAACCATG CGGGTGGCCG TCACCGCTGC CCGACCGCCG AGGGCGAAGC CCGCACCAAG GCGGAGGGCA GCGCAACCGT
```

N'term of Hax3

```
                                                                        4161
CCGACGCAAG CCCCGCAGCG CAAGTAGATT TGAGAACTTT GGGATATTCA CAGCAGCAGC AGGAAAAGAT CAAGCCCAAA
```

N'term of Hax3

```
                                                                        4241
GTGAGGTCGA CAGTCGCGCA GCATCACGAA GCGCTGGTGG GTCATGGGTT TACACATGCC CACATCGTAG CCTTGTCGCA
```

N'term of Hax3

```
                                                                        4321
GCACCCTGCA GCCCTTGGCA CGGTCGCCGT CAAGTACCAG GACATGATTG CGGCGTTGCC GGAAGCCACA CATGAGGCGA
```

N'term of Hax3

```
                                                                        4401
TCGTCGGTGT GGGGAAACAG TGGAGCGGAG CCCGAGCGCT TGAGGCCCTG TTGACGGTCG CGGGAGAGCT GAGAGGGCCT
```

N'term of Hax3

```
                                                                        4481
CCCCTTCAGC TGGACACGGG CCAGTTGCTG AAGATCGCGA AGCGGGGAGG AGTCACGGCG GTCGAGGCGG TGCACGCGTG
``` spacer 0.5

N'term of Hax3

```
                                                                        4561
GCGCAATGCG CTCACGGGAG CACCCCTCAA CCTGACCGAG ACGGTACATG AAACGCATGG CACGGCGTCT CAACTCACGC
```

0.5

C'term of Hax3

```
                                                                        4641
CTGAGCAGGT AGTGGCTATT GCATCCAATA TCGGGGGCAG ACCCGCACTG GAGTCAATCG TGGCCCAGCT TTCGAGGCCG
```

Figure 28E

```
                              C'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    4721
GACCCCGCGC TGGCCGCACT CACTAATGAT CATCTTGTAG CGCTGGCCTG CCTCGGCGGA CGACCCGCCT TGGATGCGGT C'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    4801
GAAGAAGGGG CTCCCGCACG CGCCTGCATT GATTAAGCGG ACCAACAGAA GGATTCCCGA GAGGACATCA CATCGAGTGG C'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    4881
CAGATCACGC GCAAGTGGTC CGCGTGCTCG GATTCTTCCA GTGTCACTCC CACCCCGCAC AAGCGTTCGA TGACGCCATG C'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    4961
ACTCAATTTG GTATGTCGAG ACACGGACTG CTGCAGCTCT TTCGTAGAGT CGGTGTCACA GAACTCGAGG CCCGCTCGGG C'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5041
CACACTGCCT CCCGCCTCCC AGCGGTGGGA CAGGATTCTC CAAGCGAGCG GTATGAAACG CGCGAAGCCT TCACCTACGT C'term of Hax3
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5121
CAACTCAGAC ACCTGACCAG GCGAGCCTTC ATGCGTTCGC AGACTCGCTG GAGAGGGATT TGGACGCGCC CTCGCCCATG NLS
                              ~~~~~~~~~~ ~~~~~~~~~~ ~~~~~~~~~~ ~~~
                                                                              vp64
                                                                        ~~~~~~~ ~~~~~~~~~~
           C'term of Hax3
~~~~~~~~~~ ~~~~~~~~~~ ~~~~~~~
                                                                                    5201
CATGAAGGGG ACCAAACTCG CGCGTCAGCT AGCCCCAAGA AGAAGAGAAA GGTGGAGGCC AGCGGTTCCG GACGGGCTGA vp64
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5281
CGCATTGGAC GATTTTGATC TGGATATGCT GGGAAGTGAC GCCCTCGATG ATTTTGACCT TGACATGCTT GGTTCGGATG
```

Figure 28F

```
                                           vp64
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5361
CCCTTGATGA CTTTGACCTC GACATGCTCG GCAGTGACGC CCTTGATGAT TTCGACCTGG ACATGCTGAT TAACTCTAGA

GFP
                                                                    ~~~~~~~ ~~~~~~~~~~
                               2A
~~~~~~~~~~ ~~~~~~~~~~ ~~~~~~~~~~ ~~~~~~~~~~ ~~~~~~~~~~ ~~~~~~~~~~ ~~~
                                                                                    5441
GGCAGTGGAG AGGGCAGAGG AAGTCTGCTA ACATGCGGTG ACGTCGAGGA GAATCCTGGC CCAGTGAGCA AGGGCGAGGA

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5521
GCTGTTCACC GGGGTGGTGC CCATCCTGGT CGAGCTGGAC GGCGACGTAA ACGGCCACAA GTTCAGCGTG TCCGGCGAGG

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5601
GCGAGGGCGA TGCCACCTAC GGCAAGCTGA CCCTGAAGTT CATCTGCACC ACCGGCAAGC TGCCCGTGCC CTGGCCCACC

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5681
CTCGTGACCA CCCTGACCTA CGGCGTGCAG TGCTTCAGCC GCTACCCCGA CCACATGAAG CAGCACGACT TCTTCAAGTC

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5761
CGCCATGCCC GAAGGCTACG TCCAGGAGCG CACCATCTTC TTCAAGGACG ACGGCAACTA CAAGACCCGC GCCGAGGTGA

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5841
AGTTCGAGGG CGACACCCTG GTGAACCGCA TCGAGCTGAA GGGCATCGAC TTCAAGGAGG ACGGCAACAT CCTGGGGCAC

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    5921
AAGCTGGAGT ACAACTACAA CAGCCACAAC GTCTATATCA TGGCCGACAA GCAGAAGAAC GGCATCAAGG TGAACTTCAA

GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6001
GATCCGCCAC AACATCGAGG ACGGCAGCGT GCAGCTCGCC GACCACTACC AGCAGAACAC CCCCATCGGC GACGGCCCCG
```

Figure 28G

```
                                          GFP
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6081
TGCTGCTGCC CGACAACCAC TACCTGAGCA CCCAGTCCGC CCTGAGCAAA GACCCCAACG AGAAGCGCGA TCACATGGTC

GFP
~~~~~~~~~~ ~~~~~~~~~~ ~~~~~~~~~~ ~~~~~~~~~~ ~~~~~~~~~~ ~~~~~~~
                                                                                    WPRE
                                                                              ~~~~~~
                                                                                    6161
CTGCTGGAGT TCGTGACCGC CGCCGGGATC ACTCTCGGCA TGGACGAGCT GTACAAGTAA GAATTCGATA TCAAGCTTAT

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6241
CGATAATCAA CCTCTGGATT ACAAAATTTG TGAAAGATTG ACTGGTATTC TTAACTATGT TGCTCCTTTT ACGCTATGTG

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6321
GATACGCTGC TTTAATGCCT TTGTATCATG CTATTGCTTC CCGTATGGCT TTCATTTTCT CCTCCTTGTA TAAATCCTGG

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6401
TTGCTGTCTC TTTATGAGGA GTTGTGGCCC GTTGTCAGGC AACGTGGCGT GGTGTGCACT GTGTTTGCTG ACGCAACCCC

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6481
CACTGGTTGG GGCATTGCCA CCACCTGTCA GCTCCTTTCC GGGACTTTCG CTTTCCCCCT CCCTATTGCC ACGGCGGAAC

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6561
TCATCGCCGC CTGCCTTGCC CGCTGCTGGA CAGGGGCTCG GCTGTTGGGC ACTGACAATT CCGTGGTGTT GTCGGGGAAA

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6641
TCATCGTCCT TTCCTTGGCT GCTCGCCTGT GTTGCCACCT GGATTCTGCG CGGGACGTCC TTCTGCTACG TCCCTTCGGC

WPRE
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                    6721
CCTCAATCCA GCGGACCTTC CTTCCCGCGG CCTGCTGCCG GCTCTGCGGC CTCTTCCGCG TCTTCGCCTT CGCCCTCAGA
```

Figure 28H

```
                                          WPRE
~~~~~~~~~~ ~~~~~~~~~~ ~~~~~~~~~~ ~~~~~~~~~~ ~~~
                                                                                 6801
CGAGTCGGAT CTCCCTTTGG GCCGCCTCCC CGCATCGATA CCGTCGACCT CGAGACCTAG AAAAACATGG AGCAATCACA

6881
AGTAGCAATA CAGCAGCTAC CAATGCTGAT TGTGCCTGGC TAGAAGCACA AGAGGAGGAG GAGGTGGGTT TTCCAGTCAC

6961
ACCTCAGGTA CCTTTAAGAC CAATGACTTA CAAGGCAGCT GTAGATCTTA GCCACTTTTT AAAAGAAAAG GGGGACTGG

7041
AAGGGCTAAT TCACTCCCAA CGAAGACAAG ATATCCTTGA TCTGTGGATC TACCACACAC AAGGCTACTT CCCTGATTGG

7121
CAGAACTACA CACCAGGGCC AGGGATCAGA TATCCACTGA CCTTTGGATG GTGCTACAAG CTAGTACCAG TTGAGCAAGA

7201
GAAGGTAGAA GAAGCCAATG AAGGAGAGAA CACCCGCTTG TTACACCCTG TGAGCCTGCA TGGGATGGAT GACCCGGAGA

3' LTR
                                                                              ~~~
                                                                                 7281
GAGAAGTATT AGAGTGGAGG TTTGACAGCC GCCTAGCATT TCATCACATG GCCCGAGAGC TGCATCCGGA CTGTACTGGG

3' LTR
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                 7361
TCTCTCTGGT TAGACCAGAT CTGAGCCTGG GAGCTCTCTG GCTAACTAGG GAACCCACTG CTTAAGCCTC AATAAAGCTT

3' LTR
~~~~~~~~~~ ~~~~~~~~~~ ~~~~~~~~~~ ~~~~~~~~~~ ~~~~~~~~~~ ~~~~~~~~~~ ~~~~~~~~~~ ~~~~~~~~~~
                                                                                 7441
GCCTTGAGTG CTTCAAGTAG TGTGTGCCCG TCTGTTGTGT GACTCTGGTA ACTAGAGATC CCTCAGACCC TTTTAGTCAG

3' LTR
~~~~~~~~~~ ~~~~~~~~
                                                                                 7521
TGTGGAAAAT CTCTAGCAGG GCCCGTTTAA ACCCGCTGAT CAGCCTCGAC TGTGCCTTCT AGTTGCCAGC CATCTGTTGT

7601
TTGCCCCTCC CCCGTGCCTT CCTTGACCCT GGAAGGTGCC ACTCCCACTG TCCTTTCCTA ATAAAATGAG GAAATTGCAT

7681
CGCATTGTCT GAGTAGGTGT CATTCTATTC TGGGGGGTGG GGTGGGGCAG GACAGCAAGG GGGAGGATTG GGAAGACAAT

7761
AGCAGGCATG CTGGGGATGC GGTGGGCTCT ATGGCTTCTG AGGCGGAAAG AACCAGCTGG GGCTCTAGGG GGTATCCCCA

7841
CGCGCCCTGT AGCGGCGCAT TAAGCGCGGC GGGTGTGGTG GTTACGCGCA GCGTGACCGC TACACTTGCC AGCGCCCTAG

7921
CGCCCGCTCC TTTCGCTTTC TTCCCTTCCT TTCTCGCCAC GTTCGCCGGC TTTCCCCGTC AAGCTCTAAA TCGGGGGCTC

8001
CCTTTAGGGT TCCGATTTAG TGCTTTACGG CACCTCGACC CCAAAAAACT TGATTAGGGT GATGGTTCAC GTAGTGGGCC

```
ATCGCCCTGA TAGACGGTTT TTCGCCCTTT GACGTTGGAG TCCACGTTCT TTAATAGTGG ACTCTTGTTC CAAACTGGAA
                                                                                   8161
CAACACTCAA CCCTATCTCG GTCTATTCTT TTGATTTATA AGGGATTTTG CCGATTTCGG CCTATTGGTT AAAAAATGAG
                                                                                   8241
CTGATTTAAC AAAAATTTAA CGCGAATTAA TTCTGTGGAA TGTGTGTCAG TTAGGGTGTG GAAAGTCCCC AGGCTCCCCA
                                                                                   8321
GCAGGCAGAA GTATGCAAAG CATGCATCTC AATTAGTCAG CAACCAGGTG TGGAAAGTCC CCAGGCTCCC CAGCAGGCAG
                                                                                   8401
AAGTATGCAA AGCATGCATC TCAATTAGTC AGCAACCATA GTCCCGCCCC TAACTCCGCC CATCCCGCCC CTAACTCCGC
                                                                                   8481
CCAGTTCCGC CCATTCTCCG CCCCATGGCT GACTAATTTT TTTTATTTAT GCAGAGGCCG AGGCCGCCTC TGCCTCTGAG
                                                                                   8561
CTATTCCAGA AGTAGTGAGG AGGCTTTTTT GGAGGCCTAG GCTTTTGCAA AAAGCTCCCG GGAGCTTGTA TATCCATTTT
                                                                                   8641
CGGATCTGAT CAGCACGTGT TGACAATTAA TCATCGGCAT AGTATATCGG CATAGTATAA TACGACAAGG TGAGGAACTA
                                                                                   8721
AACCATGGCC AAGTTGACCA GTGCCGTTCC GGTGCTCACC GCGCGCGACG TCGCCGGAGC GGTCGAGTTC TGGACCGACC
                                                                                   8801
GGCTCGGGTT CTCCCGGGAC TTCGTGGAGG ACGACTTCGC CGGTGTGGTC CGGGACGACG TGACCCTGTT CATCAGCGCG
                                                                                   8881
GTCCAGGACC AGGTGGTGCC GGACAACACC CTGGCCTGGG TGTGGGTGCG CGGCCTGGAC GAGCTGTACG CCGAGTGGTC
                                                                                   8961
GGAGGTCGTG TCCACGAACT TCCGGGACGC CTCCGGGCCG GCCATGACCG AGATCGGCGA GCAGCCGTGG GGGCGGGAGT
                                                                                   9041
TCGCCCTGCG CGACCCGGCC GGCAACTGCG TGCACTTCGT GGCCGAGGAG CAGGACTGAC ACGTGCTACG AGATTTCGAT
                                                                                   9121
TCCACCGCCG CCTTCTATGA AAGGTTGGGC TTCGGAATCG TTTTCCGGGA CGCCGGCTGG ATGATCCTCC AGCGCGGGGA
                                                                                   9201
TCTCATGCTG GAGTTCTTCG CCCACCCCAA CTTGTTTATT GCAGCTTATA ATGGTTACAA ATAAAGCAAT AGCATCACAA
                                                                                   9281
ATTTCACAAA TAAAGCATTT TTTTCACTGC ATTCTAGTTG TGGTTTGTCC AAACTCATCA ATGTATCTTA TCATGTCTGT
                                                                                   9361
ATACCGTCGA CCTCTAGCTA GAGCTTGGCG TAATCATGGT CATAGCTGTT TCCTGTGTGA AATTGTTATC CGCTCACAAT
                                                                                   9441
TCCACACAAC ATACGAGCCG GAAGCATAAA GTGTAAAGCC TGGGGTGCCT AATGAGTGAG CTAACTCACA TTAATTGCGT
                                                                                   9521
TGCGCTCACT GCCCGCTTTC CAGTCGGGAA ACCTGTCGTG CCAGCTGCAT TAATGAATCG GCCAACGCGC GGGGAGAGGC
                                                                                   9601
GGTTTGCGTA TTGGGCGCTC TTCCGCTTCC TCGCTCACTG ACTCGCTGCG CTCGGTCGTT CGGCTGCGGC GAGCGGTATC
                                                                                   9681
AGCTCACTCA AAGGCGGTAA TACGGTTATC CACAGAATCA GGGGATAACG CAGGAAAGAA CATGTGAGCA AAAGGCCAGC
                                                                                   9761
AAAAGGCCAG GAACCGTAAA AAGGCCGCGT TGCTGGCGTT TTTCCATAGG CTCCGCCCCC CTGACGAGCA TCACAAAAAT
                                                                                   9841
```

Figure 28J

```
CGACGCTCAA GTCAGAGGTG GCGAAACCCG ACAGGACTAT AAAGATACCA GGCGTTTCCC CCTGGAAGCT CCCTCGTGCG
                                                                                    9921
CTCTCCTGTT CCGACCCTGC CGCTTACCGG ATACCTGTCC GCCTTTCTCC CTTCGGGAAG CGTGGCGCTT TCTCATAGCT
                                                                                   10001
CACGCTGTAG GTATCTCAGT TCGGTGTAGG TCGTTCGCTC CAAGCTGGGC TGTGTGCACG AACCCCCCGT TCAGCCCGAC
                                                                                   10081
CGCTGCGCCT TATCCGGTAA CTATCGTCTT GAGTCCAACC CGGTAAGACA CGACTTATCG CCACTGGCAG CAGCCACTGG
                                                                                   10161
TAACAGGATT AGCAGAGCGA GGTATGTAGG CGGTGCTACA GAGTTCTTGA AGTGGTGGCC TAACTACGGC TACACTAGAA
                                                                                   10241
GAACAGTATT TGGTATCTGC GCTCTGCTGA AGCCAGTTAC CTTCGGAAAA AGAGTTGGTA GCTCTTGATC CGGCAAACAA
                                                                                   10321
ACCACCGCTG GTAGCGGTGG TTTTTTTGTT TGCAAGCAGC AGATTACGCG CAGAAAAAAA GGATCTCAAG AAGATCCTTT
                                                                                   10401
GATCTTTTCT ACGGGGTCTG ACGCTCAGTG GAACGAAAAC TCACGTTAAG GGATTTTGGT CATGAGATTA TCAAAAAGGA
                                                                                   10481
TCTTCACCTA GATCCTTTTA AATTAAAAAT GAAGTTTTAA ATCAATCTAA AGTATATATG AGTAAACTTG GTCTGACAGT
                                                                                   10561
TACCAATGCT TAATCAGTGA GGCACCTATC TCAGCGATCT GTCTATTTCG TTCATCCATA GTTGCCTGAC TCCCCGTCGT
                                                                                   10641
GTAGATAACT ACGATACGGG AGGGCTTACC ATCTGGCCCC AGTGCTGCAA TGATACCGCG AGACCCACGC TCACCGGCTC
                                                                                   10721
CAGATTTATC AGCAATAAAC CAGCCAGCCG GAAGGGCCGA GCGCAGAAGT GGTCCTGCAA CTTTATCCGC CTCCATCCAG
                                                                                   10801
TCTATTAATT GTTGCCGGGA AGCTAGAGTA AGTAGTTCGC CAGTTAATAG TTTGCGCAAC GTTGTTGCCA TTGCTACAGG
                                                                                   10881
CATCGTGGTG TCACGCTCGT CGTTTGGTAT GGCTTCATTC AGCTCCGGTT CCCAACGATC AAGGCGAGTT ACATGATCCC
                                                                                   10961
CCATGTTGTG CAAAAAAGCG GTTAGCTCCT TCGGTCCTCC GATCGTTGTC AGAAGTAAGT TGGCCGCAGT GTTATCACTC
                                                                                   11041
ATGGTTATGG CAGCACTGCA TAATTCTCTT ACTGTCATGC CATCCGTAAG ATGCTTTTCT GTGACTGGTG AGTACTCAAC
                                                                                   11121
CAAGTCATTC TGAGAATAGT GTATGCGGCG ACCGAGTTGC TCTTGCCCGG CGTCAATACG GGATAATACC GCGCCACATA
                                                                                   11201
GCAGAACTTT AAAAGTGCTC ATCATTGGAA AACGTTCTTC GGGGCGAAAA CTCTCAAGGA TCTTACCGCT GTTGAGATCC
                                                                                   11281
AGTTCGATGT AACCCACTCG TGCACCCAAC TGATCTTCAG CATCTTTTAC TTTCACCAGC GTTTCTGGGT GAGCAAAAAC
                                                                                   11361
AGGAAGGCAA AATGCCGCAA AAAAGGGAAT AAGGGCGACA CGGAAATGTT GAATACTCAT ACTCTTCCTT TTTCAATATT
                                                                                   11441
ATTGAAGCAT TTATCAGGGT TATTGTCTCA TGAGCGGATA CATATTTGAA TGTATTTAGA AAAATAAACA AATAGGGGTT
                                                                                   11521
CCGCGCACAT TTCCCCGAAA AGTGCCACCT GAC
```

Figure 28K

A. Module NI
```
ctgacccagagcaggtcgtggcaatcgcctccaacattggcgggaaacaggcactcgag
 L  T  P  E  Q  V  V  A  I  A  S  N  I  G  G  K  Q  A  L  E
actgtccagcgcctgcttcccgtgctgtgccaagcgcacgga
 T  V  Q  R  L  L  P  V  L  C  Q  A  H  G
```

B. Module NG
```
ctgacccagagcaggtcgtggccattgcctcgaatggaggggcaaacaggcgttggaa
 L  T  P  E  Q  V  V  A  I  A  S  N  G  G  K  Q  A  L  E
accgtacaacgattgctgccggtgctgtgccaagcgcacggc
 T  V  Q  R  L  L  P  V  L  C  Q  A  H  G
```

C. Module HD
```
ttgacccagagcaggtcgtggcgatcgcaagccacgacggaggaaagcaagccttggaa
 L  T  P  E  Q  V  V  A  I  A  S  H  D  G  G  K  Q  A  L  E
acagtacagaggctgttgcctgtgctgtgccaagcgcacggg
 T  V  Q  R  L  L  P  V  L  C  Q  A  H  G
```

D. Module NN
```
cttacccagagcaggtcgtggcaatcgcgagcaataacggcggaaaacaggctttggaa
 L  T  P  E  Q  V  V  A  I  A  S  N  N  G  G  K  Q  A  L  E
acggtgcagaggctccttccagtgctgtgccaagcgcacggg
 T  V  Q  R  L  L  P  V  L  C  Q  A  H  G
```

E. Consensus Module:
```
ctgacccagagcaggtcgtggcaatcgcctccnnnnnnggcgggaaacaggcactcgag
 L  T  P  E  Q  V  V  A  I  A  S  x  x  G  G  K  Q  A  L  E
actgtccagcgcctgcttcccgtgctgtgccaagcgcacgga
 T  V  Q  R  L  L  P  V  L  C  Q  A  H  G
```

Figure 29

```
NG    MSRTRLPSPPAPSPAFSADSFSDLLRQFDPSLFNTSLFDSLPPFGAHHTEAATGEWDEVQ
NI    MSRTRLPSPPAPSPAFSADSFSDLLRQFDPSLFNTSLFDSLPPFGAHHTEAATGEWDEVQ
NN    MSRTRLPSPPAPSPAFSADSFSDLLRQFDPSLFNTSLFDSLPPFGAHHTEAATGEWDEVQ
HD    MSRTRLPSPPAPSPAFSADSFSDLLRQFDPSLFNTSLFDSLPPFGAHHTEAATGEWDEVQ
      ************************************************************

NG    SGLRAADAPPPTMRVAVTAARPPRAKPAPRRRAAQPSDASPAAQVDLRTLGYSQQQQEKI
NI    SGLRAADAPPPTMRVAVTAARPPRAKPAPRRRAAQPSDASPAAQVDLRTLGYSQQQQEKI
NN    SGLRAADAPPPTMRVAVTAARPPRAKPAPRRRAAQPSDASPAAQVDLRTLGYSQQQQEKI
HD    SGLRAADAPPPTMRVAVTAARPPRAKPAPRRRAAQPSDASPAAQVDLRTLGYSQQQQEKI
      ************************************************************

NG    KPKVRSTVAQHHEALVGHGFTHAHIVALSQHPAALGTVAVKYQDMIAALPEATHEAIVGV
NI    KPKVRSTVAQHHEALVGHGFTHAHIVALSQHPAALGTVAVKYQDMIAALPEATHEAIVGV
NN    KPKVRSTVAQHHEALVGHGFTHAHIVALSQHPAALGTVAVKYQDMIAALPEATHEAIVGV
HD    KPKVRSTVAQHHEALVGHGFTHAHIVALSQHPAALGTVAVKYQDMIAALPEATHEAIVGV
      ************************************************************

NG    GKQWSGARALEALLTVAGELRGPPLQLDTGQLLKIAKRGGVTAVEAVHAWRNALTGAPLN
NI    GKQWSGARALEALLTVAGELRGPPLQLDTGQLLKIAKRGGVTAVEAVHAWRNALTGAPLN
NN    GKQWSGARALEALLTVAGELRGPPLQLDTGQLLKIAKRGGVTAVEAVHAWRNALTGAPLN
HD    GKQWSGARALEALLTVAGELRGPPLQLDTGQLLKIAKRGGVTAVEAVHAWRNALTGAPLN
      ************************************************************

NG    LTETVHETHGTASQLTPEQVVAIASNGGGRPALESIVAQLSRPDPALAALTNDHLVALAC
NI    LTETVHETHGTASQLTPEQVVAIASNIGGRPALESIVAQLSRPDPALAALTNDHLVALAC
NN    LTETVHETHGTASQLTPEQVVAIASNNGGRPALESIVAQLSRPDPALAALTNDHLVALAC
HD    LTETVHETHGTASQLTPEQVVAIASHDGGRPALESIVAQLSRPDPALAALTNDHLVALAC
      *************************:  ********************************

NG    LGGRPALDAVKKGLPHAPALIKRTNRRIPERTSHRVADHAQVVRVLGFFQCHSHPAQAFD
NI    LGGRPALDAVKKGLPHAPALIKRTNRRIPERTSHRVADHAQVVRVLGFFQCHSHPAQAFD
NN    LGGRPALDAVKKGLPHAPALIKRTNRRIPERTSHRVADHAQVVRVLGFFQCHSHPAQAFD
HD    LGGRPALDAVKKGLPHAPALIKRTNRRIPERTSHRVADHAQVVRVLGFFQCHSHPAQAFD
      ************************************************************

NG    DAMTQFGMSRHGLLQLFRRVGVTELEARSGTLPPASQRWDRILQASGMKRAKPSPTSTQT
NI    DAMTQFGMSRHGLLQLFRRVGVTELEARSGTLPPASQRWDRILQASGMKRAKPSPTSTQT
NN    DAMTQFGMSRHGLLQLFRRVGVTELEARSGTLPPASQRWDRILQASGMKRAKPSPTSTQT
HD    DAMTQFGMSRHGLLQLFRRVGVTELEARSGTLPPASQRWDRILQASGMKRAKPSPTSTQT
      ************************************************************

NG    PDQASLHAFADSLERDLDAPSPMHEGDQTRASASPKKKRKVEASGSGRADALDDFDLDML
NI    PDQASLHAFADSLERDLDAPSPMHEGDQTRASASPKKKRKVEASGSGRADALDDFDLDML
NN    PDQASLHAFADSLERDLDAPSPMHEGDQTRASASPKKKRKVEASGSGRADALDDFDLDML
HD    PDQASLHAFADSLERDLDAPSPMHEGDQTRASASPKKKRKVEASGSGRADALDDFDLDML
      ************************************************************

NG    GSDALDDFDLDMLGSDALDDFDLDMLGSDALDDFDLDMLINSRGSGEGRGSLLTCGDVEE
NI    GSDALDDFDLDMLGSDALDDFDLDMLGSDALDDFDLDMLINSRGSGEGRGSLLTCGDVEE
NN    GSDALDDFDLDMLGSDALDDFDLDMLGSDALDDFDLDMLINSRGSGEGRGSLLTCGDVEE
HD    GSDALDDFDLDMLGSDALDDFDLDMLGSDALDDFDLDMLINSRGSGEGRGSLLTCGDVEE
      ************************************************************

NG    NPGPVSKGEELFTGVVPILVELDGDVNGHKFSVSGEGEGDATYGKLTLKFICTTGKLPVP
NI    NPGPVSKGEELFTGVVPILVELDGDVNGHKFSVSGEGEGDATYGKLTLKFICTTGKLPVP
NN    NPGPVSKGEELFTGVVPILVELDGDVNGHKFSVSGEGEGDATYGKLTLKFICTTGKLPVP
HD    NPGPVSKGEELFTGVVPILVELDGDVNGHKFSVSGEGEGDATYGKLTLKFICTTGKLPVP
      ************************************************************
```

Figure 30A

```
NG        WPTLVTTLTYGVQCFSRYPDHMKQHDFFKSAMPEGYVQERTIFFKDDGNYKTRAEVKFEG
NI        WPTLVTTLTYGVQCFSRYPDHMKQHDFFKSAMPEGYVQERTIFFKDDGNYKTRAEVKFEG
NN        WPTLVTTLTYGVQCFSRYPDHMKQHDFFKSAMPEGYVQERTIFFKDDGNYKTRAEVKFEG
HD        WPTLVTTLTYGVQCFSRYPDHMKQHDFFKSAMPEGYVQERTIFFKDDGNYKTRAEVKFEG
          ************************************************************

NG        DTLVNRIELKGIDFKEDGNILGHKLEYNYNSHNVYIMADKQKNGIKVNFKIRHNIEDGSV
NI        DTLVNRIELKGIDFKEDGNILGHKLEYNYNSHNVYIMADKQKNGIKVNFKIRHNIEDGSV
NN        DTLVNRIELKGIDFKEDGNILGHKLEYNYNSHNVYIMADKQKNGIKVNFKIRHNIEDGSV
HD        DTLVNRIELKGIDFKEDGNILGHKLEYNYNSHNVYIMADKQKNGIKVNFKIRHNIEDGSV
          ************************************************************

NG        QLADHYQQNTPIGDGPVLLPDNHYLSTQSALSKDPNEKRDHMVLLEFVTAAGITLGMDEL
NI        QLADHYQQNTPIGDGPVLLPDNHYLSTQSALSKDPNEKRDHMVLLEFVTAAGITLGMDEL
NN        QLADHYQQNTPIGDGPVLLPDNHYLSTQSALSKDPNEKRDHMVLLEFVTAAGITLGMDEL
HD        QLADHYQQNTPIGDGPVLLPDNHYLSTQSALSKDPNEKRDHMVLLEFVTAAGITLGMDEL
          ************************************************************

```
NN    ATGTCGCGGACCCGGCTCCCTTCCCCACCCGCACCCAGCCCAGCGTTTTCGGCCGACTCG
NI    ATGTCGCGGACCCGGCTCCCTTCCCCACCCGCACCCAGCCCAGCGTTTTCGGCCGACTCG
NG    ATGTCGCGGACCCGGCTCCCTTCCCCACCCGCACCCAGCCCAGCGTTTTCGGCCGACTCG
HD    ATGTCGCGGACCCGGCTCCCTTCCCCACCCGCACCCAGCCCAGCGTTTTCGGCCGACTCG
      ************************************************************

NN    TTCTCAGACCTGCTTAGGCAGTTCGACCCCTCACTGTTTAACACATCGTTGTTCGACTCC
NI    TTCTCAGACCTGCTTAGGCAGTTCGACCCCTCACTGTTTAACACATCGTTGTTCGACTCC
NG    TTCTCAGACCTGCTTAGGCAGTTCGACCCCTCACTGTTTAACACATCGTTGTTCGACTCC
HD    TTCTCAGACCTGCTTAGGCAGTTCGACCCCTCACTGTTTAACACATCGTTGTTCGACTCC
      ************************************************************

NN    CTTCCTCCGTTTGGGGCGCACCATACGGAGGCGGCCACCGGGGAGTGGGATGAGGTGCAG
NI    CTTCCTCCGTTTGGGGCGCACCATACGGAGGCGGCCACCGGGGAGTGGGATGAGGTGCAG
NG    CTTCCTCCGTTTGGGGCGCACCATACGGAGGCGGCCACCGGGGAGTGGGATGAGGTGCAG
HD    CTTCCTCCGTTTGGGGCGCACCATACGGAGGCGGCCACCGGGGAGTGGGATGAGGTGCAG
      ************************************************************

NN    TCGGGATTGAGAGCTGCGGATGCACCACCCCCAACCATGCGGGTGGCCGTCACCGCTGCC
NI    TCGGGATTGAGAGCTGCGGATGCACCACCCCCAACCATGCGGGTGGCCGTCACCGCTGCC
NG    TCGGGATTGAGAGCTGCGGATGCACCACCCCCAACCATGCGGGTGGCCGTCACCGCTGCC
HD    TCGGGATTGAGAGCTGCGGATGCACCACCCCCAACCATGCGGGTGGCCGTCACCGCTGCC
      ************************************************************

NN    CGACCGCCGAGGGCGAAGCCCGCACCAAGGCGGAGGGCAGCGCAACCGTCCGACGCAAGC
NI    CGACCGCCGAGGGCGAAGCCCGCACCAAGGCGGAGGGCAGCGCAACCGTCCGACGCAAGC
NG    CGACCGCCGAGGGCGAAGCCCGCACCAAGGCGGAGGGCAGCGCAACCGTCCGACGCAAGC
HD    CGACCGCCGAGGGCGAAGCCCGCACCAAGGCGGAGGGCAGCGCAACCGTCCGACGCAAGC
      ************************************************************

NN    CCCGCAGCGCAAGTAGATTTGAGAACTTTGGGATATTCACAGCAGCAGCAGGAAAAGATC
NI    CCCGCAGCGCAAGTAGATTTGAGAACTTTGGGATATTCACAGCAGCAGCAGGAAAAGATC
NG    CCCGCAGCGCAAGTAGATTTGAGAACTTTGGGATATTCACAGCAGCAGCAGGAAAAGATC
HD    CCCGCAGCGCAAGTAGATTTGAGAACTTTGGGATATTCACAGCAGCAGCAGGAAAAGATC
      ************************************************************

NN    AAGCCCAAAGTGAGGTCGACAGTCGCGCAGCATCACGAAGCGCTGGTGGGTCATGGGTTT
NI    AAGCCCAAAGTGAGGTCGACAGTCGCGCAGCATCACGAAGCGCTGGTGGGTCATGGGTTT
NG    AAGCCCAAAGTGAGGTCGACAGTCGCGCAGCATCACGAAGCGCTGGTGGGTCATGGGTTT
HD    AAGCCCAAAGTGAGGTCGACAGTCGCGCAGCATCACGAAGCGCTGGTGGGTCATGGGTTT
      ************************************************************

NN    ACACATGCCCACATCGTAGCCTTGTCGCAGCACCCTGCAGCCCTTGGCACGGTCGCCGTC
NI    ACACATGCCCACATCGTAGCCTTGTCGCAGCACCCTGCAGCCCTTGGCACGGTCGCCGTC
NG    ACACATGCCCACATCGTAGCCTTGTCGCAGCACCCTGCAGCCCTTGGCACGGTCGCCGTC
HD    ACACATGCCCACATCGTAGCCTTGTCGCAGCACCCTGCAGCCCTTGGCACGGTCGCCGTC
      ************************************************************
```

Figure 31A

| | |
|---|---|
| NN | AAGTACCAGGACATGATTGCGGCGTTGCCGGAAGCCACACATGAGGCGATCGTCGGTGTG |
| NI | AAGTACCAGGACATGATTGCGGCGTTGCCGGAAGCCACACATGAGGCGATCGTCGGTGTG |
| NG | AAGTACCAGGACATGATTGCGGCGTTGCCGGAAGCCACACATGAGGCGATCGTCGGTGTG |
| HD | AAGTACCAGGACATGATTGCGGCGTTGCCGGAAGCCACACATGAGGCGATCGTCGGTGTG |
| | ************************************************************ |
| NN | GGGAAACAGTGGAGCGGAGCCCGAGCGCTTGAGGCCCTGTTGACGGTCGCGGGAGAGCTG |
| NI | GGGAAACAGTGGAGCGGAGCCCGAGCGCTTGAGGCCCTGTTGACGGTCGCGGGAGAGCTG |
| NG | GGGAAACAGTGGAGCGGAGCCCGAGCGCTTGAGGCCCTGTTGACGGTCGCGGGAGAGCTG |
| HD | GGGAAACAGTGGAGCGGAGCCCGAGCGCTTGAGGCCCTGTTGACGGTCGCGGGAGAGCTG |
| | ************************************************************ |
| NN | AGAGGGCCTCCCCTTCAGCTGGACACGGGCCAGTTGCTGAAGATCGCGAAGCGGGGAGGA |
| NI | AGAGGGCCTCCCCTTCAGCTGGACACGGGCCAGTTGCTGAAGATCGCGAAGCGGGGAGGA |
| NG | AGAGGGCCTCCCCTTCAGCTGGACACGGGCCAGTTGCTGAAGATCGCGAAGCGGGGAGGA |
| HD | AGAGGGCCTCCCCTTCAGCTGGACACGGGCCAGTTGCTGAAGATCGCGAAGCGGGGAGGA |
| | ************************************************************ |
| NN | GTCACGGCGGTCGAGGCGGTGCACGCGTGGCGCAATGCGCTCACGGGAGCACCCCTCAAC |
| NI | GTCACGGCGGTCGAGGCGGTGCACGCGTGGCGCAATGCGCTCACGGGAGCACCCCTCAAC |
| NG | GTCACGGCGGTCGAGGCGGTGCACGCGTGGCGCAATGCGCTCACGGGAGCACCCCTCAAC |
| HD | GTCACGGCGGTCGAGGCGGTGCACGCGTGGCGCAATGCGCTCACGGGAGCACCCCTCAAC |
| | ************************************************************ |
| NN | CTGACCGAGACGGTACATGAAACGCATGGCACGGCGTCTCAACTCACGCCTGAGCAGGTA |
| NI | CTGACCGAGACGGTACATGAAACGCATGGCACGGCGTCTCAACTCACGCCTGAGCAGGTA |
| NG | CTGACCGAGACGGTACATGAAACGCATGGCACGGCGTCTCAACTCACGCCTGAGCAGGTA |
| HD | CTGACCGAGACGGTACATGAAACGCATGGCACGGCGTCTCAACTCACGCCTGAGCAGGTA |
| | ************************************************************ |
| NN | GTGGCTATTGCATCCAATAACGGGGGCAGACCCGCACTGGAGTCAATCGTGGCCCAGCTT |
| NI | GTGGCTATTGCATCCAATATCGGGGGCAGACCCGCACTGGAGTCAATCGTGGCCCAGCTT |
| NG | GTGGCTATTGCATCCAATGGCGGGGGCAGACCCGCACTGGAGTCAATCGTGGCCCAGCTT |
| HD | GTGGCTATTGCATCCCATGACGGGGGCAGACCCGCACTGGAGTCAATCGTGGCCCAGCTT |
| | *************** ** ***************************************  |
| NN | TCGAGGCCGGACCCCGCGCTGGCCGCACTCACTAATGATCATCTTGTAGCGCTGGCCTGC |
| NI | TCGAGGCCGGACCCCGCGCTGGCCGCACTCACTAATGATCATCTTGTAGCGCTGGCCTGC |
| NG | TCGAGGCCGGACCCCGCGCTGGCCGCACTCACTAATGATCATCTTGTAGCGCTGGCCTGC |
| HD | TCGAGGCCGGACCCCGCGCTGGCCGCACTCACTAATGATCATCTTGTAGCGCTGGCCTGC |
| | ************************************************************ |
| NN | CTCGGCGGACGACCCGCCTTGGATGCGGTGAAGAAGGGGCTCCCGCACGCGCCTGCATTG |
| NI | CTCGGCGGACGACCCGCCTTGGATGCGGTGAAGAAGGGGCTCCCGCACGCGCCTGCATTG |
| NG | CTCGGCGGACGACCCGCCTTGGATGCGGTGAAGAAGGGGCTCCCGCACGCGCCTGCATTG |
| HD | CTCGGCGGACGACCCGCCTTGGATGCGGTGAAGAAGGGGCTCCCGCACGCGCCTGCATTG |
| | ************************************************************ |
| NN | ATTAAGCGGACCAACAGAAGGATTCCCGAGAGGACATCACATCGAGTGGCAGATCACGCG |
| NI | ATTAAGCGGACCAACAGAAGGATTCCCGAGAGGACATCACATCGAGTGGCAGATCACGCG |
| NG | ATTAAGCGGACCAACAGAAGGATTCCCGAGAGGACATCACATCGAGTGGCAGATCACGCG |
| HD | ATTAAGCGGACCAACAGAAGGATTCCCGAGAGGACATCACATCGAGTGGCAGATCACGCG |
| | ************************************************************ |

Figure 31B

| | |
|---|---|
| NN | CAAGTGGTCCGCGTGCTCGGATTCTTCCAGTGTCACTCCCACCCCGCACAAGCGTTCGAT |
| NI | CAAGTGGTCCGCGTGCTCGGATTCTTCCAGTGTCACTCCCACCCCGCACAAGCGTTCGAT |
| NG | CAAGTGGTCCGCGTGCTCGGATTCTTCCAGTGTCACTCCCACCCCGCACAAGCGTTCGAT |
| HD | CAAGTGGTCCGCGTGCTCGGATTCTTCCAGTGTCACTCCCACCCCGCACAAGCGTTCGAT |
| | ************************************************************ |
| NN | GACGCCATGACTCAATTTGGTATGTCGAGACACGGACTGCTGCAGCTCTTTCGTAGAGTC |
| NI | GACGCCATGACTCAATTTGGTATGTCGAGACACGGACTGCTGCAGCTCTTTCGTAGAGTC |
| NG | GACGCCATGACTCAATTTGGTATGTCGAGACACGGACTGCTGCAGCTCTTTCGTAGAGTC |
| HD | GACGCCATGACTCAATTTGGTATGTCGAGACACGGACTGCTGCAGCTCTTTCGTAGAGTC |
| | ************************************************************ |
| NN | GGTGTCACAGAACTCGAGGCCCGCTCGGGCACACTGCCTCCCGCCTCCCAGCGGTGGGAC |
| NI | GGTGTCACAGAACTCGAGGCCCGCTCGGGCACACTGCCTCCCGCCTCCCAGCGGTGGGAC |
| NG | GGTGTCACAGAACTCGAGGCCCGCTCGGGCACACTGCCTCCCGCCTCCCAGCGGTGGGAC |
| HD | GGTGTCACAGAACTCGAGGCCCGCTCGGGCACACTGCCTCCCGCCTCCCAGCGGTGGGAC |
| | ************************************************************ |
| NN | AGGATTCTCCAAGCGAGCGGTATGAAACGCGCGAAGCCTTCACCTACGTCAACTCAGACA |
| NI | AGGATTCTCCAAGCGAGCGGTATGAAACGCGCGAAGCCTTCACCTACGTCAACTCAGACA |
| NG | AGGATTCTCCAAGCGAGCGGTATGAAACGCGCGAAGCCTTCACCTACGTCAACTCAGACA |
| HD | AGGATTCTCCAAGCGAGCGGTATGAAACGCGCGAAGCCTTCACCTACGTCAACTCAGACA |
| | ************************************************************ |
| NN | CCTGACCAGGCGAGCCTTCATGCGTTCGCAGACTCGCTGGAGAGGGATTTGGACGCGCCC |
| NI | CCTGACCAGGCGAGCCTTCATGCGTTCGCAGACTCGCTGGAGAGGGATTTGGACGCGCCC |
| NG | CCTGACCAGGCGAGCCTTCATGCGTTCGCAGACTCGCTGGAGAGGGATTTGGACGCGCCC |
| HD | CCTGACCAGGCGAGCCTTCATGCGTTCGCAGACTCGCTGGAGAGGGATTTGGACGCGCCC |
| | ************************************************************ |
| NN | TCGCCCATGCATGAAGGGGACCAAACTCGCGCGTCAGCTAGCCCCAAGAAGAAGAGAAAG |
| NI | TCGCCCATGCATGAAGGGGACCAAACTCGCGCGTCAGCTAGCCCCAAGAAGAAGAGAAAG |
| NG | TCGCCCATGCATGAAGGGGACCAAACTCGCGCGTCAGCTAGCCCCAAGAAGAAGAGAAAG |
| HD | TCGCCCATGCATGAAGGGGACCAAACTCGCGCGTCAGCTAGCCCCAAGAAGAAGAGAAAG |
| | ************************************************************ |
| NN | _GTGGAGGCCAGCGGTTCCGGACGGGCTGACGCATTGGACGATTTTGATCTGGATATGCTG |
| NI | GTGGAGGCCAGCGGTTCCGGACGGGCTGACGCATTGGACGATTTTGATCTGGATATGCTG |
| NG | GTGGAGGCCAGCGGTTCCGGACGGGCTGACGCATTGGACGATTTTGATCTGGATATGCTG |
| HD | GTGGAGGCCAGCGGTTCCGGACGGGCTGACGCATTGGACGATTTTGATCTGGATATGCTG |
| | ************************************************************ |
| NN | GGAAGTGACGCCCTCGATGATTTTGACCTTGACATGCTTGGTTCGGATGCCCTTGATGAC |
| NI | GGAAGTGACGCCCTCGATGATTTTGACCTTGACATGCTTGGTTCGGATGCCCTTGATGAC |
| NG | GGAAGTGACGCCCTCGATGATTTTGACCTTGACATGCTTGGTTCGGATGCCCTTGATGAC |
| HD | GGAAGTGACGCCCTCGATGATTTTGACCTTGACATGCTTGGTTCGGATGCCCTTGATGAC |
| | ************************************************************ |
| NN | TTTGACCTCGACATGCTCGGCAGTGACGCCCTTGATGATTTCGACCTGGACATGCTGATT |
| NI | TTTGACCTCGACATGCTCGGCAGTGACGCCCTTGATGATTTCGACCTGGACATGCTGATT |
| NG | TTTGACCTCGACATGCTCGGCAGTGACGCCCTTGATGATTTCGACCTGGACATGCTGATT |
| HD | TTTGACCTCGACATGCTCGGCAGTGACGCCCTTGATGATTTCGACCTGGACATGCTGATT |
| | ************************************************************ |

Figure 31C

```
NN    AACTCTAGAGGCAGTGGAGAGGGCAGAGGAAGTCTGCTAACATGCGGTGACGTCGAGGAG
NI    AACTCTAGAGGCAGTGGAGAGGGCAGAGGAAGTCTGCTAACATGCGGTGACGTCGAGGAG
NG    AACTCTAGAGGCAGTGGAGAGGGCAGAGGAAGTCTGCTAACATGCGGTGACGTCGAGGAG
HD    AACTCTAGAGGCAGTGGAGAGGGCAGAGGAAGTCTGCTAACATGCGGTGACGTCGAGGAG
      ************************************************************

NN    AATCCTGGCCCAGTGAGCAAGGGCGAGGAGCTGTTCACCGGGGTGGTGCCCATCCTGGTC
NI    AATCCTGGCCCAGTGAGCAAGGGCGAGGAGCTGTTCACCGGGGTGGTGCCCATCCTGGTC
NG    AATCCTGGCCCAGTGAGCAAGGGCGAGGAGCTGTTCACCGGGGTGGTGCCCATCCTGGTC
HD    AATCCTGGCCCAGTGAGCAAGGGCGAGGAGCTGTTCACCGGGGTGGTGCCCATCCTGGTC
      ************************************************************

NN    GAGCTGGACGGCGACGTAAACGGCCACAAGTTCAGCGTGTCCGGCGAGGGCGAGGGCGAT
NI    CAGCTGGACGGCGACGTAAACGGCCACAAGTTCAGCGTGTCCGGCGAGGGCGAGGGCGAT
NG    GAGCTGGACGGCGACGTAAACGGCCACAAGTTCAGCGTGTCCGGCGAGGGCGAGGGCGAT
HD    GAGCTGGACGGCGACGTAAACGGCCACAAGTTCAGCGTGTCCGGCGAGGGCGAGGGCGAT
      ************************************************************

NN    GCCACCTACGGCAAGCTGACCCTGAAGTTCATCTGCACCACCGGCAAGCTGCCCGTGCCC
NI    GCCACCTACGGCAAGCTGACCCTGAAGTTCATCTGCACCACCGGCAAGCTGCCCGTGCCC
NG    GCCACCTACGGCAAGCTGACCCTGAAGTTCATCTGCACCACCGGCAAGCTGCCCGTGCCC
HD    GCCACCTACGGCAAGCTGACCCTGAAGTTCATCTGCACCACCGGCAAGCTGCCCGTGCCC
      ************************************************************

NN    TGGCCCACCCTCGTGACCACCCTGACCTACGGCGTGCAGTGCTTCAGCCGCTACCCCGAC
NI    TGGCCCACCCTCGTGACCACCCTGACCTACGGCGTGCAGTGCTTCAGCCGCTACCCCGAC
NG    TGGCCCACCCTCGTGACCACCCTGACCTACGGCGTGCAGTGCTTCAGCCGCTACCCCGAC
HD    TGGCCCACCCTCGTGACCACCCTGACCTACGGCGTGCAGTGCTTCAGCCGCTACCCCGAC
      ************************************************************

NN    CACATGAAGCAGCACGACTTCTTCAAGTCCGCCATGCCCGAAGGCTACGTCCAGGAGCGC
NI    CACATGAAGCAGCACGACTTCTTCAAGTCCGCCATGCCCGAAGGCTACGTCCAGGAGCGC
NG    CACATGAAGCAGCACGACTTCTTCAAGTCCGCCATGCCCGAAGGCTACGTCCAGGAGCGC
HD    CACATGAAGCAGCACGACTTCTTCAAGTCCGCCATGCCCGAAGGCTACGTCCAGGAGCGC
      ************************************************************

NN    ACCATCTTCTTCAAGGACGACGGCAACTACAAGACCCGCGCCGAGGTGAAGTTCGAGGGC
NI    ACCATCTTCTTCAAGGACGACGGCAACTACAAGACCCGCGCCGAGGTGAAGTTCGAGGGC
NG    ACCATCTTCTTCAAGGACGACGGCAACTACAAGACCCGCGCCGAGGTGAAGTTCGAGGGC
HD    ACCATCTTCTTCAAGGACGACGGCAACTACAAGACCCGCGCCGAGGTGAAGTTCGAGGGC
      ************************************************************

NN    GACACCCTGGTGAACCGCATCGAGCTGAAGGGCATCGACTTCAAGGAGGACGGCAACATC
NI    GACACCCTGGTGAACCGCATCGAGCTGAAGGGCATCGACTTCAAGGAGGACGGCAACATC
NG    GACACCCTGGTGAACCGCATCGAGCTGAAGGGCATCGACTTCAAGGAGGACGGCAACATC
HD    GACACCCTGGTGAACCGCATCGAGCTGAAGGGCATCGACTTCAAGGAGGACGGCAACATC
      ************************************************************
```

Figure 31D

| | |
|---|---|
| NN | CTGGGGCACAAGCTGGAGTACAACTACAACAGCCACAACGTCTATATCATGGCCGACAAG |
| NI | CTGGGGCACAAGCTGGAGTACAACTACAACAGCCACAACGTCTATATCATGGCCGACAAG |
| NG | CTGGGGCACAAGCTGGAGTACAACTACAACAGCCACAACGTCTATATCATGGCCGACAAG |
| HD | CTGGGGCACAAGCTGGAGTACAACTACAACAGCCACAACGTCTATATCATGGCCGACAAG |
| | ************************************************************ |
| NN | CAGAAGAACGGCATCAAGGTGAACTTCAAGATCCGCCACAACATCGAGGACGGCAGCGTG |
| NI | CAGAAGAACGGCATCAAGGTGAACTTCAAGATCCGCCACAACATCGAGGACGGCAGCGTG |
| NG | CAGAAGAACGGCATCAAGGTGAACTTCAAGATCCGCCACAACATCGAGGACGGCAGCGTG |
| HD | CAGAAGAACGGCATCAAGGTGAACTTCAAGATCCGCCACAACATCGAGGACGGCAGCGTG |
| | ************************************************************ |
| NN | CAGCTCGCCGACCACTACCAGCAGAACACCCCCATCGGCGACGGCCCCGTGCTGCTGCCC |
| NI | CAGCTCGCCGACCACTACCAGCAGAACACCCCCATCGGCGACGGCCCCGTGCTGCTGCCC |
| NG | CAGCTCGCCGACCACTACCAGCAGAACACCCCCATCGGCGACGGCCCCGTGCTGCTGCCC |
| HD | CAGCTCGCCGACCACTACCAGCAGAACACCCCCATCGGCGACGGCCCCGTGCTGCTGCCC |
| | ************************************************************ |
| NN | GACAACCACTACCTGAGCACCCAGTCCGCCCTGAGCAAAGACCCCAACGAGAAGCGCGAT |
| NI | GACAACCACTACCTGAGCACCCAGTCCGCCCTGAGCAAAGACCCCAACGAGAAGCGCGAT |
| NG | GACAACCACTACCTGAGCACCCAGTCCGCCCTGAGCAAAGACCCCAACGAGAAGCGCGAT |
| HD | GACAACCACTACCTGAGCACCCAGTCCGCCCTGAGCAAAGACCCCAACGAGAAGCGCGAT |
| | ************************************************************ |
| NN | CACATGGTCCTGCTGGAGTTCGTGACCGCCGCCGGGATCACTCTCGGCATGGACGAGCTG |
| NI | CACATGGTCCTGCTGGAGTTCGTGACCGCCGCCGGGATCACTCTCGGCATGGACGAGCTG |
| NG | CACATGGTCCTGCTGGAGTTCGTGACCGCCGCCGGGATCACTCTCGGCATGGACGAGCTG |
| HD | CACATGGTCCTGCTGGAGTTCGTGACCGCCGCCGGGATCACTCTCGGCATGGACGAGCTG |
| | ************************************************************ |
| NN | TACAAGTAA |
| NI | TACAAGTAA |
| NG | TACAAGTAA |
| HD | TACAAGTAA |
| | ********* |

```
gggcggtgcacgcgtggcgcaatgcgctcacgggagcacccctcaacctgaccccagagcaa
    A  V  H  A  W  R  N  A  L  T  G  A  P  L  N  L  T  P  E  Q
gtcgtggcaatcgcgagccacgacggcggaaaacaggctttggaaacggtgcagaggctc
 V  V  A  I  A  S  H  D  G  G  K  Q  A  L  E  T  V  Q  R  L
cttccagtgctgtgccaagcgcacggactcaccccagagcaggtcgtggcaatcgcctcc
 L  P  V  L  C  Q  A  H  G  L  T  P  E  Q  V  V  A  I  A  S
cacgacggcgggaaacaggcactcgagactgtccagcgcctgcttcccgtgctgtgccaa
 H  D  G  G  K  Q  A  L  E  T  V  Q  R  L  L  P  V  L  C  Q
gcgcacggcctcaccccagagcaggtcgtggcaatcgcgagccacgacggcggaaaacag
 A  H  G  L  T  P  E  Q  V  V  A  I  A  S  H  D  G  G  K  Q
gctttggaaacggtgcagaggctccttccagtgctgtgccaagcgcacggattaacccca
 A  L  E  T  V  Q  R  L  L  P  V  L  C  Q  A  H  G  L  T  P
gagcaggtcgtggcaatcgcgagcaatggaggcggaaaacaggctttggaaacggtgcag
 E  Q  V  V  A  I  A  S  N  G  G  K  Q  A  L  E  T  V  Q
aggctccttccagtgctgtgccaagcgcacggcttaaccccagagcaggtcgtggccatt
 R  L  L  P  V  L  C  Q  A  H  G  L  T  P  E  Q  V  V  A  I
gcctcgaatggaggggcaaacaggcgttggaaaccgtacaacgattgctgccggtgctg
 A  S  N  G  G  K  Q  A  L  E  T  V  Q  R  L  L  P  V  L
tgccaagcgcacggactcaccccagagcaggtcgtggcgatcgcaagcaataacggagga
 C  Q  A  H  G  L  T  P  E  Q  V  V  A  I  A  S  N  N  G  G
aagcaagccttggaaacagtacagaggctgttgcctgtgctgtgccaagcgcacggcctc
 K  Q  A  L  E  T  V  Q  R  L  L  P  V  L  C  Q  A  H  G  L
accccagagcaggtcgtggccattgcctcgaataacggggcaaacaggcgttggaaacc
 T  P  E  Q  V  V  A  I  A  S  N  N  G  G  K  Q  A  L  E  T
gtacaacgattgctgccggtgctgtgccaagcgcacggattaaccccagagcaggtcgtg
 V  Q  R  L  L  P  V  L  C  Q  A  H  G  L  T  P  E  Q  V  V
gcaatcgcctccaataacggcgggaaacaggcactcgagactgtccagcgcctgcttccc
 A  I  A  S  N  N  G  G  K  Q  A  L  E  T  V  Q  R  L  L  P
gtgctgtgccaagcgcacgggctcaccccagagcaggtcgtggcaatcgcctccaatgga
 V  L  C  Q  A  H  G  L  T  P  E  Q  V  V  A  I  A  S  N  G
ggcgggaaacaggcactcgagactgtccagcgcctgcttcccgtgctgtgccaagcgcac
 G  G  K  Q  A  L  E  T  V  Q  R  L  L  P  V  L  C  Q  A  H
ggactcaccccagagcaggtcgtggcgatcgcaagccacgacggaggaaagcaagccttg
 G  L  T  P  E  Q  V  V  A  I  A  S  H  D  G  G  K  Q  A  L
gaaacagtacagaggctgttgcctgtgctgtgccaagcgcacggcctcaccccagagcag
 E  T  V  Q  R  L  L  P  V  L  C  Q  A  H  G  L  T  P  E  Q
gtcgtggcgatcgcaagcaacattggaggaaagcaagccttggaaacagtacagaggctg
 V  V  A  I  A  S  N  I  G  G  K  Q  A  L  E  T  V  Q  R  L
ttgcctgtgctgtgccaagcgcacggattaaccccagagcaggtcgtggccattgcctcg
 L  P  V  L  C  Q  A  H  G  L  T  P  E  Q  V  V  A  I  A  S
aatggaggggcaaacaggcgttggaaaccgtacaacgattgctgccggtgctgtgccaa
 N  G  G  K  Q  A  L  E  T  V  Q  R  L  L  P  V  L  C  Q
gcgcacggactcacgcctgagcaggtagtggctattgcatccaataacgg
 A  H  G  L  T  P  E  Q  V  V  A  I  A  S  N  N
```

Figure 32A

B. Sequences of the variable part of TALE # 2 in pLenti-EF1α-TALE-2A-VP64-EGFP

```
Nucleotide and corresponding amino acid sequences
gggcggtgcacgcgtggcgcaatgcgctcacgggagcacccctcaacctgaccccagagcaa
    A  V  H  A  W  R  N  A  L  T  G  A  P  L  N  L  T  P  E  Q
gtcgtggcaatcgcgagccacgacggcggaaaacaggctttggaaacggtgcagaggctc
  V  V  A  I  A  S  H  D  G  G  K  Q  A  L  E  T  V  Q  R  L
cttccagtgctgtgccaagcgcacggactcaccccagagcaggtcgtggcaatcgcctcc
  L  P  V  L  C  Q  A  H  G  L  T  P  E  Q  V  V  A  I  A  S
cacgacggcgggaaacaggcactcgagactgtccagcgcctgcttccgtgctgtgccaa
  H  D  G  G  K  Q  A  L  E  T  V  Q  R  L  L  P  V  L  C  Q
gcgcacggcctcaccccagagcaggtcgtggcaatcgcgagcaatggaggcggaaaacag
  A  H  G  L  T  P  E  Q  V  V  A  I  A  S  N  G  G  K  Q
gctttggaaacggtgcagaggctccttccagtgctgtgccaagcgcacggattaacccca
  A  L  E  T  V  Q  R  L  L  P  V  L  C  Q  A  H  G  L  T  P
gagcaggtcgtggcaatcgcgagcaataacggcggaaaacaggctttggaaacggtgcag
  E  Q  V  V  A  I  A  S  N  N  G  G  K  Q  A  L  E  T  V  Q
aggctccttccagtgctgtgccaagcgcacggcttaaccccagagcaggtcgtggccatt
  R  L  L  P  V  L  C  Q  A  H  G  L  T  P  E  Q  V  V  A  I
gcctcgaataacggggcaaacaggcgttggaaaccgtacaacgattgctgccggtgctg
  A  S  N  N  G  G  K  Q  A  L  E  T  V  Q  R  L  L  P  V  L
tgccaagcgcacggactcaccccagagcaggtcgtggcgatcgcaagcaatggaggagga
  C  Q  A  H  G  L  T  P  E  Q  V  V  A  I  A  S  N  G  G
aagcaagccttggaaacagtacagaggctgttgcctgtgctgtgccaagcgcacggcctc
  K  Q  A  L  E  T  V  Q  R  L  L  P  V  L  C  Q  A  H  G  L
accccagagcaggtcgtggccattgcctcgaatggaggggcaaacaggcgttggaaacc
  T  P  E  Q  V  V  A  I  A  S  N  G  G  K  Q  A  L  E  T
gtacaacgattgctgccggtgctgtgccaagcgcacggattaaccccagagcaggtcgtg
  V  Q  R  L  L  P  V  L  C  Q  A  H  G  L  T  P  E  Q  V  V
gcaatcgcctccaataacggcgggaaacaggcactcgagactgtccagcgcctgcttccc
  A  I  A  S  N  N  G  G  K  Q  A  L  E  T  V  Q  R  L  L  P
gtgctgtgccaagcgcacgggctcaccccagagcaggtcgtggcaatcgcctcccacgac
  V  L  C  Q  A  H  G  L  T  P  E  Q  V  V  A  I  A  S  H  D
ggcgggaaacaggcactcgagactgtccagcgcctgcttccgtgctgtgccaagcgcac
  G  G  K  Q  A  L  E  T  V  Q  R  L  L  P  V  L  C  Q  A  H
ggactcaccccagagcaggtcgtggcgatcgcaagcaacattggaggaaagcaagccttg
  G  L  T  P  E  Q  V  V  A  I  A  S  N  I  G  G  K  Q  A  L
gaaacagtacagaggctgttgcctgtgctgtgccaagcgcacggcctcaccccagagcag
  E  T  V  Q  R  L  L  P  V  L  C  Q  A  H  G  L  T  P  E  Q
gtcgtggcgatcgcaagccacgacggaggaaagcaagccttggaaacagtacagaggctg
  V  V  A  I  A  S  H  D  G  G  K  Q  A  L  E  T  V  Q  R  L
ttgcctgtgctgtgccaagcgcacggattaaccccagagcaggtcgtggccattgcctcg
  L  P  V  L  C  Q  A  H  G  L  T  P  E  Q  V  V  A  I  A  S
aatggaggggcaaacaggcgttggaaaccgtacaacgattgctgccggtgctgtgccaa
  N  G  G  K  Q  A  L  E  T  V  Q  R  L  L  P  V  L  C  Q
gcgcacggactcacgcctgagcaggtagtggctattgcatcccacgacgg
  A  H  G  L  T  P  E  Q  V  V  A  I  A  S  H  D
```

Figure 32B

C. Sequences of the variable part of TALE # 3 in pLenti-EF1α-TALE-2A-VP64-EGFP

```
Nucleotide and corresponding amino acid sequences
gggcggtgcacgcgtggcgcaatgcgctcacgggagcacccctcaacctgaccccagagcaa
    A  V  H  A  W  R  N  A  L  T  G  A  P  L  N  L  T  P  E  Q
gtcgtggcaatcgcgagcaataacggcggaaaacaggctttggaaacggtgcagaggctc
 V  V  A  I  A  S  N  N  G  G  K  Q  A  L  E  T  V  Q  R  L
cttccagtgctgtgccaagcgcacggactcaccccagagcaggtcgtggcaatcgcctcc
 L  P  V  L  C  Q  A  H  G  L  T  P  E  Q  V  V  A  I  A  S
aataacggcgggaaacaggcactcgagactgtccagcgcctgcttcccgtgctgtgccaa
 N  N  G  G  K  Q  A  L  E  T  V  Q  R  L  L  P  V  L  C  Q
gcgcacggcctcaccccagagcaggtcgtggcaatcgcgagcaatggaggcggaaaacag
 A  H  G  L  T  P  E  Q  V  V  A  I  A  S  N  G  G  G  K  Q
gctttggaaacggtgcagaggctccttccagtgctgtgccaagcgcacggattaacccca
 A  L  E  T  V  Q  R  L  L  P  V  L  C  Q  A  H  G  L  T  P
gagcaggtcgtggcaatcgcgagcaatggaggcggaaaacaggctttggaaacggtgcag
 E  Q  V  V  A  I  A  S  N  G  G  G  K  Q  A  L  E  T  V  Q
aggctccttccagtgctgtgccaagcgcacggcttaaccccagagcaggtcgtggccatt
 R  L  L  P  V  L  C  Q  A  H  G  L  T  P  E  Q  V  V  A  I
gcctcgaataacgggggcaaacaggcgttggaaaccgtacaacgattgctgccggtgctg
 A  S  N  N  G  G  K  Q  A  L  E  T  V  Q  R  L  L  P  V  L
tgccaagcgcacggactcaccccagagcaggtcgtggcgatcgcaagccacgacggagga
 C  Q  A  H  G  L  T  P  E  Q  V  V  A  I  A  S  H  D  G  G
aagcaagccttggaaacagtacagaggctgttgcctgtgctgtgccaagcgcacggcctc
 K  Q  A  L  E  T  V  Q  R  L  L  P  V  L  C  Q  A  H  G  L
accccagagcaggtcgtggccattgcctcgaacattggggcaaacaggcgttggaaacc
 T  P  E  Q  V  V  A  I  A  S  N  I  G  G  K  Q  A  L  E  T
gtacaacgattgctgccggtgctgtgccaagcgcacggattaacccccagagcaggtcgtg
 V  Q  R  L  L  P  V  L  C  Q  A  H  G  L  T  P  E  Q  V  V
gcaatcgcctcccacgacggcgggaaacaggcactcgagactgtccagcgcctgcttccc
 A  I  A  S  H  D  G  G  K  Q  A  L  E  T  V  Q  R  L  L  P
gtgctgtgccaagcgcacgggctcaccccagagcaggtcgtggcaatcgcctccaatgga
 V  L  C  Q  A  H  G  L  T  P  E  Q  V  V  A  I  A  S  N  G
ggcgggaaacaggcactcgagactgtccagcgcctgcttcccgtgctgtgccaagcgcac
 G  G  K  Q  A  L  E  T  V  Q  R  L  L  P  V  L  C  Q  A  H
ggactcaccccagagcaggtcgtggcgatcgcaagccacgacggaggaaagcaagccttg
 G  L  T  P  E  Q  V  V  A  I  A  S  H  D  G  G  K  Q  A  L
gaaacagtacagaggctgttgcctgtgctgtgccaagcgcacggcctcaccccagagcag
 E  T  V  Q  R  L  L  P  V  L  C  Q  A  H  G  L  T  P  E  Q
gtcgtggcgatcgcaagccacgacggaggaaagcaagccttggaaacagtacagaggctg
 V  V  A  I  A  S  H  D  G  G  K  Q  A  L  E  T  V  Q  R  L
ttgcctgtgctgtgccaagcgcacggattaaccccagagcaggtcgtggccattgcctcg
 L  P  V  L  C  Q  A  H  G  L  T  P  E  Q  V  V  A  I  A  S
aataacgggggcaaacaggcgttggaaaccgtacaacgattgctgccggtgctgtgccaa
 N  N  G  G  K  Q  A  L  E  T  V  Q  R  L  L  P  V  L  C  Q
gcgcacggactcacgcctgagcaggtagtggctattgcatccaatgagg
 A  H  G  L  T  P  E  Q  V  V  A  I  A  S  N  G
```

Figure 32C

D. Sequences of the variable part of TALE # 4 in pLenti-EF1α-TALE-2A-VP64-EGFP

```
Nucleotide and corresponding amino acid sequences
gggcggtgcacgcgtggcgcaatgcgctcacgggagcacccctcaacctgaccccagagcaa
   A  V  H  A  W  R  N  A  L  T  G  A  P  L  N  L  T  P  E  Q
gtcgtggcaatcgcgagcaataacggcggaaaacaggctttggaaacggtgcagaggctc
 V  V  A  I  A  S  N  N  G  G  K  Q  A  L  E  T  V  Q  R  L
cttccagtgctgtgccaagcgcacggactcaccccagagcaggtcgtggcaatcgcctcc
 L  P  V  L  C  Q  A  H  G  L  T  P  E  Q  V  V  A  I  A  S
cacgacggcgggaaacaggcactcgagactgtccagcgcctgcttcccgtgctgtgccaa
 H  D  G  G  K  Q  A  L  E  T  V  Q  R  L  L  P  V  L  C  Q
gcgcacggcctcaccccagagcaggtcgtggcaatcgcgagcaatggaggcggaaaacag
 A  H  G  L  T  P  E  Q  V  V  A  I  A  S  N  G  G  G  K  Q
gctttggaaacggtgcagaggctccttccagtgctgtgccaagcgcacggattaacccca
 A  L  E  T  V  Q  R  L  L  P  V  L  C  Q  A  H  G  L  T  P
gagcaggtcgtggcaatcgcgagcaatggaggcggaaaacaggctttggaaacggtgcag
 E  Q  V  V  A  I  A  S  N  G  G  G  K  Q  A  L  E  T  V  Q
aggctccttccagtgctgtgccaagcgcacggcttaaccccagagcaggtcgtggccatt
 R  L  L  P  V  L  C  Q  A  H  G  L  T  P  E  Q  V  V  A  I
gcctcgaatggaggggcaaacaggcgttggaaaccgtacaacgattgctgccggtgctg
 A  S  N  G  G  G  K  Q  A  L  E  T  V  Q  R  L  L  P  V  L
tgccaagcgcacggactcaccccagagcaggtcgtggcgatcgcaagcaataacggagga
 C  Q  A  H  G  L  T  P  E  Q  V  V  A  I  A  S  N  N  G  G
aagcaagccttggaaacagtacagaggctgttgcctgtgctgtgccaagcgcacggcctc
 K  Q  A  L  E  T  V  Q  R  L  L  P  V  L  C  Q  A  H  G  L
accccagagcaggtcgtggccattgcctcgcacgacgggggcaaacaggcgttggaaacc
 T  P  E  Q  V  V  A  I  A  S  H  D  G  G  K  Q  A  L  E  T
gtacaacgattgctgccggtgctgtgccaagcgcacggattaaccccagagcaggtcgtg
 V  Q  R  L  L  P  V  L  C  Q  A  H  G  L  T  P  E  Q  V  V
gcaatcgcctccaacattggcgggaaacaggcactcgagactgtccagcgcctgcttccc
 A  I  A  S  N  I  G  G  K  Q  A  L  E  T  V  Q  R  L  L  P
gtgctgtgccaagcgcacgggctcaccccagagcaggtcgtggcaatcgcctcccacgac
 V  L  C  Q  A  H  G  L  T  P  E  Q  V  V  A  I  A  S  H  D
ggcgggaaacaggcactcgagactgtccagcgcctgcttcccgtgctgtgccaagcgcac
 G  G  K  Q  A  L  E  T  V  Q  R  L  L  P  V  L  C  Q  A  H
ggactcaccccagagcaggtcgtggcgatcgcaagcaacattggaggaaagcaagccttg
 G  L  T  P  E  Q  V  V  A  I  A  S  N  I  G  G  K  Q  A  L
gaaacagtacagaggctgttgcctgtgctgtgccaagcgcacggcctcaccccagagcag
 E  T  V  Q  R  L  L  P  V  L  C  Q  A  H  G  L  T  P  E  Q
gtcgtggcgatcgcaagcaacattggaggaaagcaagccttggaaacagtacagaggctg
 V  V  A  I  A  S  N  I  G  G  K  Q  A  L  E  T  V  Q  R  L
ttgcctgtgctgtgccaagcgcacggattaaccccagagcaggtcgtggccattgcctcg
 L  P  V  L  C  Q  A  H  G  L  T  P  E  Q  V  V  A  I  A  S
aacattgggggcaaacaggcgttggaaaccgtacaacgattgctgccggtgctgtgccaa
 N  I  G  G  K  Q  A  L  E  T  V  Q  R  L  L  P  V  L  C  Q
gcgcacggactcacgcctgagcaggtagtggctattgcatccaataacgg
 A  H  G  L  T  P  E  Q  V  V  A  I  A  S  N  N
```

Figure 32D

E. Sequences of the variable part of TALE # 5 in pLenti-EF1α-TALE-2A-VP64-EGFP

```
Nucleotide and corresponding amino acid sequences
gggcggtgcacgcgtggcgcaatgcgctcacgggagcacccctcaacctgaccccagagcaa
    A  V  H  A  W  R  N  A  L  T  G  A  P  L  N  L  T  P  E  Q
gtcgtggcaatcgcgagcaataacggcggaaaacaggctttggaaacggtgcagaggctc
    V  V  A  I  A  S  N  N  G  G  K  Q  A  L  E  T  V  Q  R  L
cttccagtgctgtgccaagcgcacggactcaccccagagcaggtcgtggcaatcgcctcc
    L  P  V  L  C  Q  A  H  G  L  T  P  E  Q  V  V  A  I  A  S
cacgacggcgggaaacaggcactcgagactgtccagcgcctgcttcccgtgctgtgccaa
    H  D  G  G  K  Q  A  L  E  T  V  Q  R  L  L  P  V  L  C  Q
gcgcacggcctcaccccagagcaggtcgtggcaatcgcgagcaacattggcggaaaacag
    A  H  G  L  T  P  E  Q  V  V  A  I  A  S  N  I  G  G  K  Q
gctttggaaacggtgcagaggctccttccagtgctgtgccaagcgcacggattaacccca
    A  L  E  T  V  Q  R  L  L  P  V  L  C  Q  A  H  G  L  T  P
gagcaggtcgtggcaatcgcgagccacgacggcggaaaacaggctttggaaacggtgcag
    E  Q  V  V  A  I  A  S  H  L  G  G  K  Q  A  L  E  T  V  Q
aggctccttccagtgctgtgccaagcgcacggcttaaccccagagcaggtcgtggccatt
    R  L  L  P  V  L  C  Q  A  H  G  L  T  P  E  Q  V  V  A  I
gcctcgaataacggggggcaaacaggcgttggaaaccgtacaacgattgctgccggtgctg
    A  S  N  N  G  G  K  Q  A  L  E  T  V  Q  R  L  L  P  V  L
tgccaagcgcacggactcaccccagagcaggtcgtggcgatcgcaagcaacattggagga
    C  Q  A  H  G  L  T  P  E  Q  V  V  A  I  A  S  N  I  G  G
aagcaagccttggaaacagtacagaggctgttgcctgtgctgtgccaagcgcacggcctc
    K  Q  A  L  E  T  V  Q  R  L  L  P  V  L  C  Q  A  H  G  L
accccagagcaggtcgtggccattgcctcgaacattggggggcaaacaggcgttggaaacc
    T  P  E  Q  V  V  A  I  A  S  N  I  G  G  K  Q  A  L  E  T
gtacaacgattgctgccggtgctgtgccaagcgcacggattaaccccagagcaggtcgtg
    V  Q  R  L  L  P  V  L  C  Q  A  H  G  L  T  P  E  Q  V  V
gcaatcgcctccaatggaggcgggaaacaggcactcgagactgtccagcgcctgcttccc
    A  I  A  S  N  G  G  G  K  Q  A  L  E  T  V  Q  R  L  L  P
gtgctgtgccaagcgcacgggctcaccccagagcaggtcgtggcaatcgcctccaacatt
    V  L  C  Q  A  H  G  L  T  P  E  Q  V  V  A  I  A  S  N  I
ggcgggaaacaggcactcgagactgtccagcgcctgcttcccgtgctgtgccaagcgcac
    G  G  K  Q  A  L  E  T  V  Q  R  L  L  P  V  L  C  Q  A  H
ggactcaccccagagcaggtcgtggcgatcgcaagcaataacggaggaaagcaagccttg
    G  L  T  P  E  Q  V  V  A  I  A  S  N  N  G  G  K  Q  A  L
gaaacagtacagaggctgttgcctgtgctgtgccaagcgcacggcctcaccccagagcag
    E  T  V  Q  R  L  L  P  V  L  C  Q  A  H  G  L  T  P  E  Q
gtcgtggcgatcgcaagcaatggaggaggaaagcaagccttggaaacagtacagaggctg
    V  V  A  I  A  S  N  G  G  G  K  Q  A  L  E  T  V  Q  R  L
ttgcctgtgctgtgccaagcgcacggattaaccccagagcaggtcgtggccattgcctcg
    L  P  V  L  C  Q  A  H  G  L  T  P  E  Q  V  V  A  I  A  S
aataacggggggcaaacaggcgttggaaaccgtacaacgattgctgccggtgctgtgccaa
    N  N  G  G  K  Q  A  L  E  T  V  Q  R  L  L  P  V  L  C  Q
gcgcacggactcacgcctgagcaggtagtggctattgcatcccacgacgg
    A  H  G  L  T  P  E  Q  V  V  A  I  A  S  H  D
```

Figure 32E

A. HIS-PEP1-Frataxin in pet16b

```
ccgcgaaattaatacgactcactatagggaattgtgagcggataacaatttctagaataa ttttgtttaactttaagaaggagatataccatggccatcatcatcatcatcatagcagc
                              M  G  H  H  H  H  H  H  S  S
ggcataaaagaaacctggtgggaaacctggtggaccgaatggagccagccaaaaaagaag
 G  I  K  E  T  W  W  E  T  W  W  T  E  W  S  Q  P  K  K  K
agaaaggtaagcagcggcctcgagatgtggactctcgggcgccgcgcagtagccggcctc
 R  K  V  S  S  G  L  E  M  W  T  L  G  R  R  A  V  A  G  L
ctggcgtcacccagcccggcccaggcccagaccctcacccgggtcccgcggccggcagag
 L  A  S  P  S  P  A  Q  A  Q  T  L  T  R  V  P  R  P  A  E
ttggccccactctgcggccgccgtggcctgcgcaccgacatcgatgcgacctgcacgccc
 L  A  P  L  C  G  R  R  G  L  R  T  D  I  D  A  T  C  T  P
cgccgcgcaagttcgaaccaacgtggcctcaaccagatttggaatgtcaaaaagcagagt
 R  R  A  S  S  N  Q  R  G  L  N  Q  I  W  N  V  K  K  Q  S
gtctatttgatgaatttgaggaaatctggaactttgggccacccaggctctctagatgag
 V  Y  L  M  N  L  R  K  S  G  T  L  G  H  P  G  S  L  D  E
accacctatgaaagactagcagaggaaacgctggactcttagcagagtttttgaagac
 T  T  Y  E  R  L  A  E  E  T  L  D  S  L  A  E  F  F  E  D
cttgcagacaagccatacacgtttgaggactatgatgtctcctttgggagtggtgtctta
 L  A  D  K  P  Y  T  F  E  D  Y  D  V  S  F  G  S  G  V  L
actgtcaaactggtggagatctaggaacctatgtgatcaacaagcagacgccaaacaag
 T  V  K  L  G  D  L  G  T  Y  V  I  N  K  Q  T  P  N  K
caaatctggctatcttctccatccagtggacctaagcgttatgactggactgggaaaaac
 Q  I  W  L  S  S  P  S  S  G  P  K  R  Y  D  W  T  G  K  N
tgggtgtactccacgacggcgtgtccctccatgagctgctggccgcagagctcactaaa
 W  V  Y  S  H  D  G  V  S  L  H  E  L  L  A  A  E  L  T  K
gccttaaaaaccaaactggacttgtcttccttggcctattccggaaaagatgcttgagga
 A  L  K  T  K  L  D  L  S  S  L  A  Y  S  G  K  D  A  stop
tccggctgctaacaaagcccgaaaggaagctgagttggctgctgccaccgctgagcaata actagcataa
```

Figure 33A

B. HIS-PEP1-Frataxin 248 AA
MGHHHHHHSSGIKETWWETWWTEWSQPKKKRKVSSGLEMWTLGRRAVAGLLASPSPAQAQ
TLTRVPRPAELAPLCGRRGLRTDIDATCTPRRASSNQRGLNQIWNVKKQSVYLMNLRKSG
TLGHPCSLDETTYERLAEETLDSLAEFFEDLADKPYTFEDYDVSFCSGVLTVKLGGDLGT
YVINKQTPNKQIWLSSPSSGPKRYDWTGKNWVYSHDGVSLHELLAAELTKALKTKLDLSS
LAYSGKDA
C. 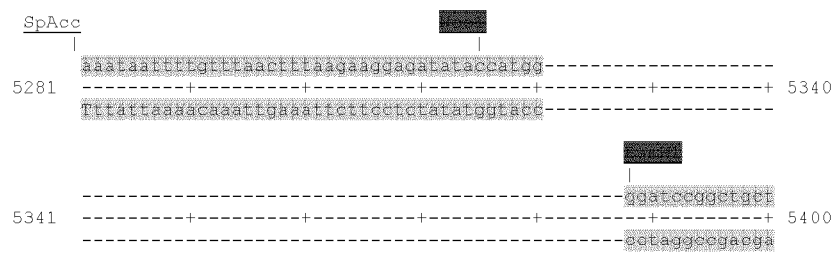
Figures 33B and C D. HIS-TAT-Frataxin in pet16b

```
tccctctagaaataattttgtttaactttaagaaggagatataccatggccatcatcat
                                          M  G  H  H  H
catcatcatagcagcggcggactgagatcttatggaaggaagaagcggagacagcgacga
 H  H  H  S  S  G  G  L  R  S  Y  G  R  K  K  R  R  Q  R  R
agaggcgctagcaccggtggtatgtggactctcgggcgccgcgcagtagccggcctcctg
 R  G  A  S  T  G  G  M  W  T  L  G  R  R  A  V  A  G  L  L
gcgtcacccagcccggcccaggcccagacccctcacccgggtcccgcggccggcagagttg
 A  S  P  S  P  A  Q  A  Q  T  L  T  R  V  P  R  P  A  E  L
gccccactctgcggccgccgtggcctgcgcaccgacatcgatgcgacctgcacgccccgc
 A  P  L  C  G  R  R  G  L  R  T  D  I  D  A  T  C  T  P  R
cgcgcaagttcgaaccaacgtggcctcaaccagatttggaatgtcaaaaagcagagtgtc
 R  A  S  S  N  Q  R  G  L  N  Q  I  W  N  V  K  K  Q  S  V
tatttgatgaatttgaggaaatctggaactttgggccacccaggctctctagatgagacc
 Y  L  M  N  L  R  K  S  G  T  L  G  H  P  G  S  L  D  E  T
acctatgaaagactagcagaggaaacgctggactctttagcagagttttttgaagacctt
 T  Y  E  R  L  A  E  E  T  L  D  S  L  A  E  F  F  E  D  L
gcagacaagccatacacgtttgaggactatgatgtctcctttgggagtggtgtcttaact
 A  D  K  P  Y  T  F  E  D  Y  D  V  S  F  G  S  G  V  L  T
gtcaaactgggtggagatctaggaacctatgtgatcaacaagcagacgccaaacaagcaa
 V  K  L  G  G  D  L  G  T  Y  V  I  N  K  Q  T  P  N  K  Q
atctggctatcttctccatccagtggacctaagcgttatgactggactgggaaaaactgg
 I  W  L  S  S  P  S  S  G  P  K  R  Y  D  W  T  G  K  N  W
gtgtactcccacgacggcgtgtccctccatgagctgctggccgcagagctcactaaagcc
 V  Y  S  H  D  G  V  S  L  H  E  L  L  A  A  E  L  T  K  A
ttaaaaaccaaactggacttgtcttccttggcctattccggaaaagatgcttgaggatcc
 L  K  T  K  L  D  L  S  S  L  A  Y  S  G  K  D  A  stop
ggctgctaacaaagcccgaaaggaagctgagttggctgctgccaccgctgagcaataact
```

E. HIS-TAT-FRATAXIN 242 aa

MGHHHHHHSSGGLRSYGRKKRRQRRRGASTGGMWTLGRRAVAGLLASPSPAQAQTLTRVP
RPAELAPLCGRRGLRTDIDATCTPRRASSNQRGLNQIWNVKKQSVYLMNLRKSGTLGHPG
SLDETTYERLAEETLDSLAEFFEDLADKPYTFEDYDVSFGSGVLTVKLGGDLGTYVINKQ
TPNKQIWLSSPSSGPKRYDWTGKNWVYSHDGVSLHELLAAELTKALKTKLDLSSLAYSGK
DA

F. 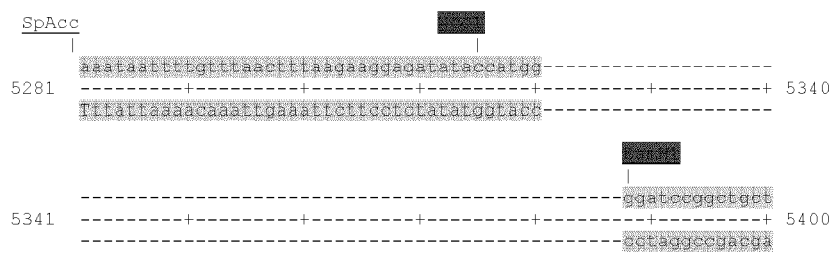 :Cloning sites of 6X HIS-TAT-Frataxin in pet 16b

Figures 33 D-F

G. HIS-Frataxin in pet16b

```
                       tagaaataattttgwttaactttaagaaggagatatacc
atgggccatcatcatcatcatcatcatcacagcagcggccatcatactagtatgtggact
 M   G   H   H   H   H   H   H   H   H   S   S   G   H   H   T   S   M   W   T
ctcgggcgccgcgcagtagccggcctcctggcgtcacccagcccggcccaggcccagacc
 L   G   R   R   A   V   A   G   L   L   A   S   P   S   P   A   Q   A   Q   T
ctcacccgggtcccgcggccggcagagttggccccactctgcggccgccgtgcctgcgc
 L   T   R   V   P   R   P   A   E   L   A   P   L   C   G   R   R   G   L   R
accgacatcgatgcgacctgcacgccccgccgcgcaagttcgaaccaacgtggcctcaac
 T   D   I   D   A   T   C   T   P   R   R   A   S   S   N   Q   R   G   L   N
cagatttggaatgtcaaaaagcagagtgtctatttgatgaatttgaggaaatctggaact
 Q   I   W   N   V   K   K   Q   S   V   Y   L   M   N   L   R   K   S   G   T
ttgggccacccaggctctctagatgagaccacctatgaagactagcagaggaaacgctg
 L   G   H   P   G   S   L   D   E   T   T   Y   E   R   L   A   E   E   T   L
gactctttagcagagttttttgaagaccttgcagacaagccatacacgtttgaggactat
 D   S   L   A   E   F   F   E   D   L   A   D   K   P   Y   T   F   E   D   Y
gatgtctcctttgggagtggtgtcttaactgtcaaactgggtggagatctagcaacctat
 D   V   S   F   G   S   G   V   L   T   V   K   L   G   G   D   L   G   T   Y
gtgatcaacaagcagacgccaaacaagcaaatctggctatcttctccatccagtggacct
 V   I   N   K   Q   T   P   N   K   Q   I   W   L   S   S   P   S   S   G   P
aagcgttatgactggactgggaaaaactgggtgtactccacgacggcgtgtccctccat
 K   R   Y   D   W   T   G   K   N   W   V   Y   S   H   D   G   V   S   L   H
gagctgctggccgcagagctcactaaagccttaaaaaccaaactggacttgtcttccttg
 E   L   L   A   A   E   L   T   K   A   L   K   T   K   L   D   L   S   S   L
gcctattcccgaaaagatgcttgaggatccggctgctaacaaagcccgaaagcaagctga
 A   Y   S   G   K   D   A   -
gttgggctgctaacaaagcccgaaaggaagctgagttggctgctgccaccgctgagcaat
```

H. HIS-FRATAXIN 227 aa

MGHHHHHHHHSSGHHTSMWTLGRRAVAGLLASPSPAQAQTLIRVPRPAELAPLCGRRGLR
TDIDATCTPRRASSNQRGLNQIWNVKKQSVYLMNLRKSGTLGHPGSLDETTYERLAEETL
DSLAEFFEDLADKPYTFEDYDVSFGSGVLTVKLGGDLGTYVINKQTPNKQIWLSSPSSGP
KRYDWTGKNWVYSHDGVSLHELLAAELTKALKTKLDLSSLAYSGKDA

I. :Cloning sites of 8X HIS -Frataxin in pet 16b

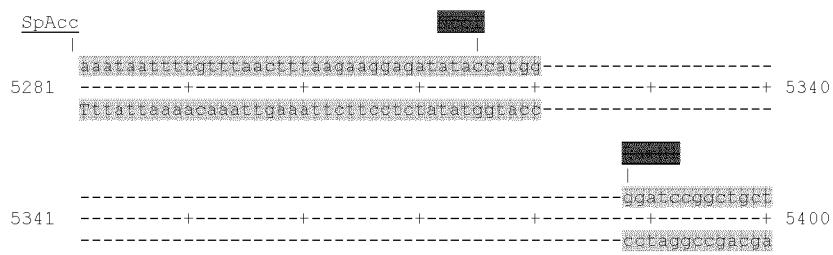

Figures 33G-I

```
ttcttgaagacgaaagggcctcgtgatacgcctattttataggttaatgtcatgataataatggtttcttagacgtcaggtggcactttt
cggggaaatgtgcgcggaaccccctatttgtttattttctaaatacattcaaatatgtatccgctcatgagacaataaccctgataaatgc
ttcaataatattgaaaaaggaagagtatgagtattcaacatttccgtgtcgcccttattccctttttttgcggcattttgccttcctgtttt
tgctcacccagaaacgctggtgaaagtaaaagatgctgaagatcagttgggtgcacgagtgggttacatcgaactggatctcaacagcggt
aagatccttgagagttttcgccccgaagaacgttttccaatgatgagcacttttaaagttctgctatgtggcgcggtattatccgtgttg
acgccgggcaagagcaactcggtcgccgcatacactattctcagaatgacttggttgagtactcaccagtcacagaaaagcatcttacgga
tggcatgacagtaagagaattatgcagtgctgccataaccatgagtgataacactgcggccaacttacttctgacaacgatcggaggaccg
aaggagctaaccgcttttttgcacaacatggggatcatgtaactcgccttgatcgttgggaaccggagctgaatgaagccataccaaacg
acgagcgtgacaccacgatgcctgcagcaatggcaacaacgttgcgcaaactattaactggcgaactacttactctagcttcccggcaaca
attaatagactggatggaggcggataaagttgcaggaccacttctgcgctcggcccttccggctggctggttttattgctgataaatctgga
gccggtgagcgtgggtctcgcggtatcattgcagcactggggccagatggtaagccctcccgtatcgtagttatctacacgacggggagtc
aggcaactatggatgaacgaaatagacagatcgctgagataggtgcctcactgattaagcattggtaactgtcagaccaagtttactcata
tatactttagattgatttaaaacttcatttttaatttaaaaggatctaggtgaagatcctttttgataatctcatgaccaaaatcccttaa
cgtgagttttcgttccactgagcgtcagacccccgtagaaaagatcaaaggatcttcttgagatcctttttttctgcgcgtaatctgctgct
tgcaaacaaaaaaaccaccgctaccagcggtggtttgtttgccggatcaagagctaccaactctttttccgaaggtaactggcttcagcag
agcgcagataccaaatactgtccttctagtgtagccgtagttaggccaccacttcaagaactctgtagcaccgcctacatacctcgctctg
ctaatcctgttaccagtggctgctgccagtggcgataagtcgtgtcttaccgggttggactcaagacgatagttaccggataaggcgcagc
ggtcgggctgaacggggggttcgtgcacacagcccagcttggagcgaacgacctacaccgaactgagatacctacagcgtgagctatgaga
aagcgccacgcttcccgaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggcggagcc
tatggaaaaacgccagcaacgcggcctttttacggttcctggccttttgctggccttttgctcacatgttctttcctgcgttatccctga
ttctgtggataaccgtattaccgcctttgagtgagctgataccgctcgccgcagccgaacgaccgagcgcagcgagtcagtgagcgaggaa
gcggaagagcgcctgatgcggtattttctccttacgcatctgtgcggtatttcacaccgcatatatggtgcactctcagtacaatctgctc
tgatgccgcatagttaagccagtatacactccgctatcgctacgtgactgggtcatggctgcgccccgacacccgccaacacccgctgacg
cgccctgacgggcttgtctgctcccggcatccgcttacagacaagctgtgaccgtctccgggagctgcatgtgtcagaggttttcaccgtc
atcaccgaaacgcgcgaggcagctgcggtaaagctcatcagcgtggtcgtgaagcgattcacagatgtctgcctgttcatccgcgtccagc
tcgttgagtttctccagaagcgttaatgtctggcttctgataaagcgggccatgttaagggcggttttttcctgtttggtcactgatgcct
ccgtgtaagggggatttctgttcatgggggtaatgataccgatgaaacgagagaggatgctcacgatacgggttactgatgatgaacatgc
ccggttactggaacgttgtgagggtaaacaactggcggtatggatgcggcgggaccagagaaaaatcactcagggtcaatgccagcgcttc
gttaatacagatgtaggtgttccacagggtagccagcagcatcctgcgatgcagatccggaacataatggtgcagggcgctgacttccgcg
tttccagacttacgaaacacggaaaccgaagaccattcatgttgttgctcaggtcgcagacgttttgcagcagcagtcgcttcacgttcg
ctcgcgtatcggtgattcattctgctaaccagtaaggcaacccgccagcctagccgggtcctcaacgacaggagcacgatcatgcgcacc
cgtggccaggacccaacgctgcccgagatgcgccgcgtgcggctgctggagatggcggacgcgatgatatgttctgccaagggttggttt
gcgcattcacagttctccgcaagaattgattggctccaattcttggagtggtgaatccgttagcgaggtgccgccggcttccattcaggtc
gaggtggcccggctccatgcaccgcgacgcaacgcggggaggcagacaaggtatagggcggcgcctacaatccatgccaacccgttccatg
tgctcgccgaggcggcataaatcgccgtgacgatcagcggtccagtgatcgaagttaggctggtaagagccgcgagcgatccttgaagctg
tccctgatggtcgtcatctacctgcctggacagcatggcctcaacgcgggcatcccgatgccgccggaagcgagaagaatcataatgggg
aaggccatccagcctcgcgtcgcgaacgccagcaagacgtagcccagcgcgtcggccgccatgccggcgataatggcctgcttctcgccga
aacgtttggtggcgggaccagtgacgaaggcttgagcgagggcgtgcaagattccgaataccgcaagcgacaggccgatcatcgtcgcgct
ccagcgaaagcggtcctcgccgaaaatgacccagagcgctgccggcacctgtcctacgagttgcatgataaagaagacagtcataagtgcg
gcgacgatagtcatgccccgcgcccaccggaaggagctgactgggttgaaggctctcaagggcatcggtcgagatcccggtgcctaatgag
tgagctaacttacattaattgcgttgcgctcactgcccgctttccagtcgggaaacctgtcgtgccagctgcattaatgaatcggccaacg
cgcggggagaggcggtttgcgtattgggcgccagggtggtttttcttttcaccagtgagacgggcaacagctgattgcccttcaccgcctg
gccctgagagagttgcagcaagcggtccacgctgttttgcccaggcagaaatcctgtttgatggtggttaacgcgggatataacat
gagctgtcttcggtatcgtcgtatcccactaccgagatatccgcaccaacgcgcagcccggactcggtaatggcgcgcattgcgcccagcg
ccatctgatcgttggcaaccagcatcgcagtgggaacgatgccctcattcagcatttgcatggttttgttgaaaaccggacatggcactcca
gtcgccttcccgttccgctatcggctgaatttgattgcgagtgagatatttatgccagccagccagacgcagacgcgccgagacagaactt
aatgggcccgctaacagcgcgatttgctggtgacccaatgcgaccagatgctccacgcccagtcgcgtaccgtcttcatgggagaaaataa
tactgttgatgggtgtctggtcagagacatcaagaaataacgccggaacattagtgcaggcagcttccacagcaatggcatcctggtcatc
cagcggatagttaatgatcagcccactgacgcgttgcgcgagaagattgtgcaccgccgctttacaggcttcgacgccgcttcgttctacc
```

Figure 33J

```
atcgacaccaccacgctggcacccagttgatcggcgcgagatttaatcgccgcgacaatttgcgacggcgcgtgcagggccagactggagg
tggcaacgccaatcagcaacgactgtttgcccgccagttgttgtgccacgcggttgggaatgtaattcagctccgccatcgccgcttccac
tttttcccgcgttttcgcagaaacgtggctggcctggttcaccacgcgggaaacggtctgataagagacaccggcatactctgcgacatcg
tataacgttactggtttcacattcaccaccctgaattgactctcttccgggcgctatcatgccataccgcgaaaggttttgcgccattcga
tggtgtccgggatctcgacgctctcccttatgcgactcctgcattaggaagcagcccagtagtaggttgaggccgttgagcaccgccgccg
caaggaatggtgcatgcaaggagatggcgcccaacagtcccccggccacggggcctgccaccatacccacgccgaaacaagcgctcatgag
cccgaagtggcgagcccgatcttccccatcggtgatgtcggcgatataggcgcagcaaccgcacctgtggcgccggtgatgccggccacg
atgcgtccggcgtagaggatcgagatctcgatcccgcgaaattaatacgactcactatagggggaattgtgagcggataacaattcccctct
agaaataattttgtttaactttaagaaggagatataccatgggccatcatcatcatcatcatcatcatcacagcagcggccatatcga
aggtcgtcatatgctcgaggatccggctgctaacaaagcccgaaaggaagctgagttggctgctgccaccgctgagcaataactagcataa
cccttggggcctctaaacgggtcttgagggggttttttgctgaaaggaggaactatatccggatatcccgcaagaggcccggcagtaccgg
cataaccaagcctatgcctacagcatccagggtgacggtgccgaggatgacgatgagcgcattgttagatttcatacacggtgcctgactg
cgttagcaatttaactgtgataaactaccgcattaaagcttatcgatgataagctgtcaaacatgagaa
```

Figure 33K

SEQUENCE LISTING

```
<160> NUMBER OF SEQ ID NOS: 143

<210> SEQ ID NO 1
<211> LENGTH: 14
<212> TYPE: DNA
<213> ORGANISM: Homo sapiens

<400> SEQUENCE: 1
tcccttgggt cagg                                                       14

<210> SEQ ID NO 2
<211> LENGTH: 442
<212> TYPE: PRT
<213> ORGANISM: Artificial sequence
<220> FEATURE:
<223> OTHER INFORMATION: synthetic construct

<400> SEQUENCE: 2

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
        130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Gly Gly Lys Gln Ala
```

```
                    245                 250                 255
Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly
        435                 440

<210> SEQ ID NO 3
<211> LENGTH: 14
<212> TYPE: DNA
<213> ORGANISM: Homo sapiens

<400> SEQUENCE: 3
tcctggttgc actc                                                                 14

<210> SEQ ID NO 4
<211> LENGTH: 442
<212> TYPE: PRT
<213> ORGANISM: Artificial sequence
<220> FEATURE:
<223> OTHER INFORMATION: synthetic construct

<400> SEQUENCE: 4

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110
```

Ser Asn Asn Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
            165                 170                 175

Val Ala Ile Ala Ser Asn Gly Gly Lys Gln Ala Leu Glu Thr Val
        180                 185                 190

Gln Arg Leu Leu Pro Val Leu Cys Gln Ala His Gly Leu Thr Pro Glu
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser His
        340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser His Asp Gly Gly Lys Gln Ala Leu Glu Thr Val Gln Arg
        420                 425                 430

Leu Leu Pro Val Leu Cys Gln Ala His Gly
        435                 440

<210> SEQ ID NO 5
<211> LENGTH: 14
<212> TYPE: DNA
<213> ORGANISM: Homo sapiens

<400> SEQUENCE: 5
tggttgcact ccgt                                                      14

<210> SEQ ID NO 6
<211> LENGTH: 410
<212> TYPE: PRT
<213> ORGANISM: Artificial sequence
<220> FEATURE:

<223> OTHER INFORMATION: synthetic construct

<400> SEQUENCE: 6

```
Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Asn Asp Leu Thr Pro Glu Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser Asn Asn Gly Gly Lys Gln Ala Leu Glu Thr Val Gln Arg Leu Leu
        355                 360                 365

Pro Val Leu Cys Gln Ala His Gly Leu Thr Pro Glu Gln Val Val Ala
    370                 375                 380

Ile Ala Ser Asn Gly Gly Gly Lys Gln Ala Leu Glu Thr Val Gln Arg
385                 390                 395                 400
```

Leu Leu Pro Val Leu Cys Gln Ala His Gly
                405                 410

<210> SEQ ID NO 7
<211> LENGTH: 14
<212> TYPE: DNA
<213> ORGANISM: Homo sapiens

<400> SEQUENCE: 7
tgctttgcac aaag                                                       14

<210> SEQ ID NO 8
<211> LENGTH: 442
<212> TYPE: PRT
<213> ORGANISM: Artificial sequence
<220> FEATURE:
<223> OTHER INFORMATION: synthetic construct

<400> SEQUENCE: 8

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

-continued

His Gly Leu Thr Pro Glu Gln Val Val Ala Ile Ala Ser Asn Ile Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly
        435                 440

<210> SEQ ID NO 9
<211> LENGTH: 14
<212> TYPE: DNA
<213> ORGANISM: Homo sapiens

<400> SEQUENCE: 9
tgcacgaata gtgc                                                            14

<210> SEQ ID NO 10
<211> LENGTH: 442
<212> TYPE: PRT
<213> ORGANISM: Artificial sequence
<220> FEATURE:
<223> OTHER INFORMATION: synthetic construct

<400> SEQUENCE: 10

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val

```
                         165                 170                 175

Val Ala Ile Ala Ser Asn Ile Gly Gly Lys Gln Ala Leu Glu Thr Val
                 180                 185                 190

Gln Arg Leu Leu Pro Val Leu Cys Gln Ala His Gly Leu Thr Pro Glu
             195                 200                 205

Gln Val Val Ala Ile Ala Ser Asn Ile Gly Gly Lys Gln Ala Leu Glu
         210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Gly Gly Gly Lys Gln Ala
                 245                 250                 255

Leu Glu Thr Val Gln Arg Leu Leu Pro Val Leu Cys Gln Ala His Gly
             260                 265                 270

Leu Thr Pro Glu Gln Val Val Ala Ile Ala Ser Asn Ile Gly Gly Lys
         275                 280                 285

Gln Ala Leu Glu Thr Val Gln Arg Leu Leu Pro Val Leu Cys Gln Ala
     290                 295                 300

His Gly Leu Thr Pro Glu Gln Val Val Ala Ile Ala Ser Asn Asn Gly
305                 310                 315                 320

Gly Lys Gln Ala Leu Glu Thr Val Gln Arg Leu Leu Pro Val Leu Cys
                 325                 330                 335

Gln Ala His Gly Leu Thr Pro Glu Gln Val Val Ala Ile Ala Ser Asn
             340                 345                 350

Gly Gly Gly Lys Gln Ala Leu Glu Thr Val Gln Arg Leu Leu Pro Val
         355                 360                 365

Leu Cys Gln Ala His Gly Leu Thr Pro Glu Gln Val Val Ala Ile Ala
     370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                 405                 410                 415

Ile Ala Ser His Asp Gly Gly Lys Gln Ala Leu Glu Thr Val Gln Arg
             420                 425                 430

Leu Leu Pro Val Leu Cys Gln Ala His Gly
         435                 440

<210> SEQ ID NO 11
<211> LENGTH: 14
<212> TYPE: DNA
<213> ORGANISM: Homo sapiens

<400> SEQUENCE: 11
tagtgctaag ctgg                                                       14

<210> SEQ ID NO 12
<211> LENGTH: 408
<212> TYPE: PRT
<213> ORGANISM: Artificial sequence
<220> FEATURE:
<223> OTHER INFORMATION: synthetic construct

<400> SEQUENCE: 12

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30
```

His Gly Leu Thr Pro Glu Gln Val Ala Ile Ala Ser Asn Asn Gly
         35                  40                  45

Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser Asn
 65                  70                  75                  80

Gly Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
                    100                 105                 110

Ser Asn Asn Gly Gly Lys Gln Ala Leu Glu Thr Val Gln Arg Leu Leu
                115                 120                 125

Pro Val Leu Cys Gln Ala His Gly Leu Thr Pro Glu Gln Val Val Ala
            130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Arg Leu Leu Pro Val Leu Cys Gln Ala His Gly
                260                 265                 270

Leu Thr Pro Glu Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
                340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly
                405

<210> SEQ ID NO 13
<211> LENGTH: 14
<212> TYPE: DNA
<213> ORGANISM: Homo sapiens

<400> SEQUENCE: 13

```
tgggaagttc ttcc                                              14
```

<210> SEQ ID NO 14
<211> LENGTH: 442
<212> TYPE: PRT
<213> ORGANISM: Artificial sequence
<220> FEATURE:
<223> OTHER INFORMATION: synthetic construct

<400> SEQUENCE: 14

```
Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350
```

-continued

```
Gly Gly Gly Lys Gln Ala Leu Glu Thr Val Gln Arg Leu Pro Val
            355                 360                 365
Leu Cys Gln Ala His Gly Leu Thr Pro Glu Gln Val Val Ala Ile Ala
    370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Ala His Gly
            435                 440

<210> SEQ ID NO 15
<211> LENGTH: 14
<212> TYPE: DNA
<213> ORGANISM: Homo sapiens

<400> SEQUENCE: 15
tcctgaggtc taac                                                      14

<210> SEQ ID NO 16
<211> LENGTH: 408
<212> TYPE: PRT
<213> ORGANISM: Artificial sequence
<220> FEATURE:
<223> OTHER INFORMATION: synthetic construct

<400> SEQUENCE: 16

Leu Thr Pro Glu Gln Val Val Ala Ile Ala Ser His Asp Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Glu Gln Val Val Ala Ile Ala Ser His Asp Gly
        35                  40                  45
Gly Lys Gln Ala Leu Glu Thr Val Gln Arg Leu Leu Pro Val Leu Cys
    50                  55                  60
Gln Ala His Gly Leu Thr Pro Glu Gln Val Val Ala Ile Ala Ser Asn
65                  70                  75                  80
Gly Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
Ser Asn Asn Gly Gly Lys Gln Ala Leu Glu Thr Val Gln Arg Leu Leu
        115                 120                 125
Pro Val Leu Cys Gln Ala His Gly Leu Thr Pro Glu Gln Val Val Ala
    130                 135                 140
Ile Ala Ser Asn Ile Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser Asn Asn Gly Gly Lys Gln Ala Leu Glu Thr Val
            180                 185                 190
Gln Arg Leu Leu Pro Val Leu Cys Gln Ala His Gly Leu Thr Pro Glu
        195                 200                 205
Gln Val Val Ala Ile Ala Ser Asn Asn Gly Gly Lys Gln Ala Leu Glu
    210                 215                 220
```

Thr Val Gln Arg Leu Leu Pro Val Leu Cys Gln Ala His Gly Leu Thr
225                 230                 235                 240

Pro Glu Gln Val Val Ala Ile Ala Ser Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser His Asp Gly Gly Lys
    275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
        340                 345                 350

Ile Gly Gly Lys Gln Ala Leu Glu Thr Val Gln Arg Leu Leu Pro Val
    355                 360                 365

Leu Cys Gln Ala His Gly Leu Thr Pro Glu Gln Val Val Ala Ile Ala
370                 375                 380

Ser Asn Ile Gly Gly Lys Gln Ala Leu Glu Thr Val Gln Arg Leu Leu
385                 390                 395                 400

Pro Val Leu Cys Gln Ala His Gly
            405

<210> SEQ ID NO 17
<211> LENGTH: 14
<212> TYPE: DNA
<213> ORGANISM: Homo sapiens

<400> SEQUENCE: 17
tgaggtctaa cctc                                                                 14

<210> SEQ ID NO 18
<211> LENGTH: 408
<212> TYPE: PRT
<213> ORGANISM: Artificial sequence
<220> FEATURE:
<223> OTHER INFORMATION: synthetic construct

<400> SEQUENCE: 18

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Asn Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
        100                 105                 110

Ser Asn Asn Gly Gly Lys Gln Ala Leu Glu Thr Val Gln Arg Leu Leu

```
                115                 120                 125
Pro Val Leu Cys Gln Ala His Gly Leu Thr Pro Glu Gln Val Val Ala
    130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly
                405

<210> SEQ ID NO 19
<211> LENGTH: 14
<212> TYPE: DNA
<213> ORGANISM: Homo sapiens

<400> SEQUENCE: 19
tgctccccca caga                                                     14

<210> SEQ ID NO 20
<211> LENGTH: 442
<212> TYPE: PRT
<213> ORGANISM: Artificial sequence
<220> FEATURE:
<223> OTHER INFORMATION: synthetic construct

<400> SEQUENCE: 20

Leu Thr Pro Glu Gln Val Val Ala Ile Ala Ser Asn Asn Gly Gly Lys
1               5                   10                  15
```

-continued

```
Gln Ala Leu Glu Thr Val Gln Arg Leu Leu Pro Val Leu Cys Gln Ala
             20                  25                  30

His Gly Leu Thr Pro Glu Gln Val Val Ala Ile Ala Ser His Asp Gly
         35                  40                  45

Gly Lys Gln Ala Leu Glu Thr Val Gln Arg Leu Leu Pro Val Leu Cys
     50                  55                  60

Gln Ala His Gly Leu Thr Pro Glu Gln Val Val Ala Ile Ala Ser Asn
 65                  70                  75                  80

Gly Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Arg
            420                 425                 430

Leu Leu Pro Val Leu Cys Gln Ala His Gly
```

<210> SEQ ID NO 21
<211> LENGTH: 14
<212> TYPE: DNA
<213> ORGANISM: Homo sapiens

<400> SEQUENCE: 21
tggccaccag gggt                                                       14

<210> SEQ ID NO 22
<211> LENGTH: 476
<212> TYPE: PRT
<213> ORGANISM: Artificial sequence
<220> FEATURE:
<223> OTHER INFORMATION: synthetic construct

<400> SEQUENCE: 22

```
Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
    290                 295                 300
```

-continued

```
His Gly Leu Thr Pro Glu Gln Val Val Ala Ile Ala Ser Asn Asn Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
        340                 345                 350

Asn Gly Gly Lys Gln Ala Leu Glu Thr Val Gln Arg Leu Leu Pro Val
    355                 360                 365

Leu Cys Gln Ala His Gly Leu Thr Pro Glu Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Asn Gly Gly Lys Gln Ala Leu Glu Thr Val Gln Arg
        420                 425                 430

Leu Leu Pro Val Leu Cys Gln Ala His Gly Leu Thr Pro Glu Gln Val
    435                 440                 445

Val Ala Ile Ala Ser Asn Gly Gly Gly Lys Gln Ala Leu Glu Thr Val
450                 455                 460

Gln Arg Leu Leu Pro Val Leu Cys Gln Ala His Gly
465                 470                 475
```

<210> SEQ ID NO 23
<211> LENGTH: 14
<212> TYPE: DNA
<213> ORGANISM: homosapiens

<400> SEQUENCE: 23
tcgccgcagc accc                                                    14

<210> SEQ ID NO 24
<211> LENGTH: 442
<212> TYPE: PRT
<213> ORGANISM: Artificial sequence
<220> FEATURE:
<223> OTHER INFORMATION: synthetic construct

<400> SEQUENCE: 24

```
Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140
```

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly
        435                 440

<210> SEQ ID NO 25
<211> LENGTH: 14
<212> TYPE: PRT
<213> ORGANISM: Artificial sequence
<220> FEATURE:
<223> OTHER INFORMATION: synthetic construct

<400> SEQUENCE: 25

Ser Gly Tyr Gly Arg Lys Lys Arg Arg Gln Arg Arg Arg Cys
1               5                   10

<210> SEQ ID NO 26
<211> LENGTH: 59
<212> TYPE: PRT
<213> ORGANISM: Artificial sequence
<220> FEATURE:
<223> OTHER INFORMATION: synthetic construct

```
<400> SEQUENCE: 26

Gly Ser Gly Arg Ala Asp Ala Leu Asp Phe Asp Leu Asp Met Leu
1               5                   10                  15

Gly Ser Asp Ala Leu Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn Ser Arg
    50                  55

<210> SEQ ID NO 27
<211> LENGTH: 7
<212> TYPE: PRT
<213> ORGANISM: Artificial sequence
<220> FEATURE:
<223> OTHER INFORMATION: synthetic construct

<400> SEQUENCE: 27

Pro Lys Lys Lys Arg Lys Val
1               5

<210> SEQ ID NO 28
<211> LENGTH: 16
<212> TYPE: PRT
<213> ORGANISM: Artificial sequence
<220> FEATURE:
<223> OTHER INFORMATION: synthetic construct

<400> SEQUENCE: 28

Lys Arg Pro Ala Ala Thr Lys Lys Ala Gly Gln Ala Lys Lys Lys Lys
1               5                   10                  15

<210> SEQ ID NO 29
<211> LENGTH: 11
<212> TYPE: PRT
<213> ORGANISM: Artificial sequence
<220> FEATURE:
<223> OTHER INFORMATION: synthetic construct

<400> SEQUENCE: 29

Ser Pro Lys Lys Lys Arg Lys Val Glu Ala Ser
1               5                   10

<210> SEQ ID NO 30
<211> LENGTH: 6
<212> TYPE: PRT
<213> ORGANISM: Artificial sequence
<220> FEATURE:
<223> OTHER INFORMATION: synthetic construct

<400> SEQUENCE: 30

Lys Lys Lys Arg Lys Val
1               5

<210> SEQ ID NO 31
<211> LENGTH: 18
<212> TYPE: PRT
<213> ORGANISM: Artificial sequence
<220> FEATURE:
<223> OTHER INFORMATION: synthetic construct

<400> SEQUENCE: 31

Ser Pro Lys Lys Lys Arg Lys Val Glu Ala Ser Pro Lys Lys Arg
1               5                   10                  15
```

-continued

Lys Val

<210> SEQ ID NO 32
<211> LENGTH: 8
<212> TYPE: PRT
<213> ORGANISM: Artificial sequence
<220> FEATURE:
<223> OTHER INFORMATION: synthetic construct

<400> SEQUENCE: 32

Lys Lys Arg Arg Gln Arg Arg Arg
1               5

<210> SEQ ID NO 33
<211> LENGTH: 12
<212> TYPE: PRT
<213> ORGANISM: Artificial sequence
<220> FEATURE:
<223> OTHER INFORMATION: synthetic construct

<400> SEQUENCE: 33

Arg Arg Gln Arg Arg Thr Ser Lys Leu Met Lys Arg
1               5                   10

<210> SEQ ID NO 34
<211> LENGTH: 27
<212> TYPE: PRT
<213> ORGANISM: Artificial sequence
<220> FEATURE:
<223> OTHER INFORMATION: synthetic construct

<400> SEQUENCE: 34

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 35
<211> LENGTH: 33
<212> TYPE: PRT
<213> ORGANISM: Artificial sequence
<220> FEATURE:
<223> OTHER INFORMATION: synthetic construct

<400> SEQUENCE: 35

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 36
<211> LENGTH: 16
<212> TYPE: PRT
<213> ORGANISM: Artificial sequence
<220> FEATURE:
<223> OTHER INFORMATION: synthetic construct

<400> SEQUENCE: 36

Arg Gln Ile Lys Ile Trp Phe Gln Asn Arg Arg Met Lys Trp Lys Lys
1               5                   10                  15

<210> SEQ ID NO 37
<211> LENGTH: 11
<212> TYPE: PRT

```
<213> ORGANISM: Artificial sequence
<220> FEATURE:
<223> OTHER INFORMATION: synthetic construct

<400> SEQUENCE: 37

Tyr Gly Arg Lys Lys Arg Arg Gln Arg Arg
1               5                   10

<210> SEQ ID NO 38
<211> LENGTH: 9
<212> TYPE: PRT
<213> ORGANISM: Artificial sequence
<220> FEATURE:
<223> OTHER INFORMATION: synthetic construct

<400> SEQUENCE: 38

Arg Lys Lys Arg Arg Gln Arg Arg Arg
1               5

<210> SEQ ID NO 39
<211> LENGTH: 9
<212> TYPE: PRT
<213> ORGANISM: Artificial sequence
<220> FEATURE:
<223> OTHER INFORMATION: synthetic construct

<400> SEQUENCE: 39

Gly Asp Val Glu Glu Asn Pro Gly Pro
1               5

<210> SEQ ID NO 40
<211> LENGTH: 960
<212> TYPE: PRT
<213> ORGANISM: Artificial sequence
<220> FEATURE:
<223> OTHER INFORMATION: synthetic construct

<400> SEQUENCE: 40

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
                20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Thr Met Arg Val Ala Val Thr Ala Ala
            115                 120                 125

Arg Pro Pro Arg Ala Lys Pro Ala Pro Arg Arg Ala Ala Gln Pro
        130                 135                 140

Ser Asp Ala Ser Pro Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
```

```
                180                 185                 190
Ile Val Ala Leu Ser Gln His Pro Ala Leu Gly Thr Val Ala Val
            195                 200                 205
Lys Tyr Gln Asp Met Ile Ala Ala Leu Pro Glu Ala Thr His Glu Ala
210                 215                 220
Ile Val Gly Val Gly Lys Gln Trp Ser Gly Ala Arg Ala Leu Glu Ala
225                 230                 235                 240
Leu Leu Thr Val Ala Gly Glu Leu Arg Gly Pro Leu Gln Leu Asp
            245                 250                 255
Thr Gly Gln Leu Leu Lys Ile Ala Lys Arg Gly Gly Val Thr Ala Val
            260                 265                 270
Glu Ala Val His Ala Trp Arg Asn Ala Leu Thr Gly Ala Pro Leu Asn
            275                 280                 285
Leu Thr Pro Glu Gln Val Ala Ile Ala Ser Asn Ile Gly Gly Lys
            290                 295                 300
Gln Ala Leu Glu Thr Val Gln Arg Leu Leu Pro Val Leu Cys Gln Ala
305                 310                 315                 320
His Gly Leu Thr Pro Gln Gln Val Val Ala Ile Ala Ser His Asp Gly
            325                 330                 335
Gly Lys Gln Ala Leu Glu Thr Val Gln Arg Leu Leu Pro Val Leu Cys
            340                 345                 350
Gln Ala His Gly Leu Thr Pro Glu Gln Val Val Ala Ile Ala Ser Asn
            355                 360                 365
Ile Gly Gly Lys Gln Ala Leu Glu Thr Val Gln Ala Leu Leu Pro Val
            370                 375                 380
Leu Cys Gln Ala His Gly Leu Thr Pro Glu Gln Val Val Ala Ile Ala
385                 390                 395                 400
Ser His Asp Gly Gly Lys Gln Ala Leu Glu Thr Val Gln Arg Leu Leu
            405                 410                 415
Pro Val Leu Cys Gln Ala His Gly Leu Thr Pro Gln Gln Val Val Ala
            420                 425                 430
Ile Ala Ser His Asp Gly Gly Lys Gln Ala Leu Glu Thr Val Gln Arg
            435                 440                 445
Leu Leu Pro Val Leu Cys Gln Ala His Gly Leu Thr Pro Gln Gln Val
            450                 455                 460
Val Ala Ile Ala Ser His Asp Gly Gly Lys Gln Ala Leu Glu Thr Val
465                 470                 475                 480
Gln Arg Leu Leu Pro Val Leu Cys Gln Ala His Gly Leu Thr Pro Gln
            485                 490                 495
Gln Val Val Ala Ile Ala Ser Asn Ser Gly Gly Lys Gln Ala Leu Glu
            500                 505                 510
Thr Val Gln Arg Leu Leu Pro Val Leu Cys Gln Ala His Gly Leu Thr
            515                 520                 525
Pro Gln Gln Val Val Ala Ile Ala Ser Asn Ser Gly Gly Lys Gln Ala
            530                 535                 540
Leu Glu Thr Val Gln Arg Leu Leu Pro Val Leu Cys Gln Ala His Gly
545                 550                 555                 560
Leu Thr Pro Gln Gln Val Val Ala Ile Ala Ser Asn Ser Gly Gly Lys
            565                 570                 575
Gln Ala Leu Glu Thr Val Gln Arg Leu Leu Pro Val Leu Cys Gln Ala
            580                 585                 590
His Gly Leu Thr Pro Glu Gln Val Val Ala Ile Ala Ser His Asp Gly
            595                 600                 605
```

Gly Lys Gln Ala Leu Glu Thr Val Gln Arg Leu Leu Pro Val Leu Cys
610                 615                 620

Gln Ala His Gly Leu Thr Pro Glu Gln Val Val Ala Ile Ala Ser Asn
625                 630                 635                 640

Ile Gly Gly Lys Gln Ala Leu Glu Thr Val Gln Arg Leu Leu Pro Val
            645                 650                 655

Leu Cys Gln Ala His Gly Leu Thr Pro Gln Gln Val Val Ala Ile Ala
            660                 665                 670

Ser Asn Gly Gly Gly Arg Pro Ala Leu Glu Ser Ile Val Ala Gln Leu
            675                 680                 685

Ser Arg Pro Asp Pro Ala Leu Ala Ala Leu Thr Asn Asp His Leu Val
690                 695                 700

Ala Leu Ala Cys Leu Gly Gly Arg Pro Ala Leu Asp Ala Val Lys Lys
705                 710                 715                 720

Gly Leu Pro His Ala Pro Ala Leu Ile Lys Arg Thr Asn Arg Arg Ile
            725                 730                 735

Pro Glu Arg Thr Ser His Arg Val Ala Asp His Ala Gln Val Val Arg
            740                 745                 750

Val Leu Gly Phe Phe Gln Cys His Ser His Pro Ala Gln Ala Phe Asp
755                 760                 765

Asp Ala Met Thr Gln Phe Gly Met Ser Arg His Gly Leu Leu Gln Leu
770                 775                 780

Phe Arg Arg Val Gly Val Thr Glu Leu Glu Ala Arg Ser Gly Thr Leu
785                 790                 795                 800

Pro Pro Ala Ser Gln Arg Trp Asp Arg Ile Leu Gln Ala Ser Gly Met
            805                 810                 815

Lys Arg Ala Lys Pro Ser Pro Thr Ser Thr Gln Thr Pro Asp Gln Ala
            820                 825                 830

Ser Leu His Ala Phe Ala Asp Ser Leu Glu Arg Asp Leu Asp Ala Pro
            835                 840                 845

Ser Pro Met His Glu Gly Asp Gln Thr Arg Ala Ser Ser Arg Lys Arg
850                 855                 860

Ser Arg Ser Asp Arg Ala Val Thr Gly Pro Ser Ala Gln Gln Ser Phe
865                 870                 875                 880

Glu Val Arg Val Pro Glu Gln Arg Asp Ala Leu His Leu Pro Leu Leu
            885                 890                 895

Ser Trp Gly Val Lys Arg Pro Arg Thr Arg Ile Gly Gly Leu Leu Asp
            900                 905                 910

Pro Gly Thr Pro Met Asp Ala Asp Leu Val Ala Ser Ser Thr Val Val
            915                 920                 925

Trp Glu Gln Asp Ala Asp Pro Phe Ala Gly Thr Ala Asp Asp Phe Pro
930                 935                 940

Ala Phe Asn Glu Glu Glu Leu Ala Trp Leu Met Glu Leu Leu Pro Gln
945                 950                 955                 960

<210> SEQ ID NO 41
<211> LENGTH: 860
<212> TYPE: DNA
<213> ORGANISM: Xanthomonas campestris

<400> SEQUENCE: 41
gtacggccac catgtcgcgg acccggctcc cttccccacc cgcacccagc ccagcgtttt    60
cggccgactc gttctcagac ctgcttaggc agttcgaccc ctcactgttt a

```
tgttcgactc ccttcctccg tttggggcgc accatacgga ggcggccacc ggggagtggg    180
atgaggtgca gtcgggattg agagctgcgg atgcaccacc cccaaccatg cgggtggccg    240
tcaccgctgc ccgaccgccg agggcgaagc ccgcaccaag gcggagggca gcgcaaccgt    300
ccgacgcaag ccccgcagcg caagtagatt tgagaacttt gggatattca cagcagcagc    360
aggaaaagat caagcccaaa gtgaggtcga cagtcgcgca gcatcacgaa gcgctggtgg    420
gtcatgggtt tacacatgcc cacatcgtag ccttgtcgca gcaccctgca gcccttggca    480
cggtcgccgt caagtaccag gacatgattg cggcgttgcc ggaagccaca catgaggcga    540
tcgtcggtgt ggggaaacag tggagcggag cccgagcgct tgaggccctg ttgacggtcg    600
cgggagagct gagagggcct ccccttcagc tggacacggg ccagttgctg aagatcgcga    660
agcggggagg agtcacggcg gtcgaggcgg tgcacgcgtg gcgcaatgcg ctcacgggag    720
cacccctcaa cctgaccgag acggtacatg aaacgcatgg cacggcgtct caactcacgc    780
ctgagcaggt agtggctatt gcatccaata tcgggggcag acccgcactg gagtcaatcg    840
tggcccagct ttcgaggccg                                                860
```

<210> SEQ ID NO 42
<211> LENGTH: 507
<212> TYPE: DNA
<213> ORGANISM: Xanthomonas campestris

<400> SEQUENCE: 42

```
gaccccgcgc tggccgcact cactaatgat catcttgtag cgctggcctg cctcggcgga     60
cgacccgcct tggatgcggt gaagaagggg ctcccgcacg cgcctgcatt gattaagcgg    120
accaacagaa ggattcccga gaggacatca catcgagtgg cagatcacgc gcaagtggtc    180
cgcgtgctcg gattcttcca gtgtcactcc caccccgcac aagcgttcga tgacgccatg    240
actcaatttg gtatgtcgag acacggactg ctgcagctct ttcgtagagt cggtgtcaca    300
gaactcgagg cccgctcggg cacactgcct cccgcctccc agcggtggga caggattctc    360
caagcgagcg gtatgaaacg cgcgaagcct tcacctacgt caactcagac acctgaccag    420
gcgagccttc atgcgttcgc agactcgctg gagagggatt tggacgcgcc ctcgcccatg    480
catgaagggg accaaactcg cgcgtca                                        507
```

<210> SEQ ID NO 43
<211> LENGTH: 5439
<212> TYPE: DNA
<213> ORGANISM: Xanthomonas campestris

<400> SEQUENCE: 43

```
aaaatattaa cgcttacaat ttacgcgcgt cgagtctaga ggcagagtac agatttacac     60
aaggcatccg tctcctggcc ccacataccc aactgctgta aacccatacc ggcggccaag    120
cagcctcaat ttgtgcatgc agggccacca ggctgcagtc tcccttgggt caggggtcct    180
ggttgcactc cgtgctttgc acaaagcagg ctctccattt ttgttaaatg cacgaatagt    240
gctaagctgg gaagttcttc ctgaggtcta acctctagct gctcccccac agaagagtgc    300
ctgcggccag tggccaccag gggtcgccgc agcacccagc gctggagggc ggagcgggcg    360
gcagaggatc ctatcacgaa ttctggatcc acgtatgtcg aggtaggcgt gtacggtggg    420
aggcctatat aagcagagct cgtttagtga accgtcagat cgcctggagg taccgccacc    480
atggtgagca agggcgagga ggataacatg gccatcatca aggagttcat gcgcttcaag    540
gtgcacatgg agggctccgt gaacggccac gagttcgaga tcgagggcga gggcgagggc    600
```

```
cgcccctacg agggcaccca gaccgccaag ctgaaggtga ccaagggtgg cccctgccc      660 ttcgcctggg acatcctgtc ccctcagttc atgtacggct ccaaggccta cgtgaagcac      720
cccgccgaca tccccgacta cttgaagctg tccttccccg agggcttcaa gtgggagcgc      780
gtgatgaact tcgaggacgg cggcgtggtg accgtgaccc aggactcctc cctgcaggac      840
ggcgagttca tctacaaggt gaagctgcgc ggcaccaact tcccctccga cggccccgta      900
atgcagaaga agaccatggg ctgggaggcc tcctccgagc ggatgtaccc cgaggacggc      960
gccctgaagg gcgagatcaa gcagaggctg aagctgaagg acggcggcca ctacgacgct     1020
gaggtcaaga ccacctacaa ggccaagaag cccgtgcagc tgcccggcgc ctacaacgtc     1080
aacatcaagt tggacatcac ctcccacaac gaggactaca ccatcgtgga acagtacgaa     1140
cgcgccgagg gccgccactc caccggcggc atggacgagc tgtacaagta agaattcgat     1200
aaacccgctg atcagcctcg actgtgcctt ctagttgcca gccatctgtt gtttgcccct     1260
cccccgtgcc ttccttgacc ctggaaggtg ccactcccac tgtcctttcc taataaaatg     1320
aggaaattgc atcgcattgt ctgagtaggt gtcattctat tctgggggt ggggtggggc      1380 aggacagcaa gggggaggat tgggaagaca atagcaggca tgctggggat gcggtgggct     1440
ctatggcttc tgaggcggaa agaaccagtg gcggtaatac ggttatccac agaatcaggg     1500
gataacgcag gaaagaacat gtgagcaaaa ggccagcaaa aggccaggaa ccgtaaaaag     1560
gccgcgttgc tggcgttttt ccataggctc cgcccccctg acgagcatca caaaaatcga     1620
cgctcaagtc agaggtggcg aaacccgaca ggactataaa gataccaggc gtttccccct     1680
ggaagctccc tcgtgcgctc tcctgttccg accctgccgc ttaccggata cctgtccgcc     1740
tttctccctt cgggaagcgt ggcgctttct catagctcac gctgtaggta tctcagttcg     1800
gtgtaggtcg ttcgctccaa gctgggctgt gtgcacgaac ccccgttca gcccgaccgc      1860 tgcgccttat ccggtaacta tcgtcttgag tccaacccgg taagacacga cttatcgcca     1920
ctggcagcag ccactggtaa caggattagc agagcgaggt atgtaggcgg tgctacagag     1980
ttcttgaagt ggtggcctaa ctacggctac actagaagga cagtatttgg tatctgcgct     2040
ctgctgaagc cagttacctt cggaaaaaga gttggtagct cttgatccgg caaacaaacc     2100
accgctggta gcggtggttt ttttgtttgc aagcagcaga ttacgcgcag aaaaaaagga     2160
tctcaagaag atcctttgat cttttctacg ggtctgacg ctcagtggaa cgaaaactca      2220
cgttaaggga ttttggtcat gagattatca aaaaggatct tcacctagat cctttaaat      2280 taaaaatgaa gttttaaatc aatctaaagt atatatgagt aacctgaggc tatggcaggg     2340
cctgccgccc cgacgttggc tgcgagccct gggccttcac ccgaacttgg ggggtggggt     2400
ggggaaaagg aagaaacgcg ggcgtattgg ccccaatggg gtctcggtgg ggtatcgaca     2460
gagtgccagc cctgggaccg aaccccgcgt ttatgaacaa cgacccaac ccgtgcgtt      2520 ttattctgtc tttttattgc cgtcatagcg cgggttcctt ccgtattgt ctccttccgt      2580 gtttcagtta gcctcccct agggtgggcg aagaactcca gcatgagatc cccgcgctgg     2640
aggatcatcc agccggcgtc ccggaaaacg attccgaagc ccaacctttc atagaaggcg     2700
gcggtggaat cgaaatctcg tgatggcagg ttggcgtcg cttggtcggt catttcgaac      2760
cccagagtcc cgctcagaag aactcgtcaa gaaggcgata gaaggcgatg cgctgcgaat     2820
cgggagcggc gataccgtaa agcacgagga agcggtcagc ccattcgccg ccaagctctt     2880
cagcaatatc acgggtagcc aacgctatgt cctgatagcg gtccgccaca cccagccggc     2940
```

```
cacagtcgat gaatccagaa aagcggccat tttccaccat gatattcggc aagcaggcat    3000
cgccatgggt cacgacgaga tcctcgccgt cgggcatgct cgccttgagc ctggcgaaca    3060
gttcggctgg cgcgagcccc tgatgctctt gatcatcctg atcgacaaga ccggcttcca    3120
tccgagtacg tgctcgctcg atgcgatgtt tcgcttggtg gtcgaatggg caggtagccg    3180
gatcaagcgt atgcagccgc cgcattgcat cagccatgat ggatactttc tcggcaggag    3240
caaggtgaga tgacaggaga tcctgccccg gcacttcgcc aatagcagc cagtcccttc     3300 ccgcttcagt gacaacgtcg agcacagctg cgcaaggaac gcccgtcgtg ccagccacg    3360 atagccgcgc tgcctcgtct tgcagttcat tcagggcacc ggacaggtcg gtcttgacaa    3420
aaagaaccgg gcgcccctgc gctgacagcc ggaacacggc ggcatcagag cagccgattg    3480
tctgttgtgc ccagtcatag ccgaatagcc tctccaccca agcggccgga gaacctgcgt    3540
gcaatccatc ttgttcaatc atgcgaaacg atcctcatcc tgtctcttga tcgatctttg    3600
caaaagccta ggcctccaaa aaagcctcct cactacttct ggaatagctc agaggccgag    3660
gcggcctcgg cctctgcata aataaaaaaa attagtcagc catggggcgg agaatgggcg    3720
gaactgggcg gagttagggg cgggatgggc ggagttaggg gcgggactat ggttgctgac    3780
taattgagat gcatgctttg catacttctg cctgctgggg agcctgggga cttccacac     3840 ctggttgctg actaattgag atgcatgctt tgcatacttc tgcctgctgg ggagcctggg    3900
gactttccac accctaactg acacacattc cacagctggt ctttccgcc tcaggactct     3960 tccttttca ataaatcaat ctaaagtata tatgagtaaa cttggtctga cagttaccaa     4020
tgcttaatca gtgaggcacc tatctcagcg atctgtctat ttcgttcatc catagttgcc    4080
tgactccccg tcgtgtagat aactacgata cgggagggct taccatctgg ccccagtgct    4140
gcaatgatac cgcgagaccc acgctcaccg gctccagatt tatcagcaat aaaccagcca    4200
gccggaaggg ccgagcgcag aagtggtcct gcaactttat ccgcctccat ccagtctatt    4260
aattgttgcc gggaagctag agtaagtagt tcgccagtta atagtttgcg caacgttgtt    4320
gccattgcta caggcatcgt ggtgtcacgc tcgtcgtttg gtatggcttc attcagctcc    4380
ggttcccaac gatcaaggcg agttacatga tcccccatgt tgtgcaaaaa agcggttagc    4440
tccttcggtc ctccgatcgt tgtcagaagt aagttggccg cagtgttatc actcatggtt    4500
atggcagcac tgcataattc tcttactgtc atgccatccg taagatgctt ttctgtgact    4560
ggtgagtact caaccaagtc attctgagaa tagtgtatgc ggcgaccgag ttgctcttgc    4620
ccggcgtcaa tacgggataa taccgcgcca catagcagaa ctttaaaagt gctcatcatt    4680
ggaaaacgtt cttcggggcg aaaactctca aggatcttac cgctgttgag atccagttcg    4740
atgtaaccca ctcgtgcacc caactgatct tcagcatctt ttactttcac cagcgtttct    4800
gggtgagcaa aaacaggaag gcaaaatgcc gcaaaaaagg gaataagggc gacacggaaa    4860
tgttgaatac tcatactctt cctttttcaa tattattgaa gcatttatca gggttattgt    4920
ctcatgagcg gatacatatt tgaatgtatt tagaaaaata acaaataggg gttccgcgc    4980 acatttcccc gaaaagtgcc acctgacgcg ccctgtagcg gcgcattaag cgcggcgggt    5040
gtggtggtta cgcgcagcgt gaccgctaca cttgccagcg ccctagcgcc cgctccttc    5100 gctttcttcc cttcctttct cgccacgttc gccggctttc cccgtcaagc tctaaatcgg    5160
gggctccctt tagggttccg atttagtgct ttacggcacc tcgaccccaa aaaacttgat    5220
tagggtgatg gttcacgtag tgggccatcg ccctgataga cggtttttcg ccctttgacg    5280
ttggagtcca cgttctttaa tagtggactc ttgttccaaa ctggaacaac actcaaccct    5340
```

```
atctcggtct attcttttga tttataaggg attttgccga tttcggccta ttggttaaaa    5400
aatgagctga tttaacaaaa atttaacgcg aattttaac                           5439
```

<210> SEQ ID NO 44
<211> LENGTH: 344
<212> TYPE: DNA
<213> ORGANISM: Homo sapiens

<400> SEQUENCE: 44

```
ggcagagtac agatttacac aaggcatccg tctcctggcc ccacataccc aactgctgta      60
aacccatacc ggcggccaag cagcctcaat ttgtgcatgc agggccacca ggctgcagtc     120
tcccttgggt cagggtcct ggttgcactc cgtgctttgc acaaagcagg ctctccattt     180
ttgttaaatg cacgaatagt gctaagctgg gaagttcttc ctgaggtcta acctctagct     240
gctcccccac agaagagtgc ctgcggccag tggccaccag gggtcgccgc agcacccagc     300
gctggagggc ggagcgggcg gcagaggatc ctatcacgaa ttct                      344
```

<210> SEQ ID NO 45
<211> LENGTH: 60
<212> TYPE: DNA
<213> ORGANISM: artificial sequence
<220> FEATURE:
<223> OTHER INFORMATION: synthetic construct

<400> SEQUENCE: 45

```
taggcgtgta cggtgggagg cctatataag cagagctcgt ttagtgaacc gtcagatcgc      60
```

<210> SEQ ID NO 46
<211> LENGTH: 711
<212> TYPE: DNA
<213> ORGANISM: artificial sequence
<220> FEATURE:
<223> OTHER INFORMATION: synthetic construct

<400> SEQUENCE: 46

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact cgaggacgg cggcgtggtg accgtgaccc aggactcctc cctgcaggac     360
ggcgagttca tctacaaggt gaagctgcgc ggcaccaact tcccctccga cggccccgta     420
atgcagaaga gaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg ccgccactc caccggcggc atggacgagc tgtacaagta a               711
```

<210> SEQ ID NO 47
<211> LENGTH: 236
<212> TYPE: PRT
<213> ORGANISM: Artificial sequence
<220> FEATURE:
<223> OTHER INFORMATION: synthetic construct

<400> SEQUENCE: 47

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 48
<211> LENGTH: 1258
<212> TYPE: DNA
<213> ORGANISM: Homo sapiens

<400> SEQUENCE: 48

```
tgcaaagatg gataaagttt taaacagaga ggaatctttg cagctaatgg accttctagg      60
tcttgaaagg agtgggaatt ggctccggtg cccgtcagtg ggcagagcgc acatcgccca     120
cagtccccga gaagttgggg ggaggggtcg gcaattgaac cggtgcctag agaaggtggc     180
gcggggtaaa ctgggaaagt gatgtcgtgt actggctccg ccttttttccc gagggtgggg    240
gagaaccgta tataagtgca gtagtcgccg tgaacgttct ttttcgcaac gggtttgccg     300
ccagaacaca ggtaagtgcc gtgtgtggtt cccgcgggcc tggcctcttt acgggttatg     360
gcccttgcgt gccttgaatt acttccactg gctgcagtac gtgattcttg atcccgagct     420
tcgggttgga agtgggtggg agagttcgag gccttgcgct taaggagccc cttcgcctcg     480
tgcttgagtt gaggcctggc ctgggcgctg gggccgccgc gtgcgaatct ggtgcacctt     540
tcgcgcctgt ctcgctgctt tcgataagtc tctagccatt taaaattttt gatgacctgc     600
tgcgacgctt tttttctggc aagatagtct tgtaaatgcg ggccaagatc tgcacactgg     660
tatttcggtt tttggggccg cgggcggcga cggggcccgt gcgtcccagc gcacatgttc     720
```

-continued

```
ggcgaggcgg ggcctgcgag cgcggccacc gagaatcgga cggggggtagt ctcaagctgg      780 ccggcctgct ctggtgcctg gcctcgcgcc gccgtgtatc gccccgccct gggcggcaag      840
gctggcccgg tcggcaccag ttgcgtgagc ggaaagatgg ccgcttcccg gccctgctgc      900
agggagctca aaatggagga cgcggcgctc gggagagcgg gcgggtgagt cacccacaca      960
aaggaaaagg gcctttccgt cctcagccgt cgcttcatgt gactccacgg agtaccgggc     1020
gccgtccagg cacctcgatt agttctcgag cttttggagt acgtcgtctt taggttgggg     1080
ggaggggttt tatgcgatgg agtttcccca cactgagtgg gtggagactg aagttaggcc     1140
agcttggcac ttgatgtaat tctccttgga atttgcccctt tttgagtttg gatcttggtt    1200
cattctcaag cctcagacag tggttcaaag tttttttctt ccatttcagg tgtcgtga       1258
```

<210> SEQ ID NO 49
<211> LENGTH: 177
<212> TYPE: DNA
<213> ORGANISM: Artificial sequence
<220> FEATURE:
<223> OTHER INFORMATION: synthetic construct

<400> SEQUENCE: 49

```
ggttccggac gggctgacgc attggacgat tttgatctgg atatgctggg aagtgacgcc       60
ctcgatgatt ttgaccttga catgcttggt tcggatgccc ttgatgactt tgacctcgac      120
atgctcggca gtgacgccct tgatgatttc gacctggaca tgctgattaa ctctaga       177
```

<210> SEQ ID NO 50
<211> LENGTH: 59
<212> TYPE: PRT
<213> ORGANISM: Artificial sequence
<220> FEATURE:
<223> OTHER INFORMATION: synthetic construct

<400> SEQUENCE: 50

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn Ser Arg
    50                  55

<210> SEQ ID NO 51
<211> LENGTH: 63
<212> TYPE: DNA
<213> ORGANISM: Artificial sequence
<220> FEATURE:
<223> OTHER INFORMATION: synthetic construct

<400> SEQUENCE: 51

```
ggcagtggag agggcagagg aagtctgcta acatgcggtg acgtcgagga gaatcctggc       60
cca                                                                    63
```

<210> SEQ ID NO 52
<211> LENGTH: 21
<212> TYPE: PRT
<213> ORGANISM: Artificial sequence
<220> FEATURE:
<223> OTHER INFORMATION: synthetic construct

<400> SEQUENCE: 52

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 53
<211> LENGTH: 717
<212> TYPE: DNA
<213> ORGANISM: Artificial sequence
<220> FEATURE:
<223> OTHER INFORMATION: synthetic construct

<400> SEQUENCE: 53
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact ctcggcatgg acgagctgta caagtaa       717

<210> SEQ ID NO 54
<211> LENGTH: 238
<212> TYPE: PRT
<213> ORGANISM: Artificial sequence
<220> FEATURE:
<223> OTHER INFORMATION: synthetic construct

<400> SEQUENCE: 54

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly

|  |  |  |  | 145 |  |  |  | 150 |  |  |  | 155 |  |  |  | 160 |
|---|---|---|---|---|---|---|---|---|---|---|---|---|---|---|---|---|
| Ile | Lys | Val | Asn | Phe | Lys | Ile | Arg | His | Asn | Ile | Glu | Asp | Gly | Ser | Val |  |
|  |  |  |  |  | 165 |  |  |  | 170 |  |  |  | 175 |  |  |  |
| Gln | Leu | Ala | Asp | His | Tyr | Gln | Gln | Asn | Thr | Pro | Ile | Gly | Asp | Gly | Pro |  |
|  |  |  | 180 |  |  |  |  | 185 |  |  |  |  | 190 |  |  |  |
| Val | Leu | Leu | Pro | Asp | Asn | His | Tyr | Leu | Ser | Thr | Gln | Ser | Ala | Leu | Ser |  |
|  |  | 195 |  |  |  |  | 200 |  |  |  | 205 |  |  |  |  |  |
| Lys | Asp | Pro | Asn | Glu | Lys | Arg | Asp | His | Met | Val | Leu | Leu | Glu | Phe | Val |  |
|  | 210 |  |  |  |  | 215 |  |  |  | 220 |  |  |  |  |  |  |
| Thr | Ala | Ala | Gly | Ile | Thr | Leu | Gly | Met | Asp | Glu | Leu | Tyr | Lys |  |  |  |
| 225 |  |  |  | 230 |  |  |  | 235 |  |  |  |  |  |  |  |  |

<210> SEQ ID NO 55
<211> LENGTH: 11553
<212> TYPE: DNA
<213> ORGANISM: Artificial sequence
<220> FEATURE:
<223> OTHER INFORMATION: synthetic construct

<400> SEQUENCE: 55

```
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa atttaagct acaacaaggc aaggcttgac cgacaattgc atgaagaatc    180
tgcttagggt taggcgtttt cgctgcttc gcgatgtacg ggccagatat acgcgttgac    240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca atagggactt   420
tccattgacg tcaatgggtg gagtatttac ggtaaactgc ccacttggca gtacatcaag   480
tgtatcatat gccaagtacg ccccctattg acgtcaatga cggtaaatgg cccgcctggc   540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagacccttt tagtcagtgt ggaaaatctc tagcagtggc  1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa  1140
ttttgactag cggaggctag aaggagagag atggtgcga gagcgtcagt attaagcggg   1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
```

```
agggacaatt ggagaagtga attatataaa tataaagtag taaaaattga accattagga       1620
gtagcaccca ccaaggcaaa gagaagagtg gtgcagagag aaaaaagagc agtgggaata       1680
ggagctttgt tccttgggtt cttgggagca gcaggaagca ctatgggcgc agcgtcaatg       1740
acgctgacgg tacaggccag acaattattg tctggtatag tgcagcagca gaacaatttg       1800
ctgagggcta ttgaggcgca acagcatctg ttgcaactca cagtctgggg catcaagcag       1860
ctccaggcaa gaatcctggc tgtggaaaga tacctaaagg atcaacagct cctgggggatt      1920
tggggttgct ctggaaaact catttgcacc actgctgtgc cttggaatgc tagttggagt       1980
aataaatctc tggaacagat ttggaatcac acgacctgga tggagtggga cagagaaatt       2040
aacaattaca caagcttaat acactcctta attgaagaat cgcaaaacca gcaagaaaag       2100
aatgaacaag aattattgga attagataaa tgggcaagtt tgtggaattg gtttaacata       2160
acaaattggc tgtggtatat aaaattattc ataatgatag taggaggctt ggtaggttta       2220
agaatagttt ttgctgtact ttctatagtg aatagagtta ggcagggata ttcaccatta       2280
tcgtttcaga cccacctccc aaccccgagg ggacccgaca ggcccgaagg aatagaagaa       2340
gaaggtggag agagagacag agacagatcc attcgattag tgaacggatc ggcactgcgt       2400
gcgccaattc tgcagacaaa tggcagtatt catccacaat tttaaaagaa aaggggggat       2460
tggggggtac agtgcagggg aaagaatagt agacataata gcaacagaca tacaaactaa       2520
agaattacaa aaacaaatta caaaaattca aaatttccgg gtttattaca gggacagcag       2580
agatccagtt tggttaatta atgcaaagat ggataaagtt ttaaacagag aggaatcttt       2640
gcagctaatg gaccttctag gtcttgaaag gagtgggaat tggctccggt gcccgtcagt       2700
gggcagagcg cacatcgccc acagtccccg agaagttggg gggagggtc ggcaattgaa       2760
ccggtgccta gagaaggtgg cgcggggtaa actgggaaag tgatgtcgtg tactggctcc       2820
gcctttttcc cgagggtggg ggagaaccgt atataagtgc agtagtcgcc gtgaacgttc       2880
tttttcgcaa cgggttttgcc gccagaacac aggtaagtgc cgtgtgtggt cccgcgggc       2940
ctggcctctt tacgggttat ggcccttgcg tgccttgaat tacttccact ggctgcagta       3000
cgtgattctt gatcccgagc ttcgggttgg aagtgggtgg gagagttcga ggccttgcgc       3060
ttaaggagcc ccttcgcctc gtgcttgagt tgaggcctgg cctgggcgct ggggccgccg       3120
cgtgcgaatc tggtggcacc ttcgcgcctg tctcgctgct ttcgataagt ctctagccat       3180
ttaaaatttt tgatgacctg ctgcgacgct ttttttctgg caagatagtc ttgtaaatgc       3240
gggccaagat ctgcacactg gtatttcggt ttttggggcc gcgggcggcg acggggcccg       3300
tgcgtcccag cgcacatgtt cggcgaggcg gggcctgcga gcgcggccac cgagaatcgg       3360
acggggtag tctcaagctg gccggcctgc tctggtgcct ggcctcgcgc cgccgtgtat        3420
cgccccgccc tgggcggcaa ggctggcccg gtcggcacca gttgcgtgag cggaaagatg       3480
gccgcttccc ggccctgctg cagggagctc aaaatggagg acgcggcgct cgggagagcg       3540
ggcgggtgag tcacccacac aaaggaaaag ggcctttccg tcctcagccg tcgcttcatg       3600
tgactccacg gagtaccggg cgccgtccag gcacctcgat tagttctcga gcttttggag       3660
tacgtcgtct ttaggttggg gggagggggtt ttatgcgatg gagtttcccc acactgagtg      3720
ggtggagact gaagttaggc cagcttggca cttgatgtaa ttctccttgg aatttgccct       3780
ttttgagttt ggatcttggt tcattctcaa gcctcagaca gtggttcaaa gttttttttct      3840
tccatttcag gtgtcgtgac gtacggccac catgtcgcgg acccggctcc cttcccacc        3900
cgcacccagc ccagcgtttt cggccgactc gttctcagac ctgcttaggc agttcgaccc       3960
```

```
ctcactgttt aacacatcgt tgttcgactc ccttcctccg tttgggcgc accatacgga      4020 ggcggccacc ggggagtggg atgaggtgca gtcgggattg agagctgcgg atgcaccacc      4080
cccaaccatg cgggtggccg tcaccgctgc ccgaccgccg agggcgaagc ccgcaccaag      4140
gcggagggca gcgcaaccgt ccgacgcaag ccccgcagcg caagtagatt tgagaacttt      4200
gggatattca cagcagcagc aggaaaagat caagcccaaa gtgaggtcga cagtcgcgca      4260
gcatcacgaa gcgctggtgg gtcatgggtt tacacatgcc cacatcgtag ccttgtcgca      4320
gcaccctgca gcccttggca cggtcgccgt caagtaccag gacatgattg cggcgttgcc      4380
ggaagccaca catgaggcga tcgtcggtgt ggggaaacag tggagcggag cccgagcgct      4440
tgaggccctg ttgacggtcg cgggagagct gagagggcct ccccttcagc tggacacggg      4500
ccagttgctg aagatcgcga agcggggagg agtcacggcg gtcgaggcgg tgcacgcgtg      4560
gcgcaatgcg ctcacgggag caccccctcaa cctgaccgag acggtacatg aaacgcatgg      4620
cacggcgtct caactcacgc ctgagcaggt agtggctatt gcatccaata tcggggggcag      4680 acccgcactg gagtcaatcg tggcccagct ttcgaggccg gaccccgcgc tggccgcact      4740
cactaatgat catcttgtag cgctggcctg cctcggcgga cgacccgcct tggatgcggt      4800
gaagaagggg ctcccgcacg cgcctgcatt gattaagcgg accaacagaa ggattcccga      4860
gaggacatca catcgagtgg cagatcacgc gcaagtggtc cgcgtgctcg gattcttcca      4920
gtgtcactcc caccccgcac aagcgttcga tgacgccatg actcaatttg gtatgtcgag      4980
acacggactg ctgcagctct ttcgtagagt cggtgtcaca gaactcgagg cccgctcggg      5040
cacactgcct cccgcctccc agcggtggga caggattctc caagcgagcg gtatgaaacg      5100
cgcgaagcct tcacctacgt caactcagac acctgaccag gcgagccttc atgcgttcgc      5160
agactcgctg gagagggatt tggacgcgcc ctcgcccatg catgaagggg accaaactcg      5220
cgcgtcagct agccccaaga agaagagaaa ggtggaggcc agcggttccg gacgggctga      5280
cgcattggac gattttgatc tggatatgct gggaagtgac gccctcgatg attttgacct      5340
tgacatgctt ggttcggatg cccttgatga ctttgacctc gacatgctcg gcagtgacgc      5400
ccttgatgat ttcgacctgg acatgctgat taactctaga ggcagtggag agggcagagg      5460
aagtctgcta acatgcggtg acgtcgagga gaatcctggc ccagtgagca agggcgagga      5520
gctgttcacc ggggtggtgc ccatcctggt cgagctggac ggcgacgtaa acggccacaa      5580
gttcagcgtg tccggcgagg gcgagggcga tgccacctac ggcaagctga ccctgaagtt      5640
catctgcacc accggcaagc tgcccgtgcc ctggcccacc ctcgtgacca ccctgaccta      5700
cggcgtgcag tgcttcagcc gctaccccga ccacatgaag cagcacgact tcttcaagtc      5760
cgccatgccc gaaggctacg tccaggagcg caccatcttc ttcaaggacg acggcaacta      5820
caagacccgc gccgaggtga agttcgaggg cgacaccctg gtgaaccgca tcgagctgaa      5880
gggcatcgac ttcaaggagg acggcaacat cctggggcac aagctggagt acaactacaa      5940
cagccacaac gtctatatca tggccgacaa gcagaagaac ggcatcaagg tgaacttcaa      6000
gatccgccac aacatcgagg acggcagcgt gcagctcgcc gaccactacc agcagaacac      6060
ccccatcggc gacggccccg tgctgctgcc cgacaaccac tacctgagca cccagtccgc      6120
cctgagcaaa gaccccaacg agaagcgcga tcacatggtc ctgctggagt tcgtgaccgc      6180
cgccgggatc actctcggca tggacgagct gtacaagtaa gaattcgata tcaagcttat      6240
cgataatcaa cctctggatt acaaaatttg tgaaagattg actggtattc ttaactatgt      6300
```

| | |
|---|---|
| tgctcctttt acgctatgtg gatacgctgc tttaatgcct ttgtatcatg ctattgcttc | 6360 |
| ccgtatggct ttcattttct cctccttgta taaatcctgg ttgctgtctc tttatgagga | 6420 |
| gttgtggccc gttgtcaggc aacgtggcgt ggtgtgcact gtgtttgctg acgcaacccc | 6480 |
| cactggttgg ggcattgcca ccacctgtca gctccttttcc gggactttcg ctttccccct | 6540 |
| ccctattgcc acggcggaac tcatcgccgc ctgccttgcc cgctgctgga caggggctcg | 6600 |
| gctgttgggc actgacaatt ccgtggtgtt gtcggggaaa tcatcgtcct ttccttggct | 6660 |
| gctcgcctgt gttgccacct ggattctgcg cgggacgtcc ttctgctacg tcccttcggc | 6720 |
| cctcaatcca gcggaccttc cttcccgcgg cctgctgccg gctctgcggc ctcttccgcg | 6780 |
| tcttcgcctt cgccctcaga cgagtcggat ctcccttttgg gccgcctccc cgcatcgata | 6840 |
| ccgtcgacct cgagacctag aaaaacatgg agcaatcaca agtagcaata cagcagctac | 6900 |
| caatgctgat tgtgcctggc tagaagcaca agaggaggag gaggtgggtt ttccagtcac | 6960 |
| acctcaggta cctttaagac caatgactta caaggcagct gtagatctta gccacttttt | 7020 |
| aaaagaaaag gggggactgg aagggctaat tcactcccaa cgaagacaag atatccttga | 7080 |
| tctgtggatc taccacacac aaggctactt ccctgattgg cagaactaca caccagggcc | 7140 |
| agggatcaga tatccactga cctttggatg gtgctacaag ctagtaccag ttgagcaaga | 7200 |
| gaaggtagaa gaagccaatg aaggagagaa caccgcttgt tacaccctg tgagcctgca | 7260 |
| tgggatggat gacccggaga gagaagtatt agagtggagg tttgacagcc gcctagcatt | 7320 |
| tcatcacatg gcccgagagc tgcatccgga ctgtactggg tctctctggt tagaccagat | 7380 |
| ctgagcctgg gagctctctg gctaactagg gaacccactg cttaagcctc aataaagctt | 7440 |
| gccttgagtg cttcaagtag tgtgtgcccg tctgttgtgt gactctggta actagagatc | 7500 |
| cctcagaccc ttttagtcag tgtggaaaat ctctagcagg gcccgtttaa acccgctgat | 7560 |
| cagcctcgac tgtgccttct agttgccagc catctgttgt ttgcccctcc cccgtgcctt | 7620 |
| ccttgaccct ggaaggtgcc actcccactg tcctttccta ataaaatgag gaaattgcat | 7680 |
| cgcattgtct gagtaggtgt cattctattc tggggggtgg ggtggggcag gacagcaagg | 7740 |
| gggaggattg ggaagacaat agcaggcatg ctggggatgc ggtgggctct atggcttctg | 7800 |
| aggcggaaag aaccagctgg ggctctaggg ggtatcccca cgcgccctgt agcggcgcat | 7860 |
| taagcgcggc gggtgtggtg gttacgcgca gcgtgaccgc tacacttgcc agcgccctag | 7920 |
| cgcccgctcc tttcgctttc ttcccttcct ttctcgccac gttcgccggc tttccccgtc | 7980 |
| aagctctaaa tcggggggctc cctttagggt tccgatttag tgctttacgg cacctcgacc | 8040 |
| ccaaaaaact tgattagggt gatggttcac gtagtgggcc atcgccctga tagacggttt | 8100 |
| ttcgcccttt gacgttggag tccacgttct ttaatagtgg actcttgttc caaactggaa | 8160 |
| caacactcaa ccctatctcg gtctattctt ttgatttata agggattttg ccgatttcgg | 8220 |
| cctattggtt aaaaaatgag ctgatttaac aaaaatttaa cgcgaattaa ttctgtggaa | 8280 |
| tgtgtgtcag ttagggtgtg gaaagtcccc aggctcccca gcaggcagaa gtatgcaaag | 8340 |
| catgcatctc aattagtcag caaccaggtg tggaaagtcc ccaggctccc cagcaggcag | 8400 |
| aagtatgcaa agcatgcatc tcaattagtc agcaaccata gtcccgcccc taactccgcc | 8460 |
| catcccgccc ctaactccgc ccagttccgc ccattctccg ccccatggct gactaatttt | 8520 |
| ttttatttat gcagaggccg aggccgcctc tgcctctgag ctattccaga agtagtgagg | 8580 |
| aggctttttt ggaggcctag gcttttgcaa aaagctcccg ggagcttgta tatccatttt | 8640 |
| cggatctgat cagcacgtgt tgacaattaa tcatcggcat agtatatcgg catagtataa | 8700 |

```
tacgacaagg tgaggaacta aaccatggcc aagttgacca gtgccgttcc ggtgctcacc   8760
gcgcgcgacg tcgccggagc ggtcgagttc tggaccgacc ggctcgggtt ctcccgggac   8820
ttcgtggagg acgacttcgc cggtgtggtc cgggacgacg tgaccctgtt catcagcgcg   8880
gtccaggacc aggtggtgcc ggacaacacc ctggcctggg tgtgggtgcg cggcctggac   8940
gagctgtacg ccgagtggtc ggaggtcgtg tccacgaact tccgggacgc ctccgggccg   9000
gccatgaccg agatcggcga gcagccgtgg gggcgggagt cgccctgcg cgacccggcc    9060 ggcaactgcg tgcacttcgt ggccgaggag caggactgac acgtgctacg agatttcgat   9120
tccaccgccg ccttctatga aaggttgggc ttcggaatcg ttttccggga cgccggctgg   9180
atgatcctcc agcgcgggga tctcatgctg gagttcttcg cccaccccaa cttgtttatt   9240
gcagcttata atggttacaa ataaagcaat agcatcacaa atttcacaaa taaagcattt   9300
ttttcactgc attctagttg tggtttgtcc aaactcatca atgtatctta tcatgtctgt   9360
ataccgtcga cctctagcta gagcttggcg taatcatggt catagctgtt tcctgtgtga   9420
aattgttatc cgctcacaat tccacacaac atacgagccg aagcataaa gtgtaaagcc    9480 tggggtgcct aatgagtgag ctaactcaca ttaattgcgt tgcgctcact gcccgctttc   9540
cagtcgggaa acctgtcgtg ccagctgcat taatgaatcg gccaacgcgc ggggagaggc   9600
ggtttgcgta ttgggcgctc ttccgcttcc tcgctcactg actcgctgcg ctcggtcgtt   9660
cggctgcggc gagcggtatc agctcactca aaggcggtaa tacggttatc cacagaatca   9720
ggggataacg caggaaagaa catgtgagca aaaggccagc aaaaggccag gaaccgtaaa   9780
aaggccgcgt tgctggcgtt tttccatagg ctccgccccc ctgacgagca tcacaaaaat   9840
cgacgctcaa gtcagaggtg gcgaaacccg acaggactat aaagatacca ggcgtttccc   9900
cctggaagct ccctcgtgcg ctctcctgtt ccgaccctgc cgcttaccgg atacctgtcc   9960
gcctttctcc cttcgggaag cgtggcgctt tctcatagct cacgctgtag gtatctcagt  10020
tcggtgtagg tcgttcgctc caagctgggc tgtgtgcacg aaccccccgt tcagcccgac  10080
cgctgcgcct tatccggtaa ctatcgtctt gagtccaacc cggtaagaca cgacttatcg  10140
ccactggcag cagccactgg taacaggatt agcagagcga ggtatgtagg cggtgctaca  10200
gagttcttga agtggtggcc taactacggc tacactagaa gaacagtatt tggtatctgc  10260
gctctgctga agccagttac cttcggaaaa agagttggta gctcttgatc cggcaaacaa  10320
accaccgctg gtagcggtgg tttttttgtt tgcaagcagc agattacgcg cagaaaaaaa  10380
ggatctcaag aagatccttt gatcttttct acggggtctg acgctcagtg gaacgaaaac  10440
tcacgttaag ggattttggt catgagatta tcaaaaagga tcttcaccta gatccttta   10500 aattaaaaat gaagttttaa atcaatctaa agtatatatg agtaaacttg gtctgacagt  10560
taccaatgct taatcagtga ggcacctatc tcagcgatct gtctatttcg ttcatccata  10620
gttgcctgac tccccgtcgt gtagataact acgatacggg agggcttacc atctggcccc  10680
agtgctgcaa tgataccgcg agacccacgc tcaccggctc cagatttatc agcaataaac  10740
cagccagccg gaagggccga gcgcagaagt ggtcctgcaa ctttatccgc ctccatccag  10800
tctattaatt gttgccggga agctagagta agtagttcgc cagttaatag tttgcgcaac  10860
gttgttgcca ttgctacagg catcgtggtg tcacgctcgt cgtttggtat ggcttcattc  10920
agctccggtt cccaacgatc aaggcgagtt acatgatccc ccatgttgtg caaaaaagcg  10980
gttagctcct tcggtcctcc gatcgttgtc agaagtaagt tggccgcagt gttatcactc  11040
```

```
atggttatgg cagcactgca taattctctt actgtcatgc catccgtaag atgctttct    11100 gtgactggtg agtactcaac caagtcattc tgagaatagt gtatgcggcg accgagttgc    11160
tcttgcccgg cgtcaatacg ggataatacc gcgccacata gcagaacttt aaaagtgctc    11220
atcattggaa aacgttcttc ggggcgaaaa ctctcaagga tcttaccgct gttgagatcc    11280
agttcgatgt aacccactcg tgcacccaac tgatcttcag catcttttac tttcaccagc    11340
gtttctgggt gagcaaaaac aggaaggcaa aatgccgcaa aaagggaat aagggcgaca    11400 cggaaatgtt gaatactcat actcttcctt tttcaatatt attgaagcat ttatcagggt    11460
tattgtctca tgagcggata catatttgaa tgtatttaga aaataaaca aatagggtt    11520 ccgcgcacat ttccccgaaa agtgccacct gac                                 11553

<210> SEQ ID NO 56
<211> LENGTH: 102
<212> TYPE: DNA
<213> ORGANISM: Artificial sequence
<220> FEATURE:
<223> OTHER INFORMATION: synthetic construct

<400> SEQUENCE: 56
ctgaccccag agcaggtcgt ggcaatcgcc tccaacattg gcgggaaaca ggcactcgag        60
actgtccagc gcctgcttcc cgtgctgtgc caagcgcacg ga                          102

<210> SEQ ID NO 57
<211> LENGTH: 34
<212> TYPE: PRT
<213> ORGANISM: Artificial sequence
<220> FEATURE:
<223> OTHER INFORMATION: synthetic construct

<400> SEQUENCE: 57

Leu Thr Pro Glu Gln Val Val Ala Ile Ala Ser Asn Ile Gly Gly Lys
1               5                   10                  15
Gln Ala Leu Glu Thr Val Gln Arg Leu Leu Pro Val Leu Cys Gln Ala
            20                  25                  30
His Gly

<210> SEQ ID NO 58
<211> LENGTH: 102
<212> TYPE: DNA
<213> ORGANISM: Artificial sequence
<220> FEATURE:
<223> OTHER INFORMATION: synthetic construct

<400> SEQUENCE: 58
ctgaccccag agcaggtcgt ggccattgcc tcgaatggag ggggcaaaca ggcgttggaa        60
accgtacaac gattgctgcc ggtgctgtgc caagcgcacg gc                          102

<210> SEQ ID NO 59
<211> LENGTH: 34
<212> TYPE: PRT
<213> ORGANISM: Artificial sequence
<220> FEATURE:
<223> OTHER INFORMATION: synthetic construct

<400> SEQUENCE: 59

Leu Thr Pro Glu Gln Val Val Ala Ile Ala Ser Asn Gly Gly Gly Lys
1               5                   10                  15
Gln Ala Leu Glu Thr Val Gln Arg Leu Leu Pro Val Leu Cys Gln Ala
            20                  25                  30
```

<210> SEQ ID NO 60
<211> LENGTH: 102
<212> TYPE: DNA
<213> ORGANISM: Artificial sequence
<220> FEATURE:
<223> OTHER INFORMATION: synthetic construct

<400> SEQUENCE: 60
ttgaccccag agcaggtcgt ggcgatcgca agccacgacg gaggaaagca agccttggaa    60
acagtacaga ggctgttgcc tgtgctgtgc aagcgcacg gg    102

<210> SEQ ID NO 61
<211> LENGTH: 34
<212> TYPE: PRT
<213> ORGANISM: Artificial sequence
<220> FEATURE:
<223> OTHER INFORMATION: synthetic construct

<400> SEQUENCE: 61

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 62
<211> LENGTH: 102
<212> TYPE: DNA
<213> ORGANISM: Artificial sequence
<220> FEATURE:
<223> OTHER INFORMATION: synthetic construct

<400> SEQUENCE: 62
cttaccccag agcaggtcgt ggcaatcgcg agcaataacg gcggaaaaca ggctttggaa    60
acggtgcaga ggctccttcc agtgctgtgc aagcgcacg gg    102

<210> SEQ ID NO 63
<211> LENGTH: 34
<212> TYPE: PRT
<213> ORGANISM: Artificial sequence
<220> FEATURE:
<223> OTHER INFORMATION: synthetic construct

<400> SEQUENCE: 63

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 64
<211> LENGTH: 102
<212> TYPE: DNA
<213> ORGANISM: Artificial sequence
<220> FEATURE:
<220> FEATURE:
<221> NAME/KEY: misc_feature
<222> LOCATION: (34)..(34)
<223> OTHER INFORMATION: n is a or c
<220> FEATURE:

```
<221> NAME/KEY: misc_feature
<222> LOCATION: (36)..(36)
<223> OTHER INFORMATION: n is c or t
<220> FEATURE:
<221> NAME/KEY: misc_feature
<222> LOCATION: (37)..(37)
<223> OTHER INFORMATION: n is a or g
<220> FEATURE:
<221> NAME/KEY: misc_feature
<222> LOCATION: (38)..(38)
<223> OTHER INFORMATION: n is t, g or a
<220> FEATURE:
<221> NAME/KEY: misc_feature
<222> LOCATION: (39)..(39)
<223> OTHER INFORMATION: n is t, a or c

<400> SEQUENCE: 64
ctgaccccag agcaggtcgt ggcaatcgcc tccnannnng gcgggaaaca ggcactcgag    60
actgtccagc gcctgcttcc cgtgctgtgc caagcgcacg ga                     102

<210> SEQ ID NO 65
<211> LENGTH: 34
<212> TYPE: PRT
<213> ORGANISM: Artificial sequence
<220> FEATURE:
<223> OTHER INFORMATION: synthetic construct
<220> FEATURE:
<221> NAME/KEY: MISC_FEATURE
<222> LOCATION: (12)..(12)
<223> OTHER INFORMATION: X is N or H
<220> FEATURE:
<221> NAME/KEY: MISC_FEATURE
<222> LOCATION: (13)..(13)
<223> OTHER INFORMATION: X is I, G or N when X at position 12 is N; and
     X is D when X at position 12 is H.

<400> SEQUENCE: 65

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 66
<211> LENGTH: 782
<212> TYPE: PRT
<213> ORGANISM: Artificial sequence
<220> FEATURE:
<223> OTHER INFORMATION: synthetic construct
<220> FEATURE:
<221> NAME/KEY: MISC_FEATURE
<222> LOCATION: (266)..(266)
<223> OTHER INFORMATION: X can be N or H
<220> FEATURE:
<221> NAME/KEY: MISC_FEATURE
<222> LOCATION: (267)..(267)
<223> OTHER INFORMATION: X is I, G or N when X at position 266 is N; and
     X is D when X at position 266 is H.

<400> SEQUENCE: 66

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60
```

-continued

```
Ala Ala Asp Ala Pro Pro Thr Met Arg Val Ala Val Thr Ala Ala
 65                  70                  75                  80

Arg Pro Pro Arg Ala Lys Pro Ala Pro Arg Arg Ala Ala Gln Pro
                 85                  90                  95

Ser Asp Ala Ser Pro Ala Ala Gln Val Asp Leu Arg Thr Leu Gly Tyr
            100                 105                 110

Ser Gln Gln Gln Glu Lys Ile Lys Pro Lys Val Arg Ser Thr Val
            115                 120                 125

Ala Gln His His Glu Ala Leu Val Gly His Gly Phe Thr His Ala His
            130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Val Thr Ala Val
210                 215                 220

Glu Ala Val His Ala Trp Arg Asn Ala Leu Thr Gly Ala Pro Leu Asn
225                 230                 235                 240

Leu Thr Glu Thr Val His Glu Thr His Gly Thr Ala Ser Gln Leu Thr
                245                 250                 255

Pro Glu Gln Val Val Ala Ile Ala Ser Xaa Xaa Gly Gly Arg Pro Ala
            260                 265                 270

Leu Glu Ser Ile Val Ala Gln Leu Ser Arg Pro Asp Pro Ala Leu Ala
            275                 280                 285

Ala Leu Thr Asn Asp His Leu Val Ala Leu Ala Cys Leu Gly Gly Arg
            290                 295                 300

Pro Ala Leu Asp Ala Val Lys Lys Gly Leu Pro His Ala Pro Ala Leu
305                 310                 315                 320

Ile Lys Arg Thr Asn Arg Arg Ile Pro Glu Arg Thr Ser His Arg Val
                325                 330                 335

Ala Asp His Ala Gln Val Val Arg Val Leu Gly Phe Phe Gln Cys His
                340                 345                 350

Ser His Pro Ala Gln Ala Phe Asp Asp Ala Met Thr Gln Phe Gly Met
            355                 360                 365

Ser Arg His Gly Leu Leu Gln Leu Phe Arg Arg Val Gly Val Thr Glu
            370                 375                 380

Leu Glu Ala Arg Ser Gly Thr Leu Pro Pro Ala Ser Gln Arg Trp Asp
385                 390                 395                 400

Arg Ile Leu Gln Ala Ser Gly Met Lys Arg Ala Lys Pro Ser Pro Thr
                405                 410                 415

Ser Thr Gln Thr Pro Asp Gln Ala Ser Leu His Ala Phe Ala Asp Ser
            420                 425                 430

Leu Glu Arg Asp Leu Asp Ala Pro Ser Pro Met His Glu Gly Asp Gln
            435                 440                 445

Thr Arg Ala Ser Ala Ser Pro Lys Lys Arg Lys Val Glu Ala Ser
            450                 455                 460

Gly Ser Gly Arg Ala Asp Ala Leu Asp Asp Phe Asp Leu Asp Met Leu
465                 470                 475                 480
```

Gly Ser Asp Ala Leu Asp Asp Phe Asp Leu Asp Met Leu Gly Ser Asp
            485                 490                 495

Ala Leu Asp Asp Phe Asp Leu Asp Met Leu Gly Ser Ala Leu Asp
        500                 505                 510

Asp Phe Asp Leu Asp Met Leu Ile Asn Ser Arg Gly Ser Gly Glu Gly
        515                 520                 525

Arg Gly Ser Leu Leu Thr Cys Gly Asp Val Glu Glu Asn Pro Gly Pro
    530                 535                 540

Val Ser Lys Gly Glu Glu Leu Phe Thr Gly Val Pro Ile Leu Val
545                 550                 555                 560

Glu Leu Asp Gly Asp Val Asn Gly His Lys Phe Ser Val Ser Gly Glu
                565                 570                 575

Gly Glu Gly Asp Ala Thr Tyr Gly Lys Leu Thr Leu Lys Phe Ile Cys
            580                 585                 590

Thr Thr Gly Lys Leu Pro Val Pro Trp Pro Thr Leu Val Thr Thr Leu
        595                 600                 605

Thr Tyr Gly Val Gln Cys Phe Ser Arg Tyr Pro Asp His Met Lys Gln
    610                 615                 620

His Asp Phe Phe Lys Ser Ala Met Pro Glu Gly Tyr Val Gln Glu Arg
625                 630                 635                 640

Thr Ile Phe Phe Lys Asp Asp Gly Asn Tyr Lys Thr Arg Ala Glu Val
                645                 650                 655

Lys Phe Glu Gly Asp Thr Leu Val Asn Arg Ile Glu Leu Lys Gly Ile
            660                 665                 670

Asp Phe Lys Glu Asp Gly Asn Ile Leu Gly His Lys Leu Glu Tyr Asn
        675                 680                 685

Tyr Asn Ser His Asn Val Tyr Ile Met Ala Asp Lys Gln Lys Asn Gly
    690                 695                 700

Ile Lys Val Asn Phe Lys Ile Arg His Asn Ile Glu Asp Gly Ser Val
705                 710                 715                 720

Gln Leu Ala Asp His Tyr Gln Gln Asn Thr Pro Ile Gly Asp Gly Pro
                725                 730                 735

Val Leu Leu Pro Asp Asn His Tyr Leu Ser Thr Gln Ser Ala Leu Ser
            740                 745                 750

Lys Asp Pro Asn Glu Lys Arg Asp His Met Val Leu Leu Glu Phe Val
        755                 760                 765

Thr Ala Ala Gly Ile Thr Leu Gly Met Asp Glu Leu Tyr Lys
    770                 775                 780

<210> SEQ ID NO 67
<211> LENGTH: 1312
<212> TYPE: DNA
<213> ORGANISM: Artificial sequence
<220> FEATURE:
<223> OTHER INFORMATION: synthetic construct

<400> SEQUENCE: 67
gggcggtgca cgcgtggcgc aatgcgctca cgggagcacc cctcaacctg accccagagc    60
aagtcgtggc aatcgcgagc cacgacggcg aaaacaggc tttggaaacg gtgcagaggc    120
tccttccagt gctgtgccaa gcgcacggac tcacccccaga gcaggtcgtg caatcgcct    180 cccacgacgg cgggaaacag gcactcgaga ctgtccagcg cctgcttccc gtgctgtgcc    240
aagcgcacgg cctcaccccca gagcaggtcg tggcaatcgc gagccacgac ggcgaaaaac    300
aggctttgga aacggtgcag aggctccttc cagtgctgtg ccaagcgcac ggattaaccc    360

-continued

```
cagagcaggt cgtggcaatc gcgagcaatg gaggcggaaa acaggctttg aaacggtgc    420 agaggctcct tccagtgctg tgccaagcgc acggcttaac cccagagcag gtcgtggcca    480
ttgcctcgaa tggaggggc aaacaggcgt tggaaaccgt acaacgattg ctgccggtgc    540
tgtgccaagc gcacggactc accccagagc aggtcgtggc gatcgcaagc aataacggag    600
gaaagcaagc cttggaaaca gtacagaggc tgttgcctgt gctgtgccaa gcgcacggcc    660 tcacccaga gcaggtcgtg gccattgcct cgaataacgg gggcaaacag gcgttggaaa    720
ccgtacaacg attgctgccg gtgctgtgcc aagcgcacgg attaacccca gagcaggtcg    780
tggcaatcgc ctccaataac ggcgggaaac aggcactcga gactgtccag cgcctgcttc    840
ccgtgctgtg ccaagcgcac gggctcaccc cagagcaggt cgtggcaatc gcctccaatg    900
gaggcgggaa acaggcactc gagactgtcc agcgcctgct cccgtgctg tgccaagcgc    960 acggactcac cccagagcag gtcgtggcga tcgcaagcca cgacggagga aagcaagcct    1020
tggaaacagt acagaggctg ttgcctgtgc tgtgccaagc gcacggcctc accccagagc    1080
aggtcgtggc gatcgcaagc aacattggag gaaagcaagc cttggaaaca gtacagaggc    1140
tgttgcctgt gctgtgccaa gcgcacggat taaccccaga gcaggtcgtg gccattgcct    1200
cgaatggagg gggcaaacag gcgttggaaa ccgtacaacg attgctgccg gtgctgtgcc    1260
aagcgcacgg actcacgcct gagcaggtag tggctattgc atccaataac gg           1312
```

<210> SEQ ID NO 68
<211> LENGTH: 436
<212> TYPE: PRT
<213> ORGANISM: Artificial sequence
<220> FEATURE:
<223> OTHER INFORMATION: synthetic construct

<400> SEQUENCE: 68

```
Ala Val His Ala Trp Arg Asn Ala Leu Thr Gly Ala Pro Leu Asn Leu
1               5                  10                  15

Thr Pro Glu Gln Val Val Ala Ile Ala Ser His Asp Gly Gly Lys Gln
            20                  25                  30

Ala Leu Glu Thr Val Gln Arg Leu Leu Pro Val Leu Cys Gln Ala His
        35                  40                  45

Gly Leu Thr Pro Glu Gln Val Val Ala Ile Ala Ser His Asp Gly Gly
    50                  55                  60

Lys Gln Ala Leu Glu Thr Val Gln Arg Leu Leu Pro Val Leu Cys Gln
65                  70                  75                  80

Ala His Gly Leu Thr Pro Glu Gln Val Val Ala Ile Ala Ser His Asp
                85                  90                  95

Gly Gly Lys Gln Ala Leu Glu Thr Val Gln Arg Leu Leu Pro Val Leu
            100                 105                 110

Cys Gln Ala His Gly Leu Thr Pro Glu Gln Val Val Ala Ile Ala Ser
        115                 120                 125

Asn Gly Gly Gly Lys Gln Ala Leu Glu Thr Val Gln Arg Leu Leu Pro
    130                 135                 140

Val Leu Cys Gln Ala His Gly Leu Thr Pro Glu Gln Val Val Ala Ile
145                 150                 155                 160

Ala Ser Asn Gly Gly Gly Lys Gln Ala Leu Glu Thr Val Gln Arg Leu
                165                 170                 175

Leu Pro Val Leu Cys Gln Ala His Gly Leu Thr Pro Glu Gln Val Val
            180                 185                 190

Ala Ile Ala Ser Asn Asn Gly Gly Lys Gln Ala Leu Glu Thr Val Gln
```

```
                    195                 200                 205
Arg Leu Leu Pro Val Leu Cys Gln Ala His Gly Leu Thr Pro Glu Gln
        210                 215                 220

Val Val Ala Ile Ala Ser Asn Asn Gly Gly Lys Gln Ala Leu Glu Thr
225                 230                 235                 240

Val Gln Arg Leu Leu Pro Val Leu Cys Gln Ala His Gly Leu Thr Pro
            245                 250                 255

Glu Gln Val Val Ala Ile Ala Ser Asn Asn Gly Gly Lys Gln Ala Leu
                260                 265                 270

Glu Thr Val Gln Arg Leu Leu Pro Val Leu Cys Gln Ala His Gly Leu
            275                 280                 285

Thr Pro Glu Gln Val Val Ala Ile Ala Ser Asn Gly Gly Lys Gln
        290                 295                 300

Ala Leu Glu Thr Val Gln Arg Leu Leu Pro Val Leu Cys Gln Ala His
305                 310                 315                 320

Gly Leu Thr Pro Glu Gln Val Val Ala Ile Ala Ser His Asp Gly Gly
            325                 330                 335

Lys Gln Ala Leu Glu Thr Val Gln Arg Leu Leu Pro Val Leu Cys Gln
                340                 345                 350

Ala His Gly Leu Thr Pro Glu Gln Val Val Ala Ile Ala Ser Asn Ile
            355                 360                 365

Gly Gly Lys Gln Ala Leu Glu Thr Val Gln Arg Leu Leu Pro Val Leu
        370                 375                 380

Cys Gln Ala His Gly Leu Thr Pro Glu Gln Val Val Ala Ile Ala Ser
385                 390                 395                 400

Asn Gly Gly Lys Gln Ala Leu Glu Thr Val Gln Arg Leu Leu Pro
            405                 410                 415

Val Leu Cys Gln Ala His Gly Leu Thr Pro Glu Gln Val Val Ala Ile
            420                 425                 430

Ala Ser Asn Asn
        435

<210> SEQ ID NO 69
<211> LENGTH: 1312
<212> TYPE: DNA
<213> ORGANISM: Artificial sequence
<220> FEATURE:
<223> OTHER INFORMATION: synthetic construct

<400> SEQUENCE: 69
gggcggtgca cgcgtggcgc aatgcgctca cgggagcacc cctcaacctg accccagagc      60
aagtcgtggc aatcgcgagc acgacggcg gaaaacaggc tttggaaacg gtgcagaggc      120
tccttccagt gctgtgccaa gcgcacggac tcaccccaga gcaggtcgtg caatcgcct      180 cccacgacgg cgggaaacag gcactcgaga ctgtccagcg cctgcttccc gtgctgtgcc      240
aagcgcacgg cctcaccca gagcaggtcg tggcaatcgc gagcaatgga ggcggaaaac      300
aggctttgga aacggtgcag aggctccttc cagtgctgtg ccaagcgcac ggattaaccc      360
cagagcaggt cgtggcaatc gcgagcaata cggcggaaa acaggctttg gaaacggtgc      420
agaggctcct ccagtgctg tgccaagcgc acggcttaac cccagagcag gtcgtggcca      480
ttgcctcgaa taacggggc aaacaggcgt ggaaaccgt acaacgattg ctgccggtgc      540
tgtgccaagc gcacggactc accccagagc aggtcgtggc gatcgcaagc aatggaggag      600
gaaagcaagc cttggaaaca gtacagaggc tgttgcctgt gctgtgccaa gcgcacggcc      660
```

| | | |
|---|---|---|
| tcaccccaga gcaggtcgtg gccattgcct cgaatggagg gggcaaacag gcgttggaaa | 720 | |
| ccgtacaacg attgctgccg gtgctgtgcc aagcgcacgg attaacccca gagcaggtcg | 780 | |
| tggcaatcgc ctccaataac ggcgggaaac aggcactcga gactgtccag cgcctgcttc | 840 | |
| ccgtgctgtg ccaagcgcac gggctcaccc cagagcaggt cgtggcaatc gcctcccacg | 900 | |
| acggcgggaa acaggcactc gagactgtcc agcgcctgct tcccgtgctg tgccaagcgc | 960 | |
| acggactcac cccagagcag gtcgtggcga tcgcaagcaa cattggagga aagcaagcct | 1020 | |
| tggaaacagt acagaggctg ttgcctgtgc tgtgccaagc gcacggcctc accccagagc | 1080 | |
| aggtcgtggc gatcgcaagc cacgacggag gaaagcaagc cttggaaaca gtacagaggc | 1140 | |
| tgttgcctgt gctgtgccaa gcgcacggat taaccccaga gcaggtcgtg gccattgcct | 1200 | |
| cgaatggagg gggcaaacag gcgttggaaa ccgtacaacg attgctgccg gtgctgtgcc | 1260 | |
| aagcgcacgg actcacgcct gagcaggtag tggctattgc atcccacgac gg | 1312 | |

<210> SEQ ID NO 70
<211> LENGTH: 436
<212> TYPE: PRT
<213> ORGANISM: Artificial sequence
<220> FEATURE:
<223> OTHER INFORMATION: synthetic construct

<400> SEQUENCE: 70

```
Ala Val His Ala Trp Arg Asn Ala Leu Thr Gly Ala Pro Leu Asn Leu
1               5                   10                  15

Thr Pro Glu Gln Val Val Ala Ile Ala Ser His Asp Gly Gly Lys Gln
            20                  25                  30

Ala Leu Glu Thr Val Gln Arg Leu Leu Pro Val Leu Cys Gln Ala His
        35                  40                  45

Gly Leu Thr Pro Glu Gln Val Val Ala Ile Ala Ser His Asp Gly Gly
    50                  55                  60

Lys Gln Ala Leu Glu Thr Val Gln Arg Leu Leu Pro Val Leu Cys Gln
65                  70                  75                  80

Ala His Gly Leu Thr Pro Glu Gln Val Val Ala Ile Ala Ser Asn Gly
                85                  90                  95

Gly Gly Lys Gln Ala Leu Glu Thr Val Gln Arg Leu Leu Pro Val Leu
            100                 105                 110

Cys Gln Ala His Gly Leu Thr Pro Glu Gln Val Val Ala Ile Ala Ser
        115                 120                 125

Asn Asn Gly Gly Lys Gln Ala Leu Glu Thr Val Gln Arg Leu Leu Pro
    130                 135                 140

Val Leu Cys Gln Ala His Gly Leu Thr Pro Glu Gln Val Val Ala Ile
145                 150                 155                 160

Ala Ser Asn Asn Gly Gly Lys Gln Ala Leu Glu Thr Val Gln Arg Leu
                165                 170                 175

Leu Pro Val Leu Cys Gln Ala His Gly Leu Thr Pro Glu Gln Val Val
            180                 185                 190

Ala Ile Ala Ser Asn Gly Gly Gly Lys Gln Ala Leu Glu Thr Val Gln
        195                 200                 205

Arg Leu Leu Pro Val Leu Cys Gln Ala His Gly Leu Thr Pro Glu Gln
    210                 215                 220

Val Val Ala Ile Ala Ser Asn Gly Gly Gly Lys Gln Ala Leu Glu Thr
225                 230                 235                 240

Val Gln Arg Leu Leu Pro Val Leu Cys Gln Ala His Gly Leu Thr Pro
                245                 250                 255
```

```
Glu Gln Val Val Ala Ile Ala Ser Asn Asn Gly Gly Lys Gln Ala Leu
                260                 265                 270

Glu Thr Val Gln Arg Leu Leu Pro Val Leu Cys Gln Ala His Gly Leu
            275                 280                 285

Thr Pro Glu Gln Val Val Ala Ile Ala Ser His Asp Gly Gly Lys Gln
        290                 295                 300

Ala Leu Glu Thr Val Gln Arg Leu Leu Pro Val Leu Cys Gln Ala His
305                 310                 315                 320

Gly Leu Thr Pro Glu Gln Val Val Ala Ile Ala Ser Asn Ile Gly Gly
                325                 330                 335

Lys Gln Ala Leu Glu Thr Val Gln Arg Leu Leu Pro Val Leu Cys Gln
            340                 345                 350

Ala His Gly Leu Thr Pro Glu Gln Val Val Ala Ile Ala Ser His Asp
        355                 360                 365

Gly Gly Lys Gln Ala Leu Glu Thr Val Gln Arg Leu Leu Pro Val Leu
    370                 375                 380

Cys Gln Ala His Gly Leu Thr Pro Glu Gln Val Val Ala Ile Ala Ser
385                 390                 395                 400

Asn Gly Gly Lys Gln Ala Leu Glu Thr Val Gln Arg Leu Leu Pro
                405                 410                 415

Val Leu Cys Gln Ala His Gly Leu Thr Pro Glu Gln Val Val Ala Ile
            420                 425                 430

Ala Ser His Asp
        435

<210> SEQ ID NO 71
<211> LENGTH: 1312
<212> TYPE: DNA
<213> ORGANISM: Artificial sequence
<220> FEATURE:
<223> OTHER INFORMATION: synthetic construct

<400> SEQUENCE: 71
gggcggtgca cgcgtggcgc aatgcgctca cgggagcacc cctcaacctg accccagagc      60
aagtcgtggc aatcgcgagc aataacggcg aaaacaggc tttggaaacg gtgcagaggc     120
tccttccagt gctgtgccaa gcgcacggac tcaccccaga gcaggtcgtg gcaatcgcct     180
ccaataacgg cgggaaacag gcactcgaga ctgtccagcg cctgcttccc gtgctgtgcc     240
aagcgcacgg cctcacccca gagcaggtcg tggcaatcgc gagcaatgga ggcggaaaac     300
aggctttgga aacggtgcag aggctccttc cagtgctgtg ccaagcgcac ggattaaccc     360
cagagcaggt cgtggcaatc gcgagcaatg gaggcggaaa acaggctttg gaaacggtgc     420
agaggctcct tccagtgctg tgccaagcgc acggcttaac cccagagcag gtcgtggcca     480
ttgcctcgaa taacggggc aaacaggcgt tggaaaccgt acaacgattg ctgccggtgc     540
tgtgccaagc gcacggactc accccagagc aggtcgtggc gatcgcaagc cacgacggag     600
gaaagcaagc cttggaaaca gtacagaggc tgttgcctgt gctgtgccaa gcgcacggcc     660
tcaccccaga gcaggtcgtg gccattgcct cgaacattgg gggcaaacag gcgttggaaa     720
ccgtacaacg attgctgccg gtgctgtgcc aagcgcacgg attaaccca gagcaggtcg     780
tggcaatcgc ctcccacgac ggcgggaaac aggcactcga gactgtccag cgcctgcttc     840
ccgtgctgtg ccaagcgcac gggctcaccc cagagcaggt cgtggcaatc gcctccaatg     900
gaggcgggaa acaggcactc gagactgtcc agcgcctgct tcccgtgctg tgccaagcgc     960
```

```
acggactcac cccagagcag gtcgtggcga tcgcaagcca cgacggagga aagcaagcct    1020
tggaaacagt acagaggctg ttgcctgtgc tgtgccaagc gcacggcctc accccagagc    1080
aggtcgtggc gatcgcaagc cacgacggag gaaagcaagc cttggaaaca gtacagaggc    1140
tgttgcctgt gctgtgccaa gcgcacggat taacccaga gcaggtcgtg gccattgcct    1200
cgaataacgg gggcaaacag gcgttggaaa ccgtacaacg attgctgccg gtgctgtgcc    1260
aagcgcacgg actcacgcct gagcaggtag tggctattgc atccaatgga gg            1312
```

<210> SEQ ID NO 72
<211> LENGTH: 436
<212> TYPE: PRT
<213> ORGANISM: Artificial sequence
<220> FEATURE:
<223> OTHER INFORMATION: synthetic construct

<400> SEQUENCE: 72

```
Ala Val His Ala Trp Arg Asn Ala Leu Thr Gly Ala Pro Leu Asn Leu
 1               5                  10                  15

Thr Pro Glu Gln Val Val Ala Ile Ala Ser Asn Asn Gly Gly Lys Gln
             20                  25                  30

Ala Leu Glu Thr Val Gln Arg Leu Leu Pro Val Leu Cys Gln Ala His
         35                  40                  45

Gly Leu Thr Pro Glu Gln Val Val Ala Ile Ala Ser Asn Asn Gly Gly
     50                  55                  60

Lys Gln Ala Leu Glu Thr Val Gln Arg Leu Leu Pro Val Leu Cys Gln
 65                  70                  75                  80

Ala His Gly Leu Thr Pro Glu Gln Val Val Ala Ile Ala Ser Asn Gly
                 85                  90                  95

Gly Gly Lys Gln Ala Leu Glu Thr Val Gln Arg Leu Leu Pro Val Leu
            100                 105                 110

Cys Gln Ala His Gly Leu Thr Pro Glu Gln Val Val Ala Ile Ala Ser
        115                 120                 125

Asn Gly Gly Gly Lys Gln Ala Leu Glu Thr Val Gln Arg Leu Leu Pro
    130                 135                 140

Val Leu Cys Gln Ala His Gly Leu Thr Pro Glu Gln Val Val Ala Ile
145                 150                 155                 160

Ala Ser Asn Asn Gly Gly Lys Gln Ala Leu Glu Thr Val Gln Arg Leu
                165                 170                 175

Leu Pro Val Leu Cys Gln Ala His Gly Leu Thr Pro Glu Gln Val Val
            180                 185                 190

Ala Ile Ala Ser His Asp Gly Gly Lys Gln Ala Leu Glu Thr Val Gln
        195                 200                 205

Arg Leu Leu Pro Val Leu Cys Gln Ala His Gly Leu Thr Pro Glu Gln
    210                 215                 220

Val Val Ala Ile Ala Ser Asn Ile Gly Gly Lys Gln Ala Leu Glu Thr
225                 230                 235                 240

Val Gln Arg Leu Leu Pro Val Leu Cys Gln Ala His Gly Leu Thr Pro
                245                 250                 255

Glu Gln Val Val Ala Ile Ala Ser His Asp Gly Gly Lys Gln Ala Leu
            260                 265                 270

Glu Thr Val Gln Arg Leu Leu Pro Val Leu Cys Gln Ala His Gly Leu
        275                 280                 285

Thr Pro Glu Gln Val Val Ala Ile Ala Ser Asn Gly Gly Gly Lys Gln
    290                 295                 300
```

```
Ala Leu Glu Thr Val Gln Arg Leu Leu Pro Val Cys Gln Ala His
305                 310                 315                 320

Gly Leu Thr Pro Glu Gln Val Val Ala Ile Ala Ser His Asp Gly Gly
            325                 330                 335

Lys Gln Ala Leu Glu Thr Val Gln Arg Leu Leu Pro Val Leu Cys Gln
                340                 345                 350

Ala His Gly Leu Thr Pro Glu Gln Val Val Ala Ile Ala Ser His Asp
            355                 360                 365

Gly Gly Lys Gln Ala Leu Glu Thr Val Gln Arg Leu Leu Pro Val Leu
370                 375                 380

Cys Gln Ala His Gly Leu Thr Pro Glu Gln Val Val Ala Ile Ala Ser
385                 390                 395                 400

Asn Asn Gly Gly Lys Gln Ala Leu Glu Thr Val Gln Arg Leu Leu Pro
                405                 410                 415

Val Leu Cys Gln Ala His Gly Leu Thr Pro Glu Gln Val Val Ala Ile
                420                 425                 430

Ala Ser Asn Gly
        435

<210> SEQ ID NO 73
<211> LENGTH: 1312
<212> TYPE: DNA
<213> ORGANISM: Artificial sequence
<220> FEATURE:
<223> OTHER INFORMATION: synthetic construct

<400> SEQUENCE: 73
gggcggtgca cgcgtggcgc aatgcgctca cgggagcacc cctcaacctg accccagagc      60
aagtcgtggc aatcgcgagc aataacggcg gaaaacaggc tttggaaacg gtgcagaggc     120
tccttccagt gctgtgccaa gcgcacggac tcaccccaga gcaggtcgtg gcaatcgcct     180
cccacgacgg cgggaaacag gcactcgaga ctgtccagcg cctgcttccc gtgctgtgcc     240
aagcgcacgg cctcacccca gagcaggtcg tggcaatcgc gagcaatgga ggcggaaaac     300
aggctttgga aacggtgcag aggctccttc cagtgctgtg ccaagcgcac ggattaaccc     360
cagagcaggt cgtggcaatc gcgagcaatg gaggcggaaa acaggctttg aaacggtgc     420 agaggctcct tccagtgctg tgccaagcgc acggcttaac cccagagcag gtcgtggcca     480
ttgcctcgaa tggagggggc aaacaggcgt tggaaaccgt acaacgattg ctgccggtgc     540
tgtgccaagc gcacggactc accccagagc aggtcgtggc gatcgcaagc aataacggag     600
gaaagcaagc cttggaaaca gtacagaggc tgttgcctgt gctgtgccaa gcgcacggcc     660
tcaccccaga gcaggtcgtg gccattgcct cgcacgacgg gggcaaacag gcgttggaaa     720
ccgtacaacg attgctgccg gtgctgtgcc aagcgcacgg attaaccccca gagcaggtcg     780 tggcaatcgc ctccaacatt ggcgggaaac aggcactcga gactgtccag cgcctgcttc     840
ccgtgctgtg ccaagcgcac gggctcaccc cagagcaggt cgtggcaatc gcctcccacg     900
acggcgggaa acaggcactc gagactgtcc agcgcctgct tcccgtgctg tgccaagcgc     960
acggactcac cccagagcag gtcgtggcga tcgcaagcaa cattggagga aagcaagcct    1020
tggaaacagt acagaggctg ttgcctgtgc tgtgccaagc gcacggcctc accccagagc    1080
aggtcgtggc gatcgcaagc aacattggag gaaagcaagc cttggaaaca gtacagaggc    1140
tgttgcctgt gctgtgccaa gcgcacggat taaccccaga gcaggtcgtg gccattgcct    1200
cgaacattgg gggcaaacag gcgttggaaa ccgtacaacg attgctgccg gtgctgtgcc    1260
```
aagcgcacgg actcacgcct gagcaggtag tggctattgc atccaataac gg    1312

<210> SEQ ID NO 74
<211> LENGTH: 436
<212> TYPE: PRT
<213> ORGANISM: Artificial sequence
<220> FEATURE:
<223> OTHER INFORMATION: synthetic construct

<400> SEQUENCE: 74

```
Ala Val His Ala Trp Arg Asn Ala Leu Thr Gly Ala Pro Leu Asn Leu
1               5                   10                  15

Thr Pro Glu Gln Val Val Ala Ile Ala Ser Asn Asn Gly Gly Lys Gln
            20                  25                  30

Ala Leu Glu Thr Val Gln Arg Leu Leu Pro Val Leu Cys Gln Ala His
        35                  40                  45

Gly Leu Thr Pro Glu Gln Val Val Ala Ile Ala Ser His Asp Gly Gly
    50                  55                  60

Lys Gln Ala Leu Glu Thr Val Gln Arg Leu Leu Pro Val Leu Cys Gln
65                  70                  75                  80

Ala His Gly Leu Thr Pro Glu Gln Val Val Ala Ile Ala Ser Asn Gly
                85                  90                  95

Gly Gly Lys Gln Ala Leu Glu Thr Val Gln Arg Leu Leu Pro Val Leu
            100                 105                 110

Cys Gln Ala His Gly Leu Thr Pro Glu Gln Val Val Ala Ile Ala Ser
        115                 120                 125

Asn Gly Gly Gly Lys Gln Ala Leu Glu Thr Val Gln Arg Leu Leu Pro
    130                 135                 140

Val Leu Cys Gln Ala His Gly Leu Thr Pro Glu Gln Val Val Ala Ile
145                 150                 155                 160

Ala Ser Asn Gly Gly Gly Lys Gln Ala Leu Glu Thr Val Gln Arg Leu
                165                 170                 175

Leu Pro Val Leu Cys Gln Ala His Gly Leu Thr Pro Glu Gln Val Val
            180                 185                 190

Ala Ile Ala Ser Asn Asn Gly Gly Lys Gln Ala Leu Glu Thr Val Gln
        195                 200                 205

Arg Leu Leu Pro Val Leu Cys Gln Ala His Gly Leu Thr Pro Glu Gln
    210                 215                 220

Val Val Ala Ile Ala Ser His Asp Gly Gly Lys Gln Ala Leu Glu Thr
225                 230                 235                 240

Val Gln Arg Leu Leu Pro Val Leu Cys Gln Ala His Gly Leu Thr Pro
                245                 250                 255

Glu Gln Val Val Ala Ile Ala Ser Asn Ile Gly Gly Lys Gln Ala Leu
            260                 265                 270

Glu Thr Val Gln Arg Leu Leu Pro Val Leu Cys Gln Ala His Gly Leu
        275                 280                 285

Thr Pro Glu Gln Val Val Ala Ile Ala Ser His Asp Gly Gly Lys Gln
    290                 295                 300

Ala Leu Glu Thr Val Gln Arg Leu Leu Pro Val Leu Cys Gln Ala His
305                 310                 315                 320

Gly Leu Thr Pro Glu Gln Val Val Ala Ile Ala Ser Asn Ile Gly Gly
                325                 330                 335

Lys Gln Ala Leu Glu Thr Val Gln Arg Leu Leu Pro Val Leu Cys Gln
            340                 345                 350

Ala His Gly Leu Thr Pro Glu Gln Val Val Ala Ile Ala Ser Asn Ile
```

355                 360                 365
Gly Gly Lys Gln Ala Leu Glu Thr Val Gln Arg Leu Leu Pro Val Leu
        370                 375                 380

Cys Gln Ala His Gly Leu Thr Pro Glu Gln Val Val Ala Ile Ala Ser
385                 390                 395                 400

Asn Ile Gly Gly Lys Gln Ala Leu Glu Thr Val Gln Arg Leu Leu Pro
                405                 410                 415

Val Leu Cys Gln Ala His Gly Leu Thr Pro Glu Gln Val Val Ala Ile
            420                 425                 430

Ala Ser Asn Asn
            435

<210> SEQ ID NO 75
<211> LENGTH: 1312
<212> TYPE: DNA
<213> ORGANISM: Artificial sequence
<220> FEATURE:
<223> OTHER INFORMATION: synthetic construct

<400> SEQUENCE: 75
gggcggtgca cgcgtggcgc aatgcgctca cgggagcacc cctcaacctg accccagagc     60
aagtcgtggc aatcgcgagc aataacggcg aaaacaggc tttggaaacg gtgcagaggc    120
tccttccagt gctgtgccaa gcgcacggac tcaccccaga gcaggtcgtg caatcgcct    180 cccacgacgg cgggaaacag gcactcgaga ctgtccagcg cctgcttccc gtgctgtgcc    240
aagcgcacgg cctcaccccca gagcaggtcg tggcaatcgc gagcaacatt ggcggaaaac    300
aggctttgga aacggtgcag aggctccttc cagtgctgtg ccaagcgcac ggattaaccc    360
cagagcaggt cgtggcaatc gcgagccacg acgcggaaaa caggctttg gaaacggtgc    420 agaggctcct tccagtgctg tgccaagcgc acggcttaac cccagagcag gtcgtggcca    480
ttgcctcgaa taacgggggc aaacaggcgt tggaaaccgt acaacgattg ctgccggtgc    540
tgtgccaagc gcacggactc accccagagc aggtcgtggc gatcgcaagc aacattggag    600
gaaagcaagc cttggaaaca gtacagaggc tgttgcctgt gctgtgccaa gcgcacggcc    660
tcaccccaga gcaggtcgtg gccattgcct cgaacattgg gggcaaacag gcgttggaaa    720
ccgtacaacg attgctgccg gtgctgtgcc aagcgcacgg attaaccca gagcaggtcg    780 tggcaatcgc ctccaatgga ggcgggaaac aggcactcga gactgtccag cgcctgcttc    840
ccgtgctgtg ccaagcgcac gggctcaccc cagagcaggt cgtggcaatc gcctccaaca    900
ttggcgggaa acaggcactc gagactgtcc agcgcctgct tcccgtgctg tgccaagcgc    960
acggactcac cccagagcag gtcgtggcga tcgcaagcaa taacggagga aagcaagcct   1020
tggaaacagt acagaggctg ttgcctgtgc tgtgccaagc gcacggcctc accccagagc   1080
aggtcgtggc gatcgcaagc aatggaggag gaaagcaagc cttggaaaca gtacagaggc   1140
tgttgcctgt gctgtgccaa gcgcacggat aaccccaga gcaggtcgtg gccattgcct   1200
cgaataacgg gggcaaacag gcgttggaaa ccgtacaacg attgctgccg gtgctgtgcc   1260
aagcgcacgg actcacgcct gagcaggtag tggctattgc atcccacgac gg           1312

<210> SEQ ID NO 76
<211> LENGTH: 436
<212> TYPE: PRT
<213> ORGANISM: Artificial sequence
<220> FEATURE:
<223> OTHER INFORMATION: synthetic construct

<400> SEQUENCE: 76

```
Ala Val His Ala Trp Arg Asn Ala Leu Thr Gly Ala Pro Leu Asn Leu
1               5                   10                  15

Thr Pro Glu Gln Val Val Ala Ile Ala Ser Asn Asn Gly Gly Lys Gln
            20                  25                  30

Ala Leu Glu Thr Val Gln Arg Leu Leu Pro Val Leu Cys Gln Ala His
        35                  40                  45

Gly Leu Thr Pro Glu Gln Val Val Ala Ile Ala Ser His Asp Gly Gly
    50                  55                  60

Lys Gln Ala Leu Glu Thr Val Gln Arg Leu Leu Pro Val Leu Cys Gln
65                  70                  75                  80

Ala His Gly Leu Thr Pro Glu Gln Val Val Ala Ile Ala Ser Asn Ile
            85                  90                  95

Gly Gly Lys Gln Ala Leu Glu Thr Val Gln Arg Leu Leu Pro Val Leu
            100                 105                 110

Cys Gln Ala His Gly Leu Thr Pro Glu Gln Val Val Ala Ile Ala Ser
        115                 120                 125

His Asp Gly Gly Lys Gln Ala Leu Glu Thr Val Gln Arg Leu Leu Pro
    130                 135                 140

Val Leu Cys Gln Ala His Gly Leu Thr Pro Glu Gln Val Val Ala Ile
145                 150                 155                 160

Ala Ser Asn Asn Gly Gly Lys Gln Ala Leu Glu Thr Val Gln Arg Leu
            165                 170                 175

Leu Pro Val Leu Cys Gln Ala His Gly Leu Thr Pro Glu Gln Val Val
            180                 185                 190

Ala Ile Ala Ser Asn Ile Gly Gly Lys Gln Ala Leu Glu Thr Val Gln
        195                 200                 205

Arg Leu Leu Pro Val Leu Cys Gln Ala His Gly Leu Thr Pro Glu Gln
    210                 215                 220

Val Val Ala Ile Ala Ser Asn Ile Gly Gly Lys Gln Ala Leu Glu Thr
225                 230                 235                 240

Val Gln Arg Leu Leu Pro Val Leu Cys Gln Ala His Gly Leu Thr Pro
            245                 250                 255

Glu Gln Val Val Ala Ile Ala Ser Asn Gly Gly Gly Lys Gln Ala Leu
            260                 265                 270

Glu Thr Val Gln Arg Leu Leu Pro Val Leu Cys Gln Ala His Gly Leu
        275                 280                 285

Thr Pro Glu Gln Val Val Ala Ile Ala Ser Asn Ile Gly Gly Lys Gln
    290                 295                 300

Ala Leu Glu Thr Val Gln Arg Leu Leu Pro Val Leu Cys Gln Ala His
305                 310                 315                 320

Gly Leu Thr Pro Glu Gln Val Val Ala Ile Ala Ser Asn Asn Gly Gly
            325                 330                 335

Lys Gln Ala Leu Glu Thr Val Gln Arg Leu Leu Pro Val Leu Cys Gln
            340                 345                 350

Ala His Gly Leu Thr Pro Glu Gln Val Val Ala Ile Ala Ser Asn Gly
        355                 360                 365

Gly Gly Lys Gln Ala Leu Glu Thr Val Gln Arg Leu Leu Pro Val Leu
    370                 375                 380

Cys Gln Ala His Gly Leu Thr Pro Glu Gln Val Val Ala Ile Ala Ser
385                 390                 395                 400

Asn Asn Gly Gly Lys Gln Ala Leu Glu Thr Val Gln Arg Leu Leu Pro
            405                 410                 415
```

Val Leu Cys Gln Ala His Gly Leu Thr Pro Glu Gln Val Val Ala Ile
            420                 425                 430

Ala Ser His Asp
        435

<210> SEQ ID NO 77
<211> LENGTH: 911
<212> TYPE: DNA
<213> ORGANISM: Artificial sequence
<220> FEATURE:
<223> OTHER INFORMATION: synthetic construct

<400> SEQUENCE: 77
ccgcgaaatt aatacgactc actatagggg aattgtgagc ggataacaat ttctagaata     60
attttgttta actttaagaa ggagatatac catgggccat catcatcatc atcatagcag    120
cggcataaaa gaaacctggt gggaaacctg gtggaccgaa tggagccagc caaaaaagaa    180
gagaaaggta agcagcggcc tcgagatgtg gactctcggg cgccgcgcag tagccggcct    240
cctggcgtca cccagcccgg cccaggccca gaccctcacc cgggtcccgc ggccggcaga    300
gttggcccca ctctgcggcc gccgtggcct gcgcaccgac atcgatgcga cctgcacgcc    360
ccgccgcgca agttcgaacc aacgtggcct caaccagatt tggaatgtca aaaagcagag    420
tgtctatttg atgaatttga ggaaatctgg aactttgggc cacccaggct ctctagatga    480
gaccacctat gaaagactag caggaaaac gctggactct ttagcagagt tttttgaaga    540
ccttgcagac aagccataca cgtttgagga ctatgatgtc tcctttggga gtggtgtctt    600
aactgtcaaa ctgggtggag atctaggaac ctatgtgatc aacaagcaga cgccaaacaa    660
gcaaatctgg ctatcttctc catccagtgg acctaagcgt tatgactgga ctgggaaaaa    720
ctgggtgtac tcccacgacg gcgtgtccct ccatgagctg ctggccgcag agctcactaa    780
agccttaaaa accaaactgg acttgtcttc cttggcctat tccggaaaag atgcttgagg    840
atccggctgc taacaaagcc cgaaaggaag ctgagttggc tgctgccacc gctgagcaat    900
aactagcata a                                                         911

<210> SEQ ID NO 78
<211> LENGTH: 248
<212> TYPE: PRT
<213> ORGANISM: Artificial sequence
<220> FEATURE:
<223> OTHER INFORMATION: synthetic construct

<400> SEQUENCE: 78

Met Gly His His His His His His Ser Ser Gly Ile Lys Glu Thr Trp
1               5                   10                  15

Trp Glu Thr Trp Trp Thr Glu Trp Ser Gln Pro Lys Lys Lys Arg Lys
            20                  25                  30

Val Ser Ser Gly Leu Glu Met Trp Thr Leu Gly Arg Arg Ala Val Ala
        35                  40                  45

Gly Leu Leu Ala Ser Pro Ser Pro Ala Gln Ala Gln Thr Leu Thr Arg
    50                  55                  60

Val Pro Arg Pro Ala Glu Leu Ala Pro Leu Cys Gly Arg Arg Gly Leu
65                  70                  75                  80

Arg Thr Asp Ile Asp Ala Thr Cys Thr Pro Arg Arg Ala Ser Ser Asn
                85                  90                  95

Gln Arg Gly Leu Asn Gln Ile Trp Asn Val Lys Lys Gln Ser Val Tyr
            100                 105                 110

```
Leu Met Asn Leu Arg Lys Ser Gly Thr Leu Gly His Pro Gly Ser Leu
        115                 120                 125

Asp Glu Thr Thr Tyr Glu Arg Leu Ala Glu Glu Thr Leu Asp Ser Leu
130                 135                 140

Ala Glu Phe Phe Glu Asp Leu Ala Asp Lys Pro Tyr Thr Phe Glu Asp
145                 150                 155                 160

Tyr Asp Val Ser Phe Gly Ser Gly Val Leu Thr Val Lys Leu Gly Gly
                165                 170                 175

Asp Leu Gly Thr Tyr Val Ile Asn Lys Gln Thr Pro Asn Lys Gln Ile
            180                 185                 190

Trp Leu Ser Ser Pro Ser Ser Gly Pro Lys Arg Tyr Asp Trp Thr Gly
        195                 200                 205

Lys Asn Trp Val Tyr Ser His Asp Gly Val Ser Leu His Glu Leu Leu
    210                 215                 220

Ala Ala Glu Leu Thr Lys Ala Leu Lys Thr Lys Leu Asp Leu Ser Ser
225                 230                 235                 240

Leu Ala Tyr Ser Gly Lys Asp Ala
                245
```

```
<210> SEQ ID NO 79
<211> LENGTH: 840
<212> TYPE: DNA
<213> ORGANISM: Artificial sequence
<220> FEATURE:
<223> OTHER INFORMATION: synthetic construct

<400> SEQUENCE: 79
tccctctaga aataattttg tttaactta agaaggagat ataccatggg ccatcatcat    60
catcatcata gcagcggcgg actgagatct tatggaagga agaagcggag acagcgacga   120
agaggcgcta gcaccggtgg tatgtggact ctcgggcgcc gcgcagtagc cggcctcctg   180
gcgtcaccca gccggcccca ggcccagacc ctcacccggg tccgcggcc ggcagagttg    240
gccccactct gcggccgccg tggcctgcgc accgacatcg atgcgacctg cacgccccgc   300
cgcgcaagtt cgaaccaacg tggcctcaac cagatttgga atgtcaaaaa gcagagtgtc   360
tatttgatga atttgaggaa atctggaact ttgggccacc caggctctct agatgagacc   420
acctatgaaa gactagcaga ggaaacgctg gactctttag cagagttttt tgaagacctt   480
gcagacaagc catacacgtt tgaggactat gatgtctcct ttgggagtgg tgtcttaact   540
gtcaaactgg gtggagatct aggaacctat gtgatcaaca gcagacgcc aaacaagcaa    600
atctggctat cttctccatc cagtggacct aagcgttatg actggactgg aaaaactgg    660
gtgtactccc acgacggcgt gtccctccat gagctgctgg ccgcagagct cactaaagcc   720
ttaaaaacca aactggactt gtcttccttg gccattccg gaaaagatgc ttgaggatcc    780
ggctgctaac aaagcccgaa aggaagctga gttggctgct gccaccgctg agcaataact   840
```

```
<210> SEQ ID NO 80
<211> LENGTH: 242
<212> TYPE: PRT
<213> ORGANISM: Artificial sequence
<220> FEATURE:
<223> OTHER INFORMATION: synthetic construct

<400> SEQUENCE: 80

Met Gly His His His His His His Ser Ser Gly Gly Leu Arg Ser Tyr
1               5                   10                  15
```

Gly Arg Lys Lys Arg Arg Gln Arg Arg Gly Ala Ser Thr Gly Gly
            20                  25                  30

Met Trp Thr Leu Gly Arg Arg Ala Val Ala Gly Leu Leu Ala Ser Pro
        35                  40                  45

Ser Pro Ala Gln Ala Gln Thr Leu Thr Arg Val Pro Arg Pro Ala Glu
    50                  55                  60

Leu Ala Pro Leu Cys Gly Arg Arg Gly Leu Arg Thr Asp Ile Asp Ala
65                  70                  75                  80

Thr Cys Thr Pro Arg Arg Ala Ser Ser Asn Gln Arg Gly Leu Asn Gln
                85                  90                  95

Ile Trp Asn Val Lys Lys Gln Ser Val Tyr Leu Met Asn Leu Arg Lys
            100                 105                 110

Ser Gly Thr Leu Gly His Pro Gly Ser Leu Asp Glu Thr Thr Tyr Glu
        115                 120                 125

Arg Leu Ala Glu Glu Thr Leu Asp Ser Leu Ala Glu Phe Phe Glu Asp
    130                 135                 140

Leu Ala Asp Lys Pro Tyr Thr Phe Glu Asp Tyr Asp Val Ser Phe Gly
145                 150                 155                 160

Ser Gly Val Leu Thr Val Lys Leu Gly Gly Asp Leu Gly Thr Tyr Val
                165                 170                 175

Ile Asn Lys Gln Thr Pro Asn Lys Gln Ile Trp Leu Ser Ser Pro Ser
            180                 185                 190

Ser Gly Pro Lys Arg Tyr Asp Trp Thr Gly Lys Asn Trp Val Tyr Ser
        195                 200                 205

His Asp Gly Val Ser Leu His Glu Leu Leu Ala Ala Glu Leu Thr Lys
    210                 215                 220

Ala Leu Lys Thr Lys Leu Asp Leu Ser Ser Leu Ala Tyr Ser Gly Lys
225                 230                 235                 240

Asp Ala

<210> SEQ ID NO 81
<211> LENGTH: 819
<212> TYPE: DNA
<213> ORGANISM: Artificial sequence
<220> FEATURE:
<223> OTHER INFORMATION: synthetic construct

<400> SEQUENCE: 81
tagaaataat tttgwttaac tttaagaagg agatatacca tgggccatca tcatcatcat    60
catcatcaca gcagcggcca tcatactagt atgtggactc tcgggcgccg cgcagtagcc   120
ggcctcctgg cgtcacccag cccggcccag gcccagaccc tcacccgggt cccgcggccg   180
gcagagttgg ccccactctg cggccgccgt ggcctgcgca ccgacatcga tgcgacctgc   240
acgccccgcc gcgcaagttc gaaccaacgt ggcctcaacc agatttggaa tgtcaaaaag   300
cagagtgtct atttgatgaa tttgaggaaa tctggaactt gggccacccc aggctctcta   360
gatgagacca cctatgaaag actagcagag gaaacgctgg actctttagc agagtttttt   420
gaagaccttg cagacaagcc atacacgttt gaggactatg atgtctcctt gggagtggt   480 gtcttaactg tcaaactggg tggagatcta ggaacctatg tgatcaacaa gcagacgcca   540
aacaagcaaa tctggctatc ttctccatcc agtggaccta agcgttatga ctggactggg   600
aaaaactggg tgtactccca cgacggcgtg tccctccatg agctgctggc cgcagagctc   660
actaaagcct taaaaaccaa actggacttg tcttccttgg cctattccgg aaaagatgct   720
tgaggatccg gctgctaaca aagcccgaaa ggaagctgag ttgggctgct aacaaagccc   780

```
gaaaggaagc tgagttggct gctgccaccg ctgagcaat                                   819
```

<210> SEQ ID NO 82
<211> LENGTH: 227
<212> TYPE: PRT
<213> ORGANISM: Artificial sequence
<220> FEATURE:
<223> OTHER INFORMATION: synthetic construct

<400> SEQUENCE: 82

```
Met Gly His His His His His His Ser Ser Gly His His Thr
1               5                   10                  15

Ser Met Trp Thr Leu Gly Arg Arg Ala Val Ala Gly Leu Leu Ala Ser
            20                  25                  30

Pro Ser Pro Ala Gln Ala Gln Thr Leu Thr Arg Val Pro Arg Pro Ala
        35                  40                  45

Glu Leu Ala Pro Leu Cys Gly Arg Arg Gly Leu Arg Thr Asp Ile Asp
    50                  55                  60

Ala Thr Cys Thr Pro Arg Arg Ala Ser Ser Asn Gln Arg Gly Leu Asn
65                  70                  75                  80

Gln Ile Trp Asn Val Lys Lys Gln Ser Val Tyr Leu Met Asn Leu Arg
                85                  90                  95

Lys Ser Gly Thr Leu Gly His Pro Gly Ser Leu Asp Glu Thr Thr Tyr
            100                 105                 110

Glu Arg Leu Ala Glu Glu Thr Leu Asp Ser Leu Ala Glu Phe Phe Glu
        115                 120                 125

Asp Leu Ala Asp Lys Pro Tyr Thr Phe Glu Asp Tyr Asp Val Ser Phe
    130                 135                 140

Gly Ser Gly Val Leu Thr Val Lys Leu Gly Gly Asp Leu Gly Thr Tyr
145                 150                 155                 160

Val Ile Asn Lys Gln Thr Pro Asn Lys Gln Ile Trp Leu Ser Ser Pro
                165                 170                 175

Ser Ser Gly Pro Lys Arg Tyr Asp Trp Thr Gly Lys Asn Trp Val Tyr
            180                 185                 190

Ser His Asp Gly Val Ser Leu His Glu Leu Leu Ala Ala Glu Leu Thr
        195                 200                 205

Lys Ala Leu Lys Thr Lys Leu Asp Leu Ser Ser Leu Ala Tyr Ser Gly
    210                 215                 220

Lys Asp Ala
225
```

<210> SEQ ID NO 83
<211> LENGTH: 5711
<212> TYPE: DNA
<213> ORGANISM: Artificial sequence
<220> FEATURE:
<223> OTHER INFORMATION: synthetic construct

<400> SEQUENCE: 83

```
ttcttgaaga cgaaagggcc tcgtgatacg cctattttta taggttaatg tcatgataat    60
aatggtttct tagacgtcag gtggcacttt tcggggaaat gtgcgcggaa ccccatttg    120 tttattttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
```

```
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540 tacgatggc atgacagtaa gagaattatg cagtgctgcc ataaccatga gtgataacac     600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct aacgtgagt tttcgttcca    1200 ctgagcgtca gaccccgtag aaaagatcaa aggatcttct tgagatcctt ttttttctgcg   1260 cgtaatctgc tgcttgcaaa caaaaaaacc accgctacca gcggtggttt gtttgccgga    1320
tcaagagcta ccaactcttt ttccgaaggt aactggcttc agcagagcgc agataccaaa    1380
tactgtcctt ctagtgtagc cgtagttagg ccaccacttc aagaactctg tagcaccgcc    1440
tacatacctc gctctgctaa tcctgttacc agtggctgct gccagtggcg ataagtcgtg    1500
tcttaccggg ttggactcaa gacgatagtt accggataag gcgcagcggt cgggctgaac   1560 gggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
```

```
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360 aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gagcggtt    3840 gcgtattggg cgccagggtg gtttttcttt tcaccagtga cgggcaac agctgattgc    3900 ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatgcgc    4080 gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga aacaagcgct catgagcccg    5100
```

```
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg ccatcatca tcatcatcat    5340 catcatcatc acagcagcgg ccatatcgaa ggtcgtcata tgctcgagga tccggctgct    5400
aacaaagccc gaaaggaagc tgagttggct gctgccaccg ctgagcaata actagcataa    5460
ccccttgggg cctctaaacg ggtcttgagg ggttttttgc tgaaaggagg aactatatcc    5520
ggatatcccg caagaggccc ggcagtaccg gcataaccaa gcctatgcct acagcatcca    5580
gggtgacggt gccgaggatg acgatgagcg cattgttaga tttcatacac ggtgcctgac    5640
tgcgttagca atttaactgt gataaactac cgcattaaag cttatcgatg ataagctgtc    5700
aaacatgaga a                                                        5711
```

<210> SEQ ID NO 84
<211> LENGTH: 782
<212> TYPE: PRT
<213> ORGANISM: Artificial sequence
<220> FEATURE:
<223> OTHER INFORMATION: synthetic construct
<220> FEATURE:
<221> NAME/KEY: MISC_FEATURE
<222> LOCATION: (266)..(266)
<223> OTHER INFORMATION: X is N or H
<220> FEATURE:
<221> NAME/KEY: MISC_FEATURE
<222> LOCATION: (267)..(267)
<223> OTHER INFORMATION: X is I, G or N when X at position 266 is N; and
      X is D when X at position 266 is H.

<400> SEQUENCE: 84

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp

```
                195                 200                 205
Thr Gly Gln Leu Leu Lys Ile Ala Lys Arg Gly Val Thr Ala Val
            210                 215                 220

Glu Ala Val His Ala Trp Arg Asn Ala Leu Thr Gly Ala Pro Leu Asn
225                 230                 235                 240

Leu Thr Glu Thr Val His Glu Thr His Gly Thr Ala Ser Gln Leu Thr
                245                 250                 255

Pro Glu Gln Val Val Ala Ile Ala Ser Xaa Xaa Gly Gly Arg Pro Ala
            260                 265                 270

Leu Glu Ser Ile Val Ala Gln Leu Ser Arg Pro Asp Pro Ala Leu Ala
            275                 280                 285

Ala Leu Thr Asn Asp His Leu Val Ala Leu Ala Cys Leu Gly Gly Arg
            290                 295                 300

Pro Ala Leu Asp Ala Val Lys Lys Gly Leu Pro His Ala Pro Ala Leu
305                 310                 315                 320

Ile Lys Arg Thr Asn Arg Arg Ile Pro Glu Arg Thr Ser His Arg Val
                325                 330                 335

Ala Asp His Ala Gln Val Val Arg Val Leu Gly Phe Phe Gln Cys His
            340                 345                 350

Ser His Pro Ala Gln Ala Phe Asp Asp Ala Met Thr Gln Phe Gly Met
            355                 360                 365

Ser Arg His Gly Leu Leu Gln Leu Phe Arg Arg Val Gly Val Thr Glu
            370                 375                 380

Leu Glu Ala Arg Ser Gly Thr Leu Pro Pro Ala Ser Gln Arg Trp Asp
385                 390                 395                 400

Arg Ile Leu Gln Ala Ser Gly Met Lys Arg Ala Lys Pro Ser Pro Thr
                405                 410                 415

Ser Thr Gln Thr Pro Asp Gln Ala Ser Leu His Ala Phe Ala Asp Ser
            420                 425                 430

Leu Glu Arg Asp Leu Asp Ala Pro Ser Pro Met His Glu Gly Asp Gln
            435                 440                 445

Thr Arg Ala Ser Ala Ser Pro Lys Lys Arg Lys Val Glu Ala Ser
            450                 455                 460

Gly Ser Gly Arg Ala Asp Ala Leu Asp Asp Phe Asp Leu Asp Met Leu
465                 470                 475                 480

Gly Ser Asp Ala Leu Asp Asp Phe Asp Leu Asp Met Leu Gly Ser Asp
                485                 490                 495

Ala Leu Asp Asp Phe Asp Leu Asp Met Leu Gly Ser Asp Ala Leu Asp
            500                 505                 510

Asp Phe Asp Leu Asp Met Leu Ile Asn Ser Arg Gly Ser Gly Glu Gly
            515                 520                 525

Arg Gly Ser Leu Leu Thr Cys Gly Asp Val Glu Glu Asn Pro Gly Pro
            530                 535                 540

Val Ser Lys Gly Glu Glu Leu Phe Thr Gly Val Val Pro Ile Leu Val
545                 550                 555                 560

Glu Leu Asp Gly Asp Val Asn Gly His Lys Phe Ser Val Ser Gly Glu
                565                 570                 575

Gly Glu Gly Asp Ala Thr Tyr Gly Lys Leu Thr Leu Lys Phe Ile Cys
            580                 585                 590

Thr Thr Gly Lys Leu Pro Val Pro Trp Pro Thr Leu Val Thr Thr Leu
            595                 600                 605

Thr Tyr Gly Val Gln Cys Phe Ser Arg Tyr Pro Asp His Met Lys Gln
            610                 615                 620
```

-continued

```
His Asp Phe Phe Lys Ser Ala Met Pro Glu Gly Tyr Val Gln Glu Arg
625                 630                 635                 640

Thr Ile Phe Phe Lys Asp Asp Gly Asn Tyr Lys Thr Arg Ala Glu Val
            645                 650                 655

Lys Phe Glu Gly Asp Thr Leu Val Asn Arg Ile Glu Leu Lys Gly Ile
        660                 665                 670

Asp Phe Lys Glu Asp Gly Asn Ile Leu Gly His Lys Leu Glu Tyr Asn
    675                 680                 685

Tyr Asn Ser His Asn Val Tyr Ile Met Ala Asp Lys Gln Lys Asn Gly
690                 695                 700

Ile Lys Val Asn Phe Lys Ile Arg His Asn Ile Glu Asp Gly Ser Val
705                 710                 715                 720

Gln Leu Ala Asp His Tyr Gln Gln Asn Thr Pro Ile Gly Asp Gly Pro
                725                 730                 735

Val Leu Leu Pro Asp Asn His Tyr Leu Ser Thr Gln Ser Ala Leu Ser
            740                 745                 750

Lys Asp Pro Asn Glu Lys Arg Asp His Met Val Leu Leu Glu Phe Val
        755                 760                 765

Thr Ala Ala Gly Ile Thr Leu Gly Met Asp Glu Leu Tyr Lys
    770                 775                 780

<210> SEQ ID NO 85
<211> LENGTH: 2349
<212> TYPE: DNA
<213> ORGANISM: Artificial sequence
<220> FEATURE:
<223> OTHER INFORMATION: synthetic construct
<220> FEATURE:
<221> NAME/KEY: misc_feature
<222> LOCATION: (796)..(796)
<223> OTHER INFORMATION: n is c or a
<220> FEATURE:
<221> NAME/KEY: misc_feature
<222> LOCATION: (799)..(799)
<223> OTHER INFORMATION: n is a or G
<220> FEATURE:
<221> NAME/KEY: misc_feature
<222> LOCATION: (800)..(800)
<223> OTHER INFORMATION: n is a, t or g

<400> SEQUENCE: 85
atgtcgcgga cccggctccc ttccccaccc gcacccagcc cagcgttttc ggccgactcg      60
ttctcagacc tgcttaggca gttcgacccc tcactgttta acacatcgtt gttcgactcc     120
cttcctccgt tggggcgca ccatacggag gcggccaccg gggagtggga tgaggtgcag     180
tcgggattga gagctgcgga tgcaccaccc caaccatgc gggtggccgt caccgctgcc     240
cgaccgccga gggcgaagcc cgcaccaagg cggagggcag cgcaaccgtc cgacgcaagc     300
cccgcagcgc aagtagattt gagaactttg ggatattcac agcagcagca ggaaaagatc     360
aagcccaaag tgaggtcgac agtcgcgcag catcacgaag cgctggtggg tcatgggttt     420
acacatgccc acatcgtagc cttgtcgcag caccctgcag cccttggcac ggtcgccgtc     480
aagtaccagg acatgattgc ggcgttgccg gaagccacac atgaggcgat cgtcggtgtg     540
gggaaacagt ggagcggagc ccgagcgctt gaggccctgt tgacggtcgc gggagagctg     600
agagggcctc cccttcagct ggacacgggc cagttgctga agatcgcgaa gcggggagga     660
gtcacggcgg tcgaggcggt gcacgcgtgg cgcaatgcgc tcacgggagc acccctcaac     720
ctgaccgaga cggtacatga aacgcatggc acggcgtctc aactcacgcc tgagcaggta     780
```

```
gtggctattg catccnatnn cgggggcaga cccgcactgg agtcaatcgt ggcccagctt    840
tcgaggccgg accccgcgct ggccgcactc actaatgatc atcttgtagc gctggcctgc    900
ctcggcggac gacccgcctt ggatgcggtg aagaaggggc tcccgcacgc gcctgcattg    960
attaagcgga ccaacagaag gattcccgag aggacatcac atcgagtggc agatcacgcg   1020
caagtggtcc gcgtgctcgg attcttccag tgtcactccc accccgcaca agcgttcgat   1080
gacgccatga ctcaatttgg tatgtcgaga cacggactgc tgcagctctt tcgtagagtc   1140
ggtgtcacag aactcgaggc ccgctcgggc acactgcctc ccgcctccca gcggtgggac   1200
aggattctcc aagcgagcgg tatgaaacgc gcgaagcctt cacctacgtc aactcagaca   1260
cctgaccagg cgagccttca tgcgttcgca gactcgctgg agagggattt ggacgcgccc   1320
tcgcccatgc atgaagggga ccaaactcgc cgtcagcta gccccaagaa gaagagaaag    1380
gtggaggcca gcggttccgg acgggctgac gcattggacg attttgatct ggatatgctg   1440
ggaagtgacg ccctcgatga ttttgacctt gacatgcttg gttcggatgc ccttgatgac   1500
tttgacctcg acatgctcgg cagtgacgcc cttgatgatt tcgacctgga catgctgatt   1560
aactctagag gcagtggaga gggcagagga agtctgctaa catgcggtga cgtcgaggag   1620
aatcctggcc cagtgagcaa gggcgaggag ctgttcaccg gggtggtgcc catcctggtc   1680
gagctggacg gcgacgtaaa cggccacaag ttcagcgtgt ccggcgaggg cgagggcgat   1740
gccacctacg gcaagctgac cctgaagttc atctgcacca ccggcaagct gcccgtgccc   1800
tggcccaccc tcgtgaccac cctgacctac ggcgtgcagt gcttcagccg ctaccccgac   1860
cacatgaagc agcacgactt cttcaagtcc gccatgcccg aaggctacgt ccaggagcgc   1920
accatcttct tcaaggacga cggcaactac aagacccgcg ccgaggtgaa gttcgagggc   1980
gacaccctgg tgaaccgcat cgagctgaag ggcatcgact tcaaggagga cggcaacatc   2040
ctggggcaca agctggagta caactacaac agccacaacg tctatatcat ggccgacaag   2100
cagaagaacg gcatcaaggt gaacttcaag atccgccaca acatcgagga cggcagcgtg   2160
cagctcgccg accactacca gcagaacacc cccatcggcg acggccccgt gctgctgccc   2220
gacaaccact acctgagcac ccagtccgcc ctgagcaaag accccaacga gaagcgcgat   2280
cacatggtcc tgctggagtt cgtgaccgcc gccgggatca ctctcggcat ggacgagctg   2340
tacaagtaa                                                           2349
```

<210> SEQ ID NO 86
<211> LENGTH: 952
<212> TYPE: PRT
<213> ORGANISM: Artificial sequence
<220> FEATURE:
<223> OTHER INFORMATION: synthetic construct

<400> SEQUENCE: 86

```
Met Gly His His His His His Ser Ser Gly Ile Lys Glu Thr Trp
1               5                   10                  15

Trp Glu Thr Trp Trp Thr Glu Trp Ser Gln Pro Lys Lys Arg Lys
                20                  25                  30

Val Ser Ser Gly Leu Glu Gly Met Ser Arg Thr Arg Leu Pro Ser
            35                  40                  45

Pro Ala Pro Ser Pro Ala Phe Ser Ala Asp Ser Phe Ser Asp Leu
        50                  55                  60

Arg Gln Phe Asp Pro Ser Leu Phe Asn Thr Ser Leu Phe Asp Ser Leu
65                  70                  75                  80
```

```
Pro Pro Phe Gly Ala His His Thr Glu Ala Thr Gly Glu Trp Asp
                85                  90                  95
Glu Val Gln Ser Gly Leu Arg Ala Ala Asp Ala Pro Pro Thr Met
            100                 105                 110
Arg Val Ala Val Thr Ala Ala Arg Pro Pro Arg Ala Lys Pro Ala Pro
            115                 120                 125
Arg Arg Arg Ala Ala Gln Pro Ser Asp Ala Ser Pro Ala Ala Gln Val
            130                 135                 140
Asp Leu Arg Thr Leu Gly Tyr Ser Glu Lys Ile Lys Pro Lys Val Arg
145                 150                 155                 160
Ser Thr Val Ala Gln His His Glu Ala Leu Val Gly His Gly Phe Thr
                165                 170                 175
His Ala His Ile Val Ala Leu Ser Gln His Pro Ala Ala Leu Gly Thr
                180                 185                 190
Val Ala Val Lys Tyr Gln Asp Met Ile Ala Ala Leu Pro Glu Ala Thr
                195                 200                 205
His Glu Ala Ile Val Gly Val Gly Lys Gln Trp Ser Gly Ala Arg Ala
            210                 215                 220
Leu Glu Ala Leu Leu Thr Val Ala Gly Glu Leu Arg Gly Pro Pro Leu
225                 230                 235                 240
Gln Leu Asp Thr Gly Gln Leu Leu Lys Ile Ala Lys Arg Gly Gly Val
                245                 250                 255
Thr Ala Val Glu Ala Val His Ala Trp Arg Asn Ala Leu Thr Gly Ala
                260                 265                 270
Pro Leu Asn Leu Thr Pro Glu Gln Val Val Ala Ile Ala Ser His Asp
                275                 280                 285
Gly Gly Lys Gln Ala Leu Glu Thr Val Gln Arg Leu Leu Pro Val Leu
            290                 295                 300
Cys Gln Ala His Gly Leu Thr Pro Glu Gln Val Val Ala Ile Ala Ser
305                 310                 315                 320
His Asp Gly Gly Lys Gln Ala Leu Glu Thr Val Gln Arg Leu Leu Pro
                325                 330                 335
Val Leu Cys Gln Ala His Gly Leu Thr Pro Glu Gln Val Val Ala Ile
                340                 345                 350
Ala Ser Asn Gly Gly Lys Gln Ala Leu Glu Thr Val Gln Arg Leu
            355                 360                 365
Leu Pro Val Leu Cys Gln Ala His Gly Leu Thr Pro Glu Gln Val Val
            370                 375                 380
Ala Ile Ala Ser Asn Gly Gly Lys Gln Ala Leu Glu Thr Val Gln
385                 390                 395                 400
Arg Leu Leu Pro Val Leu Cys Gln Ala His Gly Leu Thr Pro Glu Gln
                405                 410                 415
Val Val Ala Ile Ala Ser Asn Ile Gly Gly Lys Gln Ala Leu Glu Thr
                420                 425                 430
Val Gln Arg Leu Leu Pro Val Leu Cys Gln Ala His Gly Leu Thr Pro
            435                 440                 445
Glu Gln Val Val Ala Ile Ala Ser Asn Asn Gly Gly Lys Gln Ala Leu
            450                 455                 460
Glu Thr Val Gln Arg Leu Leu Pro Val Leu Cys Gln Ala His Gly Leu
465                 470                 475                 480
Thr Pro Glu Gln Val Val Ala Ile Ala Ser Asn Asn Gly Gly Lys Gln
                485                 490                 495
Ala Leu Glu Thr Val Gln Arg Leu Leu Pro Val Leu Cys Gln Ala His
```

```
                500             505             510
Gly Leu Thr Pro Glu Gln Val Val Ala Ile Ala Ser Asn Gly Gly Gly
            515                 520                 525

Lys Gln Ala Leu Glu Thr Val Gln Arg Leu Leu Pro Val Leu Cys Gln
            530                 535             540

Ala His Gly Leu Thr Pro Glu Gln Val Val Ala Ile Ala Ser His Asp
545                 550                 555                 560

Gly Gly Lys Gln Ala Leu Glu Thr Val Gln Arg Leu Leu Pro Val Leu
                565                 570                 575

Cys Gln Ala His Gly Leu Thr Pro Glu Gln Val Val Ala Ile Ala Ser
                580                 585                 590

Asn Gly Gly Gly Lys Gln Ala Leu Glu Thr Val Gln Arg Leu Leu Pro
            595                 600                 605

Val Leu Cys Gln Ala His Gly Leu Thr Pro Glu Gln Val Val Ala Ile
610                 615                 620

Ala Ser Asn Ile Gly Gly Lys Gln Ala Leu Glu Thr Val Gln Arg Leu
625                 630                 635                 640

Leu Pro Val Leu Cys Gln Ala His Gly Leu Thr Pro Glu Gln Val Val
                645                 650                 655

Ala Ile Ala Ser Asn Ile Gly Gly Lys Gln Ala Leu Glu Thr Val Gln
                660                 665                 670

Arg Leu Leu Pro Val Leu Cys Gln Ala His Gly Leu Thr Pro Glu Gln
                675                 680                 685

Val Val Ala Ile Ala Ser His Asp Gly Gly Arg Pro Ala Leu Glu Ser
690                 695                 700

Ile Val Ala Gln Leu Ser Arg Pro Asp Pro Ala Leu Ala Ala Leu Thr
705                 710                 715                 720

Asn Asp His Leu Val Ala Leu Ala Cys Leu Gly Gly Arg Pro Ala Leu
                725                 730                 735

Asp Ala Val Lys Lys Gly Leu Pro His Ala Pro Ala Leu Ile Lys Arg
                740                 745                 750

Thr Asn Arg Arg Ile Pro Glu Arg Thr Ser His Arg Val Ala Asp His
                755                 760                 765

Ala Gln Val Val Arg Val Leu Gly Phe Phe Gln Cys His Ser His Pro
                770                 775                 780

Ala Gln Ala Phe Asp Asp Ala Met Thr Gln Phe Gly Met Ser Arg His
785                 790                 795                 800

Gly Leu Leu Gln Leu Phe Arg Arg Val Gly Val Thr Glu Leu Glu Ala
                805                 810                 815

Arg Ser Gly Thr Leu Pro Pro Ala Ser Lys Arg Trp Asp Arg Ile Leu
                820                 825                 830

Gln Ala Ser Gly Met Lys Arg Ala Lys Pro Ser Pro Thr Ser Thr Gln
                835                 840                 845

Thr Pro Asp Gln Ala Ser Leu His Ala Phe Ala Asp Ser Leu Glu Arg
                850                 855                 860

Asp Leu Asp Ala Pro Ser Pro Met His Glu Gly Asp Gln Thr Arg Ala
865                 870                 875                 880

Ser Ala Ser Pro Lys Lys Lys Arg Lys Val Glu Ala Ser Gly Ser Gly
                885                 890                 895

Arg Ala Asp Ala Leu Asp Asp Phe Asp Leu Asp Met Leu Gly Ser Asp
                900                 905                 910

Ala Leu Asp Asp Phe Asp Leu Asp Met Leu Gly Ser Asp Ala Leu Asp
                915                 920                 925
```

Asp Phe Asp Leu Asp Met Leu Gly Ser Asp Ala Leu Asp Asp Phe Asp
            930                 935                 940

Leu Asp Met Leu Ile Asn Ser Arg
945                 950

<210> SEQ ID NO 87
<211> LENGTH: 21
<212> TYPE: PRT
<213> ORGANISM: Artificial sequence
<220> FEATURE:
<223> OTHER INFORMATION: synthetic construct

<400> SEQUENCE: 87

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 88
<211> LENGTH: 240
<212> TYPE: DNA
<213> ORGANISM: Homo sapiens

<400> SEQUENCE: 88
agtctccctt gggtcagggg tcctggttgc actccgtgct ttgcacaaag caggctctcc     60
atttttgtta aatgcacgaa tagtgctaag ctgggaagtt cttcctgagg tctaacctct    120
agctgctccc ccacagaaga gtgcctgcgg ccagtggcca ccaggggtcg ccgcagcacc    180
cagcgctgga gggcggagcg ggcggcagac ccggagcagc atgtggactc tcgggcgccg    240

<210> SEQ ID NO 89
<211> LENGTH: 5
<212> TYPE: PRT
<213> ORGANISM: Artificial sequence
<220> FEATURE:
<223> OTHER INFORMATION: synthetic construct

<400> SEQUENCE: 89

Lys Lys Lys Arg Lys
1               5

<210> SEQ ID NO 90
<211> LENGTH: 23
<212> TYPE: DNA
<213> ORGANISM: Artificial sequence
<220> FEATURE:
<223> OTHER INFORMATION: synthetic construct

<400> SEQUENCE: 90
aagccataca cgtttgagga cta                                              23

<210> SEQ ID NO 91
<211> LENGTH: 21
<212> TYPE: DNA
<213> ORGANISM: Artificial sequence
<220> FEATURE:
<223> OTHER INFORMATION: synthetic construct

<400> SEQUENCE: 91
ttggcgtctg cttgttgatc a                                                21

<210> SEQ ID NO 92
<211> LENGTH: 25

<212> TYPE: DNA
<213> ORGANISM: Artificial sequence
<220> FEATURE:
<223> OTHER INFORMATION: synthetic construct

<400> SEQUENCE: 92
agttctgtgg ccatctgctt agtag                                                25

<210> SEQ ID NO 93
<211> LENGTH: 21
<212> TYPE: DNA
<213> ORGANISM: Artificial sequence
<220> FEATURE:
<223> OTHER INFORMATION: synthetic construct

<400> SEQUENCE: 93
aaacaacaat ccgcccaaag g                                                   21

<210> SEQ ID NO 94
<211> LENGTH: 22
<212> TYPE: DNA
<213> ORGANISM: Artificial sequence
<220> FEATURE:
<223> OTHER INFORMATION: synthetic construct

<400> SEQUENCE: 94
ggctctccag aacatcatcc ct                                                  22

<210> SEQ ID NO 95
<211> LENGTH: 22
<212> TYPE: DNA
<213> ORGANISM: Artificial sequence
<220> FEATURE:
<223> OTHER INFORMATION: synthetic construct

<400> SEQUENCE: 95
acgcctgctt caccaccttc tt                                                  22

<210> SEQ ID NO 96
<211> LENGTH: 21
<212> TYPE: DNA
<213> ORGANISM: Artificial sequence
<220> FEATURE:
<223> OTHER INFORMATION: synthetic construct

<400> SEQUENCE: 96
acggaccaga gcgaaagcat t                                                   21

<210> SEQ ID NO 97
<211> LENGTH: 25
<212> TYPE: DNA
<213> ORGANISM: Artificial sequence
<220> FEATURE:
<223> OTHER INFORMATION: synthetic construct

<400> SEQUENCE: 97
tccgtcaatt cctttagttt cagct                                               25

<210> SEQ ID NO 98
<211> LENGTH: 25
<212> TYPE: DNA
<213> ORGANISM: Artificial sequence
<220> FEATURE:
<223> OTHER INFORMATION: synthetic construct

<400> SEQUENCE: 98
caggactgaa agacttgctc gagat 25

<210> SEQ ID NO 99
<211> LENGTH: 26
<212> TYPE: DNA
<213> ORGANISM: Artificial sequence
<220> FEATURE:
<223> OTHER INFORMATION: synthetic construct

<400> SEQUENCE: 99
cagcaggtca gcaaagaact tatagc 26

<210> SEQ ID NO 100
<211> LENGTH: 21
<212> TYPE: DNA
<213> ORGANISM: Artificial sequence
<220> FEATURE:
<223> OTHER INFORMATION: synthetic construct

<400> SEQUENCE: 100
acgggaagct cactggcatg g 21

<210> SEQ ID NO 101
<211> LENGTH: 23
<212> TYPE: DNA
<213> ORGANISM: Artificial sequence
<220> FEATURE:
<223> OTHER INFORMATION: synthetic construct

<400> SEQUENCE: 101
atgcctgctt caccaccttc ttg 23

<210> SEQ ID NO 102
<211> LENGTH: 24
<212> TYPE: DNA
<213> ORGANISM: Artificial sequence
<220> FEATURE:
<223> OTHER INFORMATION: synthetic construct

<400> SEQUENCE: 102
tggataccgc agctaggaat aatg 24

<210> SEQ ID NO 103
<211> LENGTH: 21
<212> TYPE: DNA
<213> ORGANISM: Artificial sequence
<220> FEATURE:
<223> OTHER INFORMATION: synthetic construct

<400> SEQUENCE: 103
tcacctctag cggcgcaata c 21

<210> SEQ ID NO 104
<211> LENGTH: 22
<212> TYPE: DNA
<213> ORGANISM: Artificial sequence
<220> FEATURE:
<223> OTHER INFORMATION: synthetic construct

<400> SEQUENCE: 104
caccccttaa gagacccatg tt 22

<210> SEQ ID NO 105
<211> LENGTH: 22
<212> TYPE: DNA
<213> ORGANISM: Artificial sequence

```
<220> FEATURE:
<223> OTHER INFORMATION: synthetic construct

<400> SEQUENCE: 105
ccctgcagag accttagaaa ac                                              22

<210> SEQ ID NO 106
<211> LENGTH: 945
<212> TYPE: PRT
<213> ORGANISM: Artificial sequence
<220> FEATURE:
<223> OTHER INFORMATION: synthetic construct

<400> SEQUENCE: 106

Met Gly His His His His His His Ser Ser Gly Gly Leu Arg Ser Tyr
1               5                   10                  15

Gly Arg Lys Lys Arg Arg Gln Arg Arg Gly Ala Ser Thr Gly Gly
            20                  25                  30

Met Ser Arg Thr Arg Leu Pro Ser Pro Pro Ala Pro Ser Pro Ala Phe
        35                  40                  45

Ser Ala Asp Ser Phe Ser Asp Leu Leu Arg Gln Phe Asp Pro Ser Leu
    50                  55                  60

Phe Asn Thr Ser Leu Phe Asp Ser Leu Pro Pro Phe Gly Ala His His
65                  70                  75                  80

Thr Glu Ala Ala Thr Gly Glu Trp Asp Glu Val Gln Ser Gly Leu Arg
                85                  90                  95

Ala Ala Asp Ala Pro Pro Pro Thr Met Arg Val Ala Val Thr Ala Ala
            100                 105                 110

Arg Pro Pro Arg Ala Lys Pro Ala Pro Arg Arg Arg Ala Ala Gln Pro
        115                 120                 125

Ser Asp Ala Ser Pro Ala Ala Gln Val Asp Leu Arg Thr Leu Gly Tyr
    130                 135                 140

Ser Glu Lys Ile Lys Pro Lys Val Arg Ser Thr Val Ala Gln His His
145                 150                 155                 160

Glu Ala Leu Val Gly His Gly Phe Thr His Ala His Ile Val Ala Leu
                165                 170                 175

Ser Gln His Pro Ala Ala Leu Gly Thr Val Ala Val Lys Tyr Gln Asp
            180                 185                 190

Met Ile Ala Ala Leu Pro Glu Ala Thr His Glu Ala Ile Val Gly Val
        195                 200                 205

Gly Lys Gln Trp Ser Gly Ala Arg Ala Leu Glu Ala Leu Leu Thr Val
    210                 215                 220

Ala Gly Glu Leu Arg Gly Pro Pro Leu Gln Leu Asp Thr Gly Gln Leu
225                 230                 235                 240

Leu Lys Ile Ala Lys Arg Gly Gly Val Thr Ala Val Glu Ala Val His
                245                 250                 255

Ala Trp Arg Asn Ala Leu Thr Gly Ala Pro Leu Asn Leu Thr Pro Glu
            260                 265                 270

Gln Val Val Ala Ile Ala Ser His Asp Gly Gly Lys Gln Ala Leu Glu
        275                 280                 285

Thr Val Gln Arg Leu Leu Pro Val Leu Cys Gln Ala His Gly Leu Thr
    290                 295                 300

Pro Glu Gln Val Val Ala Ile Ala Ser His Asp Gly Gly Lys Gln Ala
305                 310                 315                 320

Leu Glu Thr Val Gln Arg Leu Leu Pro Val Leu Cys Gln Ala His Gly
                325                 330                 335
```

```
Leu Thr Pro Glu Gln Val Val Ala Ile Ala Ser Asn Gly Gly Lys
            340                 345                 350

Gln Ala Leu Glu Thr Val Gln Arg Leu Leu Pro Val Leu Cys Gln Ala
        355                 360                 365

His Gly Leu Thr Pro Glu Gln Val Val Ala Ile Ala Ser Asn Asn Gly
370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
            405                 410                 415

Ile Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
        435                 440                 445

Ser Asn Asn Gly Gly Lys Gln Ala Leu Glu Thr Val Gln Arg Leu Leu
    450                 455                 460

Pro Val Leu Cys Gln Ala His Gly Leu Thr Pro Glu Gln Val Val Ala
465                 470                 475                 480

Ile Ala Ser Asn Asn Gly Gly Lys Gln Ala Leu Glu Thr Val Gln Arg
            485                 490                 495

Leu Leu Pro Val Leu Cys Gln Ala His Gly Leu Thr Pro Glu Gln Val
        500                 505                 510

Val Ala Ile Ala Ser Asn Gly Gly Gly Lys Gln Ala Leu Glu Thr Val
    515                 520                 525

Gln Arg Leu Leu Pro Val Leu Cys Gln Ala His Gly Leu Thr Pro Glu
    530                 535                 540

Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
            565                 570                 575

Pro Glu Gln Val Val Ala Ile Ala Ser Asn Gly Gly Gly Lys Gln Ala
        580                 585                 590

Leu Glu Thr Val Gln Arg Leu Leu Pro Val Leu Cys Gln Ala His Gly
    595                 600                 605

Leu Thr Pro Glu Gln Val Val Ala Ile Ala Ser Asn Ile Gly Gly Lys
    610                 615                 620

Gln Ala Leu Glu Thr Val Gln Arg Leu Leu Pro Val Leu Cys Gln Ala
625                 630                 635                 640

His Gly Leu Thr Pro Glu Gln Val Val Ala Ile Ala Ser Asn Ile Gly
            645                 650                 655

Gly Lys Gln Ala Leu Glu Thr Val Gln Arg Leu Leu Pro Val Leu Cys
        660                 665                 670

Gln Ala His Gly Leu Thr Pro Glu Gln Val Val Ala Ile Ala Ser His
    675                 680                 685

Asp Gly Gly Arg Pro Ala Leu Glu Ser Ile Val Ala Gln Leu Ser Arg
690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
            725                 730                 735

Pro His Ala Pro Ala Leu Ile Lys Arg Thr Asn Arg Arg Ile Pro Glu
            740                 745                 750
```

```
Arg Thr Ser His Arg Val Ala Asp His Ala Gln Val Arg Val Leu
        755                 760                 765
Gly Phe Phe Gln Cys His Ser His Pro Ala Gln Ala Phe Asp Asp Ala
770                 775                 780
Met Thr Gln Phe Gly Met Ser Arg His Gly Leu Leu Gln Leu Phe Arg
785                 790                 795                 800
Arg Val Gly Val Thr Glu Leu Glu Ala Arg Ser Gly Thr Leu Pro Pro
                805                 810                 815
Ala Ser Lys Arg Trp Asp Arg Ile Leu Gln Ala Ser Gly Met Lys Arg
            820                 825                 830
Ala Lys Pro Ser Pro Thr Ser Thr Gln Thr Pro Asp Gln Ala Ser Leu
        835                 840                 845
His Ala Phe Ala Asp Ser Leu Glu Arg Asp Leu Asp Ala Pro Ser Pro
    850                 855                 860
Met His Glu Gly Asp Gln Thr Arg Ala Ser Ala Ser Pro Lys Lys Lys
865                 870                 875                 880
Arg Lys Val Glu Ala Ser Gly Ser Gly Arg Ala Asp Ala Leu Asp Asp
                885                 890                 895
Phe Asp Leu Asp Met Leu Gly Ser Asp Ala Leu Asp Asp Phe Asp Leu
            900                 905                 910
Asp Met Leu Gly Ser Asp Ala Leu Asp Asp Phe Asp Leu Asp Met Leu
        915                 920                 925
Gly Ser Asp Ala Leu Asp Asp Phe Asp Leu Asp Met Leu Ile Asn Ser
    930                 935                 940
Arg
945

<210> SEQ ID NO 107
<211> LENGTH: 9
<212> TYPE: PRT
<213> ORGANISM: Artificial Sequence
<220> FEATURE:
<223> OTHER INFORMATION: Synthetic construct

<400> SEQUENCE: 107

Glu Thr Phe Ser Asp Leu Trp Lys Leu
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic construct

<400> SEQUENCE: 108

Asp Asp Ile Glu Gln Trp Phe Thr Glu
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic construct

<400> SEQUENCE: 109

Ser Asp Ile Met Asp Phe Val Leu Lys
1               5
```

```
<210> SEQ ID NO 110
<211> LENGTH: 9
<212> TYPE: PRT
<213> ORGANISM: Artificial Sequence
<220> FEATURE:
<223> OTHER INFORMATION: Synthetic construct

<400> SEQUENCE: 110

Asp Leu Leu Asp Phe Ser Met Met Phe
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic construct

<400> SEQUENCE: 111

Glu Thr Leu Asp Phe Ser Leu Val Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic construct

<400> SEQUENCE: 112

Arg Lys Ile Leu Asn Asp Leu Ser Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic construct

<400> SEQUENCE: 113

Glu Ala Ile Leu Ala Glu Leu Lys Lys
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic construct

<400> SEQUENCE: 114

Asp Asp Val Val Gln Tyr Leu Asn Ser
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic construct

<400> SEQUENCE: 115

Asp Asp Val Tyr Asn Tyr Leu Phe Asp
1               5

<210> SEQ ID NO 116
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 116

Asp Leu Phe Asp Tyr Asp Phe Leu Val
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic construct

<400> SEQUENCE: 117

Asp Phe Phe Asp Tyr Asp Leu Leu Phe
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic construct

<400> SEQUENCE: 118

Glu Asp Leu Tyr Ser Ile Leu Trp Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic construct

<400> SEQUENCE: 119

Thr Asp Leu Tyr His Thr Leu Trp Asn
1               5

<210> SEQ ID NO 120
<211> LENGTH: 15
<212> TYPE: PRT
<213> ORGANISM: Artificial Sequence
<220> FEATURE:
<223> OTHER INFORMATION: Synthetic construct

<400> SEQUENCE: 120

Leu Ser Pro Glu Glu Thr Phe Ser Asp Leu Trp Lys Leu Pro Glu
1               5                   10                  15

<210> SEQ ID NO 121
<211> LENGTH: 24
<212> TYPE: PRT
<213> ORGANISM: Artificial Sequence
<220> FEATURE:
<223> OTHER INFORMATION: Synthetic construct

<400> SEQUENCE: 121

Gln Ala Met Asp Asp Leu Met Leu Ser Pro Asp Asp Ile Glu Gln Trp
1               5                   10                  15

Phe Thr Glu Asp Pro Gly Pro Asp
            20
```

<210> SEQ ID NO 122
<211> LENGTH: 19
<212> TYPE: PRT
<213> ORGANISM: Artificial Sequence
<220> FEATURE:
<223> OTHER INFORMATION: Synthetic construct

<400> SEQUENCE: 122

Asp Cys Gly Asn Ile Leu Pro Ser Asp Ile Met Asp Phe Val Leu Lys
1               5                   10                  15

Asn Thr Pro

<210> SEQ ID NO 123
<211> LENGTH: 24
<212> TYPE: PRT
<213> ORGANISM: Artificial Sequence
<220> FEATURE:
<223> OTHER INFORMATION: Synthetic construct

<400> SEQUENCE: 123

Pro Val Gly Thr Asp Lys Glu Leu Ser Asp Leu Leu Leu Asp Phe Ser
1               5                   10                  15

Met Met Phe Pro Leu Pro Val Thr
            20

<210> SEQ ID NO 124
<211> LENGTH: 23
<212> TYPE: PRT
<213> ORGANISM: Artificial Sequence
<220> FEATURE:
<223> OTHER INFORMATION: Synthetic construct

<400> SEQUENCE: 124

Arg Arg Glu Ile Leu Ser Arg Arg Pro Ser Tyr Arg Lys Ile Leu Asn
1               5                   10                  15

Asp Leu Ser Ser Asp Ala Pro
            20

<210> SEQ ID NO 125
<211> LENGTH: 9
<212> TYPE: PRT
<213> ORGANISM: Artificial Sequence
<220> FEATURE:
<223> OTHER INFORMATION: Synthetic construct

<400> SEQUENCE: 125

Asp Leu Phe Asp Tyr Asp Phe Leu Val
1               5

<210> SEQ ID NO 126
<211> LENGTH: 12
<212> TYPE: PRT
<213> ORGANISM: Artificial Sequence
<220> FEATURE:
<223> OTHER INFORMATION: Synthetic construct

<400> SEQUENCE: 126

Glu Asp Leu Tyr Ser Ile Leu Trp Ser Asp Trp Tyr
1               5                   10

<210> SEQ ID NO 127
<211> LENGTH: 782
<212> TYPE: PRT
<213> ORGANISM: artificial sequence
<220> FEATURE:

<223> OTHER INFORMATION: Synthetic polypeptide

<400> SEQUENCE: 127

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
        50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
        210                 215                 220

Glu Ala Val His Ala Trp Arg Asn Ala Leu Thr Gly Ala Pro Leu Asn
225                 230                 235                 240

Leu Thr Glu Thr Val His Glu Thr His Gly Thr Ala Ser Gln Leu Thr
                245                 250                 255

Pro Glu Gln Val Val Ala Ile Ala Ser Asn Gly Gly Gly Arg Pro Ala
                260                 265                 270

Leu Glu Ser Ile Val Ala Gln Leu Ser Arg Pro Asp Pro Ala Leu Ala
            275                 280                 285

Ala Leu Thr Asn Asp His Leu Val Ala Leu Ala Cys Leu Gly Gly Arg
        290                 295                 300

Pro Ala Leu Asp Ala Val Lys Lys Gly Leu Pro His Ala Pro Ala Leu
305                 310                 315                 320

Ile Lys Arg Thr Asn Arg Arg Ile Pro Glu Arg Thr Ser His Arg Val
                325                 330                 335

Ala Asp His Ala Gln Val Val Arg Val Leu Gly Phe Phe Gln Cys His
                340                 345                 350

Ser His Pro Ala Gln Ala Phe Asp Asp Ala Met Thr Gln Phe Gly Met
            355                 360                 365

Ser Arg His Gly Leu Leu Gln Leu Phe Arg Arg Val Gly Val Thr Glu
        370                 375                 380

Leu Glu Ala Arg Ser Gly Thr Leu Pro Pro Ala Ser Gln Arg Trp Asp
385                 390                 395                 400
```

-continued

```
Arg Ile Leu Gln Ala Ser Gly Met Lys Arg Ala Lys Pro Ser Pro Thr
                405                 410                 415
Ser Thr Gln Thr Pro Asp Gln Ala Ser Leu His Ala Phe Ala Asp Ser
            420                 425                 430
Leu Glu Arg Asp Leu Asp Ala Pro Ser Pro Met His Glu Gly Asp Gln
        435                 440                 445
Thr Arg Ala Ser Ala Ser Pro Lys Lys Arg Lys Val Glu Ala Ser
    450                 455                 460
Gly Ser Gly Arg Ala Asp Ala Leu Asp Asp Phe Asp Leu Asp Met Leu
465                 470                 475                 480
Gly Ser Asp Ala Leu Asp Asp Phe Asp Leu Asp Met Leu Gly Ser Asp
                485                 490                 495
Ala Leu Asp Asp Phe Asp Leu Asp Met Leu Gly Ser Asp Ala Leu Asp
            500                 505                 510
Asp Phe Asp Leu Asp Met Leu Ile Asn Ser Arg Gly Ser Gly Glu Gly
        515                 520                 525
Arg Gly Ser Leu Leu Thr Cys Gly Asp Val Glu Glu Asn Pro Gly Pro
    530                 535                 540
Val Ser Lys Gly Glu Glu Leu Phe Thr Gly Val Val Pro Ile Leu Val
545                 550                 555                 560
Glu Leu Asp Gly Asp Val Asn Gly His Lys Phe Ser Val Ser Gly Glu
                565                 570                 575
Gly Glu Gly Asp Ala Thr Tyr Gly Lys Leu Thr Leu Lys Phe Ile Cys
            580                 585                 590
Thr Thr Gly Lys Leu Pro Val Pro Trp Pro Thr Leu Val Thr Thr Leu
        595                 600                 605
Thr Tyr Gly Val Gln Cys Phe Ser Arg Tyr Pro Asp His Met Lys Gln
    610                 615                 620
His Asp Phe Phe Lys Ser Ala Met Pro Glu Gly Tyr Val Gln Glu Arg
625                 630                 635                 640
Thr Ile Phe Phe Lys Asp Asp Gly Asn Tyr Lys Thr Arg Ala Glu Val
                645                 650                 655
Lys Phe Glu Gly Asp Thr Leu Val Asn Arg Ile Glu Leu Lys Gly Ile
            660                 665                 670
Asp Phe Lys Glu Asp Gly Asn Ile Leu Gly His Lys Leu Glu Tyr Asn
        675                 680                 685
Tyr Asn Ser His Asn Val Tyr Ile Met Ala Asp Lys Gln Lys Asn Gly
    690                 695                 700
Ile Lys Val Asn Phe Lys Ile Arg His Asn Ile Glu Asp Gly Ser Val
705                 710                 715                 720
Gln Leu Ala Asp His Tyr Gln Gln Asn Thr Pro Ile Gly Asp Gly Pro
                725                 730                 735
Val Leu Leu Pro Asp Asn His Tyr Leu Ser Thr Gln Ser Ala Leu Ser
            740                 745                 750
Lys Asp Pro Asn Glu Lys Arg Asp His Met Val Leu Leu Glu Phe Val
        755                 760                 765
Thr Ala Ala Gly Ile Thr Leu Gly Met Asp Glu Leu Tyr Lys
    770                 775                 780

<210> SEQ ID NO 128
<211> LENGTH: 782
<212> TYPE: PRT
<213> ORGANISM: artificial sequence
<220> FEATURE:
<223> OTHER INFORMATION: Synthetic polypeptide
```

```
<400> SEQUENCE: 128

Met Ser Arg Thr Arg Leu Pro Ser Pro Pro Ala Pro Ser Pro Ala Phe
  1               5                  10                  15

Ser Ala Asp Ser Phe Ser Asp Leu Leu Arg Gln Phe Asp Pro Ser Leu
             20                  25                  30

Phe Asn Thr Ser Leu Phe Asp Ser Leu Pro Pro Phe Gly Ala His His
         35                  40                  45

Thr Glu Ala Ala Thr Gly Glu Trp Asp Glu Val Gln Ser Gly Leu Arg
 50                  55                  60

Ala Ala Asp Ala Pro Pro Thr Met Arg Val Ala Val Thr Ala Ala
 65                  70                  75                  80

Arg Pro Pro Arg Ala Lys Pro Ala Pro Arg Arg Ala Ala Gln Pro
                 85                  90                  95

Ser Asp Ala Ser Pro Ala Ala Gln Val Asp Leu Arg Thr Leu Gly Tyr
                100                 105                 110

Ser Gln Gln Gln Glu Lys Ile Lys Pro Lys Val Arg Ser Thr Val
             115                 120                 125

Ala Gln His His Glu Ala Leu Val Gly His Gly Phe Thr His Ala His
130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
             180                 185                 190

Leu Leu Thr Val Ala Gly Glu Leu Arg Gly Pro Pro Leu Gln Leu Asp
         195                 200                 205

Thr Gly Gln Leu Leu Lys Ile Ala Lys Arg Gly Gly Val Thr Ala Val
210                 215                 220

Glu Ala Val His Ala Trp Arg Asn Ala Leu Thr Gly Ala Pro Leu Asn
225                 230                 235                 240

Leu Thr Glu Thr Val His Glu Thr His Gly Thr Ala Ser Gln Leu Thr
                245                 250                 255

Pro Glu Gln Val Val Ala Ile Ala Ser Asn Ile Gly Gly Arg Pro Ala
             260                 265                 270

Leu Glu Ser Ile Val Ala Gln Leu Ser Arg Pro Asp Pro Ala Leu Ala
         275                 280                 285

Ala Leu Thr Asn Asp His Leu Val Ala Leu Ala Cys Leu Gly Gly Arg
     290                 295                 300

Pro Ala Leu Asp Ala Val Lys Lys Gly Leu Pro His Ala Pro Ala Leu
305                 310                 315                 320

Ile Lys Arg Thr Asn Arg Ile Pro Glu Arg Thr Ser His Arg Val
                325                 330                 335

Ala Asp His Ala Gln Val Arg Val Leu Gly Phe Phe Gln Cys His
             340                 345                 350

Ser His Pro Ala Gln Ala Phe Asp Asp Ala Met Thr Gln Phe Gly Met
         355                 360                 365

Ser Arg His Gly Leu Leu Gln Leu Phe Arg Arg Val Gly Val Thr Glu
     370                 375                 380

Leu Glu Ala Arg Ser Gly Thr Leu Pro Pro Ala Ser Gln Arg Trp Asp
385                 390                 395                 400

Arg Ile Leu Gln Ala Ser Gly Met Lys Arg Ala Lys Pro Ser Pro Thr
```

```
            405                 410                 415
Ser Thr Gln Thr Pro Asp Gln Ala Ser Leu His Ala Phe Ala Asp Ser
            420                 425                 430

Leu Glu Arg Asp Leu Asp Ala Pro Ser Pro Met His Glu Gly Asp Gln
            435                 440                 445

Thr Arg Ala Ser Ala Ser Pro Lys Lys Lys Arg Lys Val Glu Ala Ser
450                 455                 460

Gly Ser Gly Arg Ala Asp Ala Leu Asp Asp Phe Asp Leu Asp Met Leu
465                 470                 475                 480

Gly Ser Asp Ala Leu Asp Asp Phe Asp Leu Asp Met Leu Gly Ser Asp
            485                 490                 495

Ala Leu Asp Asp Phe Asp Leu Asp Met Leu Gly Ser Asp Ala Leu Asp
            500                 505                 510

Asp Phe Asp Leu Asp Met Leu Ile Asn Ser Arg Gly Ser Gly Glu Gly
            515                 520                 525

Arg Gly Ser Leu Leu Thr Cys Gly Asp Val Glu Glu Asn Pro Gly Pro
            530                 535                 540

Val Ser Lys Gly Glu Glu Leu Phe Thr Gly Val Val Pro Ile Leu Val
545                 550                 555                 560

Glu Leu Asp Gly Asp Val Asn Gly His Lys Phe Ser Val Ser Gly Glu
            565                 570                 575

Gly Glu Gly Asp Ala Thr Tyr Gly Lys Leu Thr Leu Lys Phe Ile Cys
            580                 585                 590

Thr Thr Gly Lys Leu Pro Val Pro Trp Pro Thr Leu Val Thr Thr Leu
            595                 600                 605

Thr Tyr Gly Val Gln Cys Phe Ser Arg Tyr Pro Asp His Met Lys Gln
            610                 615                 620

His Asp Phe Phe Lys Ser Ala Met Pro Glu Gly Tyr Val Gln Glu Arg
625                 630                 635                 640

Thr Ile Phe Phe Lys Asp Asp Gly Asn Tyr Lys Thr Arg Ala Glu Val
            645                 650                 655

Lys Phe Glu Gly Asp Thr Leu Val Asn Arg Ile Glu Leu Lys Gly Ile
            660                 665                 670

Asp Phe Lys Glu Asp Gly Asn Ile Leu Gly His Lys Leu Glu Tyr Asn
            675                 680                 685

Tyr Asn Ser His Asn Val Tyr Ile Met Ala Asp Lys Gln Lys Asn Gly
            690                 695                 700

Ile Lys Val Asn Phe Lys Ile Arg His Asn Ile Glu Asp Gly Ser Val
705                 710                 715                 720

Gln Leu Ala Asp His Tyr Gln Gln Asn Thr Pro Ile Gly Asp Gly Pro
            725                 730                 735

Val Leu Leu Pro Asp Asn His Tyr Leu Ser Thr Gln Ser Ala Leu Ser
            740                 745                 750

Lys Asp Pro Asn Glu Lys Arg Asp His Met Val Leu Leu Glu Phe Val
            755                 760                 765

Thr Ala Ala Gly Ile Thr Leu Gly Met Asp Glu Leu Tyr Lys
            770                 775                 780

<210> SEQ ID NO 129
<211> LENGTH: 782
<212> TYPE: PRT
<213> ORGANISM: artificial sequence
<220> FEATURE:
<223> OTHER INFORMATION: Synthetic polypeptide
```

<400> SEQUENCE: 129

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Glu Lys Ile Lys Pro Lys Val Arg Ser Thr Val
            115                 120                 125

Ala Gln His His Glu Ala Leu Val Gly His Gly Phe Thr His Ala His
130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Val Thr Ala Val
210                 215                 220

Glu Ala Val His Ala Trp Arg Asn Ala Leu Thr Gly Ala Pro Leu Asn
225                 230                 235                 240

Leu Thr Glu Thr Val His Glu Thr His Gly Thr Ala Ser Gln Leu Thr
            245                 250                 255

Pro Glu Gln Val Val Ala Ile Ala Ser Asn Asn Gly Gly Arg Pro Ala
            260                 265                 270

Leu Glu Ser Ile Val Ala Gln Leu Ser Arg Pro Asp Pro Ala Leu Ala
            275                 280                 285

Ala Leu Thr Asn Asp His Leu Val Ala Leu Ala Cys Leu Gly Gly Arg
    290                 295                 300

Pro Ala Leu Asp Ala Val Lys Lys Gly Leu Pro His Ala Pro Ala Leu
305                 310                 315                 320

Ile Lys Arg Thr Asn Arg Arg Ile Pro Glu Arg Thr Ser His Arg Val
                325                 330                 335

Ala Asp His Ala Gln Val Val Arg Val Leu Gly Phe Phe Gln Cys His
            340                 345                 350

Ser His Pro Ala Gln Ala Phe Asp Asp Ala Met Thr Gln Phe Gly Met
            355                 360                 365

Ser Arg His Gly Leu Leu Gln Leu Phe Arg Arg Val Gly Val Thr Glu
    370                 375                 380

Leu Glu Ala Arg Ser Gly Thr Leu Pro Pro Ala Ser Gln Arg Trp Asp
385                 390                 395                 400

Arg Ile Leu Gln Ala Ser Gly Met Lys Arg Ala Lys Pro Ser Pro Thr
                405                 410                 415
```

```
Ser Thr Gln Thr Pro Asp Gln Ala Ser Leu His Ala Phe Ala Asp Ser
            420                 425                 430

Leu Glu Arg Asp Leu Asp Ala Pro Ser Pro Met His Glu Gly Asp Gln
        435                 440                 445

Thr Arg Ala Ser Ala Ser Pro Lys Lys Arg Lys Val Glu Ala Ser
    450                 455                 460

Gly Ser Gly Arg Ala Asp Ala Leu Asp Asp Phe Asp Leu Asp Met Leu
465                 470                 475                 480

Gly Ser Asp Ala Leu Asp Asp Phe Asp Leu Asp Met Leu Gly Ser Asp
                485                 490                 495

Ala Leu Asp Asp Phe Asp Leu Asp Met Leu Gly Ser Ala Leu Asp
        500                 505                 510

Asp Phe Asp Leu Asp Met Leu Ile Asn Ser Arg Gly Ser Gly Glu Gly
            515                 520                 525

Arg Gly Ser Leu Leu Thr Cys Gly Asp Val Glu Glu Asn Pro Gly Pro
530                 535                 540

Val Ser Lys Gly Glu Glu Leu Phe Thr Gly Val Val Pro Ile Leu Val
545                 550                 555                 560

Glu Leu Asp Gly Asp Val Asn Gly His Lys Phe Ser Val Ser Gly Glu
                565                 570                 575

Gly Glu Gly Asp Ala Thr Tyr Gly Lys Leu Thr Leu Lys Phe Ile Cys
            580                 585                 590

Thr Thr Gly Lys Leu Pro Val Pro Trp Pro Thr Leu Val Thr Thr Leu
        595                 600                 605

Thr Tyr Gly Val Gln Cys Phe Ser Arg Tyr Pro Asp His Met Lys Gln
    610                 615                 620

His Asp Phe Phe Lys Ser Ala Met Pro Glu Gly Tyr Val Gln Glu Arg
625                 630                 635                 640

Thr Ile Phe Phe Lys Asp Asp Gly Asn Tyr Lys Thr Arg Ala Glu Val
                645                 650                 655

Lys Phe Glu Gly Asp Thr Leu Val Asn Arg Ile Glu Leu Lys Gly Ile
            660                 665                 670

Asp Phe Lys Glu Asp Gly Asn Ile Leu Gly His Lys Leu Glu Tyr Asn
        675                 680                 685

Tyr Asn Ser His Asn Val Tyr Ile Met Ala Asp Lys Gln Lys Asn Gly
    690                 695                 700

Ile Lys Val Asn Phe Lys Ile Arg His Asn Ile Glu Asp Gly Ser Val
705                 710                 715                 720

Gln Leu Ala Asp His Tyr Gln Gln Asn Thr Pro Ile Gly Asp Gly Pro
                725                 730                 735

Val Leu Leu Pro Asp Asn His Tyr Leu Ser Thr Gln Ser Ala Leu Ser
            740                 745                 750

Lys Asp Pro Asn Glu Lys Arg Asp His Met Val Leu Leu Glu Phe Val
        755                 760                 765

Thr Ala Ala Gly Ile Thr Leu Gly Met Asp Glu Leu Tyr Lys
    770                 775                 780

<210> SEQ ID NO 130
<211> LENGTH: 782
<212> TYPE: PRT
<213> ORGANISM: artificial sequence
<220> FEATURE:
<223> OTHER INFORMATION: Synthetic polypeptide

<400> SEQUENCE: 130
```

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
50                  55                  60

Ala Ala Asp Ala Pro Pro Thr Met Arg Val Ala Val Thr Ala Ala
65              70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Glu Lys Ile Lys Pro Lys Val Arg Ser Thr Val
    115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145             150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225             230                 235                 240

Leu Thr Glu Thr Val His Glu Thr His Gly Thr Ala Ser Gln Leu Thr
                245                 250                 255

Pro Glu Gln Val Val Ala Ile Ala Ser His Asp Gly Gly Arg Pro Ala
            260                 265                 270

Leu Glu Ser Ile Val Ala Gln Leu Ser Arg Pro Asp Pro Ala Leu Ala
            275                 280                 285

Ala Leu Thr Asn Asp His Leu Val Ala Leu Ala Cys Leu Gly Gly Arg
    290                 295                 300

Pro Ala Leu Asp Ala Val Lys Lys Gly Leu Pro His Ala Pro Ala Leu
305             310                 315                 320

Ile Lys Arg Thr Asn Arg Arg Ile Pro Glu Arg Thr Ser His Arg Val
                325                 330                 335

Ala Asp His Ala Gln Val Val Arg Val Leu Gly Phe Phe Gln Cys His
            340                 345                 350

Ser His Pro Ala Gln Ala Phe Asp Asp Ala Met Thr Gln Phe Gly Met
        355                 360                 365

Ser Arg His Gly Leu Leu Gln Leu Phe Arg Arg Val Gly Val Thr Glu
    370                 375                 380

Leu Glu Ala Arg Ser Gly Thr Leu Pro Pro Ala Ser Gln Arg Trp Asp
385             390                 395                 400

Arg Ile Leu Gln Ala Ser Gly Met Lys Arg Ala Lys Pro Ser Pro Thr
                405                 410                 415
```

```
Ser Thr Gln Thr Pro Asp Gln Ala Ser Leu His Ala Phe Ala Asp Ser
            420                 425                 430

Leu Glu Arg Asp Leu Asp Ala Pro Ser Pro Met His Glu Gly Asp Gln
        435                 440                 445

Thr Arg Ala Ser Ala Ser Pro Lys Lys Arg Lys Val Glu Ala Ser
    450                 455                 460

Gly Ser Gly Arg Ala Asp Ala Leu Asp Asp Phe Asp Leu Asp Met Leu
465                 470                 475                 480

Gly Ser Asp Ala Leu Asp Asp Phe Asp Leu Asp Met Leu Gly Ser Asp
                485                 490                 495

Ala Leu Asp Asp Phe Asp Leu Asp Met Leu Gly Ser Asp Ala Leu Asp
                500                 505                 510

Asp Phe Asp Leu Asp Met Leu Ile Asn Ser Arg Gly Ser Gly Glu Gly
                515                 520                 525

Arg Gly Ser Leu Leu Thr Cys Gly Asp Val Glu Glu Asn Pro Gly Pro
        530                 535                 540

Val Ser Lys Gly Glu Glu Leu Phe Thr Gly Val Val Pro Ile Leu Val
545                 550                 555                 560

Glu Leu Asp Gly Asp Val Asn Gly His Lys Phe Ser Val Ser Gly Glu
                565                 570                 575

Gly Glu Gly Asp Ala Thr Tyr Gly Lys Leu Thr Leu Lys Phe Ile Cys
                580                 585                 590

Thr Thr Gly Lys Leu Pro Val Pro Trp Pro Thr Leu Val Thr Thr Leu
            595                 600                 605

Thr Tyr Gly Val Gln Cys Phe Ser Arg Tyr Pro Asp His Met Lys Gln
            610                 615                 620

His Asp Phe Phe Lys Ser Ala Met Pro Glu Gly Tyr Val Gln Glu Arg
625                 630                 635                 640

Thr Ile Phe Phe Lys Asp Asp Gly Asn Tyr Lys Thr Arg Ala Glu Val
                645                 650                 655

Lys Phe Glu Gly Asp Thr Leu Val Asn Arg Ile Glu Leu Lys Gly Ile
                660                 665                 670

Asp Phe Lys Glu Asp Gly Asn Ile Leu Gly His Lys Leu Glu Tyr Asn
            675                 680                 685

Tyr Asn Ser His Asn Val Tyr Ile Met Ala Asp Lys Gln Lys Asn Gly
690                 695                 700

Ile Lys Val Asn Phe Lys Ile Arg His Asn Ile Glu Asp Gly Ser Val
705                 710                 715                 720

Gln Leu Ala Asp His Tyr Gln Gln Asn Thr Pro Ile Gly Asp Gly Pro
                725                 730                 735

Val Leu Leu Pro Asp Asn His Tyr Leu Ser Thr Gln Ser Ala Leu Ser
            740                 745                 750

Lys Asp Pro Asn Glu Lys Arg Asp His Met Val Leu Leu Glu Phe Val
            755                 760                 765

Thr Ala Ala Gly Ile Thr Leu Gly Met Asp Glu Leu Tyr Lys
            770                 775                 780

<210> SEQ ID NO 131
<211> LENGTH: 2349
<212> TYPE: DNA
<213> ORGANISM: artificial sequence
<220> FEATURE:
<223> OTHER INFORMATION: Synthetic polynucleotide

<400> SEQUENCE: 131
```

```
atgtcgcgga cccggctccc ttccccaccc gcacccagcc cagcgttttc ggccgactcg    60
ttctcagacc tgcttaggca gttcgacccc tcactgttta acacatcgtt gttcgactcc   120
cttcctccgt ttggggcgca ccatacggag gcggccaccg gggagtggga tgaggtgcag   180
tcgggattga gagctgcgga tgcaccaccc ccaaccatgc gggtggccgt caccgctgcc   240
cgaccgccga gggcgaagcc cgcaccaagg cggagggcag cgcaaccgtc cgacgcaagc   300
cccgcagcgc aagtagattt gagaactttg ggatattcac agcagcagca ggaaaagatc   360
aagcccaaag tgaggtcgac agtcgcgcag catcacgaag cgctggtggg tcatgggttt   420
acacatgccc acatcgtagc cttgtcgcag caccctgcag cccttggcac ggtcgccgtc   480
aagtaccagg acatgattgc ggcgttgccg gaagccacac atgaggcgat cgtcggtgtg   540
gggaaacagt ggagcggagc ccgagcgctt gaggccctgt tgacggtcgc gggagagctg   600
agagggcctc cccttcagct ggacacgggc cagttgctga agatcgcgaa gcggggagga   660
gtcacggcgg tcgaggcggt gcacgcgtgg cgcaatgcgc tcacgggagc acccctcaac   720
ctgaccgaga cggtacatga aacgcatggc acggcgtctc aactcacgcc tgagcaggta   780
gtggctattg catccaataa cgggggcaga cccgcactgg agtcaatcgt ggcccagctt   840
tcgaggccga cccccgcgct ggccgcactc actaatgatc atcttgtagc gctggcctgc   900
ctcggcggac gacccgcctt ggatgcggtg aagaagggc tcccgcacgc gcctgcattg   960
attaagcgga ccaacagaag gattcccgag aggacatcac atcgagtggc agatcacgcg  1020
caagtggtcc gcgtgctcgg attcttccag tgtcactccc accccgcaca agcgttcgat  1080
gacgccatga ctcaatttgg tatgtcgaga cacggactgc tgcagctctt tcgtagagtc  1140
ggtgtcacag aactcgaggc ccgctcgggc acactgcctc ccgcctccca gcggtgggac  1200
aggattctcc aagcgagcgg tatgaaacgc gcgaagcctt cacctacgtc aactcagaca  1260
cctgaccagg cgagccttca tgcgttcgca gactcgctgg agagggattt ggacgcgccc  1320
tcgcccatga tgaagggga ccaaactcgc gcgtcagcta gccccaagaa gaagagaaag  1380
gtggaggcca gcggttccgg acgggctgac gcattggacg attttgatct ggatatgctg  1440
ggaagtgacg ccctcgatga ttttgacctt gacatgcttg gttcggatgc ccttgatgac  1500
tttgacctcg acatgctcgg cagtgacgcc cttgatgatt tcgacctgga catgctgatt  1560
aactctagag gcagtggaga gggcagagga agtctgctaa catgcggtga cgtcgaggag  1620
aatcctggcc cagtgagcaa gggcgaggag ctgttcaccg gggtggtgcc catcctggtc  1680
gagctggacg gcgacgtaaa cggccacaag ttcagcgtgt ccggcgaggg cgagggcgat  1740
gccacctacg gcaagctgac cctgaagttc atctgcacca ccggcaagct gcccgtgccc  1800
tggcccaccc tcgtgaccac cctgacctac ggcgtgcagt gcttcagccg ctaccccgac  1860
cacatgaagc agcacgactt cttcaagtcc gccatgcccg aaggctacgt ccaggagcgc  1920
accatcttct tcaaggacga cggcaactac aagacccgcg ccgaggtgaa gttcgagggc  1980
gacaccctgg tgaaccgcat cgagctgaag ggcatcgact tcaaggagga cggcaacatc  2040
ctggggcaca agctggagta caactacaac agccacaacg tctatatcat ggccgacaag  2100
cagaagaacg gcatcaaggt gaacttcaag atccgccaca acatcgagga cggcagcgtg  2160
cagctcgccg accactacca gcagaacacc cccatcggcg acggccccgt gctgctgccc  2220
gacaaccact acctgagcac ccagtccgcc ctgagcaaag accccaacga aaagcgcgat  2280
cacatggtcc tgctggagtt cgtgaccgcc gccgggatca ctctcggcat ggacgagctg  2340
tacaagtaa                                                          2349
```

<210> SEQ ID NO 132
<211> LENGTH: 2349
<212> TYPE: DNA
<213> ORGANISM: artificial sequence
<220> FEATURE:
<223> OTHER INFORMATION: Synthetic polynucleotide

<400> SEQUENCE: 132

```
atgtcgcgga cccggctccc ttccccaccc gcacccagcc cagcgttttc ggccgactcg     60
ttctcagacc tgcttaggca gttcgacccc tcactgttta acacatcgtt gttcgactcc    120
cttcctccgt ttggggcgca ccatacggag gcggccaccg gggagtggga tgaggtgcag    180
tcgggattga gagctgcgga tgcaccaccc caaccatgc gggtggccgt caccgctgcc    240
cgaccgccga gggcgaagcc cgcaccaagg cggagggcag cgcaaccgtc cgacgcaagc    300
cccgcagcgc aagtagattt gagaactttg ggatattcac agcagcagca ggaaaagatc    360
aagcccaaag tgaggtcgac agtcgcgcag catcacgaag cgctggtggg tcatgggttt    420
acacatgccc acatcgtagc cttgtcgcag caccctgcag cccttggcac ggtcgccgtc    480
aagtaccagg acatgattgc ggcgttgccg aagccacac atgaggcgat cgtcggtgtg    540
gggaaacagt ggagcggagc ccgagcgctt gaggccctgt tgacggtcgc gggagagctg    600
agagggcctc cccttcagct ggacacgggc cagttgctga agatcgcgaa gcggggagga    660
gtcacggcgg tcgaggcggt gcacgcgtgg cgcaatgcgc tcacgggagc accctcaac    720
ctgaccgaga cggtacatga aacgcatggc acggcgtctc aactcacgcc tgagcaggta    780
gtggctattg catccaatat cggggcaga cccgcactgg agtcaatcgt ggcccagctt    840
tcgaggccgg accccgcgct ggccgcactc actaatgatc atcttgtagc gctggcctgc    900
ctcggcggac gacccgcctt ggatgcggtg aagaagggc tcccgcacgc gcctgcattg    960
attaagcgga ccaacagaag gattcccgag aggacatcac atcgagtggc agatcacgcg   1020
caagtggtcc gcgtgctcgg attcttccag tgtcactccc accccgcaca agcgttcgat   1080
gacgccatga ctcaattggg tatgtcgaga cacggactgc tgcagctctt tcgtagagtc   1140
ggtgtcacag aactcgaggc ccgctcgggc acactgcctc ccgcctccca gcggtgggac   1200
aggattctcc aagcgagcgg tatgaaacgc gcgaagcctt cacctacgtc aactcagaca   1260
cctgaccagg cgagccttca tgcgttcgca gactcgctgg agaggatttt ggacgcgccc   1320
tcgcccatgc atgaagggga ccaaactcgc gcgtcagcta gccccaagaa gaagagaaag   1380
gtggaggcca gcggttccgg acgggctgac gcattggacg attttgatct ggatatgctg   1440
ggaagtgacg ccctcgatga ttttgacctt gacatgcttg gttcggatgc ccttgatgac   1500
tttgacctcg acatgctcgg cagtgacgcc cttgatgatt cgacctgga catgctgatt   1560
aactctagag gcagtggaga gggcagagga agtctgctaa catgcggtga cgtcgaggag   1620
aatcctggcc cagtgagcaa gggcgaggag ctgttcaccg ggtggtgcc catcctggtc   1680
gagctggacg gcgacgtaaa cggccacaag ttcagcgtgt ccggcgaggg cgagggcgat   1740
gccacctacg gcaagctgac cctgaagttc atctgcacca ccggcaagct gcccgtgccc   1800
tggcccaccc tcgtgaccac cctgacctac ggcgtgcagt gcttcagccg ctaccccgac   1860
cacatgaagc agcacgactt cttcaagtcc gccatgcccg aaggctacgt ccaggagcgc   1920
accatcttct tcaaggacga cggcaactac aagacccgcg ccgaggtgaa gttcgagggc   1980
gacaccctgg tgaaccgcat cgagctgaag ggcatcgact tcaaggagga cggcaacatc   2040
```

```
ctggggcaca agctggagta caactacaac agccacaacg tctatatcat ggccgacaag    2100
cagaagaacg gcatcaaggt gaacttcaag atccgccaca acatcgagga cggcagcgtg    2160
cagctcgccg accactacca gcagaacacc cccatcggcg acggcccgt gctgctgccc    2220 gacaaccact acctgagcac ccagtccgcc ctgagcaaag accccaacga gaagcgcgat    2280
cacatggtcc tgctggagtt cgtgaccgcc gccgggatca ctctcggcat ggacgagctg    2340
tacaagtaa                                                           2349
```

<210> SEQ ID NO 133
<211> LENGTH: 2349
<212> TYPE: DNA
<213> ORGANISM: artificial sequence
<220> FEATURE:
<223> OTHER INFORMATION: Synthetic polynucleotide

<400> SEQUENCE: 133

```
atgtcgcgga cccggctccc ttccccaccc gcacccagcc cagcgttttc ggccgactcg      60
ttctcagacc tgcttaggca gttcgacccc tcactgttta acacatcgtt gttcgactcc     120
cttcctccgt ttggggcgca ccatacggag gcggccaccg gggagtggga tgaggtgcag     180
tcgggattga gagctgcgga tgcaccaccc ccaaccatgc gggtggccgt caccgctgcc     240
cgaccgccga gggcgaagcc cgcaccaagg cggagggcag cgcaaccgtc cgacgcaagc     300
cccgcagcgc aagtagattt gagaactttg ggatattcac agcagcagca ggaaaagatc     360
aagcccaaag tgaggtcgac agtcgcgcag catcacgaag cgctggtggg tcatgggttt     420
acacatgccc acatcgtagc cttgtcgcag caccctgcag cccttggcac ggtcgccgtc     480
aagtaccagg acatgattgc ggcgttgccg gaagccacac atgaggcgat cgtcggtgtg     540
gggaaacagt ggagcggagc ccgagcgctt gaggccctgt tgacggtcgc gggagagctg     600
agagggcctc cccttcagct ggacacgggc cagttgctga agatcgcgaa gcggggagga     660
gtcacgcgcg tcgaggcggt gcacgcgtgg cgcaatgcgc tcacgggagc acccctcaac     720
ctgaccgaga cggtacatga aacgcatggc acggcgtctc aactcacgcc tgagcaggta     780
gtggctattg catccaatgg cggggggcaga cccgcactgg agtcaatcgt ggcccagctt     840
tcgaggccgg accccgcgct ggccgcactc actaatgatc atcttgtagc gctggcctgc     900
ctcggcggac gacccgcctt ggatgcggtg aagaagggc tcccgcacgc gcctgcattg     960
attaagcgga ccaacagaag gattcccgag aggacatcac atcgagtggc agatcacgcg    1020
caagtggtcc gcgtgctcgg attcttccag tgtcactccc accccgcaca agcgttcgat    1080
gacgccatga ctcaattggg tatgtcgaga cacggactgc tgcagctctt tcgtagagtc    1140
ggtgtcacag aactcgaggc ccgctcgggc acactgcctc ccgcctccca gcggtgggac    1200
aggattctcc aagcgagcgg tatgaaacgc gcgaagcctt cacctacgtc aactcagaca    1260
cctgaccagg cgagccttca tgcgttcgca gactcgctgg agagggattt ggacgcgccc    1320
tcgcccatgc atgaagggga ccaaactcgc gcgtcagcta gccccaagaa gaagagaaag    1380
gtggaggcca gcggttccgg acgggctgac gcattggacg attttgatct ggatatgctg    1440
ggaagtgacg ccctcgatga ttttgacctt gacatgcttg gttcggatgc ccttgatgac    1500
tttgacctcg acatgctcgg cagtgacgcc cttgatgatt cgacctggga catgctgatt    1560
aactctagag gcagtggaga gggcagagga agtctgctaa catgcggtga cgtcgaggag    1620
aatcctggcc cagtgagcaa gggcgaggag ctgttcaccg gggtggtgcc catcctggtc    1680
gagctggacg gcgacgtaaa cggccacaag ttcagcgtgt ccggcgaggg cgagggcgat    1740
```

```
gccacctacg gcaagctgac cctgaagttc atctgcacca ccggcaagct gcccgtgccc   1800
tggcccaccc tcgtgaccac cctgacctac ggcgtgcagt gcttcagccg ctaccccgac   1860
cacatgaagc agcacgactt cttcaagtcc gccatgcccg aaggctacgt ccaggagcgc   1920
accatcttct tcaaggacga cggcaactac aagacccgcg ccgaggtgaa gttcgagggc   1980
gacaccctgg tgaaccgcat cgagctgaag ggcatcgact tcaaggagga cggcaacatc   2040
ctggggcaca gctggagta caactacaac agccacaacg tctatatcat ggccgacaag   2100
cagaagaacg gcatcaaggt gaacttcaag atccgccaca acatcgagga cggcagcgtg   2160
cagctcgccg accactacca gcagaacacc cccatcggcg acggcccgt gctgctgccc   2220 gacaaccact acctgagcac ccagtccgcc ctgagcaaag accccaacga gaagcgcgat   2280
cacatggtcc tgctggagtt cgtgaccgcc gccgggatca ctctcggcat ggacgagctg   2340
tacaagtaa                                                           2349
```

<210> SEQ ID NO 134
<211> LENGTH: 2349
<212> TYPE: DNA
<213> ORGANISM: artificial sequence
<220> FEATURE:
<223> OTHER INFORMATION: Synthetic polynucleotide

<400> SEQUENCE: 134

```
atgtcgcgga cccggctccc ttccccaccc gcacccagcc cagcgttttc ggccgactcg     60
ttctcagacc tgcttaggca gttcgacccc tcactgttta acacatcgtt gttcgactcc    120
cttcctccgt ttggggcgca ccatacggag gcggccaccg gggagtggga tgaggtgcag    180
tcgggattga gagctgcgga tgcaccaccc ccaaccatgc gggtggccgt caccgctgcc    240
cgaccgccga gggcgaagcc cgcaccaagg cggagggcag cgcaaccgtc cgacgcaagc    300
cccgcagcgc aagtagattt gagaactttg ggatattcac agcagcagca ggaaaagatc    360
aagcccaaag tgaggtcgac agtcgcgcag catcacgaag cgctggtggg tcatgggttt    420
acacatgccc acatcgtagc cttgtcgcag caccctgcag cccttggcac ggtcgccgtc    480
aagtaccagg acatgattgc ggcgttgccg gaagccacac atgaggcgat cgtcggtgtg    540
gggaaacagt ggagcggagc ccgagcgctt gaggccctgt tgacggtcgc gggagagctg    600
agagggcctc cccttcagct ggacacgggc cagttgctga gatcgcgaa gcggggagga    660 gtcacggcgg tcgaggcggt gcacgcgtgg cgcaatgcgc tcacgggagc accctcaac   720 ctgaccgaga cggtacatga aacgcatggc acggcgtctc aactcacgcc tgagcaggta    780
gtggctattg catcccatga cggggggcaga cccgcactgg agtcaatcgt ggcccagctt    840
tcgaggccgg accccgcgct ggccgcactc actaatgatc atcttgtagc gctggcctgc    900
ctcggcggac gacccgcctt ggatgcggtg aagaaggggc tcccgcacgc gcctgcattg    960
attaagcgga ccaacagaag gattcccgag aggacatcac atcgagtggc agatcacgcg   1020
caagtggtcc gcgtgctcgg attcttccag tgtcactccc accccgcaca gcgttcgat   1080 gacgccatga ctcaatttgg tatgtcgaga cacggactgc tgcagctctt tcgtagagtc   1140
ggtgtcacag aactcgaggc cgctcgggc acactgcctc cgcctccca gcggtgggac   1200 aggattctcc aagcgagcgg tatgaaacgc gcgaagcctt cacctacgtc aactcagaca   1260
cctgaccagg cgagccttca tgcgttcgca gactcgctgg agagggattt ggacgcgccc   1320
tcgcccatgc atgaagggga ccaaactcgc gcgtcagcta gccccaagaa gaagagaaag   1380
```

```
gtggaggcca gcggttccgg acgggctgac gcattggacg attttgatct ggatatgctg    1440
ggaagtgacg ccctcgatga ttttgacctt gacatgcttg gttcggatgc ccttgatgac    1500
tttgacctcg acatgctcgg cagtgacgcc cttgatgatt tcgacctgga catgctgatt    1560
aactctagag gcagtggaga gggcagagga agtctgctaa catgcggtga cgtcgaggag    1620
aatcctggcc cagtgagcaa gggcgaggag ctgttcaccg gggtggtgcc catcctggtc    1680
gagctggacg gcgacgtaaa cggccacaag ttcagcgtgt ccggcgaggg cgagggcgat    1740
gccacctacg gcaagctgac cctgaagttc atctgcacca ccggcaagct gcccgtgccc    1800
tggcccaccc tcgtgaccac cctgacctac ggcgtgcagt gcttcagccg ctaccccgac    1860
cacatgaagc agcacgactt cttcaagtcc gccatgcccg aaggctacgt ccaggagcgc    1920
accatcttct tcaaggacga cggcaactac aagacccgcg ccgaggtgaa gttcgagggc    1980
gacaccctgg tgaaccgcat cgagctgaag ggcatcgact tcaaggagga cggcaacatc    2040
ctggggcaca gctggagta caactacaac agccacaacg tctatatcat ggccgacaag    2100
cagaagaacg gcatcaaggt gaacttcaag atccgccaca acatcgagga cggcagcgtg    2160
cagctcgccg accactacca gcagaacacc cccatcggcg acggccccgt gctgctgccc    2220
gacaaccact acctgagcac ccagtccgcc ctgagcaaag cccccaacga gaagcgcgat    2280
cacatggtcc tgctggagtt cgtgaccgcc gccgggatca ctctcggcat ggacgagctg    2340
tacaagtaa                                                           2349

<210> SEQ ID NO 135
<211> LENGTH: 40
<212> TYPE: DNA
<213> ORGANISM: artificial sequence
<220> FEATURE:
<223> OTHER INFORMATION: Synthetic polynucleotide

<400> SEQUENCE: 135
aaataatttt gtttaacttt aagaaggaga tataccatgg                          40

<210> SEQ ID NO 136
<211> LENGTH: 13
<212> TYPE: DNA
<213> ORGANISM: artificial sequence
<220> FEATURE:
<223> OTHER INFORMATION: Synthetic polynucleotide

<400> SEQUENCE: 136
ggatccggct gct                                                       13

<210> SEQ ID NO 137
<211> LENGTH: 149
<212> TYPE: PRT
<213> ORGANISM: artificial sequence
<220> FEATURE:
<223> OTHER INFORMATION: Synthetic polypeptide

<400> SEQUENCE: 137

Leu Ile Tyr Ser Tyr Gly Ser Ala Ile Ala Pro Gly Ala Ala Gly Val
1               5                   10                  15

Asn Ala Ala Leu Gly Pro Gly Glu Gly Ser Ser Pro Pro His Pro Pro
            20                  25                  30

Ser Phe Ser Ser Val Arg Ala Tyr Gln Gly Trp His Pro Arg Pro Pro
        35                  40                  45

Thr Asp Val Ser His Trp Gly Gln Ser Arg Val Gly Arg Lys His Val
    50                  55                  60
```

```
Phe Ser Gly Val Gly His Thr Lys Asn Gln Arg Lys Ile Ala Thr Met
 65                  70                  75                  80

Ala Arg Thr Gly Glu Pro Ile Thr Glu Lys Arg Thr Glu Thr Leu Arg
                 85                  90                  95

Gly Arg Pro His Ala Phe Phe Glu Leu Met Leu Asp Gly Arg Gln Leu
            100                 105                 110

Ile Met Trp Gly Ala Asp Arg Phe Val Ile Gly Phe Gly Leu Arg Glu
        115                 120                 125

Tyr Phe Ala Ala Thr Ser Asp Phe Asp Arg Ser Pro Leu Asn Pro Thr
130                 135                 140

Ala Gln Asp Thr Met
145

<210> SEQ ID NO 138
<211> LENGTH: 262
<212> TYPE: PRT
<213> ORGANISM: artificial sequence
<220> FEATURE:
<223> OTHER INFORMATION: Synthetic polypeptide

<400> SEQUENCE: 138

Phe Phe Glu Asp Leu Leu Arg Tyr Phe Ala Ile Arg Gln Ser Asp Pro
 1               5                  10                  15

Ala Ala Ile Gly Tyr Leu Val Leu Phe Arg Asp Ala Trp Glu Gly Gly
             20                  25                  30

Leu Glu Glu Ala Ile Asp Arg Thr Ala Leu Ala Ile Asp Gln Tyr Arg
         35                  40                  45

Asp Ala Val Gly Leu Arg Gly Cys Asp Ile Phe Gly Ser Phe Arg Gly
 50                  55                  60

Asn Glu Val Met Ile Asn Pro Leu Cys Ala Asp Gly His Thr Val Val
 65                  70                  75                  80

Leu Asp Glu Gly Asp Pro Met Ser Ala Lys Leu Arg Ala Phe Leu Glu
                 85                  90                  95

Ala Pro Ala Leu Gly Gln His Glu Gln Asp Asp Gln Asp Val Leu Gly
            100                 105                 110

Ala Glu Met Arg Thr Arg Ala Arg Glu Ile Arg His Lys Ala Gln His
        115                 120                 125

Asp Phe Pro Cys Thr Ala Pro Asp Leu Thr His Leu Arg Arg Met Ala
130                 135                 140

Asp Ala Met Ile Ser Val Lys Glu Ala Pro Ala Leu His Ser Ser Leu
145                 150                 155                 160

Leu Asp Gln Gly Pro Val Gly Leu Leu Leu Trp Asp Arg Gly Ala
                165                 170                 175

Glu Thr Val Val Asp Leu Val Ala Ala Cys Pro Val Gly Thr Thr Ala
            180                 185                 190

Leu Trp Ser Leu Arg Ala Ala Glu Asp Gln Leu Glu Asn Leu Ala Gly
        195                 200                 205

Ser Leu Asp Thr Lys Val Phe Leu Val Pro Arg Gly Gln Ala Ser Leu
210                 215                 220

Arg Phe Val Ala Ala Asp Ser Cys Gly Ile Thr Gln Gln Ala Trp Asp
225                 230                 235                 240

Tyr Gly Phe Leu Arg Glu Val Trp Ala Ala Pro Ser Gly Ala His Leu
                245                 250                 255

Gly Asp Gln Glu Ile Met
            260
```

<210> SEQ ID NO 139
<211> LENGTH: 285
<212> TYPE: PRT
<213> ORGANISM: artificial sequence
<220> FEATURE:
<223> OTHER INFORMATION: Synthetic polypeptide

<400> SEQUENCE: 139

```
His Lys Ile Leu Ser Ala Gly Ile Glu Ala Ile Gln Arg Asn Arg Glu
1               5                   10                  15

Asp Met Thr Ala Gln Ser Gly Thr Thr Tyr Ile Val Val Ile Arg Ser
            20                  25                  30

Pro Lys Gly Asp Pro Gly Leu Ala Ala Ile Ile Gly Arg Ser Gly Arg
        35                  40                  45

Glu Gly Ala Gly Ser Lys Asp Ala Ile Phe Trp Gly Ala Pro Leu Ala
    50                  55                  60

Ser Arg Leu Leu Pro Gly Ala Val Lys Asp Ala Glu Met Trp Asp Ile
65                  70                  75                  80

Leu Gln Gln Arg Ser Ala Leu Thr Leu Glu Gly Thr Leu Leu Lys
                85                  90                  95

Arg Leu Thr Thr Ala Met Ala Val Pro Met Thr Thr Asp Arg Glu Asp
            100                 105                 110

Asn Pro Ile Ala Glu Asn Leu Glu Pro Glu Trp Arg Asp Leu Arg Thr
        115                 120                 125

Val His Asp Gly Met Asn His Leu Phe Ala Thr Leu Glu Lys Pro Gly
    130                 135                 140

Gly Ile Thr Thr Leu Leu Leu Asn Ala Ala Thr Asn Asp Ser Met Thr
145                 150                 155                 160

Ile Ala Ala Ser Cys Leu Glu Arg Val Thr Met Gly Asp Thr Leu His
                165                 170                 175

Lys Glu Thr Val Pro Ser Tyr Glu Val Leu Asp Asn Gln Ser Tyr His
            180                 185                 190

Ile Arg Arg Gly Leu Gln Glu Gln Gly Ala Asp Ile Arg Ser Leu Val
        195                 200                 205

Ala Gly Cys Leu Leu Val Lys Phe Thr Ser Met Met Pro Phe Arg Glu
    210                 215                 220

Glu Pro Arg Phe Ser Glu Leu Ile Lys Gly Ser Asn Leu Asp Leu Glu
225                 230                 235                 240

Ile Tyr Gly Val Arg Ala Gly Leu Gln Asp Glu Ala Asp Lys Val Lys
                245                 250                 255

Val Leu Thr Glu Pro His Ala Phe Val Pro Leu Cys Phe Ala Ala Phe
            260                 265                 270

Phe Pro Ile Leu Ala Val Arg Phe His Gln Ile Ser Met
        275                 280                 285
```

<210> SEQ ID NO 140
<211> LENGTH: 34
<212> TYPE: PRT
<213> ORGANISM: Artificial sequence
<220> FEATURE:
<223> OTHER INFORMATION: Synthetic construct

<400> SEQUENCE: 140

Leu Thr Pro Glu Gln Val Val Ala Ile Ala Ser Asn Lys Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 141
<211> LENGTH: 102
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (36)..(36)
<223> OTHER INFORMATION: n is t or c
<220> FEATURE:
<221> NAME/KEY: misc_feature
<222> LOCATION: (39)..(39)
<223> OTHER INFORMATION: n is a or g

<400> SEQUENCE: 141
ctgaccccag agcaggtcgt ggcaatcgcc tccganaaag gcgggaaaca ggcactcgag     60
actgtccagc gcctgcttcc cgtgctgtgc caagcgcacg ga                       102

<210> SEQ ID NO 142
<211> LENGTH: 34
<212> TYPE: PRT
<213> ORGANISM: Artificial sequence
<220> FEATURE:
<223> OTHER INFORMATION: Synthetic construct

<400> SEQUENCE: 142

Leu Thr Pro Glu Gln Val Val Ala Ile Ala Ser Asn Ser Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 143
<211> LENGTH: 102
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (36)..(36)
<223> OTHER INFORMATION: n is t or c
<220> FEATURE:
<221> NAME/KEY: misc_feature
<222> LOCATION: (39)..(39)
<223> OTHER INFORMATION: n is t or c

<400> SEQUENCE: 143
ctgaccccag agcaggtcgt ggcaatcgcc tccganagng gcgggaaaca ggcactcgag     60
actgtccagc gcctgcttcc cgtgctgtgc caagcgcacg ga                       102

METHODS AND PRODUCTS FOR INCREASING FRATAXIN LEVELS AND USES THEREOF

CROSS REFERENCE TO RELATED APPLICATIONS

This application is a National Stage Application of PCT application no. PCT/CA2012/050817 filed on Nov. 16, 2012 and published in English under PCT Article 21(2), which claims the benefit, under 35 U.S.C. §119(e), of U.S. provisional application Ser. No. 61/561,440, filed on Nov. 18, 2011. All documents above are incorporated herein by reference in their entirety.

SEQUENCE LISTING

Pursuant to 37 C.F.R. 1.821(c), a sequence listing is submitted herewith as an ASCII compliant text file named "16189_3_161129 ST25.txt", created on Nov. 29, 2016 and having a size of ~229 Kbytes, which is incorporated herein by reference in its entirety.

FIELD OF THE INVENTION

The present invention relates to increasing frataxin expression and/or levels and uses thereof, for example for the treatment of Friedreich ataxia.

BACKGROUND OF THE INVENTION

Friedreich Ataxia

Friedreich ataxia (FRDA), an autosomal recessive neurodegenerative and cardiac disease, is caused by a trinucleotide repeat expansion mutation in the first intron of the frataxin gene (FXN) located on chromosome 9. The mutation leads to a reduced expression of the frataxin gene. Frataxin is essential for proper functioning of mitochondria. It is involved in the removal of iron and when frataxin is reduced, the iron builds up and causes free radical damage. Nerve and muscle cells are particularly sensitive to the deleterious effects. FRDA occurs in 1 in 50 000 persons in European populations but is much more frequent in the province of Quebec in Canada, because of founder effects. Males and females are affected equally. In the classic form, FRDA symptoms appear during or before the second decade of life. It is characterized by ataxia, areflexia, loss of vibratory sense and proprioception and dysarthry (Babady et al. 2007, Cooper and Schapira 2003, Harding 1981, Lynch et al. 2002, Pandolfo 1999). Moreover, FRDA patients often have systemic involvement, with cardiomyopathy, diabetes mellitus and scoliosis. Early death can result from cardiomyopathy or associated arrhythmias (Harding 1981). Degeneration of the dorsal root ganglion cells, their ascending dorsal spinal columns and the spinocerebellar tracts results in a progressive sensory ataxia. Many patients are wheelchair bound by their third decade. Associated oculomotor problems include optic atrophy, square-wave jerks and difficulty with fixation. Importantly, cognitive abilities are relatively spared. However, many patients suffer from depression (Singh et al. 2001).

Genetic Transmission

The mutation responsible for FRDA is an unstable hyperexpansion of a GAA triplet repeat located in the first intron of the frataxin gene (Campuzano et al. 1996). In normal subjects, there are 6-34 repeats, whereas in patients there are 150 or more repeats. The patients with the shorter repeats (150-200) have milder symptoms than those with longer triplex (350 to 650). In some severely affected patients there are up to 1700 repeats. Since the frataxin gene mutation is located in an intron, it does not alter the amino acid sequence of frataxin protein. There are 2-3% of FRDA patients who have a point mutation, either a missense or a non-sense (Bidichandani, Ashizawa and Patel 1997, McCormack et al. 2000, Cossee et al. 1999). Some patients with a missense mutation have less severe symptoms because the mutated protein in still functional.

Pathological Mechanism

The pathological mechanisms have been reviewed by Pandolfo et al., (Pandolfo 2006). The repeated GAA triplets would lead to the formation of triplex in the DNA, i.e., unusual non-B DNA conformations, that decrease transcription and subsequently reduce levels of the encoded protein, frataxin (level of expression is 5 to 35% of normal; Coppola et al. 2006, Coppola et al. 2009). Frataxin is a mitochondrial matrix protein and its reduction induces an iron accumulation in the mitochondria. This iron accumulation is observed in the cardiac cells of patients and in the dentate nucleus of the brain. It is associated with oxidative damage. The reduction of frataxin leads to changes in gene expression of 185 different genes (Coppola et al. 2006, Coppola et al. 2009). Thus the reduction of frataxin has profound effects of several metabolic pathways and the correction of only one of these pathways by a drug may not be ideal.

The Frataxin Protein

Frataxin is a small protein (NCBI NM_000144.4, only 210 amino acids) that promotes the biosynthesis of heme as well as the assembly and repair of iron-sulfur clusters by delivering $Fe^{2+}$ to proteins involved in these pathways. It also plays a primary role in the protection against oxidative stress through its ability to catalyze the oxidation of $Fe^{2+}$ to $Fe^{3+}$ and to store large amounts of the metal in the form of a ferrihydrite mineral. It is processed in two steps by mitochondrial processing peptidase (MPP). MPP first cleaves the precursor to intermediate form and subsequently converts the intermediate to mature size protein. Two forms exist, frataxin (56-210) and frataxin (81-210), which is the main form of mature frataxin (Schoenfeld et al. 2005, Condo et al. 2006).

Several strategies have been developed for treating Friedreich ataxia. These fall generally into the following 5 categories: 1) use of antioxidants to reduce the oxidative stress caused by iron accumulation in the mitochondria; 2) use of Iron chelators to remove iron from the mitochondria; 3) use of Histone Deacetylase Inhibitors (HDACIs) to prevent DNA condensation and permit higher expression of frataxin; 4) use of molecules such as cisplatin, 3-nitroproprionnic acid (3-NP), Pentamidine or erythropoietin (EPO) to boost frataxin expression; and 5) gene therapy. However, limited success has been reported thus far for these strategies, which are mostly non-specific or more difficult to test and apply in human trials.

Thus, there remains a need for new approaches to treat Friedreich ataxia.

The present description refers to a number of documents, the content of which is herein incorporated by reference in their entirety.

SUMMARY OF THE INVENTION

The present invention relates to inducing or increasing frataxin expression/levels in a cell, and uses thereof. In an aspect, recombinant proteins derived from a TAL (transcription activator-like) effector (also referred to as TALE) may be designed and used to specifically target the frataxin promoter to increase frataxin expression. In a further aspect, a recombinant protein comprising (a) a frataxin protein or functional fragment and/or derivative thereof; and (b) a protein transduction domain, may be designed, prepared and introduced into a cell to increase the level of frataxin protein or functional fragment and/or derivative thereof within the cell. The present invention further relates to uses of such inducing or increasing frataxin expression/levels in a cell, such as for the treatment of Friedreich ataxia.

Accordingly, in a first aspect, the present invention concerns a TAL effector based recombinant protein for increasing expression of frataxin in a cell comprising: (i) a TALE domain derived from a TAL effector protein comprising a repeat variable domain (RVD) comprising a plurality of tandem repeats monomers; (ii) a nuclear localization signal; and (ii) a transcription activation domain, wherein said RVD binds to a frataxin promoter sequence, thereby allowing expression of frataxin in said cell.

In an embodiment of the above TAL effector based recombinant protein, the monomers consist of 33 or 34 amino acid residues. In an embodiment the above RVD consist of between 6.5 and 33.5 monomers. In an embodiment, the RVD consists of 12.5, 13.5 or 14.5 monomers.

In an embodiment, the TAL effector based recombinant protein of the present invention comprises a TALE domain derived from AvrBs3, Hax2, Hax3, Hax4 or AvrXa10 TAL effector protein. In an embodiment, the TALE domain is derived from the Hax3 TAL effector protein. In an embodiment, the Hax3 TAL effector protein is from *Xanthomonas campestris* pv. *Armoraciae*.

In an embodiment of the above TAL effector based recombinant protein, the transcription activation domain is a VP64 synthetic transcription activation domain.

In an embodiment, the above-mentioned nuclear localization signal is a mammalian nuclear localization signal derived from the simian virus 40 large T antigen.

In an embodiment of the TAL effector based recombinant protein of the present invention, the above-mentioned RVD binds to:
  i) Positions 5-18 of the frataxin promoter nucleotide sequence;
  ii) Positions 21-34 of the frataxin promoter nucleotide sequence;
  iii) Positions 24-37 of the frataxin promoter nucleotide sequence;
  iv) Positions 37-50 of the frataxin promoter nucleotide sequence;
  v) Positions 73-86 of the frataxin promoter nucleotide sequence;
  vi) Positions 81-94 of the frataxin promoter nucleotide sequence;
  vii) Positions 92-105 of the frataxin promoter nucleotide sequence;
  viii) Positions 103-116 of the frataxin promoter nucleotide sequence;
  ix) Positions 106-119 of the frataxin promoter nucleotide sequence;
  x) Positions 124-137 of the frataxin promoter nucleotide sequence;
  xi) Positions 155-168 of the frataxin promoter nucleotide sequence; and/or
  xii) Positions 168-181 of the frataxin promoter nucleotide sequence;
wherein the frataxin promoter nucleotide sequence (SEQ ID NO:88) is as set forth in positions 1-240 of NCBI reference number NM_000144.4.

In an embodiment, the above-mentioned RVD comprises the amino acid sequence or one or more monomer comprising: (i) HD HD HD NG NG NN NN NN NG HD NI NG NN (SEQ ID NO:2); (ii) HD HD NG NN NN NG NG NN HD NI HD NG HD (SEQ ID NO:4); (iii) NN NN NG NG NN HD NI HD NG ND HD NN NG (SEQ ID NO:6); (iv) NN HD NG NG NG NN HD NI HD NI NI NI NN (SEQ ID NO:8); (v) NN HD NI HD NN NI NI NG NI NN NG NN HD (SEQ ID NO:10); (vi) NI NN NG NN HD NG NI NI NN HD NG NN (SEQ ID NO:12); (vii) NN HD NG HD HD HD HD HD NI HD NI NN NI (SEQ ID NO:14); (viii) HD HD NG NN NI NN NN NG HD NG NI NI (SEQ ID NO:16); (ix) NN NI NNNN NG HD NG NI NI HD HD NG (SEQ ID NO:18); (x) NN HD NG HD HD HD HD HD NI HD NI NN NI (SEQ ID NO:20); (xi) NN NN HD HD NI HD HD HD NI NN NN NN NN NG (SEQ ID NO:22); or (xii) HD NN HD HD NN HD NI NN HD NI HD HD HD (SEQ ID NO:24). In another embodiment, the above-mentioned RVD comprises one or more, preferably 6 or more, more preferably 6.5 or more monomers comprising the amino acid sequence as set forth in SEQ ID NO:65.

In an embodiment, the above-mentioned cell in which frataxin expression is increased has an abnormal number of trinucleotide repeats in intron 1 of the frataxin gene. In an embodiment, the cell comprises 35 or more trinucleotide repeats. In another embodiment, the cell comprises 150 or more trinucleotide repeats. In a further embodiment the cell comprises more than 150 trinucleotide repeats. In a further embodiment, the cell comprises 200 or more repeats. In a further embodiment, the cell comprises 500 or more repeats. In a further embodiment the cell comprises 1000 or more repeats.

The TAL effector based recombinant protein of the present invention may also comprise a protein transduction domain (or cell penetrating peptide). In an embodiment, the protein transduction domain is TAT or Pep-1. In an embodiment, the protein transduction domain is TAT and comprises the sequence SGYGRKKRRQRRRC (SEQ ID NO:25). In another embodiment, the protein transduction domain is TAT and comprises the sequence YGRKKRRQRRR (SEQ ID NO: 37). In another embodiment, the protein transduction domain is TAT and comprises the sequence KKRRQRRR (SEQ ID NO: 32). In another embodiment, the protein transduction domain is Pep-1 and comprises the sequence KETWWETWWTEWSQPKKKRKV (SEQ ID NO:87). In addition or alternatively to the above-mentioned protein transduction domain, the TAL effector based recombinant protein of the present invention may be coupled to liposomes to further facilitate translocation into the cell and mitochondria.

The present invention also provides a composition comprising a TAL effector based recombinant protein as defined above and a pharmaceutically acceptable carrier.

In an embodiment, the above-mentioned TAL effector based recombinant protein or composition comprising same is for increasing frataxin expression in a cell. In an embodiment, it is for use in the treatment of Friedreich ataxia.

The present invention further concerns the use of the above-mentioned TAL effector based recombinant protein or of a composition comprising same for increasing frataxin expression in a cell.

In another aspect, the present invention provides a use of the above-mentioned TAL effector based recombinant protein or of a composition comprising same for the treatment of Friedreich ataxia.

The present invention is also concerned with the use of above-mentioned TAL effector based recombinant protein for the preparation of a medicament for the treatment of Friedreich ataxia.

In a related aspect, the present invention provides a method for increasing frataxin expression in a cell, comprising transducing said cell with the above-mentioned TAL effector based recombinant protein or composition comprising same.

The present invention also concerns a method for treating Friedreich ataxia in a subject, comprising administering to the subject the above-mentioned TAL effector based recombinant protein or composition comprising same.

The present invention also provides an isolated nucleic acid encoding the above-mentioned TAL effector based recombinant protein of the present and a vector and host cell comprising same.

In another aspect, the present invention concerns a recombinant protein comprising: a) a frataxin protein or functional fragment and/or derivative thereof; and b) a protein transduction domain. In an embodiment, the protein transduction domain is Pep-1 or Tat. In an embodiment, the protein transduction domain is TAT and comprises the sequence SGYGRKKRRQRRRC (SEQ ID NO:25). In another embodiment, the protein transduction domain is TAT and comprises the sequence YGRKKRRQRRR (SEQ ID NO: 37). In another embodiment, the protein transduction domain is TAT and comprises the sequence KKRRQRRR (SEQ ID NO: 32). In another embodiment, the protein transduction domain is Pep-1 and comprises the sequence KETWWETWWTEWSQPKKKRKV (SEQ ID NO:87).

The present invention further provides a composition comprising the above-mentioned recombinant protein together with a pharmaceutical carrier.

The present invention also relates to the use of the above-mention recombinant protein for the treatment of Friedreich ataxia or for the preparation of a medicament for the treatment of Friedreich ataxia.

The present invention also concerns a method for treating Friedreich ataxia in a subject, comprising administering to the subject the above-mentioned recombinant protein or composition comprising same.

The present invention also provides an isolated nucleic acid encoding the above-mentioned recombinant protein, vector and host cell comprising same.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 8 shows the sequence and activity of the TALEs described herein designed to bind to frataxin promoter sequences. Nucleic acid sequences of the RVD of Tale Nos 1-12 correspond to SEQ ID NOs: 1, 3, 5, 7, 9, 11, 13, 15, 17, 19, 21 and 23 respectively. Amino acid sequences of the RVD of Tale Nos 1-12 correspond to SEQ ID NOs 2, 4, 6, 8, 10, 12, 14, 16, 18, 20, 22 and 24 respectively;

FIG. 11 shows a Western blot (A) of frataxin protein expression 60 hours following nucleofection of the plasmid coding for TALE$_{frat/VP64}$ No. 8 (see Table 3) in Friedreich fibroblasts. In (B) frataxin expression was quantified and normalized with β-actin expression (the frataxin antibody was from Mitosciences and the β-actin antibody was purchased from Sigma Aldreich);

FIG. 13 shows the amino acid sequences of fusion proteins 6×HIS-Tat-Talefrat/vp64 #8 (A, SEQ ID NO: 106) and 6×HIS-Pep1-t-Talefrat/vp64 #8 (B, SEQ ID NO:86): HHH-HHH: 6× Histidine tag. YGRKKRRQRRR (SEQ ID NO: 37) corresponds to the Tat motif. KETWWETWWTEWS-QPKKKRKV (SEQ ID NO:87) corresponds to the Pep1 motif. The 12 RVDs of tale #8 are shaded and bold. The 4 VP16 motifs are underlined (4XVP16=VP64);

FIG. 14 shows the expression in *E. coli* (BL21) of the construct 6×His-Tat-Tale$_{frat/VP64}$ of the present invention. A. Coomassie blue staining showing total protein with or without induction with IPTG. B. Purification on a Ni column of 6His-Tat-TALE$_{frat/VP64}$ construct of the present invention. Lane 1: M.W; Lane 2: *E. coli* extract, no induction; Lane 3: *E. coli* total extract; and Lane 4: Elution from the Ni column with 250 mM NPI;

FIG. 15 shows Western Blot detection of 6×His-Tat-TALE$_{frat/VP16}$ using anti-6×His antibody (A) or VP16 antibody (B). A. Lane 1: soluble extract of BL21 after induction with IPTG; and Lane 2: elution from the Ni column with 250 mM NPI. B. M: Molecular weight marker; NI: BL21 cells not induced; and I: BL21 cells induced with IPTG 1 mM for 5 hours at 37° C.;

FIG. 19 shows the amino acid sequence of Hax3 from *Xanthomonas campestris* pv. *Armoraciae* (Genbank Acc. No. AAYA3359.1 and GI 66270059, SEQ ID NO:40). The N-terminal and C-terminal sequences from Hax3 comprised in the TALE construct of the present invention (pLenti-EF1-α-TALE-VP64-2A-EGFP-WPRE) are shown in bold (N-terminal) and bold/underlined (C-terminal);

FIG. 20 shows the N-terminal (A) (SEQ ID NO:41) and C-terminal (B) (SEQ ID NO:42) nucleotide sequences of Hax3 from *Xanthomonas campestris* pv. *Armoraciae* comprised in the TALE construct of the present invention (e.g., pLenti-EF1-α-TALE-VP64-2A-EGFP-WPRE and pcr3.1-CMV-TALE-VP64?);

FIGS. 21 (A and B) shows the complete sequence of the PCR3.1-frataxin-promoter-miniCMV-mCherry plasmid (SEQ ID NO:43);

FIG. 22 (A to L) shows the restriction map of the PCR3.1-frataxin-promoter-miniCMV-mCherry plasmid (SEQ ID NO: 43—nucleic acid sequence of plasmid). ORF1: amino acid sequence of the mCherry reporter (SEQ ID NO: 47—see FIGS. 22B and C). ORF2: hypothetical protein (SEQ ID NO: 137—see FIGS. 22E and F). ORF3: Kanamycin-neomycin resistance protein (SEQ ID NO: 138—see FIGS. 22G and H). ORF4: beta-lactamase protein for ampicillin resistance (SEQ ID NO: 139—see FIGS. 22I, J and K).

FIG. 23 shows the sequence of the proximal promoter (underlined) of human frataxin included in the PCR3.1-frataxin-promoter-miniCMV-mCherry plasmid together with linking sequences in 5' and 3' (SEQ ID NO:44);

FIG. 24 shows the nucleotide sequence of the miniCMV promoter (SEQ ID NO:45);

FIG. 25 shows the nucleotide (SEQ ID NO:46) and amino acid sequences (SEQ ID NO:47) of the mCherry reporter;

FIG. 26 shows the nucleotide sequence of the human elongation factor 1 alpha promoter (A) (SEQ ID NO:48) and (B) of the nucleotide (SEQ ID NO:49) and amino acid (SEQ ID NO:50) sequences of the synthetic transcription activation domain of VP64;

FIG. 27 shows the amino acid and nucleotide sequences of the self cleavage peptide 2A (SEQ ID NOs:51 and 52) (A) and of the enhanced green fluorescent protein (EGFP, SEQ ID NOs: 53 and 54) (B);

FIG. 28 (A to K) shows the complete sequence of the pLenti-EF1α-TALE-VP64-2A-EGFP-WPRE plasmid of the present invention (SEQ ID NO:55);

FIG. 29 (A to E) shows the sequences of the various assembly modules according to the Zang technique (Nature Biotechnology, 2011). A. NI module (SEQ ID NOs:56 (nt) and 57(aa)); B. NG module (SEQ ID NOs:58 (nt) and and 59 (aa)); C. HD module (SEQ ID NOs: 60 (nt) and 61 (aa)); D. NN module (SEQ ID NOs: 62 (nt) and 63 (aa)). E. consensus module (SEQ ID NOs: 64 (nt) and 65 (aa));

FIGS. 30 (A and B) shows an alignment between the amino acid sequences of four backbone constructs (NN SEQ ID NO: 129), HD (SEQ ID NO: 130), NG (SEQ ID NO: 127) and NI (SEQ ID NO: 128) backbone) of the present invention comprising the NLS (KKKRK, bold (SEQ ID NO:89)), peptide 2A fused to GFP (underlined) and the variable di-residues (NN, HD, NG and NI, bold/underlined); The consensus sequence is shown (SEQ ID NO: 66).

FIG. 31 (A to E) shows an alignment between the nucleotide sequences of four backbone constructs of the present invention (NN (SEQ ID NO: 131), HD (SEQ ID NO: 134), NG (SEQ ID NO: 133) and NI (SEQ ID NO: 132) backbone) comprising the NLS (KKKRK, bold (SEQ ID NO:89)), peptide 2A fused to EGFP (underlined); the BsmBI cloning site for cloning the TALE customized repeat region (shade) and the variable di-residues (NN; HD, NG and NI, bold/underlined);

FIG. 32 (A to E) shows the nucleic acid and amino acid sequences of the variable part (RVD) of exemplary TALEs of the present invention. A. TALE #1 (SEQ ID NOs: 67 and 68 which binds to tcccttgggtcagg (SEQ ID NO: 1) in the frataxin promoter. The repeat variable di-residues of TALE #1 are: HD, HD, HD, NG, NG, NN, NN, NN, NG, HD, NI and NG in vector NN (this combination of modules comprising variable di-residues corresponds to SEQ ID NO: 2). B. TALE #2 (SEQ ID NOs: 69 and 70) which binds to the sequence: tcctggttgcactc (SEQ ID NO: 3) in the frataxin promoter. The repeat variable di-residues of TALE #2 are: HD, HD, NG, NN, NN, NG, NG, NN, HD, NI, HD and NG (in bold, corresponding nucleic acid sequences are underlined) in vector HD (this combination of modules comprising variable di-residues corresponds to SEQ ID NO: 4). C. TALE #3 (SEQ ID NOs: 71 et 72) which binds to the sequence: tggttgcactccgt (SEQ ID NO: 5) in the frataxin promoter. The repeat variable di-residues are in TALE #3 are: NN, NN, NG, NG, NN, HD, NI, HD, NG, HD, HD and NN in vector NG (this combination of modules comprising variable di-residues corresponds to SEQ ID NO: 6). D. TALE #4 (SEQ ID NOs: 73 and 74) which reacts with the sequence: tgctttgcacaaag (SEQ ID NO: 7) in the frataxin promoter. The repeat variable di-residues in TALE #4 are: NN, HD, NG, NG, NG, NN, HD, NI, HD, NI, NI and NI (in bold, corresponding nucleic acid sequences are underlined) in vector NN (this combination of modules comprising variable di-residues corresponds to SEQ ID NO: 8). E. TALE #5 (SEQ ID NOs: 75 and 76) which reacts with the sequence: tgcacgaatagtgc (SEQ ID NO: 9) in the frataxin promoter. The repeat variable di-residues of TALE #5 are: NN, HD, NI, HD, NN, NI, NI, NG, NI, NN, NG and NN in vector HD (this combination of modules comprising variable di-residues corresponds to SEQ ID NO: 10). See Table 3 and FIG. 8 for details on other TALEs of the present invention;

FIG. 33 shows the sequence the HIS-PEP1-Frataxin construct in vector pet-16b. A. Amino acid sequence (SEQ ID NO: 78) and corresponding nucleic acid sequence (SEQ ID NO: 77) of the HIS-PEP1-frataxin recombinant protein. B. Amino acid sequence of the HIS-PEP1-frataxin recombinant protein (SEQ ID NO: 78). C. depicts the cloning sites of the 6×HIS-PEP1-frataxin in vector pet 16B (Nco I: SEQ ID NO: 135; and bamHI: SEQ ID NO: 136). D. Amino acid sequence and corresponding nucleic acid sequence (SEQ ID NO: 79) of the HIS-Tat-frataxin recombinant protein. E. Amino acid sequence (SEQ ID NO: 80) of the HIS-TAT-frataxin recombinant protein. F. depicts the cloning sites of the 6×HIS-TAT-frataxin in vector pet 16B (Nco I: SEQ ID NO: 135; and bamHI: SEQ ID NO: 136). G. Amino acid sequence and corresponding nucleic acid sequence (SEQ ID NO: 81) of the HIS-frataxin recombinant protein. H. Amino acid sequence (SEQ ID NO: 82) of the HIS-frataxin recombinant protein. I. depicts the cloning sites of HIS-frataxin in vector pet 16B (Nco I: SEQ ID NO: 135; and bamHI: SEQ ID NO: 136). 6× His tag is underlined; the PTD (PEP1(A-B) or TAT(D-E)) is shown in bold and the frataxin sequence is shaded. J and K. Nucleic acid sequence ID NO: 83) of pet-16B vector.

DESCRIPTION OF ILLUSTRATIVE EMBODIMENTS

The present invention relates to inducing or increasing frataxin expression/levels in a cell, and uses thereof. In an aspect the present invention relates to the design of TAL-effector based recombinant proteins for inducing the expression of frataxin. In a further aspect, a recombinant protein comprising (a) a frataxin protein or functional fragment and/or derivative thereof; and (b) a protein transduction domain, may be designed, prepared and introduced into a cell, thereby to increase the level of frataxin protein or functional fragment and/or derivative thereof within the cell. The present invention further relates to uses of such induction or increasing frataxin expression/levels in a cell, such as for enhancing/increase expression of the frataxin protein in cells from a subject in need thereof, such as for the treatment of Friedreich ataxia.

Figure 1:
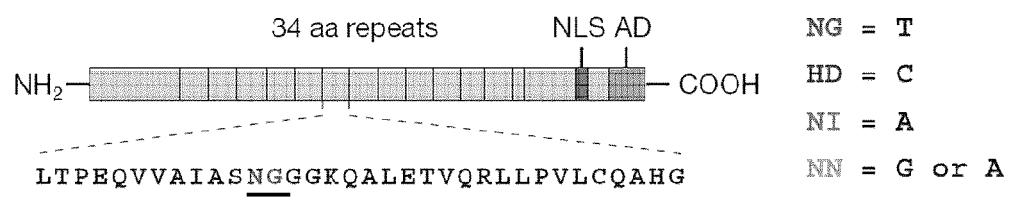
FIG. 1 is a schematic representation of the native TAL effector (TALE) hax3 from *Xanthomonas campestris* pv. *Armoraciae* depicting the tandem repeat domain and two repeat variable residues (NG, underlined) within each repeat monomer (SEQ ID NO: 57). These di-residues determine the base recognition specificity. The four most common naturally occurring di-residues used for the construction of customized artificial TAL effectors are listed together with their proposed major base specificity. NLS, nuclear localization signal; AD, transcription activation domain of the native TAL effector (Zhang et al., Nature Biotechnology, 2011)

TAL-effector based recombinant proteins (TAL Effector or TALE proteins) are naturally produced by a plant pathogen *Xanthomonas* sp (Boch et al. 2009; Boch and Bonas; Moscou and Bogdanove 2009). The TALEs have a highly conserved and repetitive region within the middle of the protein, consisting of tandem repeats of 33 or 34 amino acid segments (FIG. 1). These repeat monomers differ from each other mainly in amino acid positions 12 and 13 and there is strong correlation between this pair of amino acids and the corresponding nucleotide in the TALE-binding site (e.g., NI to A, HD to C, NG to T, and NN to G or A). A detailed Golden Gate PCR assembly method to produce TALEs targeting desired DNA sequences has been published (Zhang et al.) with reagents available commercially (e.g., Addgene Inc.).

In order to provide clear and consistent understanding of the terms in the instant application, the following definitions are provided.

Definitions

The articles "a," "an" and "the" are used herein to refer to one or to more than one (i.e., to at least one) of the grammatical object of the article.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

The TAL effector-based recombinant proteins of the present invention are derived from naturally occurring Transcription activator-like effector (TALE, see FIG. 1) and induce the transcription of the frataxin gene and expression of the frataxin protein.

TALEs are natural effector proteins secreted by numerous species of bacterial pathogens including the plant pathogen *Xanthomonas* which modulates gene expression in host plants and facilitates bacterial colonization and survival. The specific activity of TAL effectors is based on a central repeat domain of tandemly arranged nearly identical repeats of typically 33 or 34 amino acids (the repeat-variable di-residues, RVD domain).

Members of the TAL effectors family differ mainly in the number and order of their repeats. The number of repeats ranges from 1.5 to 33.5 repeats and the C-terminal repeat is usually shorter in length (i.e., about 20 amino acids) and is generally referred to as a "half-repeat". Each repeat of the TAL effector feature a one-repeat-to-one-base-pair correlation with different repeat types exhibiting different base-pair specificity (one repeat recognizes one base-pair on the target gene sequence). Generally, the smaller the number of repeats, the weaker the protein-DNA interactions. A number of 6.5 repeats has been shown to be sufficient to activate transcription of a reporter gene (Scholze et al., 2010).

Repeat to repeat variations occur predominantly at amino acid positions 12 and 13, which have therefore been termed "hypervariable" and which are responsible for the specificity of the interaction with the target DNA promoter sequence (see FIG. 29 and consensus module defined by SEQ ID NOs: 64 and 65). Accordingly, it is possible to modify the repeats of a TAL effector to target specific DNA sequences. The experimentally validated code between the repeat variable di-residues (RVD) sequence and target DNA base can be expressed as NI=A (module NI, SEQ ID NOs: 56 and 57), HD=C (module HD, SEQ ID NOs: 60 and 61), NG=T (NG module, SEQ ID NOs: 58 and 59), NN=G or A (NN module, SEQ ID NOs: 62 and 63), NK=G (SEQ ID NOs: 140 and 141), and NS=A, C, G, or T (SEQ ID NOs: 142 and 143—see also consensus module defined by SEQ ID NOs: 64 and 65). Target sites of TAL effectors also tend to include a T flanking the 5' base targeted by the first repeat, but the exact mechanism of this recognition is not known. More than 113 TAL effector sequences are known to date. Non-limiting examples of TAL effectors from *Xanthomonas* include, Hax2, Hax3, Hax4, AvrXa7, AvrXa10 and AvrBs3.

Accordingly, the "TAL domain" of the TAL effector-based recombinant protein of the present invention may be derived from a TAL effector from any bacterial species (e.g., *Xanthomonas* species such as the African strain of *Xanthomonas oryzae* pv. *Oryzae* (Yu et al. 2011), —*Xanthomonas campestris* pv. *raphani* strain 756C and *Xanthomonas oryzae* pv. *oryzicola* strain BLS256 (Bogdanove et al. 2011). As used herein, the "TAL domain" in accordance with the present invention comprises an RVD domain as well as flanking sequence(s) (sequences on the N-terminal and/or C-terminal side of the RVD domain (e.g., SEQ ID NOs: 41 (N-terminal) and 42 (C-terminal)) also from the naturally occurring TAL effector. It may comprise more of fewer repeats than the RVD of the naturally occurring TAL effector. The RVD domain of the TAL effector-based recombinant protein of the present invention is designed to target a given DNA sequence on the frataxin promoter based on the above code (i.e., NI=A (module NI, SEQ ID NOs: 56 and 57), HD=C (module HD, SEQ ID NOs: 60 and 61), NG=T (NG module, SEQ ID NOs: 58 and 59), NN=G or A (NN module, SEQ ID NOs: 62 and 63), NK=G (module NK, SEQ ID NOs: 140 and 141), and NS=A, C, G, or T (module NS, SEQ ID NOs: 142 and 143), consensus module: SEQ ID NOs: 64 and 65). The number of repeats (monomers or modules, see FIG. 29 and SEQ ID NOs: 64 and 65 for consensus module) and their specific sequence are selected based on the desired DNA target sequence on the frataxin promoter. For example repeats may be removed or added in order to suit a specific target sequence on the frataxin promoter. In an embodiment, the Tal-effector based recombinant protein of the present invention comprises between 6.5 and 33.5 repeats. In an embodiment, Tal-effector based recombinant protein of the present invention comprises between 8 and 33.5 repeats, preferably between 10 and 25 repeats and more preferably between 10 and 14 repeats.

Although a perfect match is preferred, a mismatch between a repeat and a target base-pair on the frataxin promoter sequence is also permitted as along as it still allows for an increase in frataxin expression. In general, TALE activity is inversely correlated with the number of mismatches. Preferably, the RVD domain of the recombinant protein of the present invention comprises 7 mismatches, 6 mismatches, 5 mismatches, 4 mismatches, 3 mismatches, more preferably 2 mismatches, or less, and even more preferably no mismatch, with the corresponding target frataxin promoter sequence. Of course, the smaller the number of repeat in the RVD domain the smaller the number of mismatches tolerated. The binding affinity is thought to depend on the sum of matching repeat-DNA combinations. For example, RVD domains having 25 repeats or more may be able to tolerate up to 7 mismatches.

In addition to the RVD domain, the "TALE domain" of the present invention comprises on each side of the RVD domain (i.e., on the C-terminal (e.g., SEQ ID NO:41) and N-terminal (e.g., SEQ ID NO:42) sides of the tandem repeats) additional sequences derived from a naturally occurring TAL effector (e.g., FIGS. 19 and 20). The length of the C-terminal and/or N-terminal sequence(s) included on each side of the RVD domain can vary and be selected by one skilled in the art, for example based on the studies of Zhang et al. (2011). Zhang et al., have characterized a number of C-terminal and N-terminal truncation mutants in Hax3 derived TAL-effector based proteins and have identified key elements, which contribute to optimal binding to the target sequence and thus activation of transcription. Generally, it was found that transcriptional activity is inversely correlated with the length of N-terminus. Regarding the C-terminus, an important element for DNA binding residues within the first 68 amino acids of the Hax 3 sequence was identified. Accordingly, to preserve the highest level of TALE activity, the first 68 amino acids on the C-terminal side of the RVD domain of the naturally occurring TAL effector is preferably included in the "TALE domain" of the recombinant protein of the present invention. Accordingly, in an embodiment, the "TALE domain" of the present invention comprises for example 1) an RVD domain derived from a naturally occurring TAL effector; 2) at least 70, 80, 90, 100, 110, 120, 130, 140, 150, 170, 180, 190, 200, 220, 230, 240, 250, 260, 270, 280 or more amino acids from the naturally occurring TAL effector on the N-terminal side (e.g., FIGS. 19 and 20 and SEQ ID NOs:40, 41) of RVD domain; and/or 3) at least 68, 80, 90, 100, 110, 120, 130, 140, 150, 170, 180, 190, 200, 220, 230, 240, 250, 260 or more amino acids from the naturally occurring TAL effector on the C-terminal side (e.g., FIGS. 19 and 20 and SEQ ID NOs:40, 42) of RVD domain.

The Tal effector-based recombinant protein of the present invention further comprises one or more (i.e, at least one) of a "transcription activation domain" or "trans-activating domain" (TAD), which contain binding sites for other proteins (e.g., transcription coregulators) and is essential for activating transcription of the target frataxin gene and expression of the frataxin protein.

Trans-activating domains (TADs) are named after their amino acid composition. These amino acids are either essential for the activity or simply the most abundant in the TAD. Transactivation by the Gal4 transcription factor is mediated by acidic amino acids, whereas hydrophobic residues in Gcn4 play a similar role. Hence, the TADs in Gal4 and Gcn4 are referred to as acidic or hydrophobic activation domains, respectively.

Nine-amino-acid transactivation domain (9aaTAD) defines a novel domain common to a large superfamily of eukaryotic transcription factors represented by Gal4, Oaf1, Leu3, Rtg3, Pho4, Gln3, Gcn4 in yeast and by p53, NFAT, NF-κB and VP16 in mammals. Prediction for 9aa TADs (for both acidic and hydrophilic transactivation domains) is available online from ExPASy™ and EMBnet™ Spain.

KIX domain of general coactivators Med15(Gal11) interacts with 9aaTAD transcription factors Gal4, Pdr1, Oaf1, Gcn4, VP16, Pho4, Msn2, Ino2 and P201. Interactions of Gal4, Pdr1 and Gcn4 with Taf9 were reported. 9aaTAD is a common transactivation domain recruits multiple general coactivators TAF9, MED15, CBP/p300 and GCN5. Accordingly, non-limiting examples of TAD that may be used in accordance with the present invention include TAD from Gal4, Pdr1, Oaf1, Gcn4, Pho4, Msn2, Ino2, P201, p53, VP16, MLL, E2A, HSF1, NF-16, NFAT1 and NF-kappaB. Other non-limiting examples of TAD include TAD from the SRF, TFAP2 or SP1 transcription factor, for which target sequences have been indentified in the frataxin promoter (Li et al. 2010). Of course, the choice of a TAD will depend on numerous factors including the specific type of cells in which the gene will be expressed as well as the nature of the gene. Furthermore, one can appreciate that more than one TAD may be included in a TALE construct of the present invention. In an embodiment, TAD of the recombinant protein of the present invention is VP64 which corresponds to 4 times the sequence of the VP16 TAD. In an embodiment, the TAD has the sequence GSGRADALDDFDLDM-LGSDALDDFDLDMLGSDALDDFDLDMLGSDALDD-FDLDMLINSR (SEQ ID NO:26).

TABLE 1

Exemplary TADs from transcription factors.

|  | Annotated 9aaTAD | Peptide - KIX interaction (NMR data) |
|---|---|---|
| p53TAD1 | E TFSD LWKL | LSPEET<u>FSDLWKL</u>PE |
| p53TAD2 | D DIEQ WFTE | QAMDDLMLS<u>PDDIEQW</u>FTEDPGPD |
| MLL | S DIMD FVLK | DCGNI<u>LPSDIMDFVLK</u>NTP |
| E2A | D LLDF SMMF | PVGTDKELSDL<u>LDFS</u>MMFPLPVT |
| Rtg3 | E TLDF SLVT | E2A homolog |
| CREB | R KILN DLSS | RREILSRR<u>PSYRKILNDLSS</u>DAP |
| CREBαB6 | E AILA ELKK | CREB-mutant binding to KIX |
| Gli3 | D DVVQ YLNS | TAD homology to CREB/KIX |
| Gal4 | D DVYN YLFD | Pdr1 and Oaf1 homolog |
| Oaf1 | D LFDY DFLV | DLFDYDFLV |
| Pip2 | D FFDY DLLF | Oaf1 homolog |
| Pdr1 | E DLYS ILWS | EDLYSILWSDWY |
| Pdr3 | T DLYH TLWN | Pdr1 homolog |

The sequences of the annotated 9aa TADs in Table 1 above correspond, in order of appearance from top to bottom, to SEQ ID NOs:107-119. The sequences of the Peptide-KIX interaction listed on the right hand column of Table 1 above correspond, in order of appearance from top to bottom, to SEQ ID NOs:120-126 (p53 TAD1; p53TAD2, MLL, E2A, CREB, Oaf1 and Pdr1, respectively).

The Tal effector-based recombinant protein of the present invention also comprises a Nuclear Localization Signal (NLS). Accordingly, as used herein the expression "nuclear localization signal" or "NLS" refers to an amino acid sequence, which 'tags' a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal, which targets proteins out of the nucleus. Classical NLSs can be further classified as either monopartite or bipartite. The first NLS to be discovered was the sequence PKKKRKV (SEQ ID NO: 27) in the SV40 Large T-antigen (a monopartite NLS). The NLS of nucleoplasmin, KR[PAATKKAGQA]KKKK (SEQ ID NO:28), is the prototype of the ubiquitous bipartite signal: two clusters of basic amino acids, separated by a spacer of about 10 amino acids.

There are many other types of NLS, which are said to be "non-classical", such as the acidic M9 domain of hnRNP A1, the sequence KIPIK in yeast transcription repressor Matα2, the complex signals of U snRNPs as well as a recently identified class of NLSs known as PY-NLSs. Thus, any type of NLS (classical or non-classical) may be used in accordance with the present invention as long as it targets the protein of interest into the nucleus of a target cell. Preferably, the NLS is derived from the simian virus 40 large T antigen. In an embodiment, the NLS of the TAL effector based recombinant protein of the present invention has the following amino acid sequence: SPKKKRKVEAS (SEQ ID NO:29). In an embodiment the NLS has the sequence KKKRKV (SEQ ID NO:30). In an embodiment, the NLS has the sequence SPKKKRKVEASPKKKRKV (SEQ ID NO:31). In another embodiment, the NLS has the sequence KKKRK (SEQ ID NO:89).

The TAL effector-based recombinant protein of the present invention may advantageously be coupled to a protein transduction domain to ensure entry of the protein into the target cells.

In a further aspect, the present invention provides a recombinant "frataxin-protein transduction domain" protein comprising (a) a frataxin protein or functional fragment and/or derivative thereof; and (b) a protein transduction domain.

Protein transduction domains (PTD) are of various origins and allows intracellular delivery of a given therapeutic by facilitating the translocation of the protein/polypeptide into a cell membrane, organelle membrane, or vesicle membrane. PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle including the mitochondria. In an embodiment, a PTD is covalently linked to the amino terminus of a recombinant protein of the present invention. In another embodiment, a PTD is covalently linked to the carboxyl terminus recombinant protein of the present invention. Exemplary protein transduction domains include but are not limited to a minimal undecapeptide protein transduction domain (corresponding to residues 47-57 of HIV-1 TAT comprising YGRKKRRQRRR (SEQ ID NO: 37); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an *Drosophila Antennapedia* protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:33); Transportan GWTLNSAGYLLGKINLKALAALAKKIL (SEQ ID NO:34); KALAWEAKLAKALAKA-LAKHLAKALAKALKCEA (SEQ ID NO:35); and RQIKI-WFQNRRMKWKK (SEQ ID NO:36). Further exemplary PTDs include but are not limited to, KKRRQRRR (SEQ ID NO:32), RKKRRQRRRR (SEQ ID NO:38); an arginine homopolymer of from 3 arginine residues to 50 arginine residues.

Genetic constructs to encode TAL effector-based proteins or a recombinant "frataxin-protein transduction domain" protein can be made using either conventional gene synthesis or modular assembly. A plasmid kit for assembling custom TAL effector constructs is available through the public, not-for-profit repository by AddGene. Webpages providing access to public software, protocols, and other resources for TAL effector-DNA targeting applications include the "TAL Effector-Nucleotide Targeter" (http://boglabx.plp.iastate.edu/TALENT/) and "taleffectors.com".

In an embodiment, the TAL effector-based recombinant protein of the present invention is made in accordance with the assembly protocol of Zhang et al., (2011).

In one aspect, the present TAL effector-based recombinant proteins of the present invention may be used to increase/induce expression of the frataxin nucleic acid and the frataxin protein in cells. As used herein, the expression "increasing" in "increasing the expression of frataxin in a cell" is meant to include circumstances where, in the absence of a TAL effector-based recombinant protein of the present invention, the frataxin protein is not expressed at all in said cell and where the cell already expresses a certain amount of frataxin protein. It comprises increasing/enhancing expression of frataxin in cells expressing no frataxin, a normal level or abnormal/lower level of frataxin as compared to normal conditions.

In an embodiment, the TAL effector-based recombinant proteins of the present invention may be used to increase transcription of the frataxin promoter in cells from a subject in need thereof. Non-limiting examples of a subject in need thereof include a subject having cells showing a reduced level of frataxin expression or activity as compared to cells from a normal subject. In an embodiment, the subject in need thereof is a subject having an abnormal number of trinucleotide repeats in intron 1 of the frataxin gene. In an embodiment, said number of trinucleotide repeats is 35 or more, 65 or more, 75 or more, 85 or more, 100 or more, 110 or more, 125 or more, 150 or more, 175 or more, 200 or more, 225 or more, 250 or more, 300 or more, 350 or more, 500 or more. In an embodiment, said subject in need thereof suffers from Friedreich ataxia. In an embodiment, the subject is a mammal, preferably, a human.

In a further embodiment, the recombinant "frataxin-protein transduction domain" protein may be used to increase may be used to increase levels of frataxin protein or a functional fragment and/or derivative thereof in cells, for example in cells from a subject in need thereof.

As used herein, "a subject in need thereof" is a subject, which may benefit from an increased expression of the frataxin protein or of increased levels of the frataxin protein.

In an embodiment, the present invention relates to a method of increasing frataxin expression in a subject in need thereof comprising administering an effective amount of a TAL effector-based recombinant protein of the present invention. In an embodiment, the recombinant protein is specifically formulated for crossing the plasma membrane and reaching the nucleus. In an embodiment, the present invention provides a composition comprising a TAL effector based recombinant protein of the present invention together with a pharmaceutically acceptable carrier.

In an embodiment, the present invention relates to a method of increasing frataxin (or a functional derivative and/or fragment thereof) levels in a subject in need thereof, comprising administering an effective amount of the recombinant "frataxin-protein transduction domain" protein of the present invention. In an embodiment, the present invention provides a composition comprising a recombinant "frataxin-protein transduction domain" protein of the present invention together with a pharmaceutically acceptable carrier.

Optimization of Codon Degeneracy

Because TAL effectors are expressed from bacterial pathogen infecting plants, it may be advantageous to modify their nucleic acid sequences for optimal expression in eukaryotic cells (e.g., mammalian cells) when designing and preparing TAL effector-based recombinant protein of the present invention.

Accordingly, the following codon chart (Table 2) may be used, in a site-directed mutagenic scheme, to produce nucleic acids encoding the same or slightly different amino acid sequences of a given nucleic acid:

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Sequence Similarity

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. For the sake of brevity, the units (e.g., 66, 67 . . . 81, 82, . . . 91, 92% . . . ) have not systematically been recited but are considered, nevertheless, within the scope of the present invention.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 98% or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 2010, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 2010, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In another aspect, the invention further provides a nucleic acid encoding the above-mentioned TAL effector-based recombinant protein or recombinant "frataxin-protein transduction domain" protein. The invention also provides a vector comprising the above-mentioned nucleic acid. In an embodiment, the vector further comprises a transcriptional regulatory element operably-linked to the above-mentioned nucleic acid. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, "operably-linked" DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals, which induce or control transcription of protein coding sequences with which they are operably-linked.

In yet another aspect, the present invention provides a cell (e.g., a host cell) comprising the above-mentioned nucleic acid and/or vector. The invention further provides a recombinant expression system, vectors and host cells, such as those described above, for the expression/production of a recombinant protein, using for example culture media, production, isolation and purification methods well known in the art.

In another aspect, the present invention provides a composition (e.g., a pharmaceutical composition) comprising the above-mentioned TAL effector-based recombinant protein or recombinant "frataxin-protein transduction domain" protein. In an embodiment, the composition further comprises one or more pharmaceutically acceptable carriers, excipients, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The present invention further provides a kit or package comprising the above-mentioned TAL effector-based recombinant protein or recombinant "frataxin-protein transduction domain" protein, or composition, together with instructions for increasing frataxin expression or levels in a cell or for treatment of Friedreich ataxia in a subject.

The present invention is illustrated in further details by the following non-limiting examples.

EXAMPLE 1

Tal-Effector Based Recombinant Proteins Efficiently Promote Frataxin Expression in Cells The method of Zhang et al. (2011) using a reporter plasmid has been used to design and generate several TAL effector based recombinant proteins, which are specific for various portions of the human frataxin promoter sequence. The mCherry reporter plasmid sold by AddGene™ inc. was not functional. Therefore, Applicants made their own reporter plasmid: pCR3.1-frataxin-promoter-miniCMV-mCherry, (see FIG. 21 and FIG. 22, and SEQ ID NO:43). Table 3 summarizes the nucleotide sequences, which have been targeted and the corresponding repeat-variable di-residue (RVD) (Cermak et al.) of the TAL effector based recombinant protein according to embodiments of the present invention.

TABLE 3

| TAL-effector based recombinant protein | Targeted sequence (NM_000144.4) | Targeted sequence | RVD repeats |
|---|---|---|---|
| 1 | 5-18 | tcccttgggtcagg (SEQ ID NO: 1) | HD HD HD NG NG NN NN NN NG HD NI NG NN; (SEQ ID NO: 2) |
| 2 | 21-34 | tcctggttgcactc (SEQ ID NO: 3) | HD HD NG NN NN NG NG NN HD NI HD NG HD; (SEQ ID NO: 4) |
| 3 | 24-37 | tggttgcactccgt (SEQ ID NO: 5) | NN NN NG NG NN HD NI HD NG ND HD NN NG; (SEQ ID NO: 6) |
| 4 | 37-50 | tgctttgcacaaag (SEQ ID NO: 7) | NN HD NG NG NG NN HD NI HD NI NI NI NN; (SEQ ID NO: 8) |
| 5 | 73-86 | tgccgaatagtgc (SEQ ID NO: 9) | NN HD NI HD NN NI NI NG NI NN NG NN HD; (SEQ ID NO: 10) |
| 6 | 81-94 | tagtgctaagctgg (SEQ ID NO: 11) | NI NN NG NN HD NG NI NI NN HD NG NN; (SEQ ID NO: 12) |
| 7 | 92-105 | tgggaagttcttcc (SEQ ID NO: 13) | NN NN NN NI NI NN NG NG HD NG NG HD HD; (SEQ ID NO: 14) |
| 8 | 103-116 | tcctgaggtctaac (SEQ ID NO: 15) | HD HD NG NN NI NN NN NG HD NG NI NI; (SEQ ID NO: 16) |
| 9 | 106-119 | tgaggtctaacctc (SEQ ID NO: 17) | NN NI NN NN NG HD NG NI NI HD HD NG; (SEQ ID NO: 18) |
| 10 | 124-137 | tgctcccccacaga (SEQ ID NO: 19) | NN HD NG HD HD HD HD HD NI HD NI NN NI; (SEQ ID NO: 20) |
| 11 | 155-168 | tggccaccaggggt (SEQ ID NO: 21) | NN NN HD HD NI HD HD HD NI NN NN NN NN NG; (SEQ ID NO: 22) |
| 12 | 168-181 | tcgccgcagcaccc (SEQ ID NO: 23) | HD NN HD HD NN HD NI NN HD NI HD HD HD (SEQ ID NO: 24) |

Figure 2:
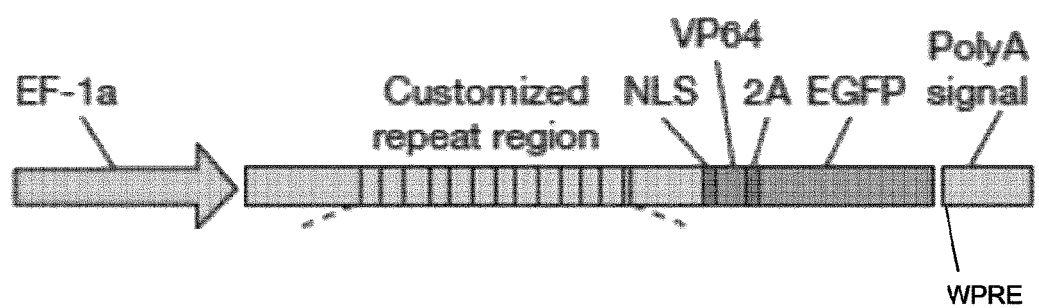
FIG. 2 is a schematic representation of the fluorescence reporter construct of the recombinant protein described herein: pLenti-EF1α-TALE-VP64-2A-EGFP-WPRE. EF-1a, EF-1a promoter sequence; VP64, synthetic transcription activation domain (TAD); NLS, nuclear localization signal; 2A; 2A self cleavage peptide; EGFP, enhanced green fluorescent protein; WPRE, woodchuck hepatitis post-transcriptional regulatory element.

PCR3.1 expression plasmids containing a gene coding for various TAL effector-based proteins under the EF1-α promoter have been produced (FIG. 2). However, in these plasmids, the TALE domain has been fused with a VP64 (SEQ ID NO:26) sequence (TALE-VP64) to induce the expression of a downstream gene following the attachment of the TALE-VP64 protein. Moreover, the TALE-VP64 gene was also fused with the gene coding for the EGFP reporter protein. A sequence coding for a 2A peptide (amino acid sequence GDVEENPGP (SEQ IS NO: 39) has been inserted between VP64 (SEQ ID NO:26) and EGFP (SEQ ID NO:54) to produce the vector pLenti-EF1α-TALE-VP64-2A-EGFP-WPRE. Following, the transfection of this plasmid in cells, there was the production of a single mRNA by transcription. However, 2 separated proteins (i.e., the TALE-VP64 and the EGFP) were produced during transcription because of the presence of the 2A peptide.

Figures 3, 4:
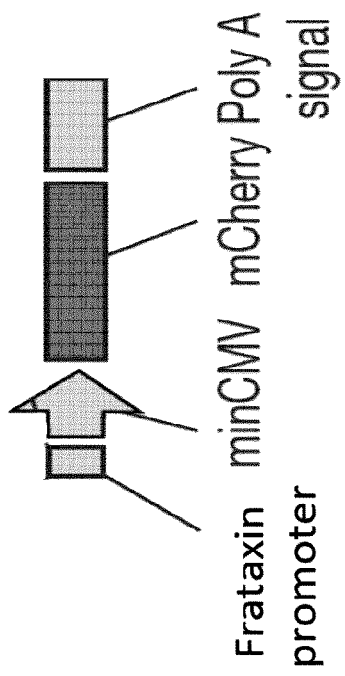
FIG. 3 shows a schematic representation of the reporter plasmid pCR3.1-frataxin-promoter-miniCMV-mCherry described herein, comprising the frataxin promoter comprising TALE DNA recognition sites. minCMV, minimal cytomegalovirus (CMV) promoter, mCherry, fluorescence reporter gene.
FIG. 4 shows the frataxin promoter nucleic acid sequence (SEQ ID NO:88) included in the reporter construct depicted in FIG. 3.

In order to determine which TALE-VP64 proteins were able to induce the expression of the frataxin gene a fluorescence-based reporter construct was prepared. The proximal frataxin promoter (SEQ ID NO: 88, Lie et al., 2010) was inserted in a reporter plasmid 3' of a minimal CMV promoter and of a mCherry reporter gene (pCR3.1-frataxin-promoter-miniCMV-mCherry, FIG. 3). The frataxin promoter sequence present in this plasmid is illustrated in FIG. 4.

Expression in 293FT Cells

Transfection:

mCherry reporter activation was tested by co-transfecting 293FT cells with plasmids carrying TALEs and mCherry reporters. 293FT cells were seeded into 24 plates the day before transfection at densities of $0.8 \times 10^4$ cells/well. Approximately 24 h after initial seeding, cells were transfected using Lipofectamine™ 2000 (Invitrogen). We used 500 ng of TALE and 30 ng of reporter plasmids per well. Transfection experiments were performed according to manufacturer's recommended protocol.

Flow Cytometry:

mCherry reporter activation was assayed by flow cytometry. Cells were trypsinized from their culturing plates about 18 h after transfection and resuspended in 200 µl of media for flow cytometry analysis. At least 10,000 events were analyzed for each transfection sample. The fold induction of mCherry reporter gene by TALEs was determined by flow cytometry analysis of mCherry expression in transfected 293FT cells, and calculated as the ratio of the total mCherry fluorescence intensity of cells from transfections with and without the specified TALE. All fold-induction values were normalized to the expression level of TALE as determined by the total GFP fluorescence for each transfection.

Figure 5:
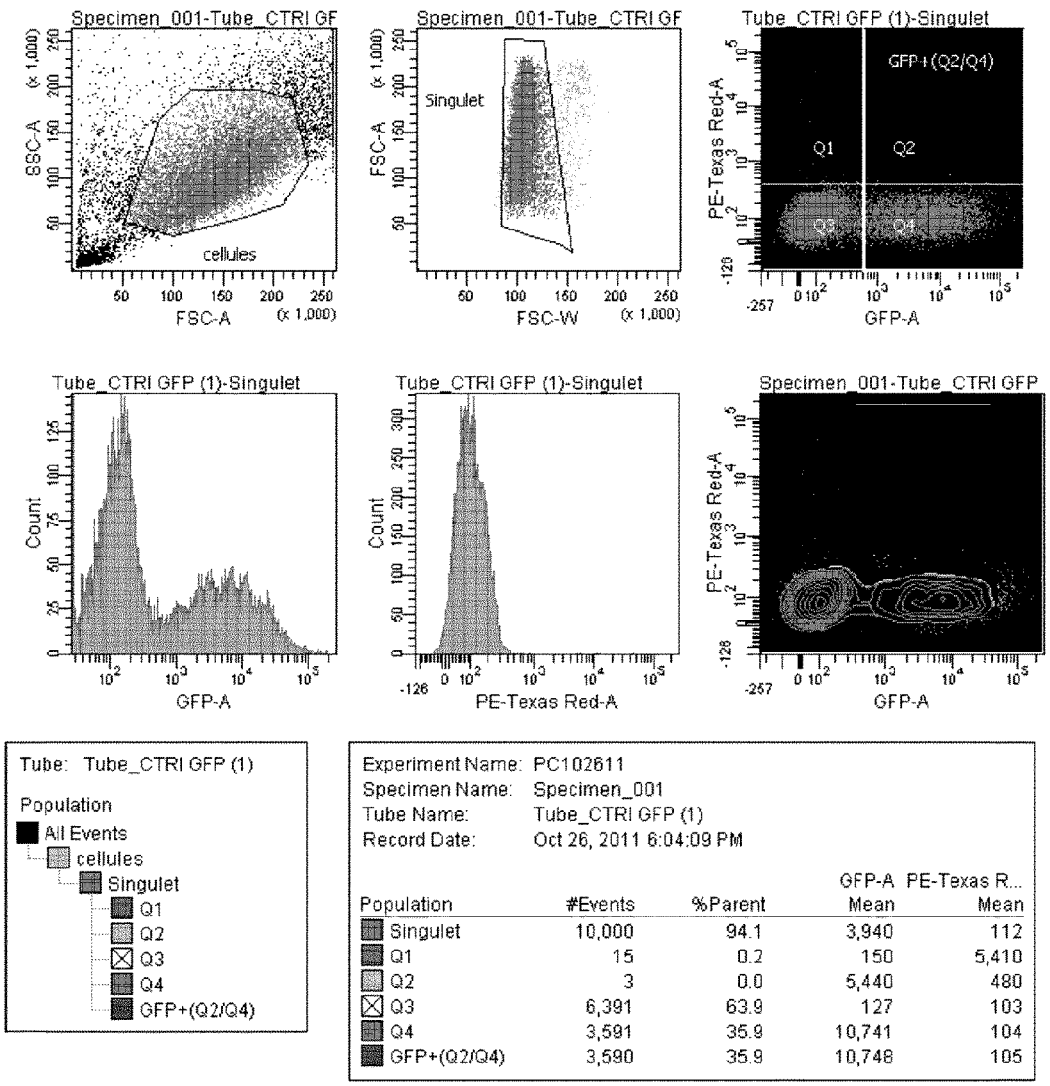
FIG. 5 shows that when the pCR3.1-TALE-VP64-EGFP expression plasmid is transfected in 293FT cells alone, only green fluorescence (Q4, lower right quadrant) was detected in the cells by flow cytometry.
Figure 6:
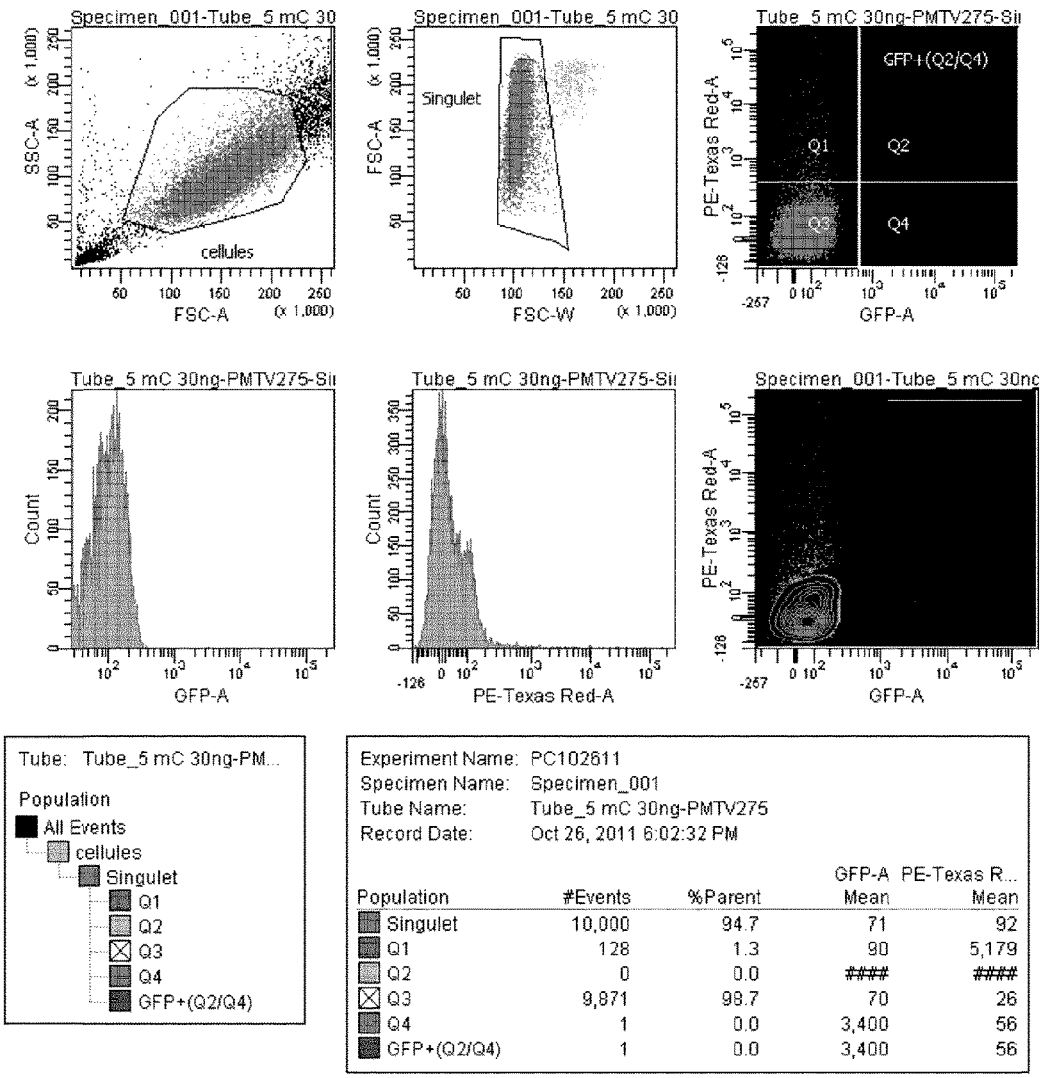
FIG. 6 shows that when the pCR3.1-frataxin-promoter-miniCMV-mCherry expression plasmid is transfected in 293FT cells alone, red fluorescence (Q1, top left quadrant) was detected in only a few cells by flow cytometry.
Figure 7:
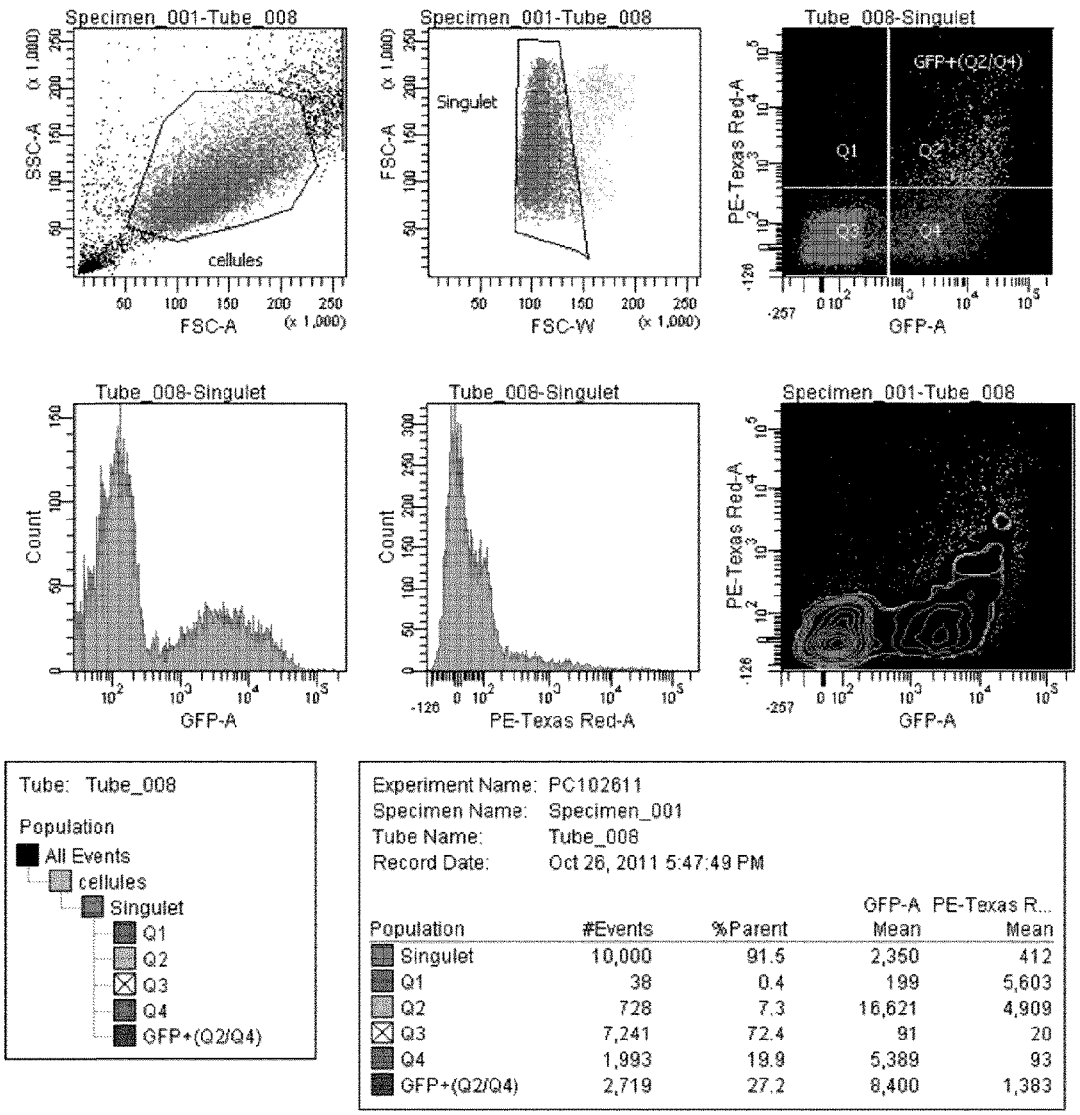
FIG. 7 shows that the co-transfection of 293FT cells with pLenti-EF1α-TALE-VP64-2A-EGFP-WPRE and pCR3.1-frataxin-promoter-miniCMV-mCherry resulted in the emission of green and red fluorescence (Q2, top right quadrant)

When human cells were transfected with pLenti-EF1α-TALE-VP64-2A-EGFP-WPRE, only green fluorescence was detected (FIG. 5). The presence of green fluorescence confirmed the expression of the EGFP protein and thus indirectly confirmed the expression of the TALE-VP64 protein. In addition, when the pCR3.1-frataxin-promoter-miniCMV-mCherry construct was initially transfected in human cells alone at 30 ng/ml, very few cells expressed the red fluorescence (FIG. 5). However, when human cells were co-transfected with vectors (pLenti-EF1α-TALE-VP64-2A-EGFP-WPRE and pCR3.1-frataxin-promoter-miniCMV-mCherry) both green fluorescence and various amounts of red fluorescence were detected confirming the activity of the TAL effector-based recombinant proteins (FIGS. 6 and 7). This indicated that the TALE-VP64 constructs were attaching to the frataxin promoter sequence inducing the expression of the mCherry reporter gene. FIG. 8 summarizes the results. The more active TAL effector based recombinant proteins of the present invention (#6, 7 and 8) are inducing the expression of mCherry (red fluorescence) in a higher proportion of the green fluorescence.

Thus, the TALE-VP64 proteins are able to attached to the frataxin promoter and drive the expression of a gene placed downstream of this promoter. These TALE-VP64 proteins may be used to increase the expression of the frataxin gene in a subject's cells. The increased expression of the frataxin will permit to reduce or prevent the symptoms associated with Friedreich ataxia.

EXAMPLE 2

Figure 9:
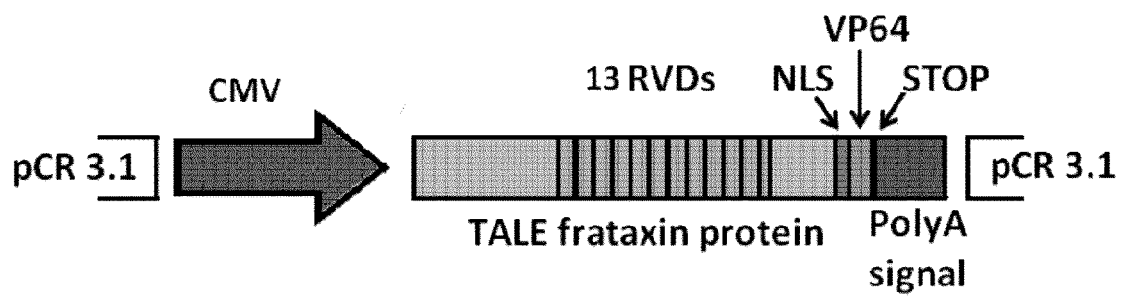
FIG. 9 shows a diagram of a plasmid coding for a TALE$_{frat/VP64}$ construct in the pCR3.1 plasmid according to an embodiment of the present invention.

$TALE_{Frat/VP16}$ Significantly Increases the Expression of the Human Frataxin Gene A plasmid coding for $TALE_{frat/VP64}$#8 (FIG. 9) was nucleofected in normal fibroblasts. Using quantitative RT-PCR, Applicants have confirmed in 3 independent experiments that the expression of the frataxin mRNA (relative to GAPDH mRNA) in human cells was doubled or triple by $TALE_{frat/VP64}$#8 when results were normalized with cells transfected with EGFP or non-transfected cells (Table 4). Two to 3 independent experiments per conditions were performed.

TABLE 4

Q-RT-PCR results

| Tale # | Normalized relative to non-transfected cells | Normalized relative to EGFP-transfected cells |
| --- | --- | --- |
| 6 | 63-140% | 73-118% |
| 7 | 94-127% | 110-148% |
| 8 | 165-313% | 192-214% |

Figure 10:
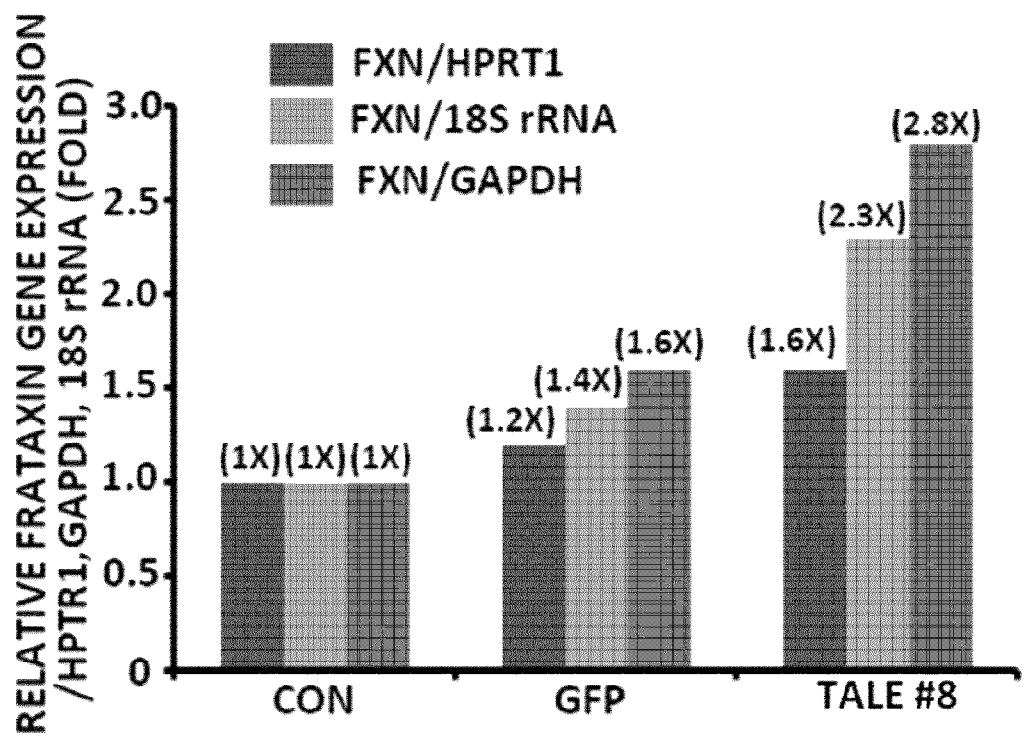
FIG. 10 shows the quantitative PCR analysis of frataxin mRNA expression 60 hours following nucleofection of a plasmid coding for TALE$_{frat/VP64}$ No. 8 (see Table 3) in Friedreich fibroblasts. Results were normalized with cells transfected with 3 different internal controls (HPRT1, GAPDH and 18S rRNA)

Applicants have also shown that TALE #8 also increased by 2 fold the frataxin mRNA in fibroblasts from a patient suffering from Friedreich ataxia. Indeed, nucleofection of pCR3.1 $TALE_{frat/VP64}$#8 significantly increased the frataxin mRNA compared with a control not nucleofected (CON) or a control nucleofected with a plasmid coding for GFP (FIG. 10). The frataxin mRNA was amplified by PCR (using primers defined in SEQ ID NOs 90 and 91) and normalized with 3 different internal controls (HPTR1 (SEQ ID NOs:92 and 93), GAPDH (SEQ ID NOs: 94 and 95) and 18S rRNA (SEQ ID NOs: 96 and 97), see also Table 5 below). The Friedreich fibroblasts used for this experiment were obtained from Coriell Institute for medical (GM 04078) and have 541 and 420 repeats on intron 1 of each allele of the gene respectively.

TABLE 5

Primer sequences used for qRT-PCR

| Gene Symbol | Description | GenBank | Size of amplicon (pb) | T annealing (° C.) | Primer sequences 5'→3' S/AS |
| --- | --- | --- | --- | --- | --- |
| FXN | Homo sapiens frataxin (FXN), nuclear gene encoding mitochondrial protein, region present in the 3 transcripts | NM_000144 | 106 | 57 | AAGCCATACACGTTTGAGGACTA/ TTGGCGTCTGCTTGTTGATCA |
| Hprt1 | Homo sapiens hypoxanthine phosphoribasyltransferase 1 | NM_000194 | 157 | 57 | AGTTCTGTGGCCATCTGCTTAGTA G/AAACAACAATCCGCCCAAAGG |

TABLE 5-continued

Primer sequences used for qRT-PCR

| Gene Symbol | Description | GenBank | Size of amplicon (pb) | T annealing (° C.) | Primer sequences 5'→3' S/AS |
|---|---|---|---|---|---|
| GAPDH | Homo sapiens glyceraldehyde-3-phosphate dehArogenase | NM_002046 | 194 | 57 | GGCTCTCCAGAACATCATCCCT/ ACGCCTGCTTCACCACCTTCTT |

For the 18S ribosomal RNA (NR_003286) primers: acggaccagagcgaaagcatt and tccgtcaattcctttagtttcagct (SEQ ID NO: 96 and SEQ ID NO:97), were used.

Results obtained at the mRNA level were also confirmed at the protein level. TALE #8 also increased by almost 2 fold the frataxin protein in fibroblasts from the same Friedreich patient (FIG. 11). Nucleofection of PCR 3.1 TALE$_{frat/VP64}$#8 significantly increased the frataxin protein compared to a non-nucleofected control (CON) or with a control nucleofected with a pCR3.1 plasmid coding for eGFP (GFP). Frataxin protein expression was normalized using β-actin as an internal standard. The mAb used to detect frataxin was #18A5DB1 from Mitosciences. Such an increase would be in the therapeutic range (i.e., 50% of normal frataxin level) for many patients.

EXAMPLE 3

Increased Expression of Frataxin mRNA and Protein in Rescued YG8 Fibroblasts

The rescued YG8 (YG8R) mouse model has 2 null mouse frataxin genes but contains a human frataxin transgene (with its human promoter) obtained from a FRDA patient. This human transgene contains 230 GAA repeats in intron 1 and thus a reduced amount of human frataxin is produced leading to the development of FRDA symptoms in this mouse model. Applicants have shown that the transfection of TALE$_{frat/VP64}$#8 plasmid in YG8R fibroblasts also increases frataxin mRNA (by about 1.4 to 1.9 fold) and protein (by about 1.5 fold) (FIG. 12).

Figure 12:
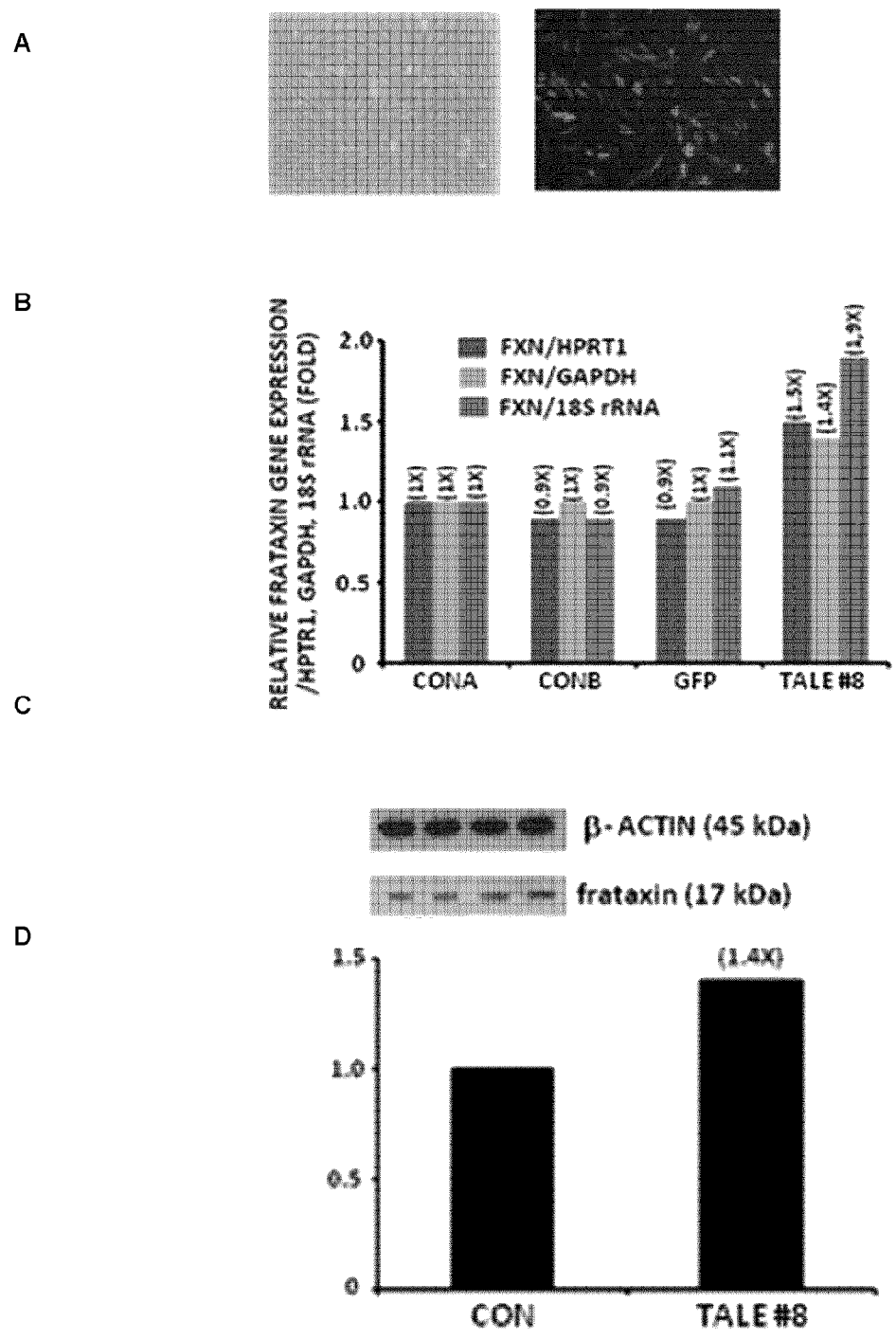
FIG. 12 shows increased expression of frataxin mRNA and protein in rescued YG8 fibroblasts. A. Nucleofection of the YG8R fibroblasts with a GFP plasmid shows that near of 40 to 50% of the cells were transfected and thus expressed the GFP fluorescent protein B. Nucleofection of pCR3.1 TALE frat/vp64#8 significantly increased frataxin mRNA (detected by Q-RT-PCR) compared with control cells not nucleofected (CONA), control cells nucleofected alone (CONB), or control cells nucleofected with a plasmid coding for a GFP. The frataxin mRNA was normalized with different internal controls (HPRT1, GAPDH and 18S rRNA. A 1.4× increase of frataxin protein expression was observed by Western blot analysis (C) when the YG8R fibroblasts were nucleofected with pCR3.1 TALE frat/vp64#8 compared to the non-nucleofected cells (CON). Frataxin protein expression was normalized using β-actin as the internal control (D). The antibodies used for this experiment are the same as for the experiments shown in FIG. 11.

As shown in FIG. 12, Applicants have analyzed the effect of PCR3.1 TALE 8 on mRNA and protein levels of frataxin as follows: YG8 cells were cultured at near of 80% confluency in a T-75 flask (medium culture: DMEM High glucose, 10% bovine serum containing non-essential amino acids (1×) and pen-strep (1×)), then the cells were trypsinized and divided equally in six tubes (15 ml sized) and centrifuged at low speed (1200×g) 5 minutes. The supernatant was discarded and cells were resuspended in 5 ml HBSS in each tube and then centrifuged as previously. At the end of centrifugation, the pellet (cells) was kept at room temperature. To each tube containing only the cells pellet was added a mix of nucleofection solution (VPD-1001)/plasmid DNA (100 µl/10 µg plasmid pCR3.1 TALE 8), cells were resuspended by pipetting up and down and transferred in a cuvette and placed inside of the Nucleofector device II™ apparatus (Amaxa biosystem)) set at the program P-022 and then nucleofected. Then, the nucleofected cells (from each nucleofection) were seeded in a well of a 6-well plate and maintained in culture overnight at 37° C. in a cells incubator. Several changes of culture medium (in the same culture medium described above) were done to remove cellular debris and culture was performed at 37° C. in an incubator during 50 to 60 hours before mRNA or protein were extracted and analysed by qRT-PCR or Western blot to evaluate Frataxin expression. Table 6 below presents the primer sequences used for qRT-PCR analysis in Y8G cells.

TABLE 6

Primers used for qRT-PCR analysis in Y8G cells following nucleofection of plasmid pCR3.1 TALE no.8.

| | | | | | |
|---|---|---|---|---|---|
| Mm Hprt1 | Mus musculus hypoxanthine guanine phosphoribosyl transferase 1 | NM_013556 | 106 | 57 | CAGGACTGAAAGACTTGCTCGAGAT/ CAGCAGGTCAGCAAAGAACTTATA GC (SEQ ID NOs: 98 and 99) |
| Mm GAPDH | Mus musculus glyceraldehyde-3-phosphate dehydrogenase | NM_008084 | 123 | 57 | ACGGGAAGCTCACTGGCATGG/ATG CCTGCTTCACCACCTTCTTG (SEQ ID NOs: 100 and 101) |
| Mm 18S | 18S ribosomal RNA (Rn18s), ribosomal RNA | NR_003278 | 119 | 57 | TGGATACCGCAGCTAGGAATAATG/ TCACCTCTAGCGGCGCAATAC (SEQ ID NOs: 102 and 103) |
| Mm ADNg | Mus musculus chromosome 3 genomic contig, strain C57BL/6J (HSD3B1 intron) | NT_039239 | 209 | 57 | CACCCCTTAAGAGACCCATGTT/CC CTGCAGAGACCTTAGAAAAC (SEQ ID NOs: 104 and 105) |
| Hs FXN | Homo sapiens frataxin (FXN), nuclear gene encoding mitochondrial protein, region commune aux 3 transcrits | NM_000144 | 106 | 57 | AAGCCATACACGTTTGAGGACTA/TT GGCGTCTGCTTGTTGATCA (SEQ ID NOs: 90 and 91) |

For Frataxin protein expression analysis by Western blot, the same human antibodies described earlier were used since as indicated above, the human frataxin gene was introduced into the mouse genome. Furthermore, the human monoclonal β-actin antibody (Sigma) was also able to recognize mouse β-actin.

EXAMPLE 4

Production and Purification of a 6×HIS-CPP-TALE$_{Frat/VP64}$ Protein

Applicants have constructed 2 plasmids (6×His-Tat-TALEFrat/VP64 and 6×His-Pep1-TALEFrat/VP64) in pET-16B (Novagen inc.) coding for a TALE$_{frat/VP64}$ protein fused with a cell penetrating peptide (CPP) and with a 6×His flag to permit the production of these recombinant proteins in *E. coli* (BL21) and their purification on a nickel affinity column. FIG. 13 shows the amino acid sequences of the proteins coded by these plasmids.

These plasmids permit the production of the recombinant protein in *E. coli* (BL21) following induction with 1 mM IPTG (FIG. 14A). The 6×His-Tat-TALE$_{frat/VP64}$ has been purified on a nickel affinity column (FIG. 14B). The recombinant protein has been detected in Western blot with an anti-6×His mAb (Qiagen #34660) (FIG. 15A) and with a polyclonal anti-VP16 mAb (ab4809, Abcam) (FIG. 15B).

Production and Purification of 6×HIS-CPP-TALE Frataxin/VP64 Protein:

The recombinant plasmids TALE No. 8 (6×HIS-TAT or PEP1) in the prokaryotic expression vector pet-16b (Novagen) have been transformed in BL21 DE3 pLysS and grown overnight at 37° C. on an agar plate containing ampicillin (150 µg/ml, chloramphenicol (34 µg/ml). The next day, three to five colonies of each recombinant were seeded separately in 25 ml of LB containing ampicillin (150 µg/ml) and chloramphenicol (34 µg/ml) and were grown under agitation at 37° C. The next day, a new culture was started by seeding 10 ml of the overnight culture in 200 ml of LB medium containing only ampicillin at 150 µg/ml. When the culture reached Absorbance (A600 nm) near 0.5-0.7, induction with 1 mM IPTG was done and the culture is kept at 37° C. during four hours under vigorous shaking conditions at 37° C. After, the culture (for each recombinant) was centrifuged at 4000 rpm 15 minutes and pellets were kept frozen at −80° C. until lysis. Lysis was performed using the lysis solution (10 ml) CelLytic B™ (Sigma) diluted at 1/10 in 50 mM NaH2PO4, 300 mM NaCl, 10 mM imidazole pH8.0. Benzonase (25 U/ml) and protease inhibitors were preferably added and vigorous shaking of the lysate was performed at room temperature during 20 minutes. Then, centrifugation was performed at 16000×g during 20 minutes and the supernatant (10 ml) (containing the soluble recombinant TALE 8) was passed through a column (NI-NTA Superflow, size 25 ml) (Qiagen). The column was washed with three volumes (30 ml) of washing buffer (50 mM NaH2PO4, 300 mM NaCl, 20 mM imidazole pH8.0) and elution was performed with 10 ml of 50 mM NaH2PO4, 300 mM NaCl, 250 mM imidazole pH8.0. The elution fraction (2 ml) was collected in the first and second tubes and were passed on a Zeba™ desalting column (Thermo Fisher Pierce) in PBS containing L-arginine 50 mM and L-Glutamine 50 mM to remove imidazole and keep soluble the recombinant protein.

EXAMPLE 5

Cell Lines and Animal Models of Friedreich Ataxia

Cell Line Models

For research on Friedreich ataxia, there is a collection of lymphoblasts and fibroblasts, from FRDA patients, their parents and their siblings available at the National Institutes of General Medical Sciences Human Genetic Cell Repository (Coriell Institute, New Jersey) (http://www.coriell.org/ nigms). These cells may be used for validating that TALEs can increase the expression of frataxin in cells of Friedreich ataxia patients. In this collection, there are FXN alleles with different repeat numbers.

Animal Models

Several animal models have been made. The first one is a heterozygous knockout mouse (KO/Normal FXN). This mouse shows reduced (50%) frataxin levels, and exhibits sporadic heart iron deposits after dietary iron load (Santos et al. 2003). The homozygous KO mouse (KO/KO) is not viable and dies during embryonic development. Further, a KI (knock-in) mouse was developed with a 230 GM repeat. The homozygous KIKI mice have frataxin protein at about 75% of the wild type mice (Miranda et al. 2002). The KI and heterozygous KO mice have been bred together to produce heterozygous KIKO. These mice expressed only 25-36% of the WT frataxin protein at 12 months of age (Miranda et al. 2002). Conditional KO/KO mouse models have been produced with absence of frataxin in muscle heart, brain or pancreas (Puccio et al. 2001), (Ristow et al. 2003). Depending on the tissue in which the gene is knocked out, these mice developed cardiac hypertrophy, large sensory neuron dysfunction or diabetes due to reactive oxygen species increase, growth arrest and apoptosis in pancreatic beta cells. In these conditional KO with a Cre under a MCK promoter, there is in the heart a progressive increase of two important mitochondrial ATP dependent proteases (Lon and ClpP), a simultaneous and significant progressive loss (loss of 80%) of mitochondrial Fe—S proteins (aconitase and ferrochelatase) and of SDHA and ND6 respiratory chain subunits (Guillon et al. 2009). These changes are detectable at 3 weeks and are very pronounced at 5 weeks.

Other researchers have developed transgenic mice containing a YAC containing a human FXN gene with either 190 or 280 GM repeats, respectively designated as YG22 and YG8. These mice showed an intergenerational and age-related somatic instability of the repeats, with the most prominent expansions occurring specifically in the cerebellum (as seen in FRDA patients) and in the dorsal root ganglia (Al-Mandawi et al. 2006, Clark et al. 2007). By crossbreeding the FXN YAC transgenic mice with heterozygous FXN KO mice obtained from Puccio and colleagues, the Pook laboratory has further shown that both transgenes are able to successfully rescue homozygous FXN knockout (KO/KO) embryonic lethality and that the rescue mice (called YG22 rescued and YG8 rescued) express no mouse frataxin and only a low level of human frataxin (because they have only one human FNX gene, which has a 190 or 280 GM repeat) and thus they exhibit an FRDA-like phenotype (Al-Mandawi et al. 2006). These rescued mice (particularly the YG8 rescued mice) exhibited decreased frataxin mRNA and protein in affected organs, decreased coordination ability (as determined by rotarod testing), decreased aconitase activity, oxidative stress (decreases CuZnSOD and MnSOD in muscles, cerebellum and heart), histopathology in DRG large sensory neurons, iron accumulation in the heart, marked reduction of activity starting at 6 months and increased weight (Al-Mandawi et al. 2006, Clark et al. 2007). Therefore, this is an excellent FRDA mouse model in which to investigate the potential therapeutic effects of the TALEs targeting the human frataxin promoter.

Other researchers have produced a FXN-EGFP reporter mouse, i.e., a transgenic mouse with a natural FXN promoter controlling the expression of EGFP (Grant et al. 2006, Sarsero et al. 2003, Sarsero et al. 2005). This transgenic model is useful to screen for compounds able to increase the activity of the FXN promoter.

Interestingly, a transgenic mouse over-expressing frataxin has been produced (Miranda et al. 2004). This transgenic mouse does not develop any pathology. This is an important result because this clearly shows that if frataxin protein is increased over the normal level by an eventual therapy in FRDA patients, the over abundance of frataxin will not produce adverse effects.

EXAMPLE 6

A Recombinant Frataxin Protein Fused with a Protein Transduction Domain Prevents the Death of Fibroblasts with a Knock Out Frataxin Gene Construction of the Frataxin Expression Vector A bacterial expression vector was produced. The human frataxin cDNA was obtained from Origene inc. (Rockville, Md.) and cloned in the pET-16b (Novagen inc., Merck inc., Darmstadt, Germany) vector under a Lac-operon inducible by Isopropyl β-D-1-thiogalactopyranoside (IPTG, BioBasic inc., Amherst, N.Y.). Various versions of the expression vector were done with the frataxin cDNA fused or not at its 5' end with a sequence coding for a protein transduction domain (PTD), i.e., either Tat or Pep-1 (Morris et al. 2001, Vives et al. 2003, Morris, Heitz and Divita 2002). However, to facilitate the protein purification this PTD was preceded by a sequence coding for a 6×His tag. Some vector variants also included a V5-tag (Invitrogen inc., Carlsbad, Calif.) at the 3' end.

Production and Purification of the Recombinant Frataxin

Figure 17:
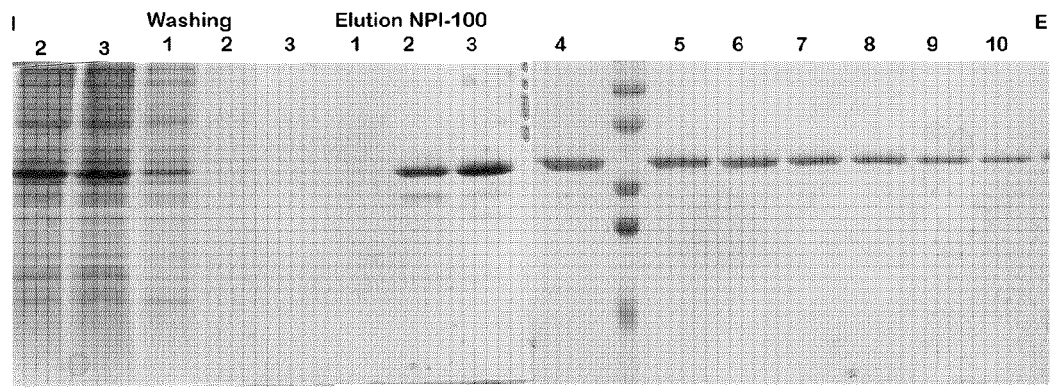
FIG. 17 shows the purification of 6×His-Tat-Frataxin The recombinant protein was produced in *E. coli* and passed through a nickel affinity column. Left lines 2 and 3 represent the proteins that when through the column without attaching to it. The column was first washed with 10 mM imidazole (lines washing 1 to 3). The protein was then eluted with 100 mM imidazole (right lines 1 to 10)

The various recombinant frataxin proteins (6×His-frataxin, 6×His-Tat-frataxin, 6×His-Pep-1-frataxin, 6×His-frataxin-V5, 6×His-Tat-frataxin-V5, 6×His-Pep-1-frataxin-V5) were produced in E. coli transformed with the pET-16b vector. Thus, all expression vectors included a sequence coding for a 6×His tag to permit the purification of the proteins on a nickel affinity column. The bacteria were grown in LB medium at 37° C. until a $DO_{600}$ between 0.5 and 1.0. The protein production was induced by adding IPTG to a final concentration of 0.5 mM. The bacteria were lysed 4 hours later with Cellytic B™ (Sigma inc., St-Louis, Mo.). The bacteria were centrifuged and the supernatant was flown through a Nickel affinity column (Qiagen inc., Valencia, Calif.). The column was first washed with the NPI-10 buffer. The frataxin protein was eluted with 100 mM imidazole. The purity of the protein was confirmed by gel electrophoresis followed by Coomassie blue staining (FIG. 17) or by western blot with a mAb against frataxin (Mito Science inc., Eugene, Oreg.).

Culture of the Conditional Knockout Fibroblasts

A murine cellular model for FRDA was used for several of our experiments (Calmels et al. 2009). This fibroblast line carries a null frataxin gene and a conditional frataxin allele. These fibroblasts were grown in DMEM media (Sigma, Saint Louis, Mo.) with 10% fetal calf serum. When these cells are transfected with an EGFP-Cre recombinase gene under a CMV promoter (AddGene inc., Cambridge, Mass.), this creates a cell model depleted of endogenous frataxin. The complete absence of murine frataxin in these fibroblasts inhibits cell division and leads to cell death.

Western Blot for the V5-Tag

To detect the V5-tag in western blot, the membrane was incubated with an anti-V5 mAb (Invitrogen inc.). The presence of the mAb was detected with an anti-mouse coupled with horseradish peroxidase (HRP) followed by chemiluminescence detection.

Transfection of 293FT Cells with Plasmids Coding for Frataxin-V5 or 6×His-Frataxin-V5

Figure 16:
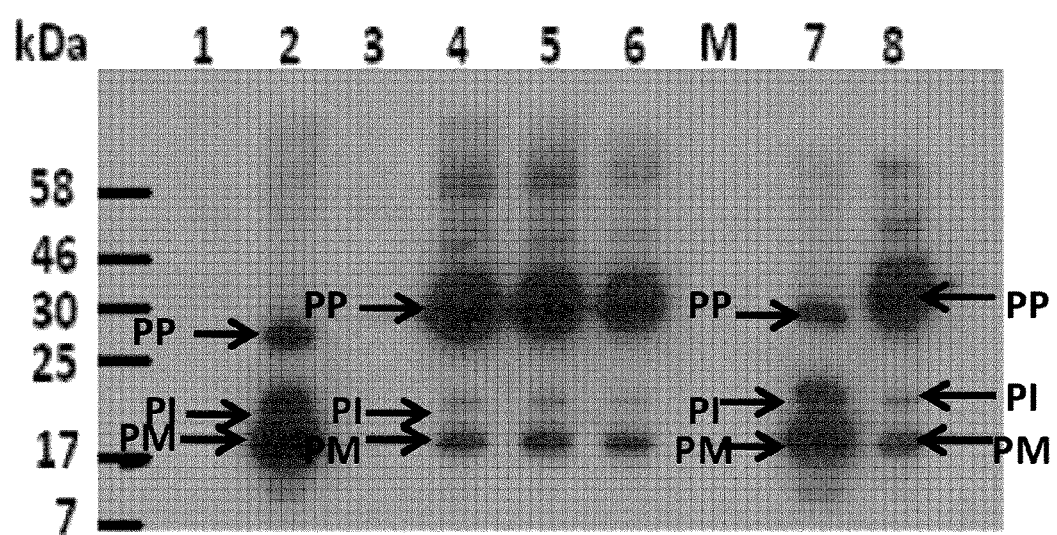
FIG. 16 shows a western blot analysis for the V5 tag. 293FT cells were transfected with plasmids coding either for frataxin fused with the V5 tag (pCR3.1-Frataxin-V5, lines 2 and 7) or for 6×His-Pep-1-frataxin fused with the V5 tag (pCR3.1-6×His-Pep-1-Frataxin-V5, lines 4, 5, 6 and 8). The proteins were extracted from the cells 36 hours later. The V5 mAb detected 3 isoforms of the frataxin protein: PP: proprotein, PI: intermediary protein, PM: mature protein.

Normally, the frataxin protein is produced in the cytoplasm as a pro-frataxin containing 210 amino acids. This pro-protein is then imported in the mitochondria where the N terminal is truncated twice to produce an intermediary and a mature frataxin. To verify whether the presence of the 6×His tag and of a PTD in the recombinant frataxin could prevent its maturation, 293FT cells were transfected with plasmids coding either for frataxin fused with the V5 tag (pCR3.1-Frataxin-V5) or for 6×His-Pep-1-frataxin fused with the V5 tag (pCR3.1-6×His-Pep-1-Frataxin-V5). The proteins were extracted from the cells 36 hours later. A V5 mAb was used to detect the recombinant proteins in a western blot. Three isoforms of the frataxin proteins were detected: PP: pro-protein, PI: intermediary protein, PM: mature protein (see FIG. 16). When the cells were transfected with the plasmid coding for Frataxin-V5, some pro-proteins and intermediary proteins were detected but most of the proteins were already mature. When the cells were transfected with the plasmid coding for the 6×His-Pep-1-Frataxin-V5, most of the proteins were in the pro-protein isoforms but some intermediary proteins and mature proteins were also detected. This indicates that although the presence of a PTD may delay the maturation of the frataxin, the protein was nevertheless able to mature.

Figure 18:
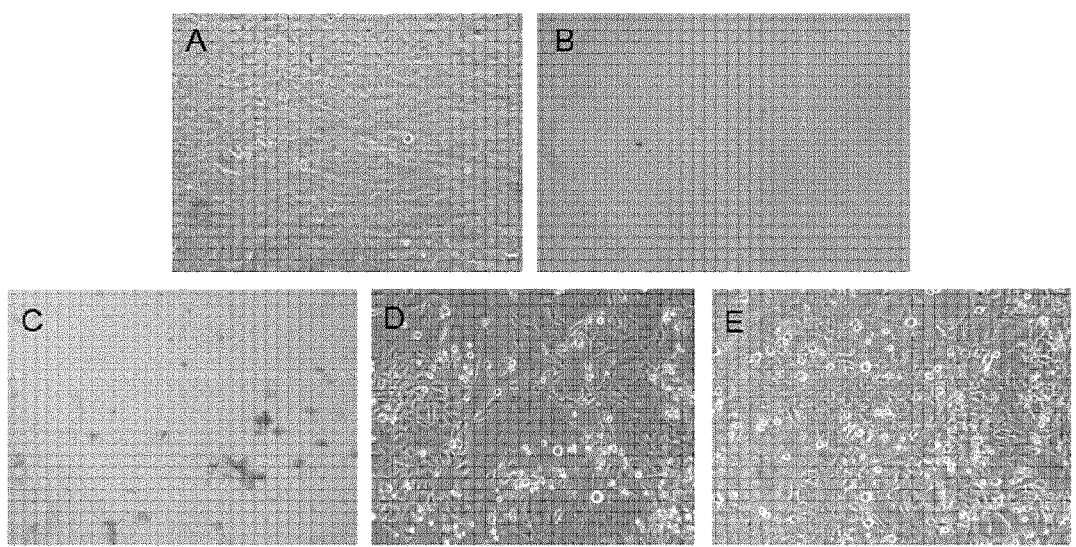
FIG. 18 shows that recombinant frataxin expressed in conditional KO cells prevents cell death. (A): cells with a conditional KO frataxin gene not transfected with Cre-recombinase. Cells in B, C, D and E were transfected with Cre-recombinase/EGFP plasmid, selected by FACS for green fluorescence and placed back in culture with either no frataxin supplement (B), with 6×His-frataxin (C), with 6×His-Tat-frataxin (D) or 6×His-Pep-1-frataxin (E). Cells cultured with 6×His-Tat-frataxin or 6×His-Pep-1-frataxin survived with cells with no frataxin or 6×His-frataxin died.

The frataxin gene in the conditional knock-out fibroblasts was knock-out by transfecting these cells with a Cre-recombinase-EGFP plasmid. The green fluorescent cells, i.e., transfected cells, were selected by FACS and placed back in culture. These cells were thus not able to produce frataxin. Some cells were cultured without any frataxin supplement in the culture medium or with 6×His-frataxin. All these cells died in less than one week (FIGS. 18 B and C). However, when Tat-frataxin or Pep-1-frataxin was added to the culture medium, the frataxin-KO fibroblasts survived and proliferated (FIGS. 18 D and E). This indicates that the recombinant proteins coupled with a PTD were not only able to enter into the fibroblasts but that they also entered in the mitochondria and were able to replace the missing frataxin protein leading to cell survival.

Although the present invention has been described hereinabove by way of specific embodiments thereof, it can be modified, without departing from the spirit and nature of the subject invention as defined in the appended claims.

REFERENCES

Al-Mandawi, S., R. M. Pinto, D. Varshney, L. Lawrence, M. B. Lowrie, S. Hughes, Z. Webster, J. Blake, J. M. Cooper, R. King & M. A. Pook (2006) GM repeat expansion mutation mouse models of Friedreich ataxia exhibit oxidative stress leading to progressive neuronal and cardiac pathology. *Genomics,* 88, 580-90.

Babady, N. E., N. Carelle, R. D. Wells, T. A. Rouault, M. Hirano, D. R. Lynch, M. B. Delatycki, R. B. Wilson, G. Isaya & H. Puccio (2007) Advancements in the pathophysiology of Friedreich's Ataxia and new prospects for treatments. *Mol Genet Metab,* 92, 23-35.

Bidichandani, S. I., T. Ashizawa & P. I. Patel (1997) Atypical Friedreich ataxia caused by compound heterozygosity for a novel missense mutation and the GM triplet-repeat expansion. *Am J Hum Genet,* 60, 1251-6.

Boch, J. & U. Bonas *Xanthomonas* AvrBs3 family-type III effectors: discovery and function. *Annu Rev Phytopathol,* 48, 419-36.

Boch, J., H. Scholze, S. Schornack, A. Landgraf, S. Hahn, S. Kay, T. Lahaye, A. Nickstadt & U. Bonas (2009) Breaking the code of DNA binding specificity of TAL-type III effectors. *Science*, 326, 1509-12.

Bogdanove, A. J., R. Koebnik, H. Lu, A. Furutani, S. V. Angiuoli, P. B. Patil, M. A. Van Sluys, R. P. Ryan, D. F. Meyer, S. W. Han, G. Aparna, M. Rajaram, A. L. Delcher, A. M. Phillippy, D. Puiu, M. C. Schatz, M. Shumway, D. D. Sommer, C. Trapnell, F. Benahmed, G. Dimitrov, R. Madupu, D. Radune, S. Sullivan, G. Jha, H. Ishihara, S. W. Lee, A. Pandey, V. Sharma, M. Sriariyanun, B. Szurek, C. M. Vera-Cruz, K. S. Dorman, P. C. Ronald, V. Verdier, J. M. Dow, R. V. Sonti, S. Tsuge, V. P. Brendel, P. D. Rabinowicz, J. E. Leach, F. F. White & S. L. Salzberg (2011) Two new complete genome sequences offer insight into host and tissue specificity of plant pathogenic *Xanthomonas* spp. J Bacteriol, 193, 5450-64.

Calmels, N., S. Schmucker, M. Wattenhofer-Donze, A. Martelli, N. Vaucamps, L. Reutenauer, N. Messaddeq, C. Bouton, M. Koenig & H. Puccio (2009) The first cellular models based on frataxin missense mutations that reproduce spontaneously the defects associated with Friedreich ataxia. *PLoS One*, 4, e6379.

Campuzano, V., L. Montermini, M. D. Molto, L. Pianese, M. Cossee, F. Cavalcanti, E. Monros, F. Rodius, F. Duclos, A. Monticelli, F. Zara, J. Canizares, H. Koutnikova, S. I. Bidichandani, C. Gellera, A. Brice, P. Trouillas, G. De Michele, A. Filla, R. De Frutos, F. Palau, P. I. Patel, S. Di Donato, J. L. Mandel, S. Cocozza, M. Koenig & M. Pandolfo (1996) Friedreich's ataxia: autosomal recessive disease caused by an intronic GM triplet repeat expansion. *Science*, 271, 1423-7.

Cermak, T., E. L. Doyle, M. Christian, L. Wang, Y. Zhang, C. Schmidt, J. A. Baller, N. V. Somia, A. J. Bogdanove & D. F. Voytas Efficient design and assembly of custom TALEN and other TAL effector-based constructs for DNA targeting. *Nucleic Acids Res*, 39, e82.

Clark, R. M., I. De Biase, A. P. Malykhina, S. Al-Mandawi, M. Pook & S. I. Bidichandani (2007) The GM triplet-repeat is unstable in the context of the human FXN locus and displays age-dependent expansions in cerebellum and DRG in a transgenic mouse model. *Hum Genet*, 120, 633-40.

Condo, I., N. Ventura, F. Malisan, B. Tomassini & R. Testi (2006) A pool of extramitochondrial frataxin that promotes cell survival. *J Biol Chem*, 281, 16750-6.

Cooper, J. M. & A. H. Schapira (2003) Friedreich's Ataxia: disease mechanisms, antioxidant and Coenzyme Q10 therapy. *Biofactors*, 18, 163-71.

Coppola, G., S. H. Choi, M. M. Santos, C. J. Miranda, D. Tentler, E. M. Wexler, M. Pandolfo & D. H. Geschwind (2006) Gene expression profiling in frataxin deficient mice: microarray evidence for significant expression changes without detectable neurodegeneration. *Neurobiol Dis*, 22, 302-11.

Coppola, G., D. Marmolino, D. Lu, Q. Wang, M. Cnop, M. Rai, F. Acquaviva, S. Cocozza, M. Pandolfo & D. H. Geschwind (2009) Functional genomic analysis of frataxin deficiency reveals tissue-specific alterations and identifies the PPARgamma pathway as a therapeutic target in Friedreich's ataxia. *Hum Mol Genet*, 18, 2452-61.

Cossee, M., A. Durr, M. Schmitt, N. Dahl, P. Trouillas, P. Allinson, M. Kostrzewa, A. Nivelon-Chevallier, K. H. Gustavson, A. Kohlschutter, U. Muller, J. L. Mandel, A. Brice, M. Koenig, F. Cavalcanti, A. Tammaro, G. De Michele, A. Filla, S. Cocozza, M. Labuda, L. Montermini, J. Poirier & M. Pandolfo (1999) Friedreich's ataxia: point mutations and clinical presentation of compound heterozygotes. *Ann Neurol*, 45, 200-6.

Guillon, B., A. L. Bulteau, M. Wattenhofer-Donze, S. Schmucker, B. Friguet, H. Puccio, J. C. Drapier & C. Bouton (2009) Frataxin deficiency causes upregulation of mitochondrial Lon and ClpP proteases and severe loss of mitochondrial Fe—S proteins. *FEBS J*, 276, 1036-47.

Grant, L., J. Sun, H. Xu, S. H. Subramony, J. B. Chaires & M. D. Hebert (2006) Rational selection of small molecules that increase transcription through the GM repeats found in Friedreich's ataxia. *FEBS Lett*, 580, 5399-405.

Harding, A. E. (1981) Friedreich's ataxia: a clinical and genetic study of 90 families with an analysis of early diagnostic criteria and intrafamilial clustering of clinical features. *Brain*, 104, 589-620.

Li, K., Singh, A., Crooks, D. A., Dai, X., Cong, Z., Pan, L., Ha, D., and Rouault, T. A., (2010) Expression of Human frataxin is regulated by transcription factors SRF and TFAP2. *Plos One*, 5(8), e12286 (www.Plosone.org).

Lynch, D. R., J. M. Farmer, L. J. Balcer & R. B. Wilson (2002) Friedreich ataxia: effects of genetic understanding on clinical evaluation and therapy. *Arch Neurol*, 59, 743-7.

McCormack, M. L., R. P. Guttmann, M. Schumann, J. M. Farmer, C. A. Stolle, V. Campuzano, M. Koenig & D. R. Lynch (2000) Frataxin point mutations in two patients with Friedreich's ataxia and unusual clinical features. *J Neurol Neurosurg Psychiatry*, 68, 661-4.

Miranda, C. J., M. M. Santos, K. Ohshima, J. Smith, L. Li, M. Bunting, M. Cossee, M. Koenig, J. Sequeiros, J. Kaplan & M. Pandolfo (2002) Frataxin knockin mouse. *FEBS Lett*, 512, 291-7.

Miranda, C. J., M. M. Santos, K. Ohshima, M. Tessaro, J. Sequeiros & M. Pandolfo (2004) Frataxin overexpressing mice. *FEBS Lett*, 572, 281-8.

Moscou, M. J. & A. J. Bogdanove (2009) A simple cipher governs DNA recognition by TAL effectors. *Science*, 326, 1501.

Pandolfo, M. (1999) Molecular pathogenesis of Friedreich ataxia. *Arch Neurol*, 56, 1201-8.

Puccio, H., D. Simon, M. Cossee, P. Criqui-Filipe, F. Tiziano, J. Melki, C. Hindelang, R. Matyas, P. Rustin & M. Koenig (2001) Mouse models for Friedreich ataxia exhibit cardiomyopathy, sensory nerve defect and Fe—S enzyme deficiency followed by intramitochondrial iron deposits. *Nat Genet*, 27, 181-6.

Ristow, M., H. Mulder, D. Pomplun, T. J. Schulz, K. Muller-Schmehl, A. Krause, M. Fex, H. Puccio, J. Muller, F. Isken, J. Spranger, D. Muller-Wieland, M. A. Magnuson, M. Mohlig, M. Koenig & A. F. Pfeiffer (2003) Frataxin deficiency in pancreatic islets causes diabetes due to loss of beta cell mass. *J Clin Invest*, 112, 527-34.

Sarsero, J. P., T. P. Holloway, L. Li, S. McLenachan, K. J. Fowler, I. Bertoncello, L. Voullaire, S. Gazeas & P. A. Ioannou (2005) Evaluation of an FRDA-EGFP genomic reporter assay in transgenic mice. *Mamm Genome*, 16, 228-41.

Sarsero, J. P., L. Li, H. Wardan, K. Sitte, R. Williamson & P. A. Ioannou (2003) Upregulation of expression from the FRDA genomic locus for the therapy of Friedreich ataxia. *J Gene Med*, 5, 72-81.

Schoenfeld, R. A., E. Napoli, A. Wong, S. Zhan, L. Reutenauer, D. Morin, A. R. Buckpitt, F. Taroni, B. Lonnerdal, M. Ristow, H. Puccio & G. A. Cortopassi (2005) Frataxin deficiency alters heme pathway transcripts and decreases mitochondrial heme metabolites in mammalian cells. *Hum Mol Genet,* 14, 3787-99.

Singh, G., B. A. Binstadt, D. F. Black, A. P. Corr & T. A. Rummans (2001) Electroconvulsive therapy and Friedreich's ataxia. *J ECT,* 17, 53-4.

Yu, Y., J. Streubel, S. Balzergue, A. Champion, J. Boch, R. Koebnik, J. Feng, V. Verdier & B. Szurek (2011) Colonization of rice leaf blades by an African strain of *Xanthomonas oryzae* pv. *oryzae* depends on a new TAL effector that induces the rice nodulin-3 Os11N3 gene. Mol Plant Microbe Interact, 24, 1102-13.

Zhang, F., L. Cong, S. Lodato, S. Kosuri, G. M. Church & P. Arlotta (2011). Efficient construction of sequence-specific TAL effectors for modulating mammalian transcription. *Nat Biotechnol,* 29(2), 149-53.

The invention claimed is:

1. A transcription activator-like (TAL) effector-based recombinant protein comprising:
   i) a TAL effector domain comprising a repeat variable domain (RVD) comprising at least 10 tandem repeat monomers, each monomer consisting of an HD, NG, NN or NI module, wherein said RVD comprises the following configuration of said HD, NG, NN and NI modules:
      a) NI-NN-NG-NN-HD-NG-NI-NI-NN-HD-NG-NN;
      b) NN-NN-NN-NI-NI-NN-NG-NG-HD-NG-NG-HD-HD; or
      c) HD-HD-NG-NN-NI-NN-NN-NG-HD-NG-NI-NI,
      wherein said HD module consists of 34 contiguous amino acids of the amino acid sequence of SEQ ID NO: 61; said NG module consists of 34 contiguous amino acids of the amino acid sequence of SEQ ID NO: 59, said NI module consists of 34 contiguous amino acids of the amino acid sequence of SEQ ID NO: 57, and said NN module consists of 34 contiguous amino acids of the amino acid sequence of SEQ ID NO: 63; and
      wherein said configuration of modules binds to a sequence within nucleotides 81-116 of SEQ ID NO: 88 of the promoter sequence of a mammalian frataxin gene;
   ii) a nuclear localization signal; and
   iii) a transcription activation domain.

2. The recombinant protein of claim 1, wherein said transcription activation domain is a VP64 synthetic transcription activation domain.

3. The recombinant protein of claim 1, wherein said nuclear localization signal is a mammalian nuclear localization signal derived from the simian virus 40 large T antigen.

4. A composition comprising the recombinant protein of claim 1 and a pharmaceutically acceptable carrier.

5. An isolated nucleic acid encoding the recombinant protein of claim 1.

6. A vector comprising the isolated nucleic acid of claim 5.

7. A host cell comprising the isolated nucleic acid of claim 5.

8. A method for increasing frataxin expression in a cell comprising transducing said cell with the recombinant protein of claim 1.

* * * * *